US011104723B2

(12) United States Patent
Goodman et al.

(10) Patent No.: US 11,104,723 B2
(45) Date of Patent: Aug. 31, 2021

(54) ANTIBODY COMPOSITIONS FOR DISRUPTING BIOFILMS

(71) Applicant: RESEARCH INSTITUTE AT NATIONWIDE CHILDREN'S HOSPITAL, Columbus, OH (US)

(72) Inventors: Steven D. Goodman, Columbus, OH (US); Lauren O. Bakaletz, Columbus, OH (US)

(73) Assignee: RESEARCH INSTITUTE AT NATIONWIDE CHILDREN'S HOSPITAL, Columbus, OH (US)

( * ) Notice: Subject to any disclaimer, the term of this patent is extended or adjusted under 35 U.S.C. 154(b) by 0 days.

(21) Appl. No.: 17/161,588

(22) Filed: Jan. 28, 2021

(65) Prior Publication Data
US 2021/0206841 A1     Jul. 8, 2021

Related U.S. Application Data

(63) Continuation of application No. PCT/US2020/041082, filed on Jul. 7, 2020.

(60) Provisional application No. 62/871,457, filed on Jul. 8, 2019, provisional application No. 63/033,109, filed on Jun. 1, 2020.

(51) Int. Cl.
| C07K 16/00 | (2006.01) |
| C07K 16/12 | (2006.01) |
| G01N 33/569 | (2006.01) |
| A61P 31/04 | (2006.01) |
| A01N 63/50 | (2020.01) |
| A61K 39/00 | (2006.01) |

(52) U.S. Cl.
CPC .......... *C07K 16/1232* (2013.01); *A01N 63/50* (2020.01); *A61P 31/04* (2018.01); *G01N 33/56911* (2013.01); *A61K 2039/505* (2013.01); *C07K 2317/21* (2013.01); *C07K 2317/24* (2013.01); *C07K 2317/40* (2013.01); *C07K 2317/41* (2013.01); *C07K 2317/52* (2013.01); *C07K 2317/54* (2013.01); *C07K 2317/55* (2013.01); *C07K 2317/565* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,663,863 B2 | 12/2003 | Horvath et al. |
| 6,696,550 B2 | 2/2004 | LaRosa et al. |
| 8,999,291 B2 * | 4/2015 | Goodman .......... C07K 16/1217 424/9.2 |
| 10,233,234 B2 | 3/2019 | Kauvar et al. |
| 10,570,193 B2 | 2/2020 | Kauvar et al. |
| 10,940,204 B2 | 3/2021 | Bakaletz et al. |
| 2010/0291177 A1 | 11/2010 | Hermans et al. |
| 2011/0236306 A1 | 9/2011 | Goodman et al. |
| 2014/0287426 A1 | 9/2014 | Arnold et al. |
| 2015/0086561 A1 * | 3/2015 | Kauvar .............. C07K 16/1275 424/139.1 |
| 2015/0166641 A1 | 6/2015 | Goodman et al. |
| 2015/0197558 A1 | 7/2015 | Kauvar et al. |
| 2015/0216971 A1 | 8/2015 | Rotolo et al. |
| 2015/0299298 A1 | 10/2015 | Kauvar et al. |
| 2016/0095316 A1 | 4/2016 | Goodman et al. |
| 2016/0175440 A1 | 6/2016 | Goodman et al. |
| 2016/0194384 A1 * | 7/2016 | Goodman ........ A61K 39/39541 424/136.1 |
| 2016/0237145 A1 | 8/2016 | Kauvar et al. |
| 2019/0000971 A1 | 1/2019 | Bakaletz et al. |
| 2019/0040127 A1 | 2/2019 | Wadehra et al. |
| 2020/0002409 A1 | 1/2020 | Goodman et al. |
| 2020/0190170 A1 | 6/2020 | Kauvar et al. |

FOREIGN PATENT DOCUMENTS

| WO | WO-2011/123396 A1 | 10/2011 | |
| WO | WO-2012/034090 A1 | 3/2012 | |
| WO | WO-2014/201305 A1 | 12/2014 | |
| WO | WO-201 5/048484 A2 | 4/2015 | |
| WO | WO-201 6/154491 A1 | 9/2016 | |
| WO | WO-201 7/023863 A1 | 2/2017 | |
| WO | WO-201 7/192594 A1 | 11/2017 | |
| WO | WO-2017192594 A1 * | 11/2017 | .......... C07K 14/195 |
| WO | WO-201 8/042385 A2 | 3/2018 | |
| WO | WO-2018129078 A1 * | 7/2018 | ............... A61K 8/64 |
| WO | WO-2019/112978 A2 | 6/2019 | |

OTHER PUBLICATIONS

Novotny et al., EBioMedicine. Aug. 2016;10:33-44. doi: 10.1016/j.ebiom.2016.06.022. Epub Jun. 16, 2016.*
Janeway et al., Immunobiology, 3rd edition, 1997 Garland Publishing Inc., pp. 3:1-3:11.*
U.S. Appl. No. 15/744,713, filed Jan. 12, 2018, The Research Institute at Nationwide Children's Hospital.
U.S. Appl. No. 15/999,215, filed Aug. 16, 2018, Goodman et al..
U.S. Appl. No. 16/746,708, filed Jan. 17, 2020, Trellis Dioscience, LLC.
U.S. Appl. No. 17/150,731, filed Jan. 15, 2021, The Research Institute at Nationwide Children's Hospital.
International Search Report and Written Opinion issued in PCT/US2020/041082 dated Jan. 21, 2021, 13 pages.
Vajdos et al. "Comprehensive Functional Maps of the Antigen-binding Site of an Anti-ErbB2 Antibody Obtained with Shotgun Scanning Mutagenesis", J Mol. Biol., Jul. 5, 2002, 320(2), pp. 415-428.

(Continued)

*Primary Examiner* — Michael Szperka
(74) *Attorney, Agent, or Firm* — Foley & Lardner LLP

(57) ABSTRACT

Provided herein are methods and compositions for disrupting biofilms in vitro and in vivo. Also disclosed are antibodies comprising a specified heavy chain (HC) immunoglobulin variable domain sequence and/or a specified light chain (LC) immunoglobulin variable domain sequence.

30 Claims, 28 Drawing Sheets
Specification includes a Sequence Listing.

(56) References Cited

OTHER PUBLICATIONS

Bakaletz et al., "New strategies to target bacterial biofilms", 28th Annual North American Cystic Fibrosis Conference (NACFC), Atlanta, GA, Oct. 9-11, 2014 (presentation), 2 pages.

Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258, Supplementary Material, 6 pages.

Brockson et al., "Evaluation of the kinetics and mechanism of action of anti-integration host factor-mediated disruption of bacterial biofilms," Molecular Microbiology, vol. 93, No. 6, Aug. 19, 2014, pp. 1246-1258.

Estelles et al., "A High-Affinity Native Human Antibody Disrupts Biofilm from *Staphylococcus aureus* Bacteria and Potentiates Antibiotic Efficacy in a Mouse Implant Infection Model," Antimicrobial Agents and Chemotherapy, vol. 60, No. 4, Apr. 2016, pp. 2292-2301.

Estrela et al., "Combining Biofilm-Controlling Compounds and Antibiotics as a Promising New Way to Control Biofilm Infections," Pharmaceuticals, vol. 3, May 11, 2010, pp. 1374-1393.

Goodman et al., "Biofilms can be dispersed by focusing the immune system on a common family of bacterial nucleoid-associated proteins," Mucosal Immunology, vol. 4, No. 6, Nov. 2011, pp. 625-637.

Goodman S D et al., "Biofilms can be dispersed by focusing the immune system on a common family of bacterial nucleoid-associated proteins", Mucosal Immuno, Nature Publishing Group, vol. 4, No. 6, Nov. 1, 2011, pp. 625-637.

Goodman, "Making and breaking biofilms", Ohio Branch American Society for Microbiology Annual Meeting, Columbus, OH, Apr. 11-12, 2014 (presentation), 12 pages.

Goodman, "The DNABII family of proteins: Diagnostic markers and therapeutic targets of bacterial biofilms", International Congress on Bacteriology and Infectious Disease, Baltimore, MD, Nov. 21, 2013, 7 pages.

Laura A. Novotny et al., "Monoclonal antibodies against DNA-binding tips of DNABII proteins disrupt biofilms in vitro and induce bacterial clearance in vivo", EBIOMEDICINE, vol. 10, Aug. 1, 2016, pp. 33-44.

M. Elizabeth Brockson et al., "Evaluation of the kinetics and mechanism of action anti-integration host factor-mediated disruption of bacterial biofilms: Anti-IHF-mediated biofilm collapse", Molecular Microbiology., Aug. 19, 2014, pp. 1-22.

Malhotra et al., "Defining the functional epitopes of Integration Host Factor (IHF) to develop a novel biofilm-focused immunotherapeutic against nontypeable Haemophilus influenzae-induced chronic and recurrent otitis media", 18th International Symposium on Recent Advances in Otitis Media, National Harbor, MD, Jun. 7-11, 2015 (poster), 1 page.

Malhotra et al., "Fine mapping the functional epitopes within integration host factor, a novel therapeutic target for nontypeable Haemophilus influenza-induced diseases of the respiratory tract", Abst. 12th Annual AMA Research Symposium, Dallas, TX, Nov. 7, 2014, 1 page.

Novotny et al., "Antibodies against the majority subunit of Type 1V pili disperse nontypeable Haemophilus influenza biofilms in a LuxS-dependent manner and confer therapeutics resolution of experimental otitis media," Mol. Microbiol., vol. 96, No. 2, Apr. 2015, pp. 1-32.

Novotny et al., "Structural Stability of Burkholderia cenocepacia Biofilms Is Reliant on eDNA Structure and Presence of a Bacterial Nucleic Acid Binding Protein," PLOS ONE, vol. 8, No. 6, e67629, Jun. 2013, 15 pages.

Novotny, "Development of a novel biofilm-focused immunotherapeutic against NTHI-induced otitis media", 18th International Symposium on Recent Advances in Otitis Media, National Harbor, MD, Jun. 7-11, 2015 (presentation), 3 pages.

Novotny, L.A., Clements, J.D., and Bakaletz, L.O. "Kinetic analysis and evaluation of the mechanisms involved in the resolution of experimental nontypeable Haemophilus influenzae-induced otitis media after transcutaneous immunization", Vaccine 31, Jul. 25, 2013, pp. 3417-3426.

Novotny, L.A., et al., "Transcutaneous immunization as preventative and therapeutic regimens to protect against experimental otitis media due to nontypeable Haemophilus influenzae", Mucosal Immunol vol. 5 No. 1, Year 2011, pp. 456-467.

\* cited by examiner

Biofilms formed for 24 hr by nontypeable *Haemophilus influenzae* were incubated for 16 h with 5 µg of:
humanized monoclonal antibody against IHF$_{NTHi}$ tip chimer peptide #1F8.F1 HC1+LC1 TP-21949
humanized monoclonal antibody against IHF$_{NTHi}$ tail chimer peptide #11E7.C7 HC1+LC1 TP-21959
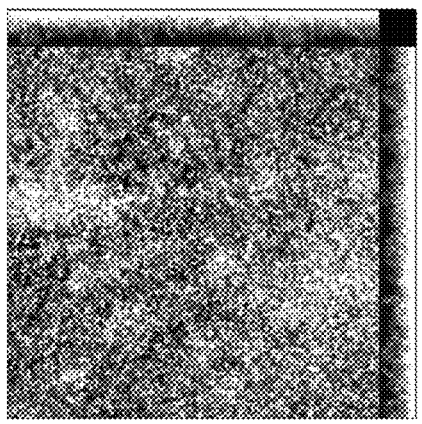
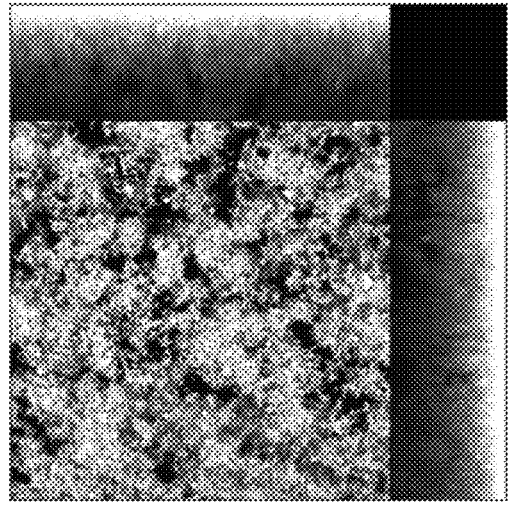
Biomass 0.4 µg$^3$/µg$^2$     Biomass 16.9 µg$^3$/µg$^2$
FIGURE 3

Organized by individual chain

IHF<sub>NTHI</sub> TIP CHIMERIC PEPTIDE-SPECIFIC

| Peptide target | Chimeric or humanized | Chain type | Chain code | Amino acid Identity[1] |
|---|---|---|---|---|
| IhfA5-mIhfB4<sub>NTHI</sub> Tip chimeric peptide | Chimeric | Heavy chain | | |
| | Chimeric | Light chain | | |
| | Humanized | Heavy chain | HC1 | 473/475 to HC2<br>452/475 to HC3 |
| | Humanized | Heavy chain | HC2 | 473/475 to HC1<br>450/475 to HC3 |
| | Humanized | Heavy chain | HC3 | 452/475 to HC1<br>450/475 to HC2 |
| | Humanized | Light chain | LC1 | 239/240 to LC2<br>224/240 to LC3 |
| | Humanized | Light chain | LC2 | 239/240 to LC1<br>223/240 to LC3 |
| | Humanized | Light chain | LC3 | 224/240 to LC1<br>223/240 to LC2 |

[1] Amino acid alignments performed with NCBI blastp

FIGURE 4A

Tip F1 HC 1 (SEQ ID NO: 1) V Tip F1 HC 2 (SEQ ID NO: 2)

Score 973 bits(2516) Except 0.0 Method- Compositional matrix adjust. Identities 473/475 Identity (99%)   positives 475/475(100%) Gaps 0/475(0%)

```
Tip F1 HC 1  MDPKGSLSWRILLFLSLAFELSYGEVKLVESGGGLVQPGGSLRLSCAASGFTFRTYAMSW  60
             MDPKGSLSWRILLFLSLAFELSYGEV+LVESGGGLVQPGGSLRLSCAASGFTFRTYAMSW
Tip F1 HC 2  MDPKGSLSWRILLFLSLAFELSYGEVQLVESGGGLVQPGGSLRLSCAASGFTFRTYAMSW  60

Tip F1 HC 1  VRQAPGKGLEWVATIGSDRRHTYYPDSVKGRFTISRDNAKNTLYLQMNSLRAEDTAVYYC  120
             VRQAPGKGLEWVATIGSDRRHTYYPDSVKGRFTISRDN+KNTLYLQMNSLRAEDTAVYYC
Tip F1 HC 2  VRQAPGKGLEWVATIGSDRRHTYYPDSVKGRFTISRDNSKNTLYLQMNSLRAEDTAVYYC  120

Tip F1 HC 1  VGPYDGYYGEFDYWGQGTLVTVSSASTKGPSVFPLAPSSKSTSGGTAALGCLVKDYFPEP  180
             VGPYDGYYGEFDYWGQGTLVTVSSASTKGPSVFPLAPSSKSTSGGTAALGCLVKDYFPEP
Tip F1 HC 2  VGPYDGYYGEFDYWGQGTLVTVSSASTKGPSVFPLAPSSKSTSGGTAALGCLVKDYFPEP  180

Tip F1 HC 1  VTVSWNSGALTSGVHTFPAVLQSSGLYSLSSVVTVPSSSLGTQTYICNVNHKPSNTKVDK  240
             VTVSWNSGALTSGVHTFPAVLQSSGLYSLSSVVTVPSSSLGTQTYICNVNHKPSNTKVDK
Tip F1 HC 2  VTVSWNSGALTSGVHTFPAVLQSSGLYSLSSVVTVPSSSLGTQTYICNVNHKPSNTKVDK  240

Tip F1 HC 1  KVEPKSCDKTHTCPPCPAPELLGGPSVFLFPPKPKDTLMISRTPEVTCVVVDVSHEDPEV  300
             KVEPKSCDKTHTCPPCPAPELLGGPSVFLFPPKPKDTLMISRTPEVTCVVVDVSHEDPEV
Tip F1 HC 2  KVEPKSCDKTHTCPPCPAPELLGGPSVFLFPPKPKDTLMISRTPEVTCVVVDVSHEDPEV  300

Tip F1 HC 1  KFNWYVDGVEVHNAKTKPREEQYNSTYRVVSVLTVLHQDWLNGKEYKCKVSNKALPAPIE  360
             KFNWYVDGVEVHNAKTKPREEQYNSTYRVVSVLTVLHQDWLNGKEYKCKVSNKALPAPIE
Tip F1 HC 2  KFNWYVDGVEVHNAKTKPREEQYNSTYRVVSVLTVLHQDWLNGKEYKCKVSNKALPAPIE  360

Tip F1 HC 1  KTISKAKGQPREPQVYTLPPSREEMTKNQVSLTCLVKGFYPSDIAVEWESNGQPENNYKT  420
             KTISKAKGQPREPQVYTLPPSREEMTKNQVSLTCLVKGFYPSDIAVEWESNGQPENNYKT
Tip F1 HC 2  KTISKAKGQPREPQVYTLPPSREEMTKNQVSLTCLVKGFYPSDIAVEWESNGQPENNYKT  420

Tip F1 HC 1  TPPVLDSDGSFFLYSKLTVDKSRWQQGNVFSCSVMHEALHNHYTQKSLSLSPG**  475
             TPPVLDSDGSFFLYSKLTVDKSRWQQGNVFSCSVMHEALHNHYTQKSLSLSPG**
Tip F1 HC 2  TPPVLDSDGSFFLYSKLTVDKSRWQQGNVFSCSVMHEALHNHYTQKSLSLSPG**  475
```

FIGURE 4B

Tip F1 HC 1 (SEQ ID NO: 1) v Tip F1 HC 3 (SEQ ID NO: 3)
Score 912 bits (2357)   Expect 0.0 Compositional matrix adjust 452/475(95%)
Identities 466/475(98%) Gaps 0/475(0%)

```
Tip F1 HC 1  MDPKGSLSWRILLFLSLAFELSYGEVKLVESGGGLVQPGGSLRLSCAASGFTFRTYAMSW  60
             MDPKGSLSWRILLFLSLAFELSYGEVKLV+SG + +PG S+++SC ASGFTFRTYAMSW
Tip F1 HC 3  MDPKGSLSWRILLFLSLAFELSYGEVKLVQSGAEVKKPGASVKVSCKASGFTFRTYAMSW  60

Tip F1 HC 1  VRQAPGKGLEWVATIGSDRRHTYYPDSVKGRFTISRDNAKNTLYLQMNSLRAEDTAVYYC  120
             VRQAPG+ LEWVATIGSDRRHTYYPD +GR TI+RDNAKNTLY++++SLR+EDTAVYYC
Tip F1 HC 3  VRQAPGQRLEWVATIGSDRRHTYYPDKFQGRVTITRDNAKNTLYMELSSLRSEDTAVYYC  120

Tip F1 HC 1  VGPYDGYYGEFDYWGQGTLVTVSSASTKGPSVFPLAPSSKSTSGGTAALGCLVKDYFPEP  180
             VGPYDGYYGEFDYWGQGTLVTVSSASTKGPSVFPLAPSSKSTSGGTAALGCLVKDYFPEP
Tip F1 HC 3  VGPYDGYYGEFDYWGQGTLVTVSSASTKGPSVFPLAPSSKSTSGGTAALGCLVKDYFPEP  180

Tip F1 HC 1  VTVSWNSGALTSGVHTFPAVLQSSGLYSLSSVVTVPSSSLGTQTYICNVNHKPSNTKVDK  240
             VTVSWNSGALTSGVHTFPAVLQSSGLYSLSSVVTVPSSSLGTQTYICNVNHKPSNTKVDK
Tip F1 HC 3  VTVSWNSGALTSGVHTFPAVLQSSGLYSLSSVVTVPSSSLGTQTYICNVNHKPSNTKVDK  240

Tip F1 HC 1  KVEPKSCDKTHTCPPCPAPELLGGPSVFLFPPKPKDTLMISRTPEVTCVVVDVSHEDPEV  300
             KVEPKSCDKTHTCPPCPAPELLGGPSVFLFPPKPKDTLMISRTPEVTCVVVDVSHEDPEV
Tip F1 HC 3  KVEPKSCDKTHTCPPCPAPELLGGPSVFLFPPKPKDTLMISRTPEVTCVVVDVSHEDPEV  300

Tip F1 HC 1  KFNWYVDGVEVHNAKTKPREEQYNSTYRVVSVLTVLHQDWLNGKEYKCKVSNKALPAPIE  360
             KFNWYVDGVEVHNAKTKPREEQYNSTYRVVSVLTVLHQDWLNGKEYKCKVSNKALPAPIE
Tip F1 HC 3  KFNWYVDGVEVHNAKTKPREEQYNSTYRVVSVLTVLHQDWLNGKEYKCKVSNKALPAPIE  360

Tip F1 HC 1  KTISKAKGQPREPQVYTLPPSREEMTKNQVSLTCLVKGFYPSDIAVEWESNGQPENNYKT  420
             KTISKAKGQPREPQVYTLPPSREEMTKNQVSLTCLVKGFYPSDIAVEWESNGQPENNYKT
Tip F1 HC 3  KTISKAKGQPREPQVYTLPPSREEMTKNQVSLTCLVKGFYPSDIAVEWESNGQPENNYKT  420

Tip F1 HC 1  TPPVLDSDGSFFLYSKLTVDKSRWQQGNVFSCSVMHEALHNHYTQKSLSLSPG**      475
             TPPVLDSDGSFFLYSKLTVDKSRWQQGNVFSCSVMHEALHNHYTQKSLSLSPG**
Tip F1 HC 3  TPPVLDSDGSFFLYSKLTVDKSRWQQGNVFSCSVMHEALHNHYTQKSLSLSPG**      475
```

FIGURE 4C

Tip F1 HC 2 (SEQ ID NO: 2) v Tip F1 HC 3 (SEQ ID NO: 3)

Score 910 bits (2351) Expect 0.0 Compositional matrix adjust. Identities 450/475(95%)

Positive 466/475(98%)   Gaps 0/475(0%)

```
Tip F1 HC 2   MDPKGSLSWRILLFLSLAFELSYGEVQLVESGGGLVQPGGSLRLSCAASGFTFRTYAMSW   60
              MDPKGSLSWRILLFLSLAFELSYGEV+LV+SG  + +PG S+++SC ASGFTFRTYAMSW
Tip F1 HC 3   MDPKGSLSWRILLFLSLAFELSYGEVKLVQSGAEVKKPGASVKVSCKASGFTFRTYAMSW   60

Tip F1 HC 2   VRQAPGKGLEWVATIGSDRRHTYYPDSVKGRFTISRDNSKNTLYLQMNSLRAEDTAVYYC   120
              VRQAPG+ LEWVATIGSDRRHTYYPD  +GR TI+RDN+KNTLY++++SLR+EDTAVYYC
Tip F1 HC 3   VRQAPGQRLEWVATIGSDRRHTYYPDKFQGRVTITRDNAKNTLYMELSSLPSEDTAVYYC   120

Tip F1 HC 2   VGPYDGYYGEFDYWGQGTLVTVSSASTKGPSVFPLAPSSKSTSGGTAALGCLVKDYFPEP   180
              VGPYDGYYGEFDYWGQGTLVTVSSASTKGPSVFPLAPSSKSTSGGTAALGCLVKDYFPEP
Tip F1 HC 3   VGPYDGYYGEFDYWGQGTLVTVSSASTKGPSVFPLAPSSKSTSGGTAALGCLVKDYFPEP   180

Tip F1 HC 2   VTVSWNSGALTSGVHTFPAVLQSSGLYSLSSVVTVPSSSLGTQTYICNVNHKPSNTKVDK   240
              VTVSWNSGALTSGVHTFPAVLQSSGLYSLSSVVTVPSSSLGTQTYICNVNHKPSNTKVDK
Tip F1 HC 3   VTVSWNSGALTSGVHTFPAVLQSSGLYSLSSVVTVPSSSLGTQTYICNVNHKPSNTKVDK   240

Tip F1 HC 2   KVEPKSCDKTHTCPPCPAPELLGGPSVFLFPPKPKDTLMISRTPEVTCVVVDVSHEDPEV   300
              KVEPKSCDKTHTCPPCPAPELLGGPSVFLFPPKPKDTLMISRTPEVTCVVVDVSHEDPEV
Tip F1 HC 3   KVEPKSCDKTHTCPPCPAPELLGGPSVFLFPPKPKDTLMISRTPEVTCVVVDVSHEDPEV   300

Tip F1 HC 2   KFNWYVDGVEVHNAKTKPREEQYNSTYRVVSVLTVLHQDWLNGKEYKCKVSNKALPAPIE   360
              KFNWYVDGVEVHNAKTKPREEQYNSTYRVVSVLTVLHQDWLNGKEYKCKVSNKALPAPIE
Tip F1 HC 3   KFNWYVDGVEVHNAKTKPREEQYNSTYRVVSVLTVLHQDWLNGKEYKCKVSNKALPAPIE   360

Tip F1 HC 2   KTISKAKGQPREPQVYTLPPSREEMTKNQVSLTCLVKGFYPSDIAVEWESNGQPENNYKT   420
              KTISKAKGQPREPQVYTLPPSREEMTKNQVSLTCLVKGFYPSDIAVEWESNGQPENNYKT
Tip F1 HC 3   KTISKAKGQPREPQVYTLPPSREEMTKNQVSLTCLVKGFYPSDIAVEWESNGQPENNYKT   420

Tip F1 HC 2   TPPVLDSDGSFFLYSKLTVDKSRWQQGNVFSCSVMHEALHNHYTQKSLSLSPG**   475
              TPPVLDSDGSFFLYSKLTVDKSRWQQGNVFSCSVMHEALHNHYTQKSLSLSPG**
Tip F1 HC 3   TPPVLDSDGSFFLYSKLTVDKSRWQQGNVFSCSVMHEALHNHYTQKSLSLSPG**   475
```

FIGURE 4D

Tip F1 LC 1 (SEQ ID NO: 7) V Tip F1 LC 2 (SEQ ID NO: 8)

Score 488 bits (1256) Expect 0.0 Compositional matrix adjust.239/240(99%) Identities 239/240(99%)  Gaps 0/240(0%)

```
Tip F1 LC 1    METDTLLLWVLLLWVPGSTGDVVMTQSPLSLPVTLGQPASISCRSSQSLLDSDGKTFLNW    60
               METDTLLLWVLLLWVPGSTGDVVMTQSPLSLPVTLGQPASISCRSSQSLLDSDGKTFLNW
Tip F1 LC 2    METDTLLLWVLLLWVPGSTGDVVMTQSPLSLPVTLGQPASISCRSSQSLLDSDGKTFLNW    60

Tip F1 LC 1    LQQRPGQSPRRLIYLVSKLDSGVPDRFSGSGSGTDFTLKISRVEAEDVGVYYCWQGTHFP   120
               LQQRPGQSPRRLIYLVSK DSGVPDRFSGSGSGTDFTLKISRVEAEDVGVYYCWQGTHFP
Tip F1 LC 2    LQQRPGQSPRRLIYLVSKRDSGVPDRFSGSGSGTDFTLKISRVEAEDVGVYYCWQGTHFP   120

Tip F1 LC 1    YTFGQGTKLEIKRTVAAPSVFIFPPSDEQLKSGTASVVCLLNNFYPREAKVQWKVDNALQ   180
               YTFGQGTKLEIKRTVAAPSVFIFPPSDEQLKSGTASVVCLLNNFYPREAKVQWKVDNALQ
Tip F1 LC 2    YTFGQGTKLEIKRTVAAPSVFIFPPSDEQLKSGTASVVCLLNNFYPREAKVQWKVDNALQ   180

Tip F1 LC 1    SGNSQESVTEQDSKDSTYSLSSTLTLSKADYEKHKVYACEVTHQGLSSPVTKSFNRGEC*   240
               SGNSQESVTEQDSKDSTYSLSSTLTLSKADYEKHKVYACEVTHQGLSSPVTKSFNRGEC*
Tip F1 LC 2    SGNSQESVTEQDSKDSTYSLSSTLTLSKADYEKHKVYACEVTHQGLSSPVTKSFNRGEC*   240
```

FIGURE 4E

Tip F1 LC 1 (SEQ ID NO: 7) V Tip F1 LC 3 (SEQ ID NO: 9)

Score 437 bits (1125) Expect 7e-16 Compositional matrix adjust. 224/240(93%) Identities 233/240(97%) Gaps 0/240(0%)

```
Tip F1 LC 1  METDTLLLWVLLLWVPGSTGDVVMTQSPLSLPVTLGQPASISCRSSQSLLDSDGKTFLNW  60
             METDTLLLWVLLLWVPGSTGDVVMTQSP SL V+LG+ A+I+C+SSQSLLDSDGKTFLNW
Tip F1 LC 3  METDTLLLWVLLLWVPGSTGDVVMTQSPDSLAVSLGERATINCKSSQSLLDSDGKTFLNW  60

Tip F1 LC 1  LQQRPGQSPRRLIYLVSKLDSGVPDRFSGSGSGTDFTLKISRVEAEDVGVYYCWQGTHFP  120
             LQQ+PGQ P+RLIYLVSKLDSGVPDRFSGSGSGTDFTL IS ++AEDV VYYCWQGTHFP
Tip F1 LC 3  LQQKPGQPPKRLIYLVSKLDSGVPDRFSGSGSGTDFTLTISSLQAEDVAVYYCWQGTHFP  120

Tip F1 LC 1  YTFGQGTKLEIKRTVAAPSVFIFPPSDEQLKSGTASVVCLLNNFYPREAKVQWKVDNALQ  180
             YTFGQGTKLEIKRTVAAPSVFIFPPSDEQLKSGTASVVCLLNNFYPREAKVQWKVDNALQ
Tip F1 LC 3  YTFGQGTKLEIKRTVAAPSVFIFPPSDEQLKSGTASVVCLLNNFYPREAKVQWKVDNALQ  180

Tip F1 LC 1  SGNSQESVTEQDSKDSTYSLSSTLTLSKADYEKHKVYACEVTHQGLSSPVTKSFNRGEC*  240
             SGNSQESVTEQDSKDSTYSLSSTLTLSKADYEKHKVYACEVTHQGLSSPVTKSFNRGEC*
Tip F1 LC 3  SGNSQESVTEQDSKDSTYSLSSTLTLSKADYEKHKVYACEVTHQGLSSPVTKSFNRGEC*  240
```

FIGURE 4F

Tip F1 LC 2 (SEQ ID NO: 8) V Tip F1 LC 3 (SEQ ID NO: 9)

Score 435 bits (1119) Expect 7e-162 Compositional matrix adjust.223/240(93%) Identities 232/240(96%) Gaps 0/240(0%)

```
Tip F1 LC 1  METDTLLLWVLLLWVPGSTGDVVMTQSPLSLPVTLGQPASISCRSSQSLLDSDGKTFLNW  60
             METDTLLLWVLLLWVPGSTGDVVMTQSP SL V+LG+ A+I+C+SSQSLLDSDGKTFLNW
Tip F1 LC 3  METDTLLLWVLLLWVPGSTGDVVMTQSPDSLAVSLGERATINCKSSQSLLDSDGKTFLNW  60

Tip F1 LC 1  LQQRPGQSPRRLIYLVSKRDSGVPDRFSGSGSGTDFTLKISRVEAEDVGVYYCWQGTHFP  120
             LQQ+PGQ P+RLIYLVSK DSGVPDRFSGSGSGTDFTL IS ++AEDV VYYCWQGTHFP
Tip F1 LC 3  LQQKPGQPPKRLIYLVSKLDSGVPDRFSGSGSGTDFTLTISSLQAEDVAVYYCWQGTHFP  120

Tip F1 LC 1  YTFGQGTKLEIKRTVAAPSVFIFPPSDEQLKSGTASVVCLLNNFYPREAKVQWKVDNALQ  180
             YTFGQGTKLEIKRTVAAPSVFIFPPSDEQLKSGTASVVCLLNNFYPREAKVQWKVDNALQ
Tip F1 LC 3  YTFGQGTKLEIKRTVAAPSVFIFPPSDEQLKSGTASVVCLLNNFYPREAKVQWKVDNALQ  180

Tip F1 LC 1  SGNSQESVTEQDSKDSTYSLSSTLTLSKADYEKHKVYACEVTHQGLSSPVTKSFNRGEC*  240
             SGNSQESVTEQDSKDSTYSLSSTLTLSKADYEKHKVYACEVTHQGLSSPVTKSFNRGEC*
Tip F1 LC 3  SGNSQESVTEQDSKDSTYSLSSTLTLSKADYEKHKVYACEVTHQGLSSPVTKSFNRGEC*  240
```

FIGURE 4G

Organized by individual chain

IHF$_{NTHi}$ TAIL CHIMERIC PEPTIDE-SPECIFIC

| Peptide target | Chimeric or humanized | Chain type | Chain code | Amino acid Identity[1] |
|---|---|---|---|---|
| IhfA3-mIhfB2$_{NTHi}$ Tail chimeric peptide | Chimeric | Heavy chain | | |
| | Chimeric | Light chain | | |
| | Humanized | Heavy chain | HC1 | 474/475 to HC2<br>469/475 to HC3 |
| | Humanized | Heavy chain | HC2 | 474/475 to HC1<br>471/475 to HC3 |
| | Humanized | Heavy chain | HC3 | 469/475 to HC1<br>471/475 to HC2 |
| | Humanized | Light chain | LC1 | 233/234 to LC2<br>218/233 to LC3 |
| | Humanized | Light chain | LC2 | 233/234 to LC1<br>218/234 to LC3 |
| | Humanized | Light chain | LC3 | 218/233 to LC1<br>218/234 to LC3 |

[1] Amino acid alignments performed with NCBI blastp

FIGURE 5A

Tail C7 HC 1 (SEQ ID NO: 4) V Tail C7 HC 2 (SEQ ID NO: 5)

Score 974 bits(2517)  Expect 0.0  Compositional matrix adjust.474/475(99%)  Identities 475/475(100%)   Gaps 0/475(0%)

```
Tail C7 HC 1  MDPKGSLSWRILLFLSLAFELSYGEVQLVESGGGLVKPGGSLRLSCAASGFTFSRYGMSW  60
              MDPKGSLSWRILLFLSLAFELSYGEVQLVESGGGLVKPGGSLRLSCAASGFTFSRYGMSW
Tail C7 HC 2  MDPKGSLSWRILLFLSLAFELSYGEVQLVESGGGLVKPGGSLRLSCAASGFTFSRYGMSW  60

Tail C7 HC 1  VRQAPGKGLEWVATISSGGSYTYYTDSVKGRFTISRDNAKNSLYLQMNSLRAEDTAVYYC  120
              VRQAPGKGLEWV+TISSGGSYTYYTDSVKGRFTISRDNAKNSLYLQMNSLRAEDTAVYYC
Tail C7 HC 2  VRQAPGKGLEWVSTISSGGSYTYYTDSVKGRFTISRDNAKNSLYLQMNSLRAEDTAVYYC  120

Tail C7 HC 1  ERHGGDGYWYFDVWGQGTMVTVSSASTKGPSVFPLAPSSKSTSGGTAALGCLVKDYFPEP  180
              ERHGGDGYWYFDVWGQGTMVTVSSASTKGPSVFPLAPSSKSTSGGTAALGCLVKDYFPEP
Tail C7 HC 2  ERHGGDGYWYFDVWGQGTMVTVSSASTKGPSVFPLAPSSKSTSGGTAALGCLVKDYFPEP  180

Tail C7 HC 1  VTVSWNSGALTSGVHTFPAVLQSSGLYSLSSVVTVPSSSLGTQTYICNVNHKPSNTKVDK  240
              VTVSWNSGALTSGVHTFPAVLQSSGLYSLSSVVTVPSSSLGTQTYICNVNHKPSNTKVDK
Tail C7 HC 2  VTVSWNSGALTSGVHTFPAVLQSSGLYSLSSVVTVPSSSLGTQTYICNVNHKPSNTKVDK  240

Tail C7 HC 1  KVEPKSCDKTHTCPPCPAPELLGGPSVFLFPPKPKDTLMISRTPEVTCVVVDVSHEDPEV  300
              KVEPKSCDKTHTCPPCPAPELLGGPSVFLFPPKPKDTLMISRTPEVTCVVVDVSHEDPEV
Tail C7 HC 2  KVEPKSCDKTHTCPPCPAPELLGGPSVFLFPPKPKDTLMISRTPEVTCVVVDVSHEDPEV  300

Tail C7 HC 1  KFNWYVDGVEVHNAKTKPREEQYNSTYRVVSVLTVLHQDWLNGKEYKCKVSNKALPAPIE  360
              KFNWYVDGVEVHNAKTKPREEQYNSTYRVVSVLTVLHQDWLNGKEYKCKVSNKALPAPIE
Tail C7 HC 2  KFNWYVDGVEVHNAKTKPREEQYNSTYRVVSVLTVLHQDWLNGKEYKCKVSNKALPAPIE  360

Tail C7 HC 1  KTISKAKGQPREPQVYTLPPSREEMTKNQVSLTCLVKGFYPSDIAVEWESNGQPENNYKT  420
              KTISKAKGQPREPQVYTLPPSREEMTKNQVSLTCLVKGFYPSDIAVEWESNGQPENNYKT
Tail C7 HC 2  KTISKAKGQPREPQVYTLPPSREEMTKNQVSLTCLVKGFYPSDIAVEWESNGQPENNYKT  420

Tail C7 HC 1  TPPVLDSDGSFFLYSKLTVDKSRWQQGNVFSCSVMHEALHNHYTQKSLSLSPG**  475
              TPPVLDSDGSFFLYSKLTVDKSRWQQGNVFSCSVMHEALHNHYTQKSLSLSPG**
Tail C7 HC 2  TPPVLDSDGSFFLYSKLTVDKSRWQQGNVFSCSVMHEALHNHYTQKSLSLSPG**  475
```

FIGURE 5B

Tail C7 HC 1 (SEQ ID NO: 4) V Tail C7 HC 3 (SEQ ID NO: 6)

Score 964 bits(2491) Expect 0.0 Compositional matrix adjust.469/475(99%) Identities 471/475(99%)Gaps 0/475(0%)

```
Tail C7 HC 1   MDPKGSLSWRILLFLSLAFELSYGEVQLVESGGGLVKPGGSLRLSCAASGFTFSRYGMSW   60
               MDPKGSLSWRILLFLSLAFELSYGEVQLVESGGGLV+PG SLRLSC ASGFTFSRYGMSW
Tail C7 HC 3   MDPKGSLSWRILLFLSLAFELSYGEVQLVESGGGLVQPGRSLRLSCTASGFTFSRYGMSW   60

Tail C7 HC 1   VRQAPGKGLEWVATISSGGSYTYYTDSVKGRFTISRDNAKNSLYLQMNSLRAEDTAVYYC   120
               VRQAPGKGLEWVATISSGGSYTYYTDSVKGRFTISRDNAKN LYLQMNSL+ EDTAVYYC
Tail C7 HC 3   VRQAPGKGLEWVATISSGGSYTYYTDSVKGRFTISRDNAKNILYLQMNSLKTEDTAVYYC   120

Tail C7 HC 1   ERHGGDGYWYFDVWGQGTMVTVSSASTKGPSVFPLAPSSKSTSGGTAALGCLVKDYFPEP   180
               ERHGGDGYWYFDVWGQGTMVTVSSASTKGPSVFPLAPSSKSTSGGTAALGCLVKDYFPEP
Tail C7 HC 3   ERHGGDGYWYFDVWGQGTMVTVSSASTKGPSVFPLAPSSKSTSGGTAALGCLVKDYFPEP   180

Tail C7 HC 1   VTVSWNSGALTSGVHTFPAVLQSSGLYSLSSVVTVPSSSLGTQTYICNVNHKPSNTKVDK   240
               VTVSWNSGALTSGVHTFPAVLQSSGLYSLSSVVTVPSSSLGTQTYICNVNHKPSNTKVDK
Tail C7 HC 3   VTVSWNSGALTSGVHTFPAVLQSSGLYSLSSVVTVPSSSLGTQTYICNVNHKPSNTKVDK   240

Tail C7 HC 1   KVEPKSCDKTHTCPPCPAPELLGGPSVFLFPPKPKDTLMISRTPEVTCVVVDVSHEDPEV   300
               KVEPKSCDKTHTCPPCPAPELLGGPSVFLFPPKPKDTLMISRTPEVTCVVVDVSHEDPEV
Tail C7 HC 3   KVEPKSCDKTHTCPPCPAPELLGGPSVFLFPPKPKDTLMISRTPEVTCVVVDVSHEDPEV   300

Tail C7 HC 1   KFNWYVDGVEVHNAKTKPREEQYNSTYRVVSVLTVLHQDWLNGKEYKCKVSNKALPAPIE   360
               KFNWYVDGVEVHNAKTKPREEQYNSTYRVVSVLTVLHQDWLNGKEYKCKVSNKALPAPIE
Tail C7 HC 3   KFNWYVDGVEVHNAKTKPREEQYNSTYRVVSVLTVLHQDWLNGKEYKCKVSNKALPAPIE   360

Tail C7 HC 1   KTISKAKGQPREPQVYTLPPSREEMTKNQVSLTCLVKGFYPSDIAVEWESNGQPENNYKT   420
               KTISKAKGQPREPQVYTLPPSREEMTKNQVSLTCLVKGFYPSDIAVEWESNGQPENNYKT
Tail C7 HC 3   KTISKAKGQPREPQVYTLPPSREEMTKNQVSLTCLVKGFYPSDIAVEWESNGQPENNYKT   420

Tail C7 HC 1   TPPVLDSDGSFFLYSKLTVDKSRWQQGNVFSCSVMHEALHNHYTQKSLSLSPG**   475
               TPPVLDSDGSFFLYSKLTVDKSRWQQGNVFSCSVMHEALHNHYTQKSLSLSPG**
Tail C7 HC 3   TPPVLDSDGSFFLYSKLTVDKSRWQQGNVFSCSVMHEALHNHYTQKSLSLSPG**   475
```

FIGURE 5C

Tail C7 HC 2 (SEQ ID NO: 5) V Tail C7 HC 3 (SEQ ID NO: 6)

Score 962 bits(2486) Expect 0.0 Compositional matrix adjust.468/475(99%) Identities 471/475(99%) Gaps 0/475(0%)

```
Tail C7 HC 2  MDPKGSLSWRILLFLSLAFELSYGEVQLVESGGGLVKPGGSLRLSCAASGFTFSRYGMSW  60
              MDPKGSLSWRILLFLSLAFELSYGEVQLVESGGGLV+PG SLRLSC ASGFTFSRYGMSW
Tail C7 HC 3  MDPKGSLSWRILLFLSLAFELSYGEVQLVESGGGLVQPGRSLRLSCTASGFTFSRYGMSW  60

Tail C7 HC 2  VRQAPGKGLEWVSTISSGGSYTYYTDSVKGRFTISRDNAKNSLYLQMNSLRAEDTAVYYC  120
              VRQAPGKGLEWV+TISSGGSYTYYTDSVKGRFTISRDNAKN LYLQMNSL+ EDTAVYYC
Tail C7 HC 3  VRQAPGKGLEWVATISSGGSYTYYTDSVKGRFTISRDNAKNILYLQMNSLKTEDTAVYYC  120

Tail C7 HC 2  ERHGGDGYWYFDVWGQGTMVTVSSASTKGPSVFPLAPSSKSTSGGTAALGCLVKDYFPEP  180
              ERHGGDGYWYFDVWGQGTMVTVSSASTKGPSVFPLAPSSKSTSGGTAALGCLVKDYFPEP
Tail C7 HC 3  ERHGGDGYWYFDVWGQGTMVTVSSASTKGPSVFPLAPSSKSTSGGTAALGCLVKDYFPEP  180

Tail C7 HC 2  VTVSWNSGALTSGVHTFPAVLQSSGLYSLSSVVTVPSSSLGTQTYICNVNHKPSNTKVDK  240
              VTVSWNSGALTSGVHTFPAVLQSSGLYSLSSVVTVPSSSLGTQTYICNVNHKPSNTKVDK
Tail C7 HC 3  VTVSWNSGALTSGVHTFPAVLQSSGLYSLSSVVTVPSSSLGTQTYICNVNHKPSNTKVDK  240

Tail C7 HC 2  KVEPKSCDKTHTCPPCPAPELLGGPSVFLFPPKPKDTLMISRTPEVTCVVVDVSHEDPEV  300
              KVEPKSCDKTHTCPPCPAPELLGGPSVFLFPPKPKDTLMISRTPEVTCVVVDVSHEDPEV
Tail C7 HC 3  KVEPKSCDKTHTCPPCPAPELLGGPSVFLFPPKPKDTLMISRTPEVTCVVVDVSHEDPEV  300

Tail C7 HC 2  KFNWYVDGVEVHNAKTKPREEQYNSTYRVVSVLTVLHQDWLNGKEYKCKVSNKALPAPIE  360
              KFNWYVDGVEVHNAKTKPREEQYNSTYRVVSVLTVLHQDWLNGKEYKCKVSNKALPAPIE
Tail C7 HC 3  KFNWYVDGVEVHNAKTKPREEQYNSTYRVVSVLTVLHQDWLNGKEYKCKVSNKALPAPIE  360

Tail C7 HC 2  KTISKAKGQPREPQVYTLPPSREEMTKNQVSLTCLVKGFYPSDIAVEWESNGQPENNYKT  420
              KTISKAKGQPREPQVYTLPPSREEMTKNQVSLTCLVKGFYPSDIAVEWESNGQPENNYKT
Tail C7 HC 3  KTISKAKGQPREPQVYTLPPSREEMTKNQVSLTCLVKGFYPSDIAVEWESNGQPENNYKT  420

Tail C7 HC 2  TPPVLDSDGSFFLYSKLTVDKSRWQQGNVFSCSVMHEALHNHYTQKSLSLSPG**  475
              TPPVLDSDGSFFLYSKLTVDKSRWQQGNVFSCSVMHEALHNHYTQKSLSLSPG**
Tail C7 HC 3  TPPVLDSDGSFFLYSKLTVDKSRWQQGNVFSCSVMHEALHNHYTQKSLSLSPG**  475
```

FIGURE 5D

Tail C7 LC 1 (SEQ ID NO: 10) V Tail C7 LC 2 (SEQ ID NO: 11)

Score 480 bits(1235) Expect 8e-180 Compositional matrix adjust.233/234(99%) Identities 234/234(100%) Gaps 0/234(0%)

```
Tail C7 LC 1    METDTLLLWVLLLWVPGSTGDIQMTQSPSSLSASVGDRVTITCRASQDISNYLNWYQQKP    60
                METDTLLLWVLLLWVPGSTGDIQMTQSPSSLSASVGDRVTITCRASQDISNYLNWYQQKP
Tail C7 LC 2    METDTLLLWVLLLWVPGSTGDIQMTQSPSSLSASVGDRVTITCRASQDISNYLNWYQQKP    60

Tail C7 LC 1    GKAVKLLIYYTSRLHSGVPSRFSGSGSGTDYTLTISSLQPEDFATYFCQQGNPLRTFGGG    120
                GKAVKLLIYYTSRLHSGVPSRFSGSGSGTDYTLTISSLQPEDFATY+CQQGNPLRTFGGG
Tail C7 LC 2    GKAVKLLIYYTSRLHSGVPSRFSGSGSGTDYTLTISSLQPEDFATYYCQQGNPLRTFGGG    120

Tail C7 LC 1    TKVEIKRTVAAPSVFIFPPSDEQLKSGTASVVCLLNNFYPREAKVQWKVDNALQSGNSQE    180
                TKVEIKRTVAAPSVFIFPPSDEQLKSGTASVVCLLNNFYPREAKVQWKVDNALQSGNSQE
Tail C7 LC 2    TKVEIKRTVAAPSVFIFPPSDEQLKSGTASVVCLLNNFYPREAKVQWKVDNALQSGNSQE    180

Tail C7 LC 1    SVTEQDSKDSTYSLSSTLTLSKADYEKHKVYACEVTHQGLSSPVTKSFNRGEC*    234
                SVTEQDSKDSTYSLSSTLTLSKADYEKHKVYACEVTHQGLSSPVTKSFNRGEC*
Tail C7 LC 2    SVTEQDSKDSTYSLSSTLTLSKADYEKHKVYACEVTHQGLSSPVTKSFNRGEC*    234
```

FIGURE 5E

Tail C7 LC 1 (SEQ ID NO: 10) V Tail C7 LC 3 (SEQ ID NO: 12)

Score 434 bits(1115)   Expect 1e-161   Compositional matrix adjust. 218/233(94%)

Identities 228/233(97%) Gaps 0/233(0%)

```
Tail C7 LC 1    METDTLLLWVLLLWVPGSTGDIQMTQSPSSLSASVGDRVTITCRASQDISNYLNWYQQKP    60
                METDTLLLWVLLLWVPGSTGDI MTQSP++LS S G+R T++CRASQDISNYLNWYQQKP
Tail C7 LC 3    METDTLLLWVLLLWVPGSTGDIVMTQSPATLSLSPGERATLSCRASQDISNYLNWYQQKP    60

Tail C7 LC 1    GKAVKLLIYYTSRLHSGVPSRFSGSGSGTDYTLTISSLQPEDFATYFCQQGNPLRTFGGG   120
                G+AV+LLIYYTSRLHSG+P+RFSGSGSGTDYTLTISSL+PEDFA YFCQQGNPLRTFGGG
Tail C7 LC 3    GQAVRLLIYYTSRLHSGIPARFSGSGSGTDYTLTISSLEPEDFAVYFCQQGNPLRTFGGG   120

Tail C7 LC 1    TKVEIKRTVAAPSVFIFPPSDEQLKSGTASVVCLLNNFYPREAKVQWKVDNALQSGNSQE   180
                TKVEIKRTVAAPSVFIFPPSDEQLKSGTASVVCLLNNFYPREAKVQWKVDNALQSGNSQE
Tail C7 LC 3    TKVEIKRTVAAPSVFIFPPSDEQLKSGTASVVCLLNNFYPREAKVQWKVDNALQSGNSQE   180

Tail C7 LC 1    SVTEQDSKDSTYSLSSTLTLSKADYEKHKVYACEVTHQGLSSPVTKSFNRGEC   233
                SVTEQDSKDSTYSLSSTLTLSKADYEKHKVYACEVTHQGLSSPVTKSFNRGEC
Tail C7 LC 3    SVTEQDSKDSTYSLSSTLTLSKADYEKHKVYACEVTHQGLSSPVTKSFNRGEC   233
```

FIGURE 5F

Tail C7 LC2 (SEQ ID NO: 11) V Tail C7 LC 3 (SEQ ID NO: 12)

Score 432 bits(1112) Expect 4: 1e-161 Compositional matrix adjust.   218/234(93%)

Identities 229/234(97%)     Gaps 0/234(0%)

```
Tail C7 LC 2  METDTLLLWVLLLWVPGSTGDIQMTQSPSSLSASVGDRVTITCRASQDISNYLNWYQQKP  60
              METDTLLLWVLLLWVPGSTGDI MTQSP++LS S G+R T++CRASQDISNYLNWYQQKP
Tail C7 LC 3  METDTLLLWVLLLWVPGSTGDIVMTQSPATLSLSPGERATLSCRASQDISNYLNWYQQKP  60

Tail C7 LC 2  GKAVKLLIYYTSRLHSGVPSRFSGSGSGTDYTLTISSLQPEDFATYYCQQGNPLRTFGGG  120
              G+AV+LLIYYTSRLHSG+P+RFSGSGSGTDYTLTISSL+PEDFA Y+CQQGNPLRTFGGG
Tail C7 LC 3  GQAVRLLIYYTSRLHSGIPARFSGSGSGTDYTLTISSLEPEDFAVYFCQQGNPLRTFGGG  120

Tail C7 LC 2  TKVEIKRTVAAPSVFIFPPSDEQLKSGTASVVCLLNNFYPREAKVQWKVDNALQSGNSQE  180
              TKVEIKRTVAAPSVFIFPPSDEQLKSGTASVVCLLNNFYPREAKVQWKVDNALQSGNSQE
Tail C7 LC 3  TKVEIKRTVAAPSVFIFPPSDEQLKSGTASVVCLLNNFYPREAKVQWKVDNALQSGNSQE  180

Tail C7 LC 2  SVTEQDSKDSTYSLSSTLTLSKADYEKHKVYACEVTHQGLSSPVTKSFNRGEC*   234
              SVTEQDSKDSTYSLSSTLTLSKADYEKHKVYACEVTHQGLSSPVTKSFNRGEC*
Tail C7 LC 3  SVTEQDSKDSTYSLSSTLTLSKADYEKHKVYACEVTHQGLSSPVTKSFNRGEC*   234
```

FIGURE 5G

Organized by chain combination

IHF$_{NTHi}$ TIP CHIMERIC PEPTIDE-SPECIFIC

| Peptide target | Heavy and light chain combination | | Biofilm disruption[2] (NCH) Value indicates remaining biomass ($\mu m^3/\mu m^2$) |
| --- | --- | --- | --- |
| | Heavy chain | Light chain | Nontypeable *Haemophilus influenzae* |
| IhfA5-mIhfB4 Tip chimeric peptide | HC1 | LC1 | 4.41 |
| | HC1 | LC2 | 12.9 |
| | HC1 | LC3 | 8.3 |
| | HC2 | LC1 | 7.1 |
| | HC2 | LC2 | 6.9 |
| | HC2 | LC3 | 12.1 |
| | HC3 | LC1 | 7.4 |
| | HC3 | LC2 | 7.6 |
| | HC3 | LC3 | 14.1 |

FIGURE 6

Organized by chain combination

IHF$_{NTHi}$ TAIL CHIMERIC PEPTIDE-SPECIFIC

| Heavy and light chain combination | | Biofilm disruption[2] (NCH) Value indicates remaining biomass ($\mu m^3/\mu m^2$) |
|---|---|---|
| Heavy chain | Light chain | Nontypeable *Haemophilus influenzae* |
| HC1 | LC1 | 24.1 |
| HC1 | LC2 | 16.9 |
| HC1 | LC3 | 14.3 |
| HC2 | LC1 | 17.6 |
| HC2 | LC2 | 18.3 |
| HC2 | LC3 | 21.0 |
| HC3 | LC1 | 18.1 |
| HC3 | LC2 | 15.7 |
| HC3 | LC3 | 15.6 |

FIGURE 7

ANTIBODY COMPOSITIONS FOR DISRUPTING BIOFILMS

CROSS-REFERENCE TO RELATED APPLICATIONS

This application is a continuation application filed under 35 U.S.C. § 111 (a) claiming the benefit under 35 U.S.C. § 120 and 365(c) of International Patent Application No. PCT/US2020/041082, filed on Jul. 7, 2020, which claims priority under 35 U.S.C. § 119(e) to U.S. Provisional Application Nos. 63/033,109, filed Jun. 1, 2020, and 62/871,457, filed Jul. 8, 2019, the contents of each of which are incorporated herein by reference in their entireties into the present disclosure.

STATEMENT OF GOVERNMENT SUPPORT

This invention was made with government support under Grant No. RO1 DC011818 awarded by the National Institute on Deafness and Other Communication Disorders (NIDCD) of the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Jan. 25, 2021, is named 106887-0861_SL.txt and is 106,496 bytes in size.

FIELD OF THE DISCLOSURE

The present disclosure generally relates to the methods and compositions to lessen and/or eradicate bacterial biofilms.

BACKGROUND

The DNABII family of proteins are naturally found outside of the bacterial cell and contribute to biofilm formation. At least one protein from the DNABII family is found in all known eubacteria. While these proteins elicit a strong innate and acquired immune response, host subjects fail to naturally produce immunoprotective antibodies to family members as a result of infection. The major problem with bacterial biofilms is the inability of the host immune system and/or antibiotics and other antimicrobials to gain access to the bacteria protected within the biofilm.

Biofilms are present in an industrial setting as well. For example, biofilms are implicated in a wide range of petroleum process problems, from the production field to the gas station storage tank. In the field, sulfate reducing biofilm bacteria produce hydrogen sulfide (soured oil). In the process pipelines, biofilm activity develops slimes which impede filters and orifices. Biofilm and biofilm organisms also cause corrosion of pipeline and petroleum process equipment. These problems can be manifested throughout an oil or gas production facility, to the point where fouling and corrosive biofilm organisms have even been found on the surfaces of final product storage tanks.

Biofilms are implicated in a wide range of water processes, both domestic and industrial. They can grow on the surface of process equipment and impede the performance of the equipment, such as degradation of heat transfer or plugging of filters and membranes. Biofilms growing on a cooling tower fill can add enough weight to cause collapse of the fill. Biofilms cause corrosion of even highly specialized stainless steels. Biofilms in a water process can degrade the value of a final product such as biofilm contamination in a paper process or the attachment of even a single cell on a silicon chip. Biofilms growing in drinking water distribution systems can harbor potential pathogenic organisms, corrosive organisms or bacteria that degrade the aesthetic quality of the water. In the home, biofilms are found in or on any surface that supports microbial growth, e.g., in drains, on food preparation surfaces, in toilets, and in swimming pools and spas.

Thus, a need exists to break through the protective barrier of biofilms to treat or kill the associated bacterial infections and clear them from surfaces and in water systems.

SUMMARY

Within bacterial cells, the DNABII proteins are DNA-binding proteins that necessarily bend DNA substrates upon binding. Similarly, DNA that is already in a bent conformation is an exemplary substrate as the energy required for bending is rendered unnecessary.

The DNABII family is a member of a class of proteins referred to as nucleoid associated proteins (NAPs), bacterial proteins that, in part, shape the intracellular bacterial nucleoid (Browning et al. (2010) Curr. Opin. Microbiol. 13:773-780). In addition, this family is ubiquitous, expressed by virtually all eubacteria. All characterized family members to date function as either a homodimer or heterodimer of subunits. The family is divided into two types, HU (histone-like protein) and IHF (integration host factor) with *B. cenocepacia* capable of expressing both (strain J2315 genes: BCAL3530, hupA; BCAL1585, hupB; BCAL1487, ihfA and BCAL2949, ihfb), while many other bacteria also express both HU and IHF. The primary distinction between these family members is that HU binds DNA in a sequence independent manner, while IHF binds a consensus sequence (WATCAANNNNTTR where W is A or T and R is a purine, SEQ ID NO: 28) conserved across genera (Swinger et al. (2004) Curr. Opin. Struct. Biol. 14:28-35). All DNABII proteins bind to and bend DNA considerably e.g. *E. coli* IHF can bend DNA into a virtual U-turn (Rice et al. (1996) Cell 87: 1295-1306). In addition, all family members have a preference for pre-bent or curved DNA structures e.g. Holliday junctions, a cruciform-like structure central to DNA recombination. In fact, DNABII proteins function as accessory factors facilitating all intracellular DNA functions, including gene expression, recombination, repair and replication (Swinger et al. (2004) Curr. Opin. Struct. Biol. 14:28-35).

The DNABII family of proteins is found outside of bacterial cells in the biofilm state. Applicants have shown that these proteins are in fact bound to the extracellular DNA at critical branched junctions.

Thus, provided herein is an antibody or an antigen binding fragment thereof, that comprises, or consists essentially of, or yet further consists of: a heavy chain (HC) immunoglobulin variable domain sequence comprising, or consisting essentially of, or yet further consisting of a sequence of amino acid (aa) 25 to aa 144 of SEQ ID NO: 13 or an equivalent thereof, and/or a light chain (LC) immunoglobulin variable domain sequence comprising, or consisting essentially of, or yet further consisting of a sequence selected from the group of aa 21 to aa 132 of SEQ ID NO: 14, or an equivalent thereof. Further provided herein is an antibody or an antigen binding fragment thereof, that comprises or consists essentially of, or yet further consists of: a heavy chain (HC) immunoglobulin variable domain sequence comprising, or consisting essentially of, or yet further consisting of a sequence selected from the group of aa 25 to aa 144 of SEQ ID NO: 13, 24 or 26, or an equivalent of each thereof, and/or a light chain (LC) immunoglobulin variable domain sequence comprising, or consisting essentially of, or yet further consisting of a sequence selected from the group of aa 21 to aa 132 of SEQ ID NOs: 14 or 25, aa 21 to aa 126 of SEQ ID NO: 27, or an equivalent of each thereof. In certain embodiments, the antibody or fragment thereof binds to a DNABII peptide (such as the tip region of the DNABII peptide including but not limited to: a tip region of IHF or HU, a tip region of IHFA or IHFB, and/or the tip-chimeric peptide IhfA5-mIhfB4$_{NTHi}$; and/or the tail region of the DNABII peptide, including but not limited to: a tail region of IHF or HU, a tail region of IHFA or IHFB, and/or the tail-chimeric peptide IhfA3-IhfB2$_{NTHi}$). In one embodiment, the antibody or fragment thereof binds to the tip-chimeric peptide IhfA5-mIhfB4$_{NTHi}$ or the tail-chimeric peptide IhfA3-IhfB2$_{NTHi}$.

Also provided herein is an antibody or an antigen binding fragment thereof, that comprises or consists essentially of, or yet further consists of: a heavy chain (HC) immunoglobulin variable domain sequence comprising, or consisting essentially of, or yet further consisting of a sequence selected from the group of aa 25 to aa 144 of SEQ ID NO: 13 or 24, or an equivalent of each thereof, and/or a light chain (LC) immunoglobulin variable domain sequence comprising, or consisting essentially of, or yet further consisting of a sequence selected from the group of aa 21 to aa 132 of SEQ ID NO: 14 or 25 or an equivalent of each thereof. In certain embodiments, the antibody or fragment thereof binds to a DNABII peptide (such as the tip region of the DNABII peptide including but not limited to: a tip region of IHF or HU, a tip region of IHFA or IHFB, and/or the tip-chimeric peptide IhfA5-mIhfB4$_{NTHi}$). In one embodiment, the antibody or fragment thereof binds to the tip-chimeric peptide IhfA5-mIhfB4$_{NTHi}$.

Yet further provided is an antibody or an antigen binding fragment thereof, that comprises or consists essentially of, or yet further consists of: a heavy chain (HC) immunoglobulin variable domain sequence comprising, or consisting essentially of, or yet further consisting of a sequence selected from the group of aa 25 to aa 144 of SEQ ID NOs: 1-6, 24 or 26 or an equivalent of each thereof, and/or a light chain (LC) immunoglobulin variable domain sequence comprising, or consisting essentially of, or yet further consisting of a sequence selected from the group of aa 21 to aa 132 of SEQ ID NOs: 7-9 or 25, aa 21 to aa 126 of SEQ ID NOs: 10-12 or 27, or an equivalent of each thereof. In certain embodiments, the antibody or fragment thereof binds to a DNABII peptide (such as the tip region of the DNABII peptide including but not limited to: a tip region of IHF or HU, a tip region of IHFA or IHFB, and/or the tip-chimeric peptide IhfA5-mIhfB4$_{NTHi}$; and/or the tail region of the DNABII peptide, including but not limited to: a tail region of IHF or HU, a tail region of IHFA or IHFB, and/or the tail-chimeric peptide IhfA3-IhfB2$_{NTHi}$). In one embodiment, the antibody or fragment thereof binds to the tip-chimeric peptide IhfA5-mIhfB4$_{NTHi}$ or the tail-chimeric peptide IhfA3-IhfB2$_{NTHi}$.

Also provided is an antibody or an antigen binding fragment thereof, that comprises or consists essentially of, or yet further consists of: a heavy chain (HC) comprising, or consisting essentially of, or yet further consisting of a sequence selected from the group of aa 25 to aa 473 of SEQ ID NOs: 1-6, 13, 24 or 26 or an equivalent of each thereof, and/or a light chain (LC) comprising, or consisting essentially of, or yet further consisting of a sequence selected from the group of aa 21 to aa 239 of SEQ ID NOs: 7-9, 14, or 25, aa 21 to aa 233 of SEQ ID NOs: 10-12 or 27, or an equivalent of each thereof. In certain embodiments, the antibody or fragment thereof binds to a DNABII peptide (such as the tip region of the DNABII peptide including but not limited to: a tip region of IHF or HU, a tip region of IHFA or IHFB, and/or the tip-chimeric peptide IhfA5-mIhfB4$_{NTHi}$; and/or the tail region of the DNABII peptide, including but not limited to: a tail region of IHF or HU, a tail region of IHFA or IHFB, and/or the tail-chimeric peptide IhfA3-IhfB2$_{NTHi}$). In one embodiment, the antibody or fragment thereof binds to the tip-chimeric peptide IhfA5-mIhfB4$_{NTHi}$ or the tail-chimeric peptide IhfA3-IhfB2$_{NTHi}$.

Additionally provided is an antibody or a fragment thereof that comprises or consists essentially of, or yet further consists of: any one or any two or all three CDRs of a sequence selected from the group of: SEQ ID NOs: 1-6, 13, 24 or 26, or an equivalent of each thereof and/or any one or any two or all three CDRs of a sequence selected from the group of: SEQ ID NOs: 7-12, 14, 25 or 27, or an equivalent of each thereof. In certain embodiments, the antibody or fragment thereof binds to a DNABII peptide (such as the tip region of the DNABII peptide including but not limited to: a tip region of IHF or HU, a tip region of IHFA or IHFB, and/or the tip-chimeric peptide IhfA5-mIhfB4$_{NTHi}$; and/or the tail region of the DNABII peptide, including but not limited to: a tail region of IHF or HU, a tail region of IHFA or IHFB, and/or the tail-chimeric peptide IhfA3-IhfB2$_{NTHi}$). In one embodiment, the antibody or fragment thereof binds to the tip-chimeric peptide IhfA5-mIhfB4$_{NTHi}$ or the tail-chimeric peptide IhfA3-IhfB2$_{NTHi}$.

Non-limiting examples of antigen binding fragments are selected from a Fab, F(ab')$_2$, Fab', scFv, or Fv.

In another aspect, a Fab fragment of the antibody is provided herein, wherein the antibody specifically binds the tip region of a DNABII peptide (including but not limited to: a tip region of IHF or HU, a tip region of IHFA or IHFB, and/or the tip-chimeric peptide IhfA5-mIhfB4$_{NTHi}$). Also, provided is a fragment of an antibody disclosed herein. In one embodiment, the fragment is antigen binding fragment selected from the group of Fab, F(ab')$_2$, Fab', scFv, or Fv. In a further embodiment, the fragment specifically binds the tip region of a DNABII peptide.

Further provided are formulations comprising the Fab fragment.

In another aspect, the antibody or fragment thereof is modified. Non-limiting examples of modifications include PEGylation, a PEG mimetic, polysialyation, HESylation or glycosylation.

The antibodies and antigen binding fragments can be detectably labeled or comprise a detectable label and/or a purification marker.

Also provided herein are polypeptides comprising, consisting essentially of or consisting of, a complementarity-determining region (CDR) of an antibody or antigen binding fragment or region as disclosed above. The CDR can be selected from the group of CDR1, CDR2 or CDR3. The CDRs can be detectably labeled or comprise a detectable label and/or a purification marker.

Further provided are isolated polypeptides, wherein the polypeptides comprise, consist essentially of, or yet further consist of, an amino acid sequence selected from the group of: SEQ ID NOs: 1-14 or 24-27; amino acid (aa) 25 to aa 144 of SEQ ID NOs: 1-6, 13, 24 or 26; aa 21 to aa 132 of SEQ ID NOs: 7-9, 14 or 25; aa 21 to aa 126 of SEQ ID NOS: 10-12 or 27; or an equivalent of each thereof. Also provided is an isolated polypeptide comprising, or alternatively consisting essentially of, or yet further consisting of one or more of amino acid sequences of the antibodies or fragments thereof as disclosed herein. The polypeptides can be detectably labeled and/or comprise a detectable label and/or a purification marker. In a further embodiment, the polypeptides further comprise a signal peptide.

Further provided are isolated polynucleotides encoding the antibodies or antigen binding fragments thereof, or the CDRs of the antigen binding fragments or antibodies, as well as the polypeptides of this disclosure, or an equivalent of each thereof, that are optionally operatively linked to a promoter and/or enhancer element. The polynucleotides can be detectably labeled and/or comprise a detectable label and/or a purification marker. The polynucleotides can further comprise a signal peptide polynucleotide sequence located upstream of the immunoglobulin variable domain of the antibody. They can be contained within a vector and/or a host cell. Thus, further provided is a vector comprising, or alternatively consisting essentially of, or yet further consisting of one or more of the isolated polynucleotides as disclosed herein. Such vector may be a plasmid or a viral vector, optionally selected from a group consisting of a retroviral vector, a lentiviral vector, an adenoviral vector, and an adeno-associated viral vector. Also provided is a host cell comprising one or more of the polynucleotides and/or the vectors as disclosed herein.

Further provided are compositions comprising, or alternatively consisting of, or yet further consisting of, a carrier and one or more of: the antibody or fragment thereof, the CDRs, the polypeptides, the isolated polynucleotides, the vectors, or the host cells. In one embodiment, the carrier is a pharmaceutically acceptable carrier. Additionally or alternatively, the carrier is a solid phase carrier or a solid phase support. In another embodiment, the carrier is suitable for use in an industrial setting. Also provided is a non-physiological surface coated with an antibody or a thereof as disclosed herein. In one embodiment, the surface is in an industrial setting. In certain embodiments, the fragment is an antigen binding fragment.

Also provided are methods to produce the antibodies, fragments, CDRs, or polypeptides comprising, or alternatively consisting of, or yet further consisting of, culturing a host cell comprising a polynucleotide encoding the antibody, antigen binding fragment, polypeptide, or CDR under conditions for expression of the polynucleotide, and optionally isolating the antibody, fragment, CDR and/or polypeptide from the cell and/or culture. In one embodiment, the host cell is a mammalian cell.

In one aspect, provided is a method for inhibiting or competing with the binding of a DNABII polypeptide or protein to a microbial DNA. The method comprises or consists essentially of, or yet further consists of contacting the DNABII polypeptide or protein with one or more of an antibody, a fragment thereof, a polypeptide, or a CDR as disclosed herein. In one embodiment, the antibody, fragment thereof, polypeptide, or CDR binds a tip region of a DNABII peptide (including but not limited to: a tip region of IHF or HU, a tip region of IHFA or IHFB, and/or the tip-chimeric peptide IhfA5-mIhfB4$_{NTHI}$). In a further embodiment, the antibody, fragment thereof, polypeptide, or CDR binds the tip-chimeric peptide IhfA5-mIhfB4$_{NTHI}$. In yet a further embodiment, the contacting is in vivo or in vitro.

In another aspect, provided is a method to disrupt a biofilm. The method comprises or consists essentially of, or yet further consists of contacting the biofilm with one or more of an antibody, a fragment thereof, a polypeptide, or a CDR as disclosed herein. In one embodiment, the antibody, fragment thereof, polypeptide, or CDR binds a tip region of a DNABII peptide (including but not limited to: a tip region of IHF or HU, a tip region of IHFA or IHFB, the tip-chimeric peptide IhfA5-mIhfB4$_{NTHI}$). In a further embodiment, the antibody, fragment thereof, polypeptide, or CDR binds the tip-chimeric peptide IhfA5-mIhfB4$_{NTHI}$. In yet a further embodiment, the contacting is in vivo or in vitro.

Yet further provided are methods to prevent formation of, or to disrupt a biofilm on a surface comprising, or alternatively consisting of, or yet further consisting of, treating the surface susceptible to or containing a biofilm with, e.g., one or more of the antibody, antigen binding fragment, polypeptide, or CDR as described herein, wherein the antibody, fragment thereof, polypeptide, or CDR binds a tip region of a DNABII peptide (including but not limited to: a tip region of IHF or HU, a tip region of IHFA or IHFB, the tip-chimeric peptide IhfA5-mIhfB4$_{NTHI}$). In a further embodiment, the antibody, fragment thereof, polypeptide, or CDR binds the tip-chimeric peptide IhfA5-mIhfB4$_{NTHI}$. In yet a further embodiment, the treating is in vivo or in vitro.

Also further provided are methods to detect a biofilm on a surface comprising, or alternatively consisting of, or yet further consisting of, contacting the surface (in one aspect susceptible to or containing a biofilm) with one or more of the antibody, antigen binding fragment, polypeptide or CDR as described herein, wherein the antibody, fragment thereof, polypeptide or CDR binds a tail or tip region of a DNABII peptide (including but not limited to: a tip region of IHF or HU, a tip region of IHFA or IHFB, the tip-chimeric peptide IhfA5-mIhfB4$_{NTHI}$, tail region of IHF or HU, a tail region of IHFA or IHFB, and/or or the tail-chimeric peptide IhfA3-IhfB2$_{NTHI}$). In a further embodiment, the antibody, fragment thereof, polypeptide, or CDR binds the tip-chimeric peptide IhfA5-mIhfB4$_{NTHI}$. In one embodiment, the contacting is in vivo or in vitro.

In one aspect, provided is a method for detecting a microbial infection that produces a biofilm in a subject. The method comprises, or alternatively consists of, or yet further consists of contacting one or more of the antibody, fragment thereof, polypeptide, or CDR as disclosed herein with a biological sample suspected of comprising the biofilm and isolated from the subject and detecting the binding of the antibody, fragment thereof, polypeptide, or CDR to any biofilm in the sample. The amount can be determined by the treating physician or veterinarian, e.g., an effective amount for the subject. In one embodiment, the antibody, fragment thereof, polypeptide or CDR binds a tail or tip region of a DNABII peptide (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$). In a further embodiment, the contacting is in vivo or in vitro.

In another aspect, provided is a method for screening subjects having a biofilm, comprising or alternatively consisting of, or yet further consisting of, contacting one or more of an antibody, a fragment thereof, a polypeptide, or a CDR as disclosed herein with a biological sample comprising the biofilm and isolated from the subject, and detecting the binding of the antibody, fragment thereof, polypeptide, or CDR to any biofilm in the sample. In one embodiment, the antibody, fragment thereof, polypeptide or CDR binds a tail or tip region of a DNABII peptide (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$). In a further embodiment, a subject detected with the binding is selected for administration with one or more of an antibody, a fragment thereof, a polypeptide, or a CDR as disclosed herein, and/or one or more of a polynucleotide or a vector encoding the antibody, fragment thereof, polypeptide or CDR, wherein the antibody, fragment thereof, polypeptide, or CDR binds a tip region of a DNABII peptide (including but not limited to: a tip region of IHF or HU, a tip region of IHFA or IHFB, and/or the tip-chimeric peptide IhfA5-mIhfB4$_{NTHI}$). The amount can be determined by the treating physician or veterinarian, e.g., an effective amount for the subject. In yet a further embodiment, the contacting is in vivo or in vitro.

Provided herein are methods to detect a biofilm in a subject by administering to the subject one or more of the antibody or the fragment thereof as disclosed herein, and detecting any binding of the antibody, the fragment thereof, polypeptide or CDR as disclosed herein to the biofilm. In one aspect, the antibody, fragment thereof, polypeptide or CDR binds a tail or tip region of a DNABII peptide (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$). In another embodiment, the method further comprises detecting binding of the antibody, fragment thereof, polypeptide or CDR to the biofilm.

In one aspect, methods to prevent or disrupt a biofilm in a subject are provided, comprising, or alternatively consisting of, or yet further consisting of, administering to the subject one or more of the antibody, fragment thereof, polypeptide, or CDR as disclosed herein, and/or one or more of a polynucleotide or a vector encoding the antibody, fragment thereof, polypeptide or CDR, wherein such binds to a tip region of a DNABII peptide (including but not limited to: a tip region of IHF or HU, a tip region of IHFA or IHFB, and/or the tip-chimeric peptide IhfA5-mIhfB4$_{NTHI}$). The amount can be determined by the treating physician or veterinarian, e.g., an effective amount for the subject. In one embodiment, the method further comprises detecting a biofilm by contacting one or more of an antibody, a fragment thereof, a polypeptide, or a CDR as disclosed herein with a sample suspected of containing a biofilm, and detecting the binding of the biofilm and the antibody, fragment thereof, polypeptide, or CDR, and wherein the antibody, fragment thereof, polypeptide, or CDR binds to the tip region or the tail region of a DNABII peptide (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$).

In another aspect, methods for inhibiting, preventing or treating a microbial infection that produces a biofilm in a subject are provided, comprising, or alternatively consisting of, or yet further consisting of, administering to the subject one or more of the antibody, fragment thereof, polypeptide, or CDR as disclosed herein, and/or of one or more of a polynucleotide or a vector encoding the antibody, fragment thereof, polypeptide or CDR, wherein such binds to a tip region of a DNABII peptide (including but not limited to: a tip region of IHF or HU, a tip region of IHFA or IHFB, and/or the tip-chimeric peptide IhfA5-mIhfB4$_{NTHI}$). The amount can be determined by the treating physician or veterinarian, e.g., an effective amount for the subject. In one embodiment, the method further comprises detecting a biofilm by contacting one or more of an antibody, a fragment thereof, a polypeptide, or a CDR as disclosed herein with a sample suspected of containing a biofilm, and detecting the binding of the biofilm and the antibody, fragment thereof, polypeptide, or CDR, and wherein the antibody, fragment thereof, polypeptide, or CDR binds to the tip region or the tail region of a DNABII peptide (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$).

In yet another aspect, methods to prevent or treat a condition characterized by the formation of biofilm in a subject are provided by administering to the subject one or more of the antibody, the fragment thereof, polypeptide, or CDR as disclosed herein, and/or one or more of a polynucleotide or a vector encoding the antibody, fragment thereof, polypeptide or CDR, wherein such binds to a tip region of a DNABII peptide (including but not limited to: a tip region of IHF or HU, a tip region of IHFA or IHFB, and/or the tip-chimeric peptide IhfA5-mIhfB4$_{NTHI}$). The amount can be determined by the treating physician or veterinarian, e.g., an effective amount for the subject. Non-limiting examples of condition include chronic non-healing wounds, infections of the lung due to *Burkholderia* sp., venous ulcers, diabetic foot ulcers, ear infections, sinus infections, urinary tract infections, gastrointestinal tract ailments, hospital acquired pneumonia, ventilator-associated pneumonia, surgical implant-associated infections, pulmonary infections, respiratory tract infections, cystic fibrosis, chronic obstructive pulmonary disease, catheter-associated infections, indwelling devices associated infections, infections associated with implanted prostheses, osteomyelitis, cellulitis, abscesses, and periodontal disease. In one embodiment, the method further comprises detecting a biofilm by contacting one or more of an antibody, a fragment thereof, a polypeptide, or a CDR as disclosed herein with a sample suspected of containing a biofilm, and detecting the binding of the biofilm and the antibody, fragment thereof, polypeptide, or CDR, and wherein the antibody, fragment thereof, polypeptide, or CDR binds to the tip region or the tail region of a DNABII peptide (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$).

In certain embodiments of a method disclosed herein, administration of one or more of the antibody, fragment thereof, polypeptide, or CDR reduces one or more of pro-inflammatory cytokines in the subject. Non-limiting examples of the pro-inflammatory cytokines includes: IL-10, IL6, IL8, IL12p70, IL17A, Interferon (IFN) and tumor necrosis factor (TNF). Additionally or alternatively, administration of one or more of the antibody, fragment thereof, polypeptide, or CDR increases one or more of anti-inflammatory cytokines in the subject. In one embodiment, the anti-inflammatory cytokines include, but are not limited to, IL10, IL13, IL-1ra, IL-4, IL-11, and transforming growth factor-β (TGF-β).

Also provided is a method for conferring passive immunity in a subject, comprising, or alternatively consisting essentially of, or yet further consisting of administering to the subject one or more of an antibody, fragment thereof of, polypeptide, or CDR as disclosed herein, and/or one or more of a polynucleotide or a vector encoding the antibody, fragment thereof, polypeptide or CDR, wherein the antibody, fragment, polypeptide or CDR binds to a tip region of a DNABII peptide (including but not limited to: a tip region of IHF or HU, a tip region of IHFA or IHFB, and/or the tip-chimeric peptide IhfA5-mIhfB4$_{NTHI}$). The amount can be determined by the treating physician or veterinarian, e.g., an effective amount for the subject.

In one aspect, the therapeutic methods are combined with diagnostic methods to detect and/or monitor biofilm formation and disruption, using an antibody, a fragment thereof, a polypeptide or a CDR as disclosed herein.

In certain embodiments, the biofilm is derived from (i.e., produced by) a gram negative or a gram positive biofilm producing bacteria. In certain embodiments, the biofilm comprises a DNABII protein. In a further embodiment, the biofilm comprises a histone-like protein from E. coli strain U93 (HU) or an integration host factor (IHF) binding protein. In certain embodiments, the DNABII peptide is an IHF peptide. Additionally or alternatively, the DNABII peptide is an HU peptide. In certain embodiments, the tip region of DNABII peptide is the tip region of IHFA and/or the tip region of IHFB. In a further embodiment, the tip region of DNABII peptide is an IHFA tip region conjugated directly or indirectly (for example via a linker) to an IHFB tip region. In yet a further embodiment, the tip region of DNABII peptide is the IhfA5-mIhfB4$_{NTHI}$ Tip chimeric peptide. In certain embodiments, the tail region of DNABII peptide is the tail region of IHFA and/or the tail region of IHFB. In a further embodiment, the tail region of DNABII peptide is an IHFA tail region conjugated directly or indirectly (for example via a linker) to an IHFB tail region. In yet a further embodiment, the tail region of DNABII peptide is the IhfA3-IhfB2$_{NTHI}$ Tail chimeric peptide.

Yet further provided are methods to prepare an interfering nucleic acid, or alternatively consisting of, or yet further consisting of, preparing a nucleic acid consisting of about 10-20 nucleotides that specifically binds a specific binding partner to the antibody or fragment thereof as disclosed herein, and optionally isolating the interfering nucleic acid prepared by the method.

In another aspect, provided herein is a non-physiological surface coated with one or more of an antibody, a fragment thereof, a polypeptide, or a CDR as disclosed herein, and optionally, wherein in one aspect, the surface is in an industrial setting.

Also provided are methods to obtain antisera effective to disrupt a biofilm comprising immunizing a subject with a small molecule, and recovering antiserum from the subject, and optionally isolating polyclonal antiserum or monoclonal antibodies from the subject.

Kits also are provided. The kits comprise one or more of an antibody, a fragment thereof, a polypeptide, or CDR, a polynucleotide, a vector, a host cell, or a composition as disclosed herein and optionally, instructions for use.

BRIEF DESCRIPTION OF THE DRAWINGS

FIG. 3 is an in vitro model for reversal of an established biofilm in 8-well chamber slide using a humanized tip or tail chimer peptide monoclonal antibody of this disclosure.

FIGS. 4A to 4G provide a comparison (tabulated, FIG. 4A and detailed alignments, FIGS. 4B to 4G) between amino acid identities of heavy chains and light chains of humanized monoclonal antibodies designed to target the tip-chimeric peptide IhfA5-mIhfB4$_{NTHI}$. Amino acid alignments were performed with NCBI blastp.

FIGS. 5A to 5G provide a comparison (tabulated, FIG. 5A and detailed alignments, FIGS. 5B to 5G) between amino acid identities of heavy chains and light chains of humanized monoclonal antibodies designed to target the tail-chimeric peptide IhfA3-IhfB2$_{NTHI}$. Amino acid alignments were performed with NCBI blastp.

FIG. 6 provides relative biofilm disruption data using humanized monoclonal antibodies designed to target IhfA5-mIhfB4$_{NTHI}$ tip-chimeric peptide. Biofilm disruption: NTHI 86-028NP colonies were collected from overnight culture on chocolate agar and suspended in brain heart infusion broth supplemented with 2 µg β-NAD and heme per ml medium (sBHI). The optical density at 490 nm was then adjusted to 0.65 and the culture diluted 1:6 in sBHI prior to incubation at 37° C. with 5% CO2 for 3 hr, static. Next, the culture was diluted 1:2500 in fresh sBHI and 200 µl of the suspension aliquotted into each well of an 8-well chamber slide. The slide was then incubated at 37° C. with 5% CO2 for 3 hr, static. After 16 hr, 200 µl fresh sBHI was added to each well, and the slide incubated an additional 8 hr. At this time point, medium was aspirated from each well and 5 µg monoclonal antibody added per well. The biofilms were incubated an additional 16 hr. Biofilms were then washed and stained with FM1-43FX bacterial cell membrane stain (Invitrogen) and fixed overnight at 4° C. in 16% paraformaldehyde, 2.5% glutaraldehyde, 4.0% acetic acid in 0.1 M phosphate buffer (pH 7.4). Fixative was aspirated and 200 µl Hank's Balanced Salt Solution was added to each well prior to viewing of biofilms on a Zeiss 800 Meta-laser scanning confocal microscope. Images were compiled with Zeiss Zen Black software and biofilm biomass calculated with COMSTAT2.1 software. The K$_A$ for the IhfA5-mIhfB4$_{NTHI}$ Tip chimeric peptide (in 1/M) is about 4E+05 to about 2E+08.

FIG. 7 provides relative biofilm disruption data using humanized monoclonal antibodies designed to target IhfA3-IhfB2$_{NTHI}$ tail-chimeric peptide. Biofilm disruption: NTHI 86-028NP colonies were collected from overnight culture on chocolate agar and suspended in brain heart infusion broth supplemented with 2 µg β-NAD and heme per ml medium (sBHI). The optical density at 490 nm was then adjusted to 0.65 and the culture diluted 1:6 in sBHI prior to incubation at 37° C. with 5% CO2 for 3 hr, static. Next, the culture was diluted 1:2500 in fresh sBHI and 200 µl of the suspension aliquotted into each well of an 8-well chamber slide. The slide was then incubated at 37° C. with 5% CO2 for 3 hr, static. After 16 hr, 200 µl fresh sBHI was added to each well, and the slide incubated an additional 8 hr. At this time point, medium was aspirated from each well and 5 µg monoclonal antibody added per well. The biofilms were incubated an additional 16 hr. Biofilms were then washed and stained with FM1-43FX bacterial cell membrane stain (Invitrogen) and fixed overnight at 4° C. in 16% paraformaldehyde, 2.5% glutaraldehyde, 4.0% acetic acid in 0.1 M phosphate buffer (pH 7.4). Fixative was aspirated and 200 μl Hank's Balanced Salt Solution was added to each well prior to viewing of biofilms on a Zeiss 800 Meta-laser scanning confocal microscope. Images were compiled with Zeiss Zen Black software and biofilm biomass calculated with COMSTAT2.1 software. The $K_A$ for the IhfA3-IhfB2$_{NTHI}$ Tail chimeric peptide (in 1/M) is from about 8E+06 to about 2E+09.

FIG. 8A shows representative images of bacterial biofilms (pseudo-coloured white) revealed significant biofilm disruption by 170 nM intact IgG or Fabs directed against the β-tip domain of IHF. Orthogonal projections show a top-down view to depict spatial distribution of biofilm in x-y plane and side view indicates biofilm height in z-plane (arrowheads). Scale bars, 20 μm. FIG. 8B shows biomass within each image as quantitated by COMSTAT2 software. Each assay was repeated three times on different days and the mean±SEM shown. *P≤0.05, **P≤0.01 compared to respective intact IgG or fabs (one-way ANOVA with multiple comparisons).

FIG. 9A shows a study timeline and treatments given. A dose of 342 nM Fabs was delivered into each middle ear. FIG. 9B shows the relative quantity of NTHI within mucosal biofilms and adherent to the middle ear mucosa amongst treated cohorts. FIG. 9C shows relative mucosal biofilm score determined by six reviewers blinded to treatment amongst treated cohorts. FIGS. 9B and 9C: 6-8 middle ears per cohort, values for individual ears and mean for cohort shown, and cohorts for each panel from left to right are isotypy control Fabs, 0-tail Fabs, and β-tip Fabs. *P≤0.05, P≤0.01, *P≤0.001 (One-way ANOVA with multiple comparisons). FIG. 9D shows representative images of chinchilla middle ears from each cohort, mean mucosal biofilm score for the ear indicated within the box at the bottom right corner. TM, tympanic membrane; S, bony septae; MEM, middle ear mucosa; B, biofilm (encircled). In one embodiment, delivery of murine monoclonal antibody β-tip Fabs both significantly reduced the bacterial load in the middle ears and eradicated mucosal biofilms however the β-tail Fabs not only failed to do so but also were associated with significant inflammation.

FIG. 10A shows relative quantity of pro-inflammatory cytokines in chinchilla middle ear fluids after NTHI challenge and Fab fragment therapy as determined by cytometric bead array. *P≤0.05, **P≤0.01 vs. β-tip Fabs (one-way ANOVA with multiple comparisons), #P≤0.05 vs. isotype control Fabs (unpaired t-test). FIG. 10B shows relative mean concentration of the anti-inflammatory cytokine IL-10 amongst the three Fab fragment treated cohorts. *P≤0.05 vs. β-tail Fabs, ++P≤0.01 vs. β-tail Fabs or isotype control Fabs (one-way ANOVA with multiple comparisons). 5-7 middle ear fluids tested per cohort. Mean cytokine concentration ±SD shown. For either panel (FIG. 10A or 10B), shown from left to right are cytokine results for cohorts of isotypy control Fabs, β-tail Fabs, and β-tip Fabs. In one embodiment, delivery of β-tip Fabs resulted in a significantly reduced concentration of 6 pro-inflammatory cytokines and significantly greater concentration of the anti-inflammatory cytokine IL-10 which supports the relative inflammation or lack thereof as shown in FIG. 9D.

FIG. 11A shows a study timeline. A dose of 342 nM Fabs was delivered into each middle ear. FIG. 11B shows a relative quantity of NTHI resident within mucosal biofilms and adherent to the middle ear mucosa one or seven days after completion of antibody therapy. FIG. 11C shows relative amount of remaining mucosal biofilm as determined by six reviewers blinded to treatment delivered. FIGS. 11B and 11C: 6 middle ears per cohort, values for individual ears and mean for each cohort shown. Cohorts for each plotting from left to right are naïve serum Fabs, tail chimeric Fabs, and tip chimeric Fabs. *P≤0.05, P≤0.01, *P≤0.001 (one-way ANOVA with multiple comparisons). FIG. 11D shows representative images of middle ear mucosal biofilms; mean mucosal biofilm score indicated within the box at the bottom right corner. TM, tympanic membrane; S, bony septae; MEM, middle ear mucosa; B, biofilm (encircled). Rabbit polyclonal antibody Fabs directed against the tip-chimeric peptide mediated rapid and durable clearance of biofilm resident NTHI, eradication of established mucosal biofilms and resolution of experimental OM. Rabbit polyclonal antibody Fabs directed against the tail-chimeric peptide did not induce clearance of biofilm resident NTHI or disease resolution, and were instead associated with significant inflammation (FIG. 11D) as were those murine monoclonal antibodies Fabs directed against the β-tail (see FIG. 9D).

FIG. 12A shows representative images of bacterial biofilms (pseudocoloured white) after 16 h incubation with HuTipMab or HuTailMab. Orthogonal projections show a top-down view to depict spatial distribution of biofilm in x-y plane and side view indicates biofilm height in z-plane (arrowheads). Scale bars, 20 μm. As used herein, the term "HuTipMab" refers to a monoclonal antibody (Mab or mAb) comprising anti-tip HCl having an amino acid sequence of SEQ ID NO: 1 and anti-tip LC1 having an amino acid sequence of SEQ ID NO: 7. FIG. 12B show percentage of biofilm biomass that remained after exposure to HuTipMab compared to HuTailMab, determined by COMSTAT2 analysis. Mean±SD shown. Experiments were performed three times on separate days. ***P≤0.001 (unpaired t-test). HuTipMab significantly disrupted biofilms formed by diverse respiratory tract pathogens in vitro. As used herein, the term "HuTailMab" refers to a monoclonal antibody (Mab or mAb) comprising anti-tail HCl having an amino acid sequence of SEQ ID NO: 4 and anti-tail LC1 having an amino acid sequence of SEQ ID NO: 10.

FIG. 13A shows a study timeline and treatments. FIG. 13B shows a relative quantity of NTHI within the middle ear. FIG. 13C shows a relative amount of NTHI mucosal biofilm that remained in the middle ear after treatment with human monoclonal antibodies. FIGS. 13B and 13C: six middle ears per cohort, values for individual ears and mean for cohort shown. Cohorts for each plotting from left to right are saline, a humanized monoclonal antibody against the tail chimeric peptide, and a humanized monoclonal antibody against the tip chimeric peptide. ****P≤0.0001 (one-way ANOVA with multiple comparisons). FIG. 13D provides representative images of middle ears from each cohort; mean mucosal biofilm score for the ear indicated within the box at the bottom right corner. S, bony septae; MEM, middle ear mucosa; B, biofilm, encircled. The HuTipMab eradicated NTHI by resolution of mucosal biofilms, an outcome that was rapid and sustained. Also note that once humanized, monoclonal antibody directed at the tail-chimeric peptide no longer is associated with significant inflammatory changes as had been consistently observed with either the murine monoclonal directed to the β-tail (see FIG. 9D) or to the rabbit polyclonal antibody Fabs directed tail-chimeric peptide (see FIG. 11D).

FIG. 15A is a study timeline and vaccine formulations delivered. FIG. 15B is a relative quantity of NTHI within nasopharyngeal lavage fluids one day after bacterial challenge to ensure all cohorts were equivalently colonized. 8 lavage fluids per cohort, NS, no significance, one-way ANOVA. FIG. 15C shows a number of animals in each cohort with signs of experimental OM, i.e. inflammation and/or middle ear fluid, visualized by blinded video otoscopy. Eight animals per cohort, ****P≤0.001 vs. dmLT or tail chimeric peptide, Mantel-Cox test. FIG. 15D shows a representative images of tympanic membranes from each cohort on day 11, which was the day of maximum disease incidence in the cohort immunized with the tip chimeric peptide. TM, tympanic membrane. Immunization with tip chimeric peptide prevented ascending polymicrobial OM and promoted rapid resolution of the limited disease observed.

DETAILED DESCRIPTION

Figure 1:
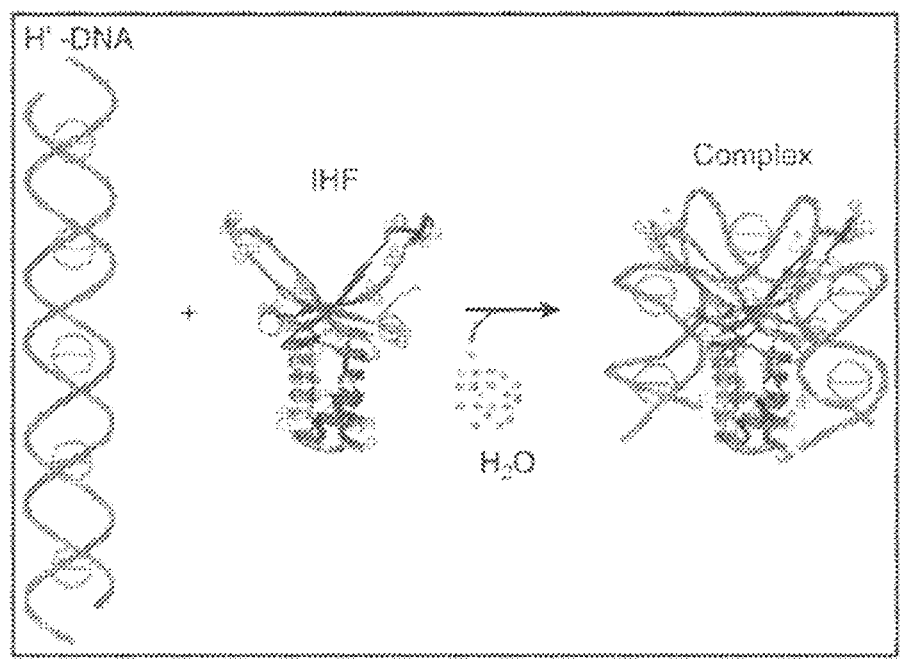
FIG. 1 provides a diagram showing how a DNABII protein (for example, an IHF) binds to double stranded DNA as well as the two arms of the DNABII protein.
Figures 2A, 2B:
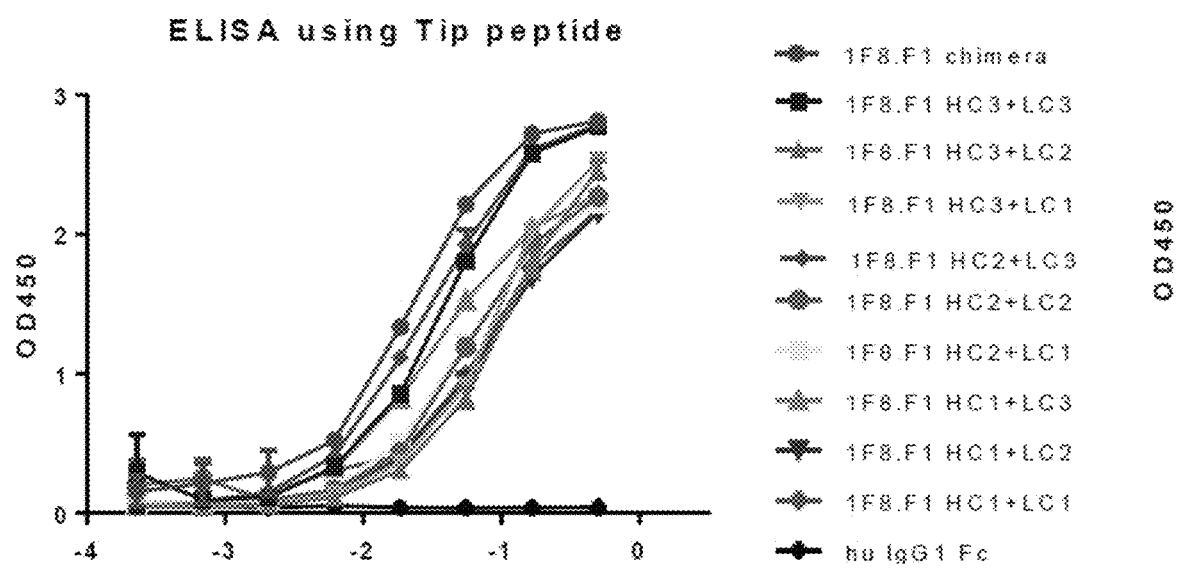
FIGS. 2A to 2D show results of a direct binding ELISA performed to assess the binding of the humanized monoclonal antibody variants against the corresponding peptides. Tip or tail chimeric peptide was coated onto a 96-well plate at 2 ug/mL and an 8-point dilution series of the antibodies were added (starting concentration of 50 ug/mL, 1:3 dilution). An anti-human IgG Fc HRP conjugated antibody (1:7000, Jackson ImmunoResearch Laboratories, 109-035-098) was used as the secondary detection antibody. A standard direct ELISA protocol was followed and the read the absorbance at 450 nm using a microplate reader. EC$_{50}$ values were calculated, and the humanized variants were determined to have comparable binding. Humanized tip-chimeric peptide antibodies shown in FIGS. 2A and 2B. Humanized tail-chimeric peptide antibodies shown in FIGS. 2C and 2D.
Figures 2C, 2D:
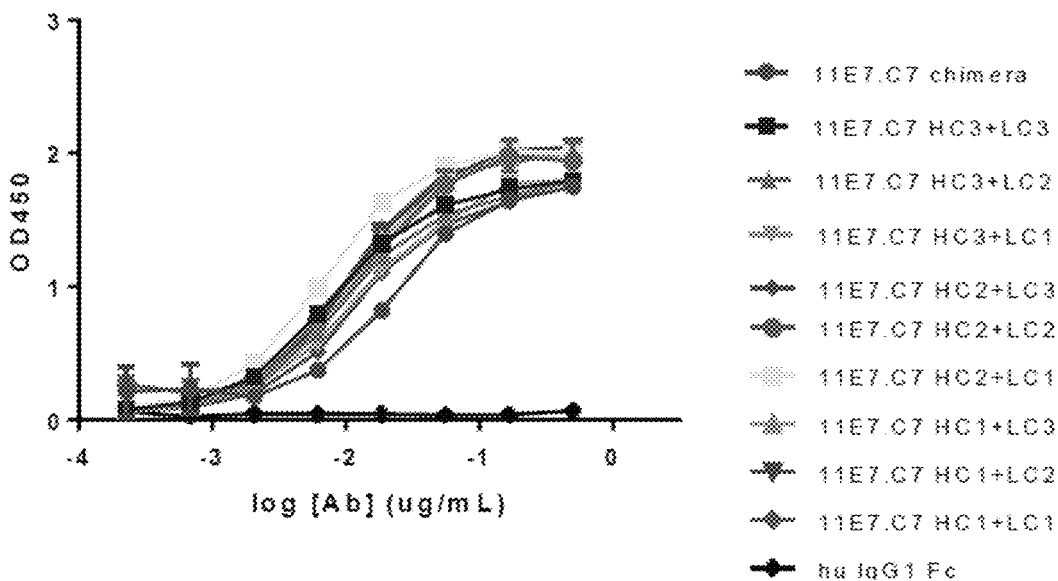

Unless defined otherwise, all technical and scientific terms used herein have the same meanings as commonly understood by one of ordinary skill in the art to which this disclosure belongs. All nucleotide sequences provided herein are presented in the 5' to 3' direction. Although any methods and materials similar or equivalent to those described herein can be used in the practice or testing of the present disclosure, particular, non-limiting exemplary methods, devices, and materials are now described. All technical and patent publications cited herein are incorporated herein by reference in their entirety. Nothing herein is to be construed as an admission that the disclosure is not entitled to antedate such disclosure by virtue of prior invention.

The practice of the present disclosure will employ, unless otherwise indicated, conventional techniques of tissue culture, immunology, molecular biology, microbiology, cell biology and recombinant DNA, which are within the skill of the art. See, e.g., Sambrook and Russell eds, (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds, (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate or alternatively by a variation of +/−15%, or alternatively 10% or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polypeptide" includes a plurality of polypeptides, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions disclosed herein. Embodiments defined by each of these transition terms are within the scope of this disclosure.

A "biofilm" intends an organized community of microorganisms that at times adhere to the surface of a structure, that may be organic or inorganic, together with the polymers such as DNA that they secrete, release and/or become available in the extracellular milieu due to bacterial lysis. The biofilms are very resistant to microbiotics and antimicrobial agents. They live on gingival tissues, teeth and restorations, causing caries and periodontal disease, also known as periodontal plaque disease. They also cause chronic middle ear infections. Biofilms can also form on the surface of dental implants, stents, catheter lines and contact lenses. They grow on pacemakers, heart valve replacements, artificial joints and other surgical implants. The Centers for Disease Control) estimate that over 65% of nosocomial (hospital-acquired) infections are caused by biofilms. They cause chronic vaginal infections and lead to life-threatening systemic infections in people with hobbled immune systems. Biofilms also are involved in numerous diseases. For instance, cystic fibrosis patients have *Pseudomonas* infections that often result in antibiotic resistant biofilms. In one embodiment, the biofilm comprises a DNABII polypeptide or protein. In a further embodiment, the biofilm comprises an IHF and/or an HU. In yet a further embodiment, the biofilm comprises an IHFA and/or an IHFB.

The term "disrupt" intends a reduction in the formation of the DNA/protein matrix that is a component of a microbial biofilm. In certain embodiments, disrupting a biofilm refers to dispersing the biofilm, releasing microorganisms from the DNA/protein matrix of the biofilm, and optionally allowing killing the microorganisms by host immune effectors and/or antibiotics.

A "DNABII polypeptide or protein" intends a DNA-binding protein or polypeptide that is composed of DNA-binding domains and thus have a specific or general affinity for microbial DNA. In one aspect, they bind DNA in the minor grove. Non-limiting examples of DNABII proteins are an integration host factor (IHF) protein and a histone-like protein from *E. coli* strain U93 (HU). Other DNA binding proteins that may be associated with the biofilm include DPS (Genbank Accession No.: CAA49169), H-NS (Genbank Accession No.: CAA47740), Hfq (Genbank Accession No.: ACE63256), CbpA (Genbank Accession No.: BAA03950) and CbpB (Genbank Accession No.: NP_418813).

An "integration host factor" or "IHF" protein is a bacterial protein that is used by bacteriophages to incorporate their DNA into the host bacteria. They also bind extracellular microbial DNA. The genes that encode the IHF protein subunits in *E. coli* are himA (Genbank Accession No.: POA6X7.1) and himD (POA6Y1.1) genes. Homologs for these genes are found in other organisms. In certain embodiments, the term "IHF" refers to one or both of the two IHF subunits: integration host factor subunit alpha (IHFA or IhfA) and integration host factor subunit beta (IHFB or IhfB).

"HU" or "histone-like protein from *E. coli* strain U93" refers to a class of heterodimeric proteins typically associate with *E. coli*. HU proteins are known to bind DNA junctions. Related proteins have been isolated from other microorganisms. The complete amino acid sequence of *E. coli* HU was reported by Laine et al. (1980) Eur. J. Biochem 103(3) 447-481. Antibodies to the HU protein are commercially available from Abeam. The genes that encode the HU protein subunits in *E. coli* are hupA and hupB corresponding to SEQ ID NOs: 29 and 30, respectively. Homologs for these genes are found in other organisms, and peptides corresponding to these genes from other organisms can be found in Table 10 of WO 2011/123396.

The term "surface antigens" or "surface proteins" refers to proteins or peptides on the surface of cells such as bacterial cells. Examples of outer membrane proteins such as OMP P5 (Genbank Accession No.: YP_004139079.1), OMP P2 (Genbank Accession No.: ZZX87199.1) and OMP P26 (Genbank Accession No.: YP_665091.1) whereas examples of surface antigens are rsPilA or recombinant soluble PilA (Genbank Accession No.: EFU96734.1) and Type IV Pilin (Genbank Accession No.: Yp_003864351.1).

The term "*Haemophilus influenzae*" refers to pathogenic bacteria that can cause many different infections such as, for example, ear infections, eye infections, and sinusitis. Many different strains of *Haemophilus influenzae* have been isolated and have an IhfA, ihfB and hupA genes or protein. Some non-limiting examples of different strains of *Haemophilus influenzae* include Rd KW20, 86-028NP, R2866, PittGG, PittEE, R2846, and 2019.

"Microbial DNA" intends single or double stranded DNA from a microorganism that is incorporated into a biofilm.

"Inhibiting, preventing or disrupting" a biofilm intends the prophylactic or therapeutic reduction in the structure of a biofilm.

A "bent polynucleotide" intends a double strand polynucleotide that contains a small loop on one strand which does not pair with the other strand. In some embodiments, the loop is from 1 base to about 20 bases long, or alternatively from 2 bases to about 15 bases long, or alternatively from about 3 bases to about 12 bases long, or alternatively from about 4 bases to about 10 bases long, or alternatively has about 4, 5, or 6, or 7, or 8, or 9, or 10 bases.

"Polypeptides that compete with DNABII binding, such as IHF in DNA binding" intend proteins or peptides that compete with DNABII (e.g., IHF) in binding bent or distorted DNA structures but do not form a biofilm with the DNA. Examples, without limitation, include fragments of IHF that include one or more DNA binding domains of the IHF, or the biological equivalents thereof.

A "subject" of diagnosis or treatment is a cell or an animal such as a mammal, or a human. Non-human animals subject to diagnosis or treatment and are those subject to infections or animal models, for example, simians, murines, such as, rats, mice, chinchilla, canine, such as dogs, leporids, such as rabbits, livestock, sport animals, and pets. The term "subject," "host," "individual," and "patient" are as used interchangeably herein to refer to animals, typically mammalian animals. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. In some embodiments a subject is a human.

The term "protein", "peptide" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

A "C-terminal polypeptide" intends at least the 10, or alternatively at least the 15, or alternatively at least 20, or at least the 25 C-terminal amino acids or alternatively half of a polypeptide. In another aspect, for polypeptides containing 90 amino acids, the C-terminal polypeptide would comprise amino acids 46 through 90. In one aspect, the term intends the C-terminal 20 amino acids from the carboxyl terminus.

A "tip fragment" of a DNABII polypeptide intends a DNABII polypeptide that, using IHFalpha and IHFbeta as examples, forms the two arms of the proteins. (see FIG. 1). Non-limiting examples of such include IhfA, A tip fragment: NFELRDKSSRPGRNPKTGDVV, SEQ ID NO: 31, and IhfB, B tip fragment: SLHHRQPRLGRNPKTGDSVNL, SEQ ID NO: 32.

A "tail fragment" of a DNABII polypeptide intends a region of the protein that is both exposed to the bulk medium and not occluded by DNA or other polypeptides.

An immunodominant antigen intends a region of the protein that is recognized and binds with high affinity to an antibody.

An immunoprotective antigen intends a region of the protein that is recognized and binds with high affinity to an antibody to interfere with protein function; the antibodies generated against an immuonprotective antigen are characterized by enhanced or optimal effect against a target indication as a result to the interference with protein function— in this case, an improve capability to clear biofilms.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "isolated" or "recombinant" as used herein with respect to nucleic acids, such as DNA or RNA, refers to molecules separated from other DNAs or RNAs, respectively that are present in the natural source of the macromolecule as well as polypeptides. The term "isolated or recombinant nucleic acid" is meant to include nucleic acid fragments which are not naturally occurring as fragments and would not be found in the natural state. The term "isolated" is also used herein to refer to polynucleotides, polypeptides and proteins that are isolated from other cellular proteins and is meant to encompass both purified and recombinant polypeptides. In other embodiments, the term "isolated or recombinant" means separated from constituents, cellular and otherwise, in which the cell, tissue, polynucleotide, peptide, polypeptide, protein, antibody or fragment(s) thereof, which are normally associated in nature. For example, an isolated cell is a cell that is separated from tissue or cells of dissimilar phenotype or genotype. An isolated polynucleotide is separated from the 3' and 5' contiguous nucleotides with which it is normally associated in its native or natural environment, e.g., on the chromosome. As is apparent to those of skill in the art, a non-naturally occurring polynucleotide, peptide, polypeptide, protein, antibody or fragment(s) thereof, does not require "isolation" to distinguish it from its naturally occurring counterpart.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, fragment, polypeptide or nucleic acid, intends those having minimal homology while still maintaining desired structure or functionality. Unless specifically recited herein, it is contemplated that any polynucleotide, polypeptide or protein mentioned herein also includes equivalents thereof. In one aspect, an equivalent polynucleotide is one that hybridizes under stringent conditions to the polynucleotide or complement of the polynucleotide as described herein for use in the described methods. In another aspect, an equivalent antibody or antigen binding polypeptide intends one that binds with at least 70%, or alternatively at least 75%, or alternatively at least 80%, or alternatively at least 85%, or alternatively at least 90%, or alternatively at least 95% affinity or higher affinity to a reference antibody or antigen binding fragment. In another aspect, the equivalent thereof competes with the binding of the antibody or antigen binding fragment to its antigen under a competitive ELISA assay. In another aspect, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide or nucleic acid. Examples of biologically equivalent polypeptides are provided in Table 9 of WO 2011/123396 which identifies conservative amino acid substitutions to the disclosed amino acid sequences.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+

PDB+GenBank CDS translations+SwissProtein+SPupdate+ PIR. Details of these programs can be found at the following Internet address: ncbi.nlm.nih.gov/cgi-bin/BLAST. Sequence identity and percent identity were determined by incorporating them into clustalW (available at the web address: align.genome.jp, last accessed on Mar. 7, 2011).

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder. As used herein, "treating" or "treatment" of a disease in a subject can also refer to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, treatment excludes prophylaxis.

To prevent intends to prevent a disorder or effect in vitro or in vivo in a system or subject that is predisposed to the disorder or effect. An example of such is preventing the formation of a biofilm in a system that is infected with a microorganism known to produce one.

A "composition" is intended to mean a combination of active agent and another compound or composition, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

A "pharmaceutical composition" is intended to include the combination of an active agent with a carrier, inert or active, making the composition suitable for diagnostic or therapeutic use in vitro, in vivo or ex vivo.

"Pharmaceutically acceptable carriers" refers to any diluents, excipients, or carriers that may be used in the compositions disclosed herein. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They may be selected with respect to the intended form of administration, that is, oral tablets, capsules, elixirs, syrups and the like, and consistent with conventional pharmaceutical practices.

The compositions used in accordance with the disclosure can be packaged in dosage unit form for ease of administration and uniformity of dosage. The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions are administered in a manner compatible with the dosage formulation and in such amount as is therapeutically or prophylactically effective. The formulations are easily administered in a variety of dosage forms, such as the type of injectable solutions described herein.

A "biologically active agent" or an active agent disclosed herein intends one or more of an isolated or recombinant polypeptide, an isolated or recombinant polynucleotide, a vector, an isolated host cell, or an antibody, as well as compositions comprising one or more of same.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

An agent of the present disclosure can be administered for therapy by any suitable route of administration. It will also be appreciated that the optimal route will vary with the condition and age of the recipient, and the disease being treated.

As used herein, the term "contacting" means direct or indirect binding or interaction between two or more molecules. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of an immunogenic composition, in some embodiments the effective amount is the amount sufficient to result in a protective response against a pathogen. In other embodiments, the effective amount of an immunogenic composition is the amount sufficient to result in antibody generation against the antigen. In some embodiments, the effective amount is the amount required to confer passive immunity on a subject in need thereof. With respect to immunogenic compositions, in some embodiments the effective amount will depend on the intended use, the degree of immunogenicity of a particular antigenic compound, and the health/responsiveness of the subject's immune system, in addition to the factors described above. The skilled artisan will be able to determine appropriate amounts depending on these and other factors.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The term "contacting" means direct or indirect binding or interaction between two or more molecules. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

The term "conjugated moiety" refers to a moiety that can be added to an isolated chimeric polypeptide by forming a covalent bond with a residue of chimeric polypeptide. The moiety may bond directly to a residue of the chimeric polypeptide or may form a covalent bond with a linker which in turn forms a covalent bond with a residue of the chimeric polypeptide.

A "peptide conjugate" refers to the association by covalent or non-covalent bonding of one or more polypeptides and another chemical or biological compound. In a non-limiting example, the "conjugation" of a polypeptide with a chemical compound results in improved stability or efficacy of the polypeptide for its intended purpose. In one embodiment, a peptide is conjugated to a carrier, wherein the carrier is a liposome, a micelle, or a pharmaceutically acceptable polymer.

"Liposomes" are microscopic vesicles consisting of concentric lipid bilayers. Structurally, liposomes range in size and shape from long tubes to spheres, with dimensions from a few hundred Angstroms to fractions of a millimeter. Vesicle-forming lipids are selected to achieve a specified degree of fluidity or rigidity of the final complex providing the lipid composition of the outer layer. These are neutral (cholesterol) or bipolar and include phospholipids, such as phosphatidylcholine (PC), phosphatidylethanolamine (PE), phosphatidylinositol (PI), and sphingomyelin (SM) and other types of bipolar lipids including but not limited to dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanol-amine, phosphatidylserine, phosphatidylinositol, sphingomyelin, cephalin, cardiolipin, phosphatidic acid, cerebrosides, di stearoylphosphatidylethanolamine (DSPE), dioleoylphosphatidylcholine (DOPC), dipalmitoylphosphatidylcholine (DPPC), palmitoyloteoylphosphatidylcholine (POPC), palmitoyloleoylphosphatidylethanolamine (POPE) and dioleoylphosphatidylethanolamine 4-(N-maleimido-triethyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, and the cationic lipids mentioned above (DDAB, DODAC, DMRIE, DMTAP, DOGS, DOTAP (DOTMA), DOSPA, DPTAP, DSTAP, DC-Chol). Negatively charged lipids include phosphatidic acid (PA), dipalmitoylphosphatidylglycerol (DPPG), dioteoylphosphatidylglycerol and (DOPG), dicetylphosphate that are able to form vesicles. Typically, liposomes can be divided into three categories based on their overall size and the nature of the lamellar structure. The three classifications, as developed by the New York Academy Sciences Meeting, "Liposomes and Their Use in Biology and Medicine," December 1977, are multi-lamellar vesicles (MLVs), small uni-lamellar vesicles (SUVs) and large uni-lamellar vesicles (LUVs). The biological active agents can be encapsulated in such for administration in accordance with the methods described herein.

A "micelle" is an aggregate of surfactant molecules dispersed in a liquid colloid. A typical micelle in aqueous solution forms an aggregate with the hydrophilic "head" regions in contact with surrounding solvent, sequestering the hydrophobic tail regions in the micelle center. This type of micelle is known as a normal phase micelle (oil-in-water micelle). Inverse micelles have the head groups at the center with the tails extending out (water-in-oil micelle). Micelles can be used to attach a polynucleotide, polypeptide, antibody or composition described herein to facilitate efficient delivery to the target cell or tissue.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof. The biological active agents can be conjugated to a pharmaceutically acceptable polymer for administration in accordance with the methods described herein.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue or a subject using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

As used herein the term "eDNA" refers to extracellular DNA found as a component to pathogenic biofilms.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors". Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene. This is a cheap and easy way of mass-producing a gene or the protein it then codes for.

A "yeast artificial chromosome" or "YAC" refers to a vector used to clone large DNA fragments (larger than 100 kb and up to 3000 kb). It is an artificially constructed chromosome and contains the telomeric, centromeric, and replication origin sequences needed for replication and preservation in yeast cells. Built using an initial circular plasmid, they are linearized by using restriction enzymes, and then DNA ligase can add a sequence or gene of interest within the linear molecule by the use of cohesive ends. Yeast expression vectors, such as YACs, YIps (yeast integrating plasmid), and YEps (yeast episomal plasmid), are extremely useful as one can get eukaryotic protein products with posttranslational modifications as yeasts are themselves eukaryotic cells, however YACs have been found to be more unstable than BACs, producing chimeric effects.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. See, e.g., PCT International Application Publication No. WO 95/27071. Ads do not require integration into the host cell genome. Recombinant Ad derived vectors, particularly those that reduce the potential for recombination and generation of wild-type virus, have also been constructed. See, PCT International Application Publication Nos. WO 95/00655 and WO 95/11984, Wild-type AAV has high infectivity and specificity integrating into the host cell's genome. See, Hermonat & Muzyczka (1984) Proc. Natl. Acad. Sci. USA 81:6466-6470 and Lebkowski et al. (1988) Mol. Cell. Biol. 8:3988-3996.

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include DNA/liposome complexes, micelles and targeted viral protein-DNA complexes. Liposomes that also comprise a targeting antibody or fragment thereof can be used in the methods disclosed herein. In addition to the delivery of polynucleotides to a cell or cell population, direct introduction of the proteins described herein to the cell or cell population can be done by the non-limiting technique of protein transfection, alternatively culturing conditions that can enhance the expression and/or promote the activity of the proteins disclosed herein are other non-limiting techniques.

As used herein, the terms "antibody," "antibodies" and "immunoglobulin" includes whole antibodies and any antigen binding fragment or a single chain thereof. Thus, the term "antibody" includes any protein or peptide containing molecule that comprises at least a portion of an immunoglobulin molecule. The terms "antibody," "antibodies" and "immunoglobulin" also include immunoglobulins of any isotype, fragments of antibodies which retain specific binding to antigen, including, but not limited to, Fab, Fab', F(ab)$_2$, Fv, scFv, dsFv, Fd fragments, dAb, VH, VL, VhH, and V-NAR domains; minibodies, diabodies, triabodies, tetrabodies and kappa bodies; multispecific antibody fragments formed from antibody fragments and one or more isolated. Examples of such include, but are not limited to a complementarity determining region (CDR) of a heavy or light chain or a ligand binding portion thereof, a heavy chain or light chain variable region (which is also referred to herein as a variable domain), a heavy chain or light chain constant region (which is also referred to herein as a constant domain), a framework (FR) region, or any portion thereof, at least one portion of a binding protein, chimeric antibodies, humanized antibodies, single-chain antibodies, and fusion proteins comprising an antigen-binding portion of an antibody and a non-antibody protein. The variable regions of the heavy and light chains of the immunoglobulin molecule contain a binding domain that interacts with an antigen. The constant regions of the antibodies (Abs) may mediate the binding of the immunoglobulin to host tissues. The term "anti-" when used before a protein name, anti-DNABII, anti-IHF, anti-HU, anti-OMP P5, for example, refers to a monoclonal or polyclonal antibody that binds and/or has an affinity to a particular protein. For example, "anti-IHF" refers to an antibody that binds to the IHF protein. The specific antibody may have affinity or bind to proteins other than the protein it was raised against. For example, anti-IHF, while specifically raised against the IHF protein, may also bind other proteins that are related either through sequence homology or through structure homology.

Complementarity determining regions (CDRs) are part of the variable region of an antibody or a T cell receptor generated by B-cell s and T-cells respectively, wherein these molecules bind to their specific antigen (also called epitope). In certain embodiments, the terms "variable region" and "variable domain" are used interchangeably, referring to the polypeptide of a light or heavy chain of an antibody that varies greatly in its sequence of amino acid residues from one antibody to another, and that determines the conformation of the combining site which confers the specificity of the antibody for a particular antigen. In a further embodiment, the variable region is about 90 amino acids long to about 200 amino acids long, including but not limited to about 100 amino acids long, or alternatively about 110 amino acids long, or alternatively about 120 amino acids long, or alternatively about 130 amino acids long, or alternatively about 140 amino acids long, or alternatively about 150 amino acids long, or alternatively about 160 amino acids long, or alternatively about 170 amino acids long, or alternatively about 180 amino acids long, or alternatively about 190 amino acids long. In certain embodiments, a variable region of an amino acid sequence, as used herein, refers to that the first about 100 amino acids, or alternatively about 110 amino acids, or alternatively about 120 amino acids, or alternatively about 130 amino acids, or alternatively about 140 amino acids, or alternatively about 150 amino acids of the amino acid sequence (including or excluding a signal peptide if applicable) is the variable region.

A set of CDRs constitutes a paratope also called an antigen-binding site, which is a part of an antibody that recognizes and binds to an antigen. There are three CDRs (CDR1, CDR2 and CDR3), arranged non-consecutively, optionally from the amino terminus to the carboxyl terminus, on the amino acid sequence of a variable region of an antigen receptor, such as a heavy chain or a light chain. As used herein, CDRn refers to a CDRn in an immunoglobulin chain or derived from an immunoglobulin chain, wherein the number n is selected from 1-3. In one embodiment, CDRLn refers to a CDRn in a light chain or derived from a light chain, wherein the number n is selected from 1-3; while CDRHn refers to a CDRn in a heavy chain or derived from a heavy chain, wherein the number n is selected from 1-3. In certain embodiments, framework region (FR) refers to the part of a variable region which is not a CDR. In certain embodiments, FRn refers to a FR in a heavy chain or a light chain or derived from a heavy chain or a light chain, and wherein the number n is selected from 1-4. In certain embodiments, a varabile region comprises or consists essentially of, or yet further consists of the following (optionally following the order as provided, and further optionally from the amino terminus to the carboxyl terminus): FR1, CDR1, FR2, CDR2, FR3, CDR3 and FR4.

Variable regions and/or CDRs of an antibody or a fragment thereof can be determined by one of skill in the art, for example, using publically or commercially available tools. Non-limiting examples of such tools include, IgBlast (accessible at www.ncbi.nlm.nih.gov/igblast/), Scaligner (available from drugdesigntech at www.scaligner.com/), IMGT rules and/or tools (see, for example, www.imgt.org/EVIGT-ScientificChart/Nomenclature/IMGT-FRCDRdefinition-.html, also accessible at www.imgt.org/), Chothia Canonical Assignment (accessible at www.bioinforg.uk/abs/chothia.html), Antigen receptor Numbering And Receptor Calssificatilon (ANARCI, accessible at opig.stats.ox.ac.uk/webapps/newsabdab/sabpred/anarci/), the Kabat numbering method/scheme (e.g., Kabat, E. A., et al., (1991) Sequences of Proteins of Immunological Interest, Fifth Edition, U.S. Department of Health and Human Services, NIH Publication No. 91-3242) or the Paratome web server (accessible at www.ofranlab.org/paratome/, see Vered Kunik, et al, Nucleic Acids Research, Volume 40, Issue W1, 1 Jul. 2012, Pages W521-W524).

The antibodies can be polyclonal, monoclonal, multispecific (e.g., bispecific antibodies), and antibody fragments, so long as they exhibit the desired biological activity. Antibodies can be isolated from any suitable biological source, e.g., murine, rat, sheep and canine.

The terms "polyclonal antibody" or "polyclonal antibody composition" as used herein refer to a preparation of antibodies that are derived from different B-cell lines. They are a mixture of immunoglobulin molecules secreted against a specific antigen, each recognizing a different epitope.

As used herein, "monoclonal antibody" refers to an antibody obtained from a substantially homogeneous antibody population. Monoclonal antibodies are highly specific, as each monoclonal antibody is directed against a single determinant on the antigen. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like.

Monoclonal antibodies may be generated using hybridoma techniques or recombinant DNA methods known in the art. A hybridoma is a cell that is produced in the laboratory from the fusion of an antibody-producing lymphocyte and a non-antibody producing cancer cell, usually a myeloma or lymphoma. A hybridoma proliferates and produces a continuous sample of a specific monoclonal antibody. Alternative techniques for generating or selecting antibodies include in vitro exposure of lymphocytes to antigens of interest, and screening of antibody display libraries in cells, phage, or similar systems.

The term "human antibody" as used herein, is intended to include antibodies having variable and constant regions derived from human germline immunoglobulin sequences. The human antibodies disclosed herein may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, $C_L$, $C_H$ domains (e.g., $C_{H1}$, $C_{H2}$, $C_{H3}$), hinge, (VL, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

As used herein, the term "humanized antibody" or "humanized immunoglobulin" refers to a human/non-human chimeric antibody that contains a minimal sequence derived from non-human immunoglobulin. For the most part, humanized antibodies are human immunoglobulins (recipient antibody) in which residues from a variable region or a fragment thereof (for example, 1, 2, 3, 4, 5, or all 6 CDRs) of the recipient are replaced by residues from a variable region or a fragment thereof (for example, 1, 2, 3, 4, 5, or all 6 CDRs) of a non-human species (donor antibody) such as mouse, rat, rabbit, or non-human primate having the desired specificity, affinity and capacity. Humanized antibodies may comprise residues that are not found in the recipient antibody or in the donor antibody. The humanized antibody can optionally also comprise at least a portion of an immunoglobulin constant region (Fc), typically that of a human immunoglobulin, a non-human antibody containing one or more amino acids in a framework region, a constant region or a CDR, that have been substituted with a correspondingly positioned amino acid from a human antibody. Without wishing to be bound by the theory, humanized antibodies produce a reduced immune response in a human host, as compared to a non-humanized version of the same antibody. The humanized antibodies may have conservative amino acid substitutions which have substantially no effect on antigen binding or other antibody functions. Conservative substitutions groupings include: glycine-alanine, valine-leucine-isoleucine, phenylalanine-tyrosine, lysine-arginine, alanine-valine, serine-threonine and asparagine-glutamine. Specifically, the humanized antibodies as disclosed herein specifically binds to a DNABII polypeptide or a fragment thereof (such as the tip chimeric peptide or the tail chimeric peptide) with certain range(s) of one or more of the following: $EC_{50}$, $K_{on}$, $K_{off}$, $K_A$ and/or $K_D$, and inhibits or releases certain cytokine(s) upon treating a subject. In a further embodiment, the humanized antibody specifically binding to the tip region of a DNABII polypeptide (such as the tip chimeric peptide) disrupts biofilm both in vivo and in vitro. In addition, the process of humanization, while a rational design process, may produce unexpected changes (positive or negative) in e.g. binding affinity, antigen specificity, or physical properties such as solubility or aggregatability; hence, properties of humanized antibodies are not inherently predictable from the properties of the starting non-human antibody.

In one embodiment, an antibody as used herein may be a recombinant antibody. The term "recombinant antibody", as used herein, includes all antibodies that are prepared, expressed, created or isolated by recombinant means, such as antibodies isolated from an animal (e.g., a mouse) that is transgenic or transchromosomal for immunoglobulin genes or a hybridoma prepared therefrom, antibodies isolated from a host cell transformed to express the antibody, e.g., from a transfectoma, antibodies isolated from a recombinant, combinatorial antibody library, and antibodies prepared, expressed, created or isolated by any other means that involve splicing of immunoglobulin (Ig) gene sequences to other DNA sequences. In certain embodiments, however, such recombinant antibodies can be subjected to in vitro mutagenesis (or, when an animal transgenic for Ig sequences is used, in vivo somatic mutagenesis) and thus the amino acid sequences of the VH and VL regions of the recombinant antibodies are sequences that may not naturally exist within the antibody germline repertoire in vivo. Methods to making these antibodies are described herein.

In one embodiment, an antibody as used herein may be a chimeric antibody. As used herein, chimeric antibodies are antibodies whose light and heavy chain genes have been constructed, typically by genetic engineering, from antibody variable and constant region genes belonging to different species.

As used herein, the term "antibody derivative", comprises a full-length antibody or a fragment of an antibody, wherein one or more of the amino acids are chemically modified by alkylation, pegylation, acylation, ester formation or amide formation or the like, e.g., for linking the antibody to a second molecule. This includes, but is not limited to, pegylated antibodies, cysteine-pegylated antibodies, and variants thereof.

As used herein, the term "label" intends a directly or indirectly detectable compound or composition that is conjugated directly or indirectly to the composition to be detected, e.g., N-terminal histidine tags (N-His), magnetically active isotopes, e.g., $^{115}Sn$, $^{117}Sn$ and $^{119}Sn$, a non-radioactive isotopes such as $^{13}C$ and $^{15}N$, polynucleotide or protein such as an antibody so as to generate a "labeled" composition. The term also includes sequences conjugated to the polynucleotide that will provide a signal upon expression of the inserted sequences, such as green fluorescent protein (GFP) and the like. The label may be detectable by itself (e.g., radioisotope labels or fluorescent labels) or, in the case of an enzymatic label, may catalyze chemical alteration of a substrate compound or composition which is detectable. The labels can be suitable for small scale detection or more suitable for high-throughput screening. As such, suitable labels include, but are not limited to magnetically active isotopes, non-radioactive isotopes, radioisotopes, fluorochromes, chemiluminescent compounds, dyes, and proteins, including enzymes. The label may be simply detected or it may be quantified. A response that is simply detected generally comprises a response whose existence merely is confirmed, whereas a response that is quantified generally comprises a response having a quantifiable (e.g., numerically reportable) value such as an intensity, polarization, and/or other property. In luminescence or fluorescence assays, the detectable response may be generated directly using a luminophore or fluorophore associated with an assay component actually involved in binding, or indirectly using a luminophore or fluorophore associated with another (e.g., reporter or indicator) component. Examples of luminescent labels that produce signals include, but are not limited to bioluminescence and chemiluminescence. Detectable luminescence response generally comprises a change in, or an occurrence of a luminescence signal. Suitable methods and luminophores for luminescently labeling assay components are known in the art and described for example in Haugland, Richard P. (1996) Handbook of Fluorescent Probes and Research Chemicals ($6^{th}$ ed). Examples of luminescent probes include, but are not limited to, aequorin and luciferases.

As used herein, the term "immunoconjugate" comprises an antibody or an antibody derivative associated with or linked to a second agent, such as a cytotoxic agent, a detectable agent, a radioactive agent, a targeting agent, a human antibody, a humanized antibody, a chimeric antibody, a synthetic antibody, a semisynthetic antibody, or a multispecific antibody.

Examples of suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, and Texas Red. Other suitable optical dyes are described in the Haugland, Richard P. (1996) Handbook of Fluorescent Probes and Research Chemicals ($6^{th}$ ed.).

In another aspect, the fluorescent label is functionalized to facilitate covalent attachment to a cellular component present in or on the surface of the cell or tissue such as a cell surface marker. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to either a linker, the agent, the marker, or the second labeling agent.

"Eukaryotic cells" comprise all of the life kingdoms except Monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

"Prokaryotic cells" that usually lack a nucleus or any other membrane-bound organelles and are divided into two domains, bacteria and archaea. In addition to chromosomal DNA, these cells can also contain genetic information in a circular loop called on episome. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission. Examples include but are not limited to *Bacillus* bacteria, *E. coli* bacterium, and *Salmonella* bacterium.

A "native" or "natural" antigen is a polypeptide, protein or a fragment which contains an epitope, which has been isolated from a natural biological source, and which can specifically bind to an antigen receptor, in particular a T cell antigen receptor (TCR), in a subject.

The terms "antigen" and "antigenic" refer to molecules with the capacity to be recognized by an antibody or otherwise act as a member of an antibody-ligand pair. "Specific binding" or "binding" refers to the interaction of an antigen with the variable regions of immunoglobulin heavy and light chains. Antibody-antigen binding may occur in vivo or in vitro. The skilled artisan will understand that macromolecules, including proteins, nucleic acids, fatty acids, lipids, lipopolysaccharides and polysaccharides have the potential to act as an antigen. The skilled artisan will further understand that nucleic acids encoding a protein with the potential to act as an antibody ligand necessarily encode an antigen. The artisan will further understand that antigens are not limited to full-length molecules, but can also include partial molecules. The term "antigenic" is an adjectival reference to molecules having the properties of an antigen. The term encompasses substances which are immunogenic, i.e., immunogens, as well as substances which induce immunological unresponsiveness, or anergy, i.e., anergens.

An "altered antigen" is one having a primary sequence that is different from that of the corresponding wild-type antigen. Altered antigens can be made by synthetic or recombinant methods and include, but are not limited to, antigenic peptides that are differentially modified during or after translation, e.g., by phosphorylation, glycosylation, cross-linking, acylation, proteolytic cleavage, linkage to an antibody molecule, membrane molecule or other ligand. (Ferguson et al. (1988) Ann. Rev. Biochem. 57:285-320). A synthetic or altered antigen disclosed herein is intended to bind to the same TCR as the natural epitope.

A "self-antigen" also referred to herein as a native or wild-type antigen is an antigenic peptide that induces little or no immune response in the subject due to self-tolerance to the antigen. An example of a self-antigen is the melanoma specific antigen gp100.

"Immune response" broadly refers to the antigen-specific responses of lymphocytes to foreign substances. The terms "immunogen" and "immunogenic" refer to molecules with the capacity to elicit an immune response. All immunogens are antigens, however, not all antigens are immunogenic. An immune response disclosed herein can be humoral (via antibody activity) or cell-mediated (via T cell activation). The response may occur in vivo or in vitro. The skilled artisan will understand that a variety of macromolecules, including proteins, nucleic acids, fatty acids, lipids, lipopolysaccharides and polysaccharides have the potential to be immunogenic. The skilled artisan will further understand that nucleic acids encoding a molecule capable of eliciting an immune response necessarily encode an immunogen. The artisan will further understand that immunogens are not limited to full-length molecules, but may include partial molecules.

The term "passive immunity" refers to the transfer of immunity from one subject to another through the transfer of antibodies. Passive immunity may occur naturally, as when maternal antibodies are transferred to a fetus. Passive immunity may also occur artificially as when antibody compositions are administered to non-immune subjects. Antibody donors and recipients may be human or non-human subjects. Antibodies may be polyclonal or monoclonal, may be generated in vitro or in vivo, and may be purified, partially purified, or unpurified depending on the embodiment. In some embodiments described herein, passive immunity is conferred on a subject in need thereof through the administration of antibodies or antigen binding fragments that specifically recognize or bind to a particular antigen. In some embodiments, passive immunity is conferred through the administration of an isolated or recombinant polynucleotide encoding an antibody or antigen binding fragment that specifically recognizes or binds to a particular antigen.

In the context of this disclosure, a "ligand" is a polypeptide. In one aspect, the term "ligand" as used herein refers to any molecule that binds to a specific site on another molecule. In other words, the ligand confers the specificity of the protein in a reaction with an immune effector cell or an antibody to a protein or DNA to a protein. In one aspect it is the ligand site within the protein that combines directly with the complementary binding site on the immune effector cell.

As used herein, "solid phase support" or "solid support", used interchangeably, is not limited to a specific type of support. Rather a large number of supports are available and are known to one of ordinary skill in the art. Solid phase supports include silica gels, resins, derivatized plastic films, glass beads, cotton, plastic beads, alumina gels. As used herein, "solid support" also includes synthetic antigen-presenting matrices, cells, and liposomes. A suitable solid phase support may be selected on the basis of desired end use and suitability for various protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, Calif.).

An example of a solid phase support include glass, polystyrene, polypropylene, polyethylene, dextran, nylon, amylases, natural and modified celluloses, polyacrylamides, gabbros, and magnetite. The nature of the carrier can be either soluble to some extent or insoluble. The support material may have virtually any possible structural configuration so long as the coupled molecule is capable of binding to a polynucleotide, polypeptide or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

As used herein, a biological sample, or a sample, can be obtained from a subject, cell line or cultured cell or tissue. Exemplary samples include, but are not limited to, cell sample, tissue sample, liquid samples such as blood and other liquid samples of biological origin (including, but not limited to, ocular fluids (aqueous and vitreous humor), peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, tears, cyst fluid, pleural and peritoneal fluid, pericardial fluid, ascites, lymph, chyme, chyle, bile, interstitial fluid, menses, pus, sebum, vomit, vaginal secretions/flushing, synovial fluid, mucosal secretion, stool water, pancreatic juice, lavage fluids from sinus cavities, bronchopulmonary aspirates, blastocyl cavity fluid, or umbilical cord blood. In one embodiment, the biological sample is suspect of having a biofilm. In another embodiment, the biological sample comprise a biofilm.

As used herein, the term "signal peptide" or "signal polypeptide" intends an amino acid sequence usually present at the N-terminal end of newly synthesized secretory or membrane polypeptides or proteins. It acts to direct the polypeptide to a specific cellular location, e.g. across a cell membrane, into a cell membrane, or into the nucleus. In some embodiments, the signal peptide is removed following localization. Examples of signal peptides are well known in the art. Non-limiting examples are those described in U.S. Pat. Nos. 8,853,381, 5,958,736, and 8,795,965.

As used herein, the term "chimer" or "chimeric peptide" refers to a recombinant polypeptide comprising or alternatively consisting essentially of, or yet further consisting of, two or more fragments or domains of a DNABII polypeptide conjugated directly or indirectly (such as via a linker) with each other. In one embodiment, the domains are conformational tip domains and/or conformational tail domains. Additionally or alternatively, the two or more fragments or domains is derived from the same or different DNABII polypeptide(s). In one embodiment, the chimeric peptide comprises or alternatively consists essentially of, or yet further consists of, a tip domain of IhfA and a tip domain of IhfB conjugated directly or indirectly (such as via a linker) with each other. In another embodiment, the chimeric peptide comprises or alternatively consists essentially of, or yet further consists of, a tail domain of IhfA and a tail domain of IhfB conjugated directly or indirectly (such as via a linker) with each other. "A conformational tip domain" of a polypeptide refers to a polypeptide that comprises a primary amino acid sequence wherein the structure has an anti-parallel beta ribbon with a sharp turn that is typically mediated by a proline residue. The "tip" of an IHF polypeptide is shown in FIG. 1 of WO2018/129078.

In certain embodiments, the tip-chimeric peptide IhfA5-mIhfB4$_{NTHI}$ comprises, or consists essentially of, or yet further consists of: a polypeptide sequence of RPGRNPX$_1$TGDVVPVSARRVV-X-FSLHHRQPRLGRNPX$_1$TGDSV (SEQ ID NO: 38), wherein "X" is an optional amino acid linker sequence, optionally comprising, or consisting essentially of, or yet further consisting of between 1 to 20 amino acids; and wherein "X$_1$" is any amino acid or alternatively "X$_1$" is selected from the amino acids Q, R, K, S, or T. In a further aspect, "X$_1$" is a K or Q. In a further embodiment, the tip-chimeric peptide IhfA5-mIhfB4$_{NTHI}$ comprises, or consists essentially of, or yet further consists of: a polypeptide sequence of RPGRNPKTGDVVPVSARRVV-X-FSLHHRQPRLGRNPKTGDSV (SEQ ID NO: 39), wherein "X" is an optional amino acid linker sequence optionally comprising, or consisting essentially of, or yet further consisting of between 1 to 20 amino acids. In yet a further embodiment, the tip-chimeric peptide IhfA5-mIhfB4$_{NTHI}$ comprises or consists essentially of, or yet further consists of: a polypeptide sequence of (SEQ ID NO: 40)
RPGRNPKTGDVVPVSARRVVGPSLFSLHHRQPRLGRNPKTGDSV.

In certain embodiments, the tail-chimeric peptide IhfA3-IhfB2$_{NTHI}$ comprises, or consists essentially of, or yet further consists of: a polypeptide sequence of FLEE- IRLSLESGQDVKLSGF-X-TLSAKEIENMVKDILEFISQ (SEQ ID NO: 41), wherein "X" is an optional amino acid linker sequence optionally comprising, or consisting essentially of, or yet further consisting of between 1 to 20 amino acids. In certain embodiments, the linker is selected from any one or more of SEQ ID NOs: 42-49. In one embodiment, the tail-chimeric peptide IhfA3-IhfB2$_{NTHI}$ comprises, or consists essentially of, or yet further consists of (SEQ ID NO: 50)
FLEEIRLSLESGQDVKLSGFGPSLTLSAKEIENIVIVKDILEFISQ.

As used herein, the term "EC$_{50}$" refers to the concentration of an antibody or a fragment thereof which induces a response (for example, binding between the antibody or a fragment thereof and its target) halfway between the baseline and maximum after a specified exposure time.

Several parameters are used herein to described the binding and unbinding reaction of receptor (R, such as an antibody or a fragment thereof) and ligand (L, such as the target of the antibody or a fragment thereof) molecules, which is formalized as: R+L⇌RL. The reaction is characterized by the on-rate constant k$_{on}$ and the off-rate constant k$_{off}$ which have units of $M^{-1} s^{-1}$ and $s^{-1}$, respectively. In equilibrium, the forward binding transition R+L→RL should be balanced by the backward unbinding transition RL→R+L. That is k$_{on}$ [R] [L]=k$_{off}$[RL] where [R], [L] and [RL] represent the concentration of unbound free receptors, the concentration of unbound free ligand and the concentration of receptor-ligand complexes. Further, the equilibrium dissociation constant "K$_D$" can be calculated as k$_{off}$/k$_{on}$ which is [R]×[L]/[RL], while the equilibrium association constant "K$_A$" can be calculated as k$_{on}$/k$_{off}$ which is [RL]/([R]×[L]).

As used herein, the term "cytokine" refers to small proteins (about 5-20 kDa) important in cell signaling, including but not limited to chemokines, interferons, interleukins (ILs), lymphokines, and tumour necrosis factors, but generally not hormones. Cytokines are peptides and cannot cross the lipid bilayer of cells to enter the cytoplasm. An inflammatory cytokine or pro-inflammatory cytokine is a type of signaling molecule (a cytokine) that is secreted from immune cells like helper T cells (Th) and macrophages, and certain other cell types that promote inflammation. They include (but are not limited to) interleukin-1 (IL-1), IL-12, and IL-18, tumor necrosis factor alpha (TNF-α), interferon gamma (IFNγ), and granulocyte-macrophage colony stimulating factor (GM-CSF) and play an important role in mediating the innate immune response. Inflammatory cytokines are predominantly produced by and involved in the upregulation of inflammatory reactions. The term "anti-inflammatory cytokines" includes immunoregulatory molecules that control the proinflammatory cytokine response. Cytokines act together with specific cytokine inhibitors and soluble cytokine receptors to regulate the human immune response. Major anti-inflammatory cytokines include interleukin (IL)-1 receptor antagonist, IL-4, IL-6, IL-10, IL-11, and IL-13. Specific cytokine receptors for IL-1, tumor necrosis factor-alpha, and IL-18 also function as proinflammatory cytokine inhibitors. Methods of measuring cytokine, including anti-inflammatory cytokine and pro-inflammatory cytokine, levels thereof are well known in the art. For example, serum cytokine levels can be measured using commercially available enzyme-linked immuno-sorbent assay (ELISA) kits.

As used herein, the term "anti-infective" refers to a medicine that is capable of inhibiting the spread of an infectious organism or by killing the infectious organism outright. This term encompasses, but is not limited to, antibiotics, antifungals, anthelmintics, antimalarials, anti-protozoals, antituberculosis agents, and antivirals. Antifungal agents are also called antimycotic agents. They kill or inactivate fungi and are used to treat fungal infections (including yeast infections). One non-limiting example, polyene antifungals are not absorbed when given orally, so are used to treat fungal infections of the gastrointestinal tract, such as oral thrush. Another non-limiting examples are azole antifungals which are synthetic, fungistatic agents with broad-spectrum activity, Echinocandins which are lipopeptide molecules that noncompetitively inhibit (1,3) beta-d-glucan synthase enzyme and target the fungal cell wall, Fulvicin U/F (i.e., griseofulvin), Grifulvin V (Pro) (i.e., griseofulvin), Lamisil (Pro) (i.e., terbinafine), Gris-PEG (Pro) (i.e., griseofulvin), Ancobon (Pro) (i.e., flucytosine), Fulvicin P/G (i.e., griseofulvin) and Terbinex (Pro) (i.e., terbinafine). More anti-infective agents can be found, for example, at www.drugbank.ca/categories/DBCAT000065. The term "anti-viral" or "antiviral" refers to a class of medication used for treating viral infections. Most antivirals target specific viruses, while a broad-spectrum antiviral is effective against a wide range of viruses. Unlike most antibiotics, antiviral drugs do not destroy their target pathogen; instead they inhibit their development. Some of the ways they may act include preventing viral replication by inhibiting viral DNA polymerase; binding to specific cell-surface receptors and inhibiting viral penetration or uncoating; inhibiting viral protein synthesis; or blocking late stages of virus assembly. Non-limiting examples of anti-viral agents can be found, for example, at www.drugbank.ca/categories/DBCAT000066.

As used herein, the term "anti-parasitic" refers to a class of medications which are indicated for the treatment of parasitic diseases, such as those caused by helminths, amoeba, ectoparasites, parasitic fungi, and protozoa, among others. Non-limiting examples of anti-parastics can be found, for example, at www.drugbank.ca/categories/DB-CAT000522.

Modes for Carrying Out the Disclosure

Antibody Compositions

The present disclosure provides an isolated antibody comprising a heavy chain (HC) variable domain sequence and a light chain (LC) variable domain sequence, wherein the heavy chain and light chain immunoglobulin variable domain sequences form an antigen binding site that binds to an epitope of a DNABII protein. In certain embodiments, the antibody or fragment thereof binds to a DNABII peptide (such as the tip region of the DNABII peptide including but not limited to: a tip region of IHF or HU, a tip region of IHFA or IHFB, and/or the tip-chimeric peptide IhfA5-mIhfB4$_{NTHI}$; and/or the tail region of the DNABII peptide, including but not limited to: a tail region of IHF or HU, a tail region of IHFA or IHFB, and/or the tail-chimeric peptide IhfA3-IhfB2$_{NTHI}$). In one embodiment, the antibody or fragment thereof binds to the tip-chimeric peptide IhfA5-mIhfB4$_{NTHI}$. In another embodiment, the antibody or fragment thereof binds to the tail-chimeric peptide IhfA3-IhfB2$_{NTHI}$.

In one aspect, provided herein are antibodies and antigen binding fragments thereof that comprise, or consist essentially of or yet consist of, a heavy chain (HC) immunoglobulin variable domain sequence comprising, consisting essentially of, or consisting of, a sequence selected from the group of amino acid (aa) 25 to aa 144 of SEQ ID NOs: 1-6, 13, 24 or 26 or an equivalent of each thereof; and/or a light chain (LC) immunoglobulin variable domain sequence comprising, consisting essentially of, or consisting of, a sequence selected from the group of aa 21 to aa 132 of SEQ ID NOs: 7-9, 14 or 25, aa 21 to aa 126 of SEQ ID NOs: 10-12 or 27, or an equivalent of each thereof.

In a further aspect, provided are antibodies and antigen binding fragments thereof that comprise, or consist essentially of or yet consist of, a heavy chain (HC) comprising, consisting essentially of, or consisting of, a sequence selected from the group of aa 25 to aa 473 of SEQ ID NOs: 1-6, 13, 24 or 26 or an equivalent of each thereof; and/or a light chain (LC) comprising, consisting essentially of, or consisting of, a sequence selected from the group of aa 21 to aa 239 of SEQ ID NOs: 7-9, 14, or 25, aa 21 to aa 233 of SEQ ID NOs: 10-12 or 27, or an equivalent of each thereof.

In yet a further aspect, provided are antibodies and antigen binding fragments thereof that comprise, or consist essentially of or yet consist of, a heavy chain (HC) comprising, consisting essentially of, or consisting of, a sequence selected from the group of SEQ ID NOs: 1-6, 13, 24 or 26 or an equivalent of each thereof; and/or a light chain (LC) comprising, consisting essentially of, or consisting of, a sequence selected from the group of SEQ ID NOs: 7-12, 14, 25, or 27, or an equivalent of each thereof.

In another aspect, provided herein are antibodies and antigen binding fragments thereof that comprise, or consist essentially of or yet consist of, a heavy chain (HC) immunoglobulin variable domain sequence comprising, consisting essentially of, or consisting of, a sequence selected from the group of amino acid (aa) 25 to 144 of SEQ ID NO: 1-6, 13, 24 or 26, or an equivalent thereof; and/or a light chain (LC) immunoglobulin variable domain sequence comprising, consisting essentially of, or consisting of, a sequence selected from the group of aa 21 to aa 132 of SEQ ID NO: 6-9, 14 or 25, aa 21 to aa 126 of SEQ ID NOs: 10-12, or 27, or an equivalent of each thereof.

In yet another aspect, provided is an antibody or a fragment thereof that comprises or consists essentially of, or yet further consists of: any one or any two or all three CDRs of a sequence selected from the group of: SEQ ID NOs: 1-6, 13, 24 or 26, or an equivalent of each thereof; and/or any one or any two or all three CDRs of a sequence selected from the group of: SEQ ID NOs: 7-12, 14, 25 or 27, or an equivalent of each thereof.

In another aspect, provided herein are antibodies and antigen binding fragments thereof that comprise, or consist essentially of or yet consist of, a heavy chain (HC) immunoglobulin variable domain sequence comprising, consisting essentially of, or consisting of a sequence selected from the group of aa 25 to aa 144 of SEQ ID NO: 13, 24 or 26, or an equivalent thereof; and a light chain (LC) immunoglobulin variable domain sequence comprising, consisting essentially of, or consisting of, a sequence selected from the group of aa 21 to aa 132 of SEQ ID NOs: 14 or 25, aa 21 to aa 126 of SEQ ID NO: 27, or an equivalent thereof. In a further aspect, provided herein are antibodies and antigen binding fragments thereof that comprise, or consist essentially of or yet consist of, a heavy chain (HC) immunoglobulin variable domain sequence comprising, consisting essentially of, or consisting of a sequence selected from the group of aa 25 to aa 144 of SEQ ID NOs: 1-6, 13, 24 or 26, or an equivalent of each thereof; and/or a light chain (LC) immunoglobulin variable domain sequence comprising, consisting essentially of, or consisting of a sequence selected from the group of aa 21 to aa 132 of SEQ ID NOs: 7-9, 14 or 25, aa 21 to aa 126 of SEQ ID NOs: 10-12 or 27, or an equivalent of each thereof.

Also provided are antibodies and antigen binding fragments thereof that comprise, or consist essentially of, or yet consist of a heavy chain (HC) immunoglobulin variable domain sequence that comprises, consisting essentially of, or consisting of, an amino acid sequence of aa 25 to aa 144 of SEQ ID NO: 1 or an equivalent thereof and a light chain (LC) immunoglobulin variable domain sequence that comprises, consisting essentially of, or consisting of, an amino acid sequence of any one of aa 21 to aa 132 of SEQ ID NOs: 7-9, 14 or 25, aa 21 to aa 126 of SEQ ID NOs: 10-12 or 27,or an equivalent of each thereof. In another aspect, provided herein are antibodies or fragments thereof comprising, or alternatively consisting essentially, or consisting of, a heavy chain (HC) immunoglobulin variable domain sequence that comprises, consisting essentially of, or consisting of, an amino acid sequence of aa 25 to aa 144 of SEQ ID NO: 2 or an equivalent thereof and a light chain (LC) immunoglobulin variable domain sequence that comprises, consists essentially of, or alternatively consists of, an amino acid sequence of any one of aa 21 to aa 132 of SEQ ID NOs: 7-9, 14 or 25, aa 21 to aa 126 of SEQ ID NOs: 10-12 or 27, or an equivalent of each thereof. In a further aspect, provided herein are antibodies and antigen binding fragments thereof that comprise, or consist essentially of, or yet consist of, a heavy chain (HC) immunoglobulin variable domain sequence comprises, consisting essentially of, or consisting of, an amino acid sequence of aa 25 to aa 144 of SEQ ID NO: 3 or an equivalent thereof and a light chain (LC) immunoglobulin variable domain sequence comprises, consisting essentially of, or consisting of, an amino acid sequence of any one of aa 21 to aa 132 of SEQ ID NOs: 7-9, 14 or 25, aa 21 to aa 126 of SEQ ID NOs: 10-12 or 27, or an equivalent of each thereof.

In a yet further aspect, provided herein are antibodies and antigen binding fragments thereof that comprise, or consist essentially of, or yet consist of, a heavy chain (HC) immunoglobulin variable domain sequence that comprises, consisting essentially of, or consisting of, an amino acid sequence of aa 25 to aa 144 of SEQ ID NO: 4 or an equivalent thereof and a light chain (LC) immunoglobulin variable domain sequence that comprises, consisting essentially of, or consisting of, an amino acid sequence of any one of aa 21 to aa 132 of SEQ ID NOs: 7-9, 14 or 25, aa 21 to aa 126 of SEQ ID NOs: 10-12 or 27, or an equivalent of each thereof. Also provided are antibodies and antigen binding fragments thereof comprising, or alternatively consisting essentially of, or yet consisting of, a heavy chain (HC) immunoglobulin variable domain sequence that comprises, consisting essentially of, or consisting of, an amino acid sequence of aa 25 to aa 144 of SEQ ID NO: 5 or an equivalent thereof and a light chain (LC) immunoglobulin variable domain sequence that comprises, consisting essentially of, or consisting of, an amino acid sequence of any one of aa 21 to aa 132 of SEQ ID NOs: 7-9, 14 or 25, aa 21 to aa 126 of SEQ ID NOs: 10-12 or 27, or an equivalent of each thereof. Yet further provided are antibodies and antigen binding fragments thereof comprising, or alternatively consisting essentially or consisting of, a heavy chain (HC) immunoglobulin variable domain sequence that comprises, consisting essentially of, or consisting of, an amino acid sequence of aa 25 to aa 144 of SEQ ID NO: 6 or an equivalent thereof, and a light chain (LC) immunoglobulin variable domain sequence that comprises, consisting essentially of, or consisting of, an amino acid sequence of any one of aa 21 to aa 132 of SEQ ID NOs: 7-9, 14 or 25, aa 21 to aa 126 of SEQ ID NOs: 10-12 or 27, or an equivalent of each thereof.

In another aspect, provided herein are antibodies or antigen binding fragments thereof, that comprise, or consisting essentially of, or consisting of, a heavy chain (HC) immunoglobulin variable domain sequence that comprises, consisting essentially of, or consisting of an amino acid sequence of aa 25 to aa 144 of any one of SEQ ID NOs: 1-6, 13, 24 or 26, or an equivalent of each thereof, and a light chain (LC) immunoglobulin variable domain sequence comprises, consisting essentially of, or consisting of, an amino acid sequence of aa 21 to aa 132 of SEQ ID NO 7, or an equivalent thereof. Yet further provided are antibodies or antigen binding fragments thereof comprising, or consisting essentially of, or yet further consisting of, a heavy chain (HC) immunoglobulin variable domain sequence that comprises, consisting essentially of, or consisting of, an amino acid sequence of aa 25 to aa 144 of any one of SEQ ID NOs: 1-6, 13, 24 or 26 or an equivalent of each thereof, and a light chain (LC) immunoglobulin variable domain sequence that comprises, consisting essentially of, or consisting of, an amino acid sequence of aa 21 to aa 132 of SEQ ID NO: 8, or an equivalent thereof. In another aspect, also provided are antibodies or antigen binding fragments thereof that comprise, or consist essentially of, or yet further consist of, a heavy chain (HC) immunoglobulin variable domain sequence that comprises, consisting essentially of, or consisting of, an amino acid sequence of aa 25 to aa 144 of any one of SEQ ID NOs: 1-6, 13, 24 or 26, or an equivalent of each thereof, and a light chain (LC) immunoglobulin variable domain sequence that comprises, consisting essentially of, or consisting of, an amino acid sequence of aa 21 to aa 132 of SEQ ID NO: 9, or an equivalent thereof.

In a further aspect, also provided are antibodies or antigen binding fragments thereof, that comprise, or consist essentially of, or yet further consist of, a heavy chain (HC) immunoglobulin variable domain sequence that comprises, or alternatively consists essentially of, or yet further consists of, an amino acid sequence of aa 25 to aa 144 of any one of SEQ ID NOs: 1-6, 13, 24 or 26, or an equivalent of each thereof, and a light chain (LC) immunoglobulin variable domain sequence that comprises, or consists essentially of, or yet further consists of, an amino acid sequence of aa 21 to aa 126 of SEQ ID NO: 10, or an equivalent thereof. Also provided are antibodies and antigen binding fragments thereof that comprise, or consist essentially of, or yet further consist of, a heavy chain (HC) immunoglobulin variable domain sequence that comprises, or consist essentially of, or yet further consists of, an amino acid sequence of aa 25 to aa 144 of any one off SEQ ID NOs: 1-6, 13, 24 or 26, or an equivalent of each thereof, and a light chain (LC) immunoglobulin variable domain that comprises, or consists essentially thereof, or consists of, an amino acid sequence of aa 21 to aa 126 of SEQ ID NO: 11, or an equivalent thereof. Also provided are antibodies and antigen binding fragments thereof, comprising, or consisting essentially of, or yet further consisting of, a heavy chain (HC) immunoglobulin variable domain sequence that comprises, or consists essentially thereof, or consisting of, an amino acid sequence of aa 25 to aa 144 of any one of SEQ ID NOs: 1-6, 13, 24 or 26, or an equivalent of each thereof, and the light chain (LC) immunoglobulin variable domain sequence comprises an amino acid sequence of aa 21 to aa 126 of SEQ ID NO: 12, or an equivalent thereof.

In one aspect, provided herein are antibodies and antigen binding fragments thereof are provided, that comprise or alternatively consist essentially of, or yet further consist of, a heavy chain (HC) immunoglobulin variable domain sequence that comprises, or alternatively consists essentially of, or yet further consists of, an amino acid sequence of aa 25 to aa 144 of SEQ ID NO: 1 or an equivalent thereof and a light chain (LC) immunoglobulin variable domain sequence that comprises, or alternatively consists essentially thereof, or consists of, an amino acid sequence of aa 21 to aa 132 of SEQ ID NO: 7, or an equivalent thereof. In one embodiment, antibodies and antigen binding fragments thereof are provided, that comprise or alternatively consist essentially of, or yet further consist of, a heavy chain (HC) immunoglobulin variable domain sequence that comprises, or alternatively consists essentially of, or yet further consists of, an amino acid sequence of aa 25 to aa 144 of SEQ ID NO: 1 or an equivalent thereof and a light chain (LC) immunoglobulin variable domain sequence that comprises, or alternatively consists essentially thereof, or consists of, an amino acid sequence of aa 21 to aa 132 of SEQ ID NO: 8, or an equivalent thereof. In an another embodiment, provided herein are antibodies and antigen binding fragments thereof that comprise, or alternatively consist essentially thereof, or consist of, a heavy chain (HC) immunoglobulin variable domain sequence that comprises, or consists essentially thereof, or consists of, an amino acid sequence of aa 25 to aa 144 of SEQ ID NO: 1 or an equivalent thereof and a light chain (LC) immunoglobulin variable domain sequence that comprises, or consists essentially thereof, or consists of, an amino acid sequence of aa 21 to aa 132 of SEQ ID NO: 9, or an equivalent thereof.

In an another aspect, provided herein are antibodies and antigen binding fragments thereof that comprise, or alternatively consist essentially thereof, or consist of a heavy chain (HC) immunoglobulin variable domain sequence that comprises, or alternatively consists essentially thereof, or consists of, an amino acid sequence of aa 25 to aa 144 of SEQ ID NO: 2 or an equivalent thereof and a light chain (LC) immunoglobulin variable domain sequence that comprises, or consists essentially thereof, of consists of, an amino acid sequence of aa 21 to aa 132 of SEQ ID NO: 7, or an equivalent thereof. In an another aspect, provided herein are antibodies and antigen binding fragments thereof that comprise, or alternatively consist essentially thereof, or consist of a heavy chain (HC) immunoglobulin variable domain sequence comprises an amino acid sequence of aa 25 to aa 144 of SEQ ID NO: 2 or an equivalent thereof, and a light chain (LC) immunoglobulin variable domain sequence that comprises, or consists essentially thereof, or yet further consists of, an amino acid sequence of aa 21 to aa 132 of SEQ ID NO: 8, or an equivalent thereof. In a further another aspect, provided herein are antibodies and antigen binding fragments thereof that comprise, or alternatively consist essentially thereof, or consist of a heavy chain (HC) immunoglobulin variable domain sequence that comprises, or consisting essentially thereof, or consisting of, an amino acid sequence of aa 25 to aa 144 of SEQ ID NO: 2 or an equivalent thereof, and a light chain (LC) immunoglobulin variable domain sequence that comprises, consisting essentially thereof, or consists of, an amino acid sequence of aa 21 to aa 132 of SEQ ID NO: 9, or an equivalent thereof.

In an another aspect, provided herein are antibodies and antigen binding fragments thereof that comprise, or alternatively consist essentially thereof, or consist of a heavy chain (HC) immunoglobulin variable domain sequence that comprises, or consists essentially thereof, or consists of, an amino acid sequence of aa 25 to aa 144 of SEQ ID NO: 3 or an equivalent thereof and a light chain (LC) immunoglobulin variable domain sequence comprises, or consists of an amino acid sequence of aa 21 to aa 132 of SEQ ID NO: 7, or an equivalent thereof. In a further aspect, provided herein are antibodies and antigen binding fragments thereof that comprise, or alternatively consist essentially thereof, or consist of a heavy chain (HC) immunoglobulin variable domain sequence that comprises, or consists essentially of, or yet further consists of, an amino acid sequence of aa 25 to aa 144 of SEQ ID NO: 3 or an equivalent thereof, and the light chain (LC) immunoglobulin variable domain sequence comprises, or consists essentially thereof, or consists of, an amino acid sequence of aa 21 to aa 132 of SEQ ID NO: 8, or an equivalent thereof. In one embodiment, provided herein are antibodies and antigen binding fragments thereof that comprise, or alternatively consist essentially thereof, or consist of a heavy chain (HC) immunoglobulin variable domain sequence that comprises, or consists essentially thereof, or consists of, an amino acid sequence of aa 25 to aa 144 of SEQ ID NO: 3 or an equivalent thereof and the light chain (LC) immunoglobulin variable domain sequence comprises an amino acid sequence of aa 21 to aa 132 of SEQ ID NO: 9, or an equivalent thereof.

Also provided are antibodies and antigen binding fragments thereof that comprise, or alternatively consist essentially thereof, or consist of a heavy chain (HC) immunoglobulin variable domain sequence that comprises, or consists essentially thereof, or consists of, an amino acid sequence of aa 25 to aa 144 of SEQ ID NO: 4 or an equivalent thereof and a light chain (LC) immunoglobulin variable domain sequence comprises, or consists essentially thereof, or consists of, an amino acid sequence of aa 21 to aa 126 of SEQ ID NO: 10, or an equivalent thereof. In an another aspect, provided herein are antibodies and antigen binding fragments thereof that comprise, or alternatively consist essentially thereof, or consist of a heavy chain (HC) immunoglobulin variable domain sequence that comprises, or consists essentially thereof, or consists of, an amino acid sequence of aa 25 to aa 144 of SEQ ID NO: 4 or an equivalent thereof, and a light chain (LC) immunoglobulin variable domain sequence that comprises, or consists essentially thereof, or consists of, an amino acid sequence of aa 21 to aa 126 of SEQ ID NO: 11, or an equivalent thereof. In a further aspect, provided herein are antibodies and antigen binding fragments thereof that comprise, or alternatively consist essentially thereof, or consist of a heavy chain (HC) immunoglobulin variable domain sequence that comprises, or consists essentially thereof, or consists of, an amino acid sequence of aa 25 to aa 144 of SEQ ID NO: 4 or an equivalent thereof, and a light chain (LC) immunoglobulin variable domain sequence that comprises, or consists essentially thereof, or consists thereof, an amino acid sequence of aa 21 to aa 126 of SEQ ID NO: 12, or an equivalent thereof.

In one embodiment, provided herein are antibodies and antigen binding fragments thereof that comprise, or alternatively consist essentially thereof, or consist of a heavy chain (HC) immunoglobulin variable domain sequence that comprises, or consists essentially thereof, or consists of, an amino acid sequence of aa 25 to aa 144 of SEQ ID NO: 5 or an equivalent thereof, and a light chain (LC) immunoglobulin variable domain sequence that comprises, or consists essentially thereof, or consists of, an amino acid sequence of aa 21 to aa 126 of SEQ ID NO: 10, or an equivalent thereof. In an another embodiment, provided herein are antibodies and antigen binding fragments thereof that comprise, or alternatively consist essentially thereof, or consist of a heavy chain (HC) immunoglobulin variable domain sequence that comprises, or consists essentially thereof, or consists of, an amino acid sequence of aa 25 to aa 144 of SEQ ID NO: 5 or an equivalent thereof, and a light chain (LC) immunoglobulin variable domain sequence that comprises, or consists essentially thereof, or consists of, an amino acid sequence of aa 21 to aa 126 of SEQ ID NO: 11, or an equivalent thereof. In a further aspect, provided herein are antibodies and antigen binding fragments thereof that comprise, or alternatively consist essentially thereof, or consist of a heavy chain (HC) immunoglobulin variable domain sequence that comprises, or consists essentially thereof, or consists of, an amino acid sequence of aa 25 to aa 144 of SEQ ID NO: 5 or an equivalent thereof, and a light chain (LC) immunoglobulin variable domain sequence that comprises, or consists essentially thereof, an amino acid sequence of aa 21 to aa 126 of SEQ ID NO: 12, or an equivalent thereof.

In another embodiment, provided herein are antibodies and antigen binding fragments thereof that comprise, or alternatively consist essentially thereof, or consist of a heavy chain (HC) immunoglobulin variable domain sequence that comprises, or consists essentially thereof, or consists of, an amino acid sequence of aa 25 to aa 144 of SEQ ID NO: 6 or an equivalent thereof, and a light chain (LC) immunoglobulin variable domain sequence that comprises, or consists essentially thereof, or consists of, an amino acid sequence of aa 21 to aa 126 of SEQ ID NO: 10, or an equivalent thereof. In one aspect, provided herein are antibodies and antigen binding fragments thereof that comprise, or alternatively consist essentially thereof, or consist of a heavy chain (HC) immunoglobulin variable domain sequence that comprises, or consisting essentially thereof, or consists thereof, an amino acid sequence of aa 25 to aa 144 of SEQ ID NO: 6 or an equivalent thereof, and a light chain (LC) immunoglobulin variable domain sequence that comprises, or consists essentially thereof, or consists of, an amino acid sequence of aa 21 to aa 126 of SEQ ID NO: 11, or an equivalent thereof. In one embodiment, provided herein are antibodies and antigen binding fragments thereof that comprise, or alternatively consist essentially thereof, or consist of a heavy chain (HC) immunoglobulin variable domain sequence that comprises, consisting essentially thereof, or consisting of, an amino acid sequence of aa 25 to aa 144 of SEQ ID NO: 6 or an equivalent thereof, and a light chain (LC) immunoglobulin variable domain sequence that comprises, consists essentially thereof, or consists of, an amino acid sequence of aa 21 to aa 126 of SEQ ID NO: 12, or an equivalent thereof.

In one aspect, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 24 or an equivalent thereof, and/or a light chain (LC) immunoglobulin variable domain sequence comprising, or consisting essentially of, or yet further consisting of an amino acid sequence of aa 21 to aa 132 of SEQ ID NO: 25 or an equivalent thereof. In a further embodiment, the antibody or fragment thereof binds to a tip region of a DNABII peptide (including but not limited to: a tip region of IHF or HU, a tip region of IHFA or IHFB, and/or the tip-chimeric peptide IhfA5-mIhfB4$_{NTHI}$). In one embodiment, the antibody or fragment thereof binds to the tip-chimeric peptide IhfA5-mIhfB4$_{NTHI}$. In yet a further embodiment, the fragment is an antigen binding fragment. In one embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 1 or an equivalent thereof, and/or a light chain (LC) immunoglobulin variable domain sequence comprising, or consisting essentially of, or yet further consisting of an amino acid sequence of aa 21 to aa 132 of SEQ ID NO: 7 or an equivalent thereof. In another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 1 or an equivalent thereof, and/or a light chain (LC) immunoglobulin variable domain sequence comprising, or consisting essentially of, or yet further consisting of an amino acid sequence of aa 21 to aa 132 of SEQ ID NO: 8 or an equivalent thereof. In yet another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 1 or an equivalent thereof, and/or a light chain (LC) immunoglobulin variable domain sequence comprising, or consisting essentially of, or yet further consisting of an amino acid sequence of aa 21 to aa 132 of SEQ ID NO: 9 or an equivalent thereof. In one embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 2 or an equivalent thereof, and/or a light chain (LC) immunoglobulin variable domain sequence comprising, or consisting essentially of, or yet further consisting of an amino acid sequence of aa 21 to aa 132 of SEQ ID of NO: 7 or an equivalent thereof. In another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 2 or an equivalent thereof, and/or a light chain (LC) immunoglobulin variable domain sequence comprising, or consisting essentially of, or yet further consisting of an amino acid sequence of aa 21 to aa 132 of SEQ ID NO: 8 or an equivalent thereof. In yet another embodiment, the antibody or fragment thereof comprises or consists essentially of, or yet further consists of: a the heavy chain (HC) immunoglobulin variable domain sequence comprising, or consisting essentially of, or yet further consisting of an amino acid sequence of aa 25 to aa 144 of SEQ ID NO: 2 or an equivalent thereof, and/or a light chain (LC) immunoglobulin variable domain sequence comprising, or consisting essentially of, or yet further consisting of an amino acid sequence of aa 21 to aa 132 of SEQ ID NO: 9 or an equivalent thereof. In one embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 3 or an equivalent thereof, and/or a light chain (LC) immunoglobulin variable domain sequence comprising, or consisting essentially of, or yet further consisting of an amino acid sequence of aa 21 to aa 132 of SEQ ID NO: 7 or an equivalent thereof. In another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 3 or an equivalent thereof, and/or a light chain (LC) immunoglobulin variable domain sequence comprising, or consisting essentially of, or yet further consisting of an amino acid sequence of aa 21 to aa 132 of SEQ ID NO: 8 or an equivalent thereof. In yet another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 3 or an equivalent thereof, and/or a light chain (LC) immunoglobulin variable domain sequence comprising, or consisting essentially of, or yet further consisting of an amino acid sequence of aa 21 to aa 132 of SEQ ID NO: 9 or an equivalent thereof.

In another aspect, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 26 or an equivalent thereof, and a light chain (LC) immunoglobulin variable domain sequence comprising, or consisting essentially of, or yet further consisting of an amino acid sequence of aa 21 to aa 126 of SEQ ID NO: 27 or an equivalent thereof. In a further embodiment, the antibody or fragment thereof binds to a tail region of a DNABII peptide (including but not limited to: a tail region of IHF or HU, a tail region of IHFA or IHFB, and/or the tail-chimeric peptide IhfA3-IhfB2$_{NTHI}$). In one embodiment, the antibody of fragment thereof binds to the tail-chimeric peptide IhfA3-IhfB2$_{NTHI}$. In yet a further embodiment, the fragment is an antigen binding fragment. In one embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 4 or an equivalent thereof, and/or a light chain (LC) immunoglobulin variable domain sequence comprising, or consisting essentially of, or yet further consisting of an amino acid sequence of aa 21 to aa 126 of SEQ ID NO: 10 or an equivalent thereof. In another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 4 or an equivalent thereof, and/or a light chain (LC) immunoglobulin variable domain sequence comprising, or consisting essentially of, or yet further consisting of an amino acid sequence of aa 21 to aa 126 of SEQ ID NO: 11 or an equivalent thereof. In yet another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 4 or an equivalent thereof, and/or a light chain (LC) immunoglobulin variable domain sequence comprising, or consisting essentially of, or yet further consisting of an amino acid sequence of aa 21 to aa 126 of SEQ ID NO: 12 or an equivalent thereof. In one embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 5 or an equivalent thereof, and/or a light chain (LC) immunoglobulin variable domain sequence comprising, or consisting essentially of, or yet further consisting of an amino acid sequence of aa 21 to aa 126 of SEQ ID NO: 10 or an equivalent thereof. In another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 5 or an equivalent thereof, and/or a light chain (LC) immunoglobulin variable domain sequence comprising, or consisting essentially of, or yet further consisting of an amino acid sequence of aa 21 to aa 126 of SEQ ID NO: 11 or an equivalent thereof. In yet another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 5 or an equivalent thereof, and/or a light chain (LC) immunoglobulin variable domain sequence comprising, or consisting essentially of, or yet further consisting of an amino acid sequence of aa 21 to aa 126 of SEQ ID NO: 12 or an equivalent thereof. In one embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 6 or an equivalent thereof, and/or a light chain (LC) immunoglobulin variable domain sequence comprising, or consisting essentially of, or yet further consisting of an amino acid sequence of aa 21 to aa 126 of SEQ ID NO: 10 or an equivalent thereof. In another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 6 or an equivalent thereof, and/or a light chain (LC) immunoglobulin variable domain sequence comprising, or consisting essentially of, or yet further consisting of an amino acid sequence of aa 21 to aa 126 of SEQ ID NO: 11 or an equivalent thereof. In yet another embodiment, the antibody or fragment thereof comprises or consists essentially of, or yet further consists of: a heavy chain (HC) immunoglobulin variable domain sequence comprising, or consisting essentially of, or yet further consisting of an amino acid sequence of aa 25 to aa 144 of SEQ ID NO: 6 or an equivalent thereof, and/or a light chain (LC) immunoglobulin variable domain sequence comprising, or consisting essentially of, or yet further consisting of an amino acid sequence of aa 21 to aa 126 of SEQ ID NO: 12 or an equivalent thereof.

In one aspect, provided is an antibody or a fragment thereof, that comprises or consists essentially of, or yet further consists of: a heavy chain (HC) comprising, or consisting essentially of, or yet further consisting of an amino acid sequence of SEQ ID NO: 24 or an equivalent thereof, and/or a light chain (LC) comprising, or consisting essentially of, or yet further consisting of an amino acid sequence of SEQ ID NO: 25 or an equivalent thereof. In a further embodiment, the antibody or fragment thereof binds to a tip region of a DNABII peptide (including but not limited to: a tip region of IHF or HU, a tip region of IHFA or IHFB, and/or the tip-chimeric peptide IhfA5-mIhfB4$_{NTHI}$). In one embodiment, the antibody or fragment thereof binds to the tip-chimeric peptide IhfA5-mIhfB4$_{NTHI}$. In yet a further embodiment, the fragment is an antigen binding fragment. In one embodiment, the antibody or fragment thereof comprises or consists essentially of, or yet further consists of: a heavy chain (HC) comprising, or consisting essentially of, or yet further consisting of an amino acid sequence of SEQ ID NO: 1 or an equivalent thereof, and/or a light chain (LC) comprising, or consisting essentially of, or yet further consisting of an amino acid sequence of SEQ ID NO: 7 or an equivalent thereof. In another embodiment, the antibody or fragment thereof comprises or consists essentially of, or yet further consists of: a heavy chain (HC) comprising, or consisting essentially of, or yet further consisting of an amino acid sequence of SEQ ID NO: 1 or an equivalent thereof, and/or a light chain (LC) comprising, or consisting essentially of, or yet further consisting of an amino acid sequence of SEQ ID NO: 8 or an equivalent thereof. In yet another embodiment, the antibody or fragment thereof comprises or consists essentially of, or yet further consists of: a heavy chain (HC) comprising, or consisting essentially of, or yet further consisting of an amino acid sequence of SEQ ID NO: 1 or an equivalent thereof, and/or a light chain (LC) comprising, or consisting essentially of, or yet further consisting of an amino acid sequence of SEQ ID NO: 9 or an equivalent thereof. In one embodiment, the antibody or fragment thereof comprises or consists essentially of, or yet further consists of: a heavy chain (HC) comprising, or consisting essentially of, or yet further consisting of an amino acid sequence of SEQ ID NO: 2 or an equivalent thereof, and/or a light chain (LC) comprising, or consisting essentially of, or yet further consisting of an amino acid sequence of SEQ ID of NO: 7 or an equivalent thereof. In another embodiment, the antibody or fragment thereof comprises or consists essentially of, or yet further consists of: a heavy chain (HC) comprising, or consisting essentially of, or yet further consisting of an amino acid sequence of SEQ ID NO: 2 or an equivalent thereof, and/or a light chain (LC) comprising, or consisting essentially of, or yet further consisting of an amino acid sequence of SEQ ID NO: 8 or an equivalent thereof. In yet another embodiment, the antibody or fragment thereof comprises or consists essentially of, or yet further consists of: a the heavy chain (HC) comprising, or consisting essentially of, or yet further consisting of an amino acid sequence of SEQ ID NO: 2 or an equivalent thereof, and/or a light chain (LC) comprising, or consisting essentially of, or yet further consisting of an amino acid sequence of SEQ ID NO: 9 or an equivalent thereof. In one embodiment, the antibody or fragment thereof comprises or consists essentially of, or yet further consists of: a heavy chain (HC) comprising, or consisting essentially of, or yet further consisting of an amino acid sequence of SEQ ID NO: 3 or an equivalent thereof, and/or a light chain (LC) comprising, or consisting essentially of, or yet further consisting of an amino acid sequence of SEQ ID NO: 7 or an equivalent thereof. In another embodiment, the antibody or fragment thereof comprises or consists essentially of, or yet further consists of: a heavy chain (HC) comprising, or consisting essentially of, or yet further consisting of an amino acid sequence of SEQ ID NO: 3 or an equivalent thereof, and/or a light chain (LC) comprising, or consisting essentially of, or yet further consisting of an amino acid sequence of SEQ ID NO: 8 or an equivalent thereof. In yet another embodiment, the antibody or fragment thereof comprises or consists essentially of, or yet further consists of: a heavy chain (HC) comprising, or consisting essentially of, or yet further consisting of an amino acid sequence of SEQ ID NO: 3 or an equivalent thereof, and/or a light chain (LC) comprising, or consisting essentially of, or yet further consisting of an amino acid sequence of SEQ ID NO: 9 or an equivalent thereof.

In another aspect, provided is an antibody or a fragment thereof, that comprises or consists essentially of, or yet further consists of: a heavy chain (HC) comprising, or consisting essentially of, or yet further consisting of an amino acid sequence of SEQ ID NO: 26 or an equivalent thereof, and a light chain (LC) comprising, or consisting essentially of, or yet further consisting of an amino acid sequence of SEQ ID NO: 27 or an equivalent thereof. In a further embodiment, the antibody or fragment thereof binds to a tail region of a DNABII peptide (including but not limited to: a tail region of IHF or HU, a tail region of IHFA or IHFB, and/or the tail-chimeric peptide IhfA3-IhfB2$_{NTHI}$). In one embodiment, the antibody of fragment thereof binds to the tail-chimeric peptide IhfA3-IhfB2$_{NTHI}$. In yet a further embodiment, the fragment is an antigen binding fragment. In one embodiment, the antibody or fragment thereof comprises or consists essentially of, or yet further consists of: a heavy chain (HC) comprising, or consisting essentially of, or yet further consisting of an amino acid sequence of SEQ ID NO: 4 or an equivalent thereof, and/or a light chain (LC) comprising, or consisting essentially of, or yet further consisting of an amino acid sequence of SEQ ID NO: 10 or an equivalent thereof. In another embodiment, the antibody or fragment thereof comprises or consists essentially of, or yet further consists of: a heavy chain (HC) comprising, or consisting essentially of, or yet further consisting of an amino acid sequence of SEQ ID NO: 4 or an equivalent thereof, and/or a light chain (LC) comprising, or consisting essentially of, or yet further consisting of an amino acid sequence of SEQ ID NO: 11 or an equivalent thereof. In yet another embodiment, the antibody or fragment thereof comprises or consists essentially of, or yet further consists of: a heavy chain (HC) comprising, or consisting essentially of, or yet further consisting of an amino acid sequence of SEQ ID NO: 4 or an equivalent thereof, and/or a light chain (LC) comprising, or consisting essentially of, or yet further consisting of an amino acid sequence of SEQ ID NO: 12 or an equivalent thereof. In one embodiment, the antibody or fragment thereof comprises or consists essentially of, or yet further consists of: a heavy chain (HC) comprising, or consisting essentially of, or yet further consisting of an amino acid sequence of SEQ ID NO: 5 or an equivalent thereof, and/or a light chain (LC) comprising, or consisting essentially of, or yet further consisting of an amino acid sequence of SEQ ID NO: 10 or an equivalent thereof. In another embodiment, the antibody or fragment thereof comprises or consists essentially of, or yet further consists of: a heavy chain (HC) comprising, or consisting essentially of, or yet further consisting of an amino acid sequence of SEQ ID NO: 5 or an equivalent thereof, and/or a light chain (LC) comprising, or consisting essentially of, or yet further consisting of an amino acid sequence of SEQ ID NO: 11 or an equivalent thereof. In yet another embodiment, the antibody or fragment thereof comprises or consists essentially of, or yet further consists of: a heavy chain (HC) comprising, or consisting essentially of, or yet further consisting of an amino acid sequence of SEQ ID NO: 5 or an equivalent thereof, and/or a light chain (LC) comprising, or consisting essentially of, or yet further consisting of an amino acid sequence of SEQ ID NO: 12 or an equivalent thereof. In one embodiment, the antibody or fragment thereof comprises or consists essentially of, or yet further consists of: a heavy chain (HC) comprising, or consisting essentially of, or yet further consisting of an amino acid sequence of SEQ ID NO: 6 or an equivalent thereof, and/or a light chain (LC) comprising, or consisting essentially of, or yet further consisting of an amino acid sequence of SEQ ID NO: 10 or an equivalent thereof. In another embodiment, the antibody or fragment thereof comprises or consists essentially of, or yet further consists of: a heavy chain (HC) comprising, or consisting essentially of, or yet further consisting of an amino acid sequence of SEQ ID NO: 6 or an equivalent thereof, and/or a light chain (LC) comprising, or consisting essentially of, or yet further consisting of an amino acid sequence of SEQ ID NO: 11 or an equivalent thereof. In yet another embodiment, the antibody or fragment thereof comprises or consists essentially of, or yet further consists of: a heavy chain (HC) comprising, or consisting essentially of, or yet further consisting of an amino acid sequence of SEQ ID NO: 6 or an equivalent thereof, and/or a light chain (LC) comprising, or consisting essentially of, or yet further consisting of an amino acid sequence of SEQ ID NO: 12 or an equivalent thereof.

In one aspect, provided is an antibody or a fragment thereof, that comprises or consists essentially of, or yet further consists of: a heavy chain (HC) comprising, or consisting essentially of, or yet further consisting of an amino acid sequence of aa 25 to aa 473 of SEQ ID NO: 24 or an equivalent thereof, and/or a light chain (LC) comprising, or consisting essentially of, or yet further consisting of an amino acid sequence of aa 21 to aa 239 of SEQ ID NO: 25 or an equivalent thereof. In a further embodiment, the antibody or fragment thereof binds to a tip region of a DNABII peptide (including but not limited to: a tip region of IHF or HU, a tip region of IHFA or IHFB, and/or the tip-chimeric peptide IhfA5-mIhfB4$_{NTHI}$). In one embodiment, the antibody or fragment thereof binds to the tip-chimeric peptide IhfA5-mIhfB4$_{NTHI}$. In yet a further embodiment, the fragment is an antigen binding fragment. In one embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 1 or an equivalent thereof, and/or a light chain (LC) comprising, or consisting essentially of, or yet further consisting of an amino acid sequence of aa 21 to aa 239 of SEQ ID NO: 7 or an equivalent thereof. In another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 1 or an equivalent thereof, and/or a light chain (LC) comprising, or consisting essentially of, or yet further consisting of an amino acid sequence of aa 21 to aa 239 of SEQ ID NO: 8 or an equivalent thereof. In yet another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 1 or an equivalent thereof, and/or a light chain (LC) comprising, or consisting essentially of, or yet further consisting of an amino acid sequence of aa 21 to aa 239 of SEQ ID NO: 9 or an equivalent thereof. In one embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 2 or an equivalent thereof, and/or a light chain (LC) comprising, or consisting essentially of, or yet further consisting of an amino acid sequence of aa 21 to aa 239 of SEQ ID of NO: 7 or an equivalent thereof. In another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 2 or an equivalent thereof, and/or a light chain (LC) comprising, or consisting essentially of, or yet further consisting of an amino acid sequence of aa 21 to aa 239 of SEQ ID NO: 8 or an equivalent thereof. In yet another embodiment, the antibody or fragment thereof comprises or consists essentially of, or yet further consists of: a the heavy chain (HC) comprising, or consisting essentially of, or yet further consisting of an amino acid sequence of aa 25 to aa 473 of SEQ ID NO: 2 or an equivalent thereof, and/or a light chain (LC) comprising, or consisting essentially of, or yet further consisting of an amino acid sequence of aa 21 to aa 239 of SEQ ID NO: 9 or an equivalent thereof. In one embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 3 or an equivalent thereof, and/or a light chain (LC) comprising, or consisting essentially of, or yet further consisting of an amino acid sequence of aa 21 to aa 239 of SEQ ID NO: 7 or an equivalent thereof. In another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 3 or an equivalent thereof, and/or a light chain (LC) comprising, or consisting essentially of, or yet further consisting of an amino acid sequence of aa 21 to aa 239 of SEQ ID NO: 8 or an equivalent thereof. In yet another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 3 or an equivalent thereof, and/or a light chain (LC) comprising, or consisting essentially of, or yet further consisting of an amino acid sequence of aa 21 to aa 239 of SEQ ID NO: 9 or an equivalent thereof.

In another aspect, provided is an antibody or a fragment thereof, that comprises or consists essentially of, or yet further consists of: a heavy chain (HC) comprising, or consisting essentially of, or yet further consisting of an amino acid sequence of aa 25 to aa 473 of SEQ ID NO: 26 or an equivalent thereof, and a light chain (LC) comprising, or consisting essentially of, or yet further consisting of an amino acid sequence of aa 21 to aa 233 of SEQ ID NO: 27 or an equivalent thereof. In a further embodiment, the antibody or fragment thereof binds to a tail region of a DNABII peptide (including but not limited to: a tail region of IHF or HU, a tail region of IHFA or IHFB, and/or the tail-chimeric peptide IhfA3-IhfB2$_{NTHI}$). In one embodiment, the antibody of fragment thereof binds to the tail-chimeric peptide IhfA3-IhfB2$_{NTHI}$. In yet a further embodiment, the fragment is an antigen binding fragment. In one embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 4 or an equivalent thereof, and/or a light chain (LC) comprising, or consisting essentially of, or yet further consisting of an amino acid sequence of aa 21 to aa 233 of SEQ ID NO: 10 or an equivalent thereof. In another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 4 or an equivalent thereof, and/or a light chain (LC) comprising, or consisting essentially of, or yet further consisting of an amino acid sequence of aa 21 to aa 233 of SEQ ID NO: 11 or an equivalent thereof. In yet another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 4 or an equivalent thereof, and/or a light chain (LC) comprising, or consisting essentially of, or yet further consisting of an amino acid sequence of aa 21 to aa 233 of SEQ ID NO: 12 or an equivalent thereof. In one embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 5 or an equivalent thereof, and/or a light chain (LC) comprising, or consisting essentially of, or yet further consisting of an amino acid sequence of aa 21 to aa 233 of SEQ ID NO: 10 or an equivalent thereof. In another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 5 or an equivalent thereof, and/or a light chain (LC) comprising, or consisting essentially of, or yet further consisting of an amino acid sequence of aa 21 to aa 233 of SEQ ID NO: 11 or an equivalent thereof. In yet another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 5 or an equivalent thereof, and/or a light chain (LC) comprising, or consisting essentially of, or yet further consisting of an amino acid sequence of aa 21 to aa 233 of SEQ ID NO: 12 or an equivalent thereof. In one embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 6 or an equivalent thereof, and/or a light chain (LC) comprising, or consisting essentially of, or yet further consisting of an amino acid sequence of aa 21 to aa 233 of SEQ ID NO: 10 or an equivalent thereof. In another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 6 or an equivalent thereof, and/or a light chain (LC) comprising, or consisting essentially of, or yet further consisting of an amino acid sequence of aa 21 to aa 233 of SEQ ID NO: 11 or an equivalent thereof. In yet another embodiment, the antibody or fragment thereof comprises or consists essentially of, or yet further consists of: a heavy chain (HC) comprising, or consisting essentially of, or yet further consisting of an amino acid sequence of aa 25 to aa 473 of SEQ ID NO: 6 or an equivalent thereof, and/or a light chain (LC) comprising, or consisting essentially of, or yet further consisting of an amino acid sequence of aa 21 to aa 233 of SEQ ID NO: 12 or an equivalent thereof.

In one aspect, provided is an antibody or a fragment thereof that comprises or consists essentially of, or yet further consists of: any one or any two or all three CDRs of a sequence selected from the group of: SEQ ID NOs: 1-3 or 24, or an equivalent of each thereof; and/or any one or any two or all three CDRs of a sequence selected from the group of: SEQ ID NOs: 7-9 or 25, or an equivalent of each thereof. In a further embodiment, the antibody or fragment thereof binds to a tip region of a DNABII peptide (including but not limited to: a tip region of IHF or HU, a tip region of IHFA or IHFB, and/or the tip-chimeric peptide IhfA5-mIhfB4$_{NTHI}$). In one embodiment, the antibody or fragment thereof binds to the tip-chimeric peptide IhfA5-mIhfB4$_{NTHI}$. In yet a further embodiment, the fragment is an antigen binding fragment. In one embodiment, provided is an antibody or a fragment thereof that comprises or consists essentially of, or yet further consists of: all three CDRs of a sequence selected from the group of: SEQ ID NOs: 1-3 or 24, or an equivalent of each thereof; and/or all three CDRs of a sequence selected from the group of: SEQ ID NOs: 7-9 or 25, or an equivalent of each thereof.

In another embodiment, provided is an antibody or a fragment thereof that comprises or consists essentially of, or yet further consists of: any one or any two or all three CDRs of a sequence selected from the group of: SEQ ID NOs: 4-6 or 26, or an equivalent of each thereof; and/or any one or any two or all three CDRs of a sequence selected from the group of: SEQ ID NOs: 10-12 or 27, or an equivalent of each thereof. In a further embodiment, the antibody or fragment thereof binds to a tail region of a DNABII peptide (including but not limited to: a tail region of IHF or HU, a tail region of IHFA or IHFB, and/or the tail-chimeric peptide IhfA3-IhfB2$_{NTHI}$). In one embodiment, the antibody of fragment thereof binds to the tail-chimeric peptide IhfA3-IhfB2$_{NTHI}$. In yet a further embodiment, the fragment is an antigen binding fragment. In one embodiment, provided is an antibody or a fragment thereof that comprises or consists essentially of, or yet further consists of: all three CDRs of a sequence selected from the group of: SEQ ID NOs: 4-6 or 26, or an equivalent of each thereof; and/or all three CDRs of a sequence selected from the group of: SEQ ID NOs: 10-12 or 27, or an equivalent of each thereof.

In certain embodiments, the antibody or fragment thereof as provided herein further comprises one or more signal peptide(s). In one embodiment, the signal peptide comprises or consists essentially of, or yet further consists of amino acid (aa) 1 to aa 24 of any one of SEQ ID NOs: 1-6, 13, 24 or 26. In another embodiment, the signal peptide comprises or consists essentially of, or yet further consists of aa 1 to aa 20 of any one of SEQ ID NOs: 7-12, 14, 25 and 27. In a further embodiment, the signal peptide is located at the amino terminus of the light chain variable region. Additionally or alternatively, the same signal peptide or a different signal peptide is located at the amino terminus of the heavy chain variable region.

The antibody or fragment thereof as provided herein may be monospecific or bispecific. In one embodiment, the antibody or fragment thereof is trispecific, or tetraspecific, or pentaspecific. Additionally or alternatively, the antibody is selected from the group of an IgA (such as an IgA1 or an IgA2), an IgD, an IgE, an IgG (such as an IgG1, an IgG2, an IgG3, or an IgG4), or an IgM antibody. In one embodiment, the antibody further comprises a constant region selected from the group of: an IgA constant region (such as an IgA1 constant region or an IgA2 constant region), an IgD constant region, an IgE constant region, an IgG constant region (such as an IgG1 constant region, an IgG2 constant region, an IgG3 constant region, or an IgG4 constant region) or an IgM constant region.

In certain embodiments, an equivalent to an amino acid sequence comprises or consists essentially of, or yet further consists of a polypeptide having at least about 80% (including about 80% to 100%, at least about 85%, at least about 90%, at least about 91%, at least about 92%, at least about 93%, at least about 94%, at least about 95%, at least about 96%, at least about 97%, at least about 98%, or at least about 99%) amino acid identity to the amino acid sequence. Additionally or alternatively, an equivalent to the amino acid sequence comprises or consists essentially of, or yet further consists of a polypeptide that is encoded by a polynucleotide that hybridizes under conditions of high stringency to the complement of the polynucleotide encoding the amino acid sequence. In a further embodiment, an equivalent to an amino acid sequence comprises or consists essentially of, or yet further consists of a polypeptide at least 80% (including about 80% to 100%, at least about 85%, at least about 90%, at least about 91%, at least about 92%, at least about 93%, at least about 94%, at least about 95%, at least about 96%, at least about 97%, at least about 98%, or at least about 99%) identity to the amino acid sequence. In certain embodiments, an equivalent to an amino acid sequence (such as an antibody or a fragment thereof, or any one or more of SEQ ID NOs: 1-14 and 24-26 or a fragment thereof as disclosed herein, including but not limited to: 25 to aa 144 of SEQ ID NOs: 13, 24 or 26, aa 21 to aa 132 of SEQ ID NOs: 14 or 25, aa 21 to aa 126 of SEQ ID NO: 27, aa 25 to aa 473 of SEQ ID NOs: 13, 24 or 26, aa 21 to aa 239 of SEQ ID NOs: 14 or 25, aa 21 to aa 233 of SEQ ID NO: 27) comprises, or consists essentially of, or yet further consists of a polypeptide comprises one or more or all CDRs of the amino acid sequence. Additionally or alternatively, the polypeptide is at least about 80% (including about 80% to 100%, at least about 85%, at least about 90%, at least about 91%, at least about 92%, at least about 93%, at least about 94%, at least about 95%, at least about 96%, at least about 97%, at least about 98%, or at least about 99%) amino acid identity to the amino acid sequence.

In certain embodiments, the equivalent to an amino acid sequence, such as an antibody, a fragment thereof, a complementarity-determining region (CDR) thereof, or a CDR-containing polypeptide, lacks an amino acid difference to the amino acid sequence in the CDR(s). However, the equivalent to an amino acid sequence, such as an antibody, a fragment thereof, a CDR thereof, or a CDR-containing polypeptide, may comprises one or more of (for example but not limited to 1, 2, 3, 4, 5, 6, 7, 8, 9, 10, 11, 12, 13, 14, 15, 16, 17, 18, 19, 20, 21, 22, 23, 24 or 25) amino acid differences compared to the amino acid sequence in the non-CDR region(s) with the proviso that the three-dimensional arrangement of the CDR(s) and/or the CDRs is/are retained. In certain embodiments, the equivalent polypeptide to an amino acid sequence, such as an antibody, a fragment thereof, a CDR thereof, or a CDR-containing polypeptide, is at least about 80% (including about 80% to 100%, at least about 85%, at least about 90%, at least about 91%, at least about 92%, at least about 93%, at least about 94%, at least about 95%, at least about 96%, at least about 97%, at least about 98%, or at least about 99%) amino acid identity to the amino acid sequence with the proviso that the three-dimensional arrangement of the CDR(s) and/or the CDR(s) is/are retained.

Non-limiting examples of such non-CDR regions includes a framework region (FR), a constant region, a Fc region, a pFc' region, a constant heavy chain (CH) domain (such as CH1, CH2, CH3 or CH4), a constant light chain (CL) domain, or a hinge region. In one embodiment, such amino acid differences may be a conservative amino acid substitution and/or does not change the three-dimensional arrangement of the antibody, fragment thereof, CDR thereof, or the CDR-containing polypeptide. In another embodiment, the equivalent may comprises a conservative amino acid substitution in the boundaries of a CDR, such as one or two amino acid(s) at the amino termini, the carboxyl termini or both of the CDR.

In one aspect, provided is one or more of CDRs (such as any 1, or 2, or 3, or 4, or 5, or 6 CDR(s)) of an antibody or fragment thereof as disclosed herein. In one embodiment, provided is a set of CDRs comprising or alternatively consisting essentially of, or yet further consisting of one or more of CDRs (such as any 1, or 2, or 3, or 4, or 5, or 6 CDR(s)) of an antibody or fragment thereof as disclosed herein. In one embodiment, provided is a set of CDRs comprising, or alternatively consisting essentially of, or yet further consisting of CDRL1, CDRL2, and CDRL3 of a variable region as disclosed herein. In a further embodiment, provided is a set of CDRs comprising, or alternatively consisting essentially of, or yet further consisting of CDRH1, CDRH2, and CDRH3 of a variable region as disclosed herein. In yet a further embodiment, provided is a set of CDRs comprising, or alternatively consisting essentially of, or yet further consisting of CDRL1, CDRL2, and CDRL3 of a variable region as disclosed herein and CDRH1, CDRH2, CDRH3 of another variable region as disclosed herein. In certain embodiments, the CDR set constitutes a paratope. Additionally or alternatively, the CDR set specifically binds to a DNABII peptide (such as the tip region and/or the tail region, including but not limited to: a tip region of IHF or HU, a tip region of IHFA or IHFB, the tip-chimeric peptide IhfA5-mIhfB4$_{NTHi}$, a tail region of IHF or HU, a tail region of IHFA or IHFB, and/or the tail-chimeric peptide IhfA3-IhfB2$_{NTHi}$). In a further embodiment, provided is an antibody, a fragment thereof, or an equivalent of each thereof, comprising, or alternatively consisting essentially of, or yet further consisting of any one or more CDRs as disclosed herein. In yet a further embodiment, provided is an antibody, a fragment thereof, or an equivalent of each thereof, comprising, or alternatively consisting essentially of, or yet further consisting of a CDR set as disclosed herein.

In certain embodiments, CDRs of SEQ ID NOs: 1-13 are illustrated in the following table. In certain embodiments, CDRH1 of any one of SEQ ID NOs: 1-6, 13, 24 or 26 comprises or consists essentially of, or yet further consists of amino acid (aa) 50 to aa 57 of SEQ ID NO: 1-6, 13, 24 or 26, respectively. In certain embodiments, CDRH2 of any one of SEQ ID NOs: 1-6, 13, 24 or 26 comprises or consists essentially of, or yet further consists of amino acid (aa) 75 to aa 82 of SEQ ID NO: 1-6, 13, 24 or 26, respectively. In certain embodiments, CDRH3 of any one of SEQ ID NOs: 1-6, 13, 24 or 26 comprises or consists essentially of, or yet further consists of amino acid (aa) 121 to aa 133 of SEQ ID NO: 1-6, 13, 24 or 26, respectively. In certain embodiments, CDRL1 of any one of SEQ ID NOs: 7-9, 14 or 25 comprises or consists essentially of, or yet further consists of amino acid (aa) 47 to aa 57 of SEQ ID NO: 7-9, 14 or 25, respectively. In certain embodiments, CDRL2 of any one of SEQ ID NOs: 7-9, 14 or 25 comprises or consists essentially of, or yet further consists of amino acid (aa) 75 to aa 77 of SEQ ID NO: 7-9, 14 or 25, respectively. In certain embodiments, CDRL3 of any one of SEQ ID NOs: 7-9, 14 or 25 comprises or consists essentially of, or yet further consists of amino acid (aa) 114 to aa 122 of SEQ ID NO: 7-9, 14 or 25, respectively. In certain embodiments, CDRL1 of any one of SEQ ID NOs: 10-12 or 27 comprises or consists essentially of, or yet further consists of amino acid (aa) 47 to aa 52 of SEQ ID NO: 10-12 or 27, respectively. In certain embodiments, CDRL2 of any one of SEQ ID NOs: 10-12 or 27 comprises or consists essentially of, or yet further consists of amino acid (aa) 70 to aa 72 of SEQ ID NO: 10-12 or 27, respectively. In certain embodiments, CDRL3 of any one of SEQ ID NOs: 10-12 or 27 comprises or consists essentially of, or yet further consists of amino acid (aa) 109 to aa 116 of SEQ ID NO: 10-12 or 27, respectively.

| SEQ ID NO: | CDR1 | CDR2 | CDR3 | Variable Region |
|---|---|---|---|---|
| 4 | GFTFSRYG (residues 50-57 of SEQ ID NO: 4) | ISSGGSYT (residues 75-82 of SEQ ID NO: 4) | ERHGGDGYWYFDV (residues 121-133 of SEQ ID NO: 4) | EVQLVESGGGLVKPGGSLRLSCAASGFTFSRYGM SWVRQAPGKGLEWVATISSGGSYTYYTDSVKGRF TISRDNAKNSLYLQMNSLRAEDTAVYYCERHGGD GYWYFDVWGQGTMVTVSS (residues 25-144 of SEQ ID NO: 4) |
| 5 | GFTFSRYG (residues 50-57 of SEQ ID NO: 5) | ISSGGSYT (residues 75-82 of SEQ ID NO: 5) | ERHGGDGYWYFDV (residues 121-133 of SEQ ID NO: 5) | EVQLVESGGGLVKPGGSLRLSCAASGFTFSRYGM SWVRQAPGKGLEWVSTISSGGSYTYYTDSVKGRF TISRDNAKNSLYLQMNSLRAEDTAVYYCERHGGD GYWYFDVWGQGTMVTVSS (residues 25-144 of SEQ ID NO: 5) |
| 6 | GFTFSRYG (residues 50-57 of SEQ ID NO: 6) | ISSGGSYT (residues 75-82 of SEQ ID NO: 6) | ERHGGDGYWYFDV (residues 121-133 of SEQ ID NO: 6) | EVQLVESGGGLVQPGRSLRLSCTASGFTFSRYGM SWVRQAPGKGLEWVATISSGGSYTYYTDSVKGRF TISRDNAKNILYLQMNSLKTEDTAVYYCERHGGD GYWYFDVWGQGTMVTVSS (residues 25-144 of SEQ ID NO: 6) |
| 10 | QDISNY (residues 47-52 Of SEQ ID NO: 10) | YTS (residues 70-72 Of SEQ ID NO: 10) | QQGNPLRT (residues 109-116 Of SEQ ID NO: 10) | DIQMTQSPSSLSASVGDRVTITCRASQDISNYLNW YQQKPGKAVKLLIYYTSRLHSGVPSRFSGSGSGTD YTLTISSLQPEDFATYFCQQGNPLRTFGGGTKVE IK (residues 21-126 of SEQ ID NO: 10) |

| SEQ ID NO: | CDR1 | CDR2 | CDR3 | Variable Region |
|---|---|---|---|---|
| 11 | QDISNY (residues 47-52 of SEQ ID NO: 11) | YTS (residues 70-72 of SEQ ID NO: 11) | QQGNPLRT (residues 109-116 of SEQ ID NO: 11) | DIQMTQSPSSLSASVGDRVTITCRASQDISNYLNW YQQKPGKAVKLLIYYTSRLHSGVPSRFSGSGSGTD YTLTISSLQPEDFATYYCQQGNPLRTFGGGTKVEIK (residues 21-126 of SEQ ID NO: 11) |
| 12 | QDISNY (residues 47-52 of SEQ ID NO: 12) | YTS (residues 70-72 of SEQ ID NO: 12) | QQGNPLRT (residues 109-116 of SEQ ID NO: 12) | DIVMTQSPATLSLSPGERATLSCRASQDISNYLNW YQQKPGQAVRLLIYYTSRLHSGIPARFSGSGSGTD YTLTISSLEPEDFAVYFCQQGNPLRTFGGGTKVE IK (residues 21-126 of SEQ ID NO: 12) |
| 1 | GFTFRTYA (residues 50-57 of SEQ ID NO: 1) | IGSDRRHT (residues 75-82 of SEQ ID NO: 1) | VGPYDGYY GEFDY (residues 121-133 of SEQ ID NO: 1) | EVKLVESGGGLVQPGGSLRLSCAASGFTFRTYAM SWVRQAPGKGLEWVATIGSDRRHTYYPDSVKGRF TISRDNAKNTLYLQMNSLRAEDTAVYYCVGPYDGY YGEFDYWGQGTLVTVSS (residues 25-144 of SEQ ID NO: 1) |
| 2 | GFTFRTYA (residues 50-57 of SEQ ID NO: 2) | IGSDRRHT (residues 75-82 of SEQ ID NO: 2) | VGPYDGYY GEFDY (residues 121-133 of SEQ ID NO: 2) | EVQLVESGGGLVQPGGSLRLSCAASGFTFRTYAM SWVRQAPGKGLEWVATIGSDRRHTYYPDSVKGRF TISRDNSKNTLYLQMNSLRAEDTAVYYCVGPYDGY YGEFDYWGQGTLVTVSS (residues 25-144 of SEQ ID NO: 2) |
| 3 | GFTFRTYA (residues 50-57 of SEQ ID NO: 3) | IGSDRRHT (residues 75-82 of SEQ ID NO: 3) | VGPYDGYY GEFDY (residues 121-133 of SEQ ID NO: 3) | EVKLVQSGAEVKKPGASVKVSCKASGFTFRTYAM SWVRQAPGQRLEWVATIGSDRRHTYYPDKFQGR VTITRDNAKNTLYMELSSLRSEDTAVYYCVGPYD GYYGEFDYWGQGTLVTVSS (residues 25-144 of SEQ ID NO: 3) |
| 7 | QSLLDSD GKTF (residues 47-57 of SEQ ID NO: 7) | LVS (residues 75-77 of SEQ ID NO: 7) | WQGTHFPY T (residues 114-122 of SEQ ID NO: 7) | DVVMTQSPLSLPVTLGQPASISCRSSQSLLDSDGK TFLNWLQQRPGQSPRRLIYLVSKLDSGVPDRFSG SGSGTDFTLKISRVEAEDVGVYYCWQGTHFPYTF GQGTKLEIK (residues 21-132 of SEQ ID NO: 7) |
| 8 | QSLLDSD GKTF (residues 47-57 of SEQ ID NO: 8) | LVS (residues 75-77 of SEQ ID NO: 8) | WQGTHFPY T (residues 114-122 of SEQ ID NO: 8) | DVVMTQSPLSLPVTLGQPASISCRSSQSLLDSDGK TFLNWLQQRPGQSPRRLIYLVSKRDSGVPDRFSG SGSGTDFTLKISRVEAEDVGVYYCWQGTHFPYTF GQGTKLEIK (residues 21-132 of SEQ ID NO: 8) |
| 9 | QSLLDSD GKTF (residues 47-57 of SEQ ID NO: 9) | LVS (residues 75-77 Of SEQ ID NO: 9) | WQGTHFPY T (residues 114-122 Of SEQ ID NO: 9) | DVMTQSPDSLAVSLGERATINCKSSQSLLDSDG KTFLNWLQQKPGQPPKRLIYLVSKLDSGVPDRFS GFSGSGTDFTLTISSLQAEDVAVYYCWQGTHFP YTFGQGTKLEIK (residues 21-132 of SEQ ID NO: 9) |

In certain embodiments, provided are CDRs as identified in the following two Tables below.

| SEQ | | 1 | 2 | 3 | 4 | 5 | 6 | 7 | 8 |
|---|---|---|---|---|---|---|---|---|---|
| 1 | VH1 CDR1 | AASGFTF RTYAMS (residues 47-59 of SEQ ID NO: 1) | GFTFR TYA (residues 50-57 of SEQ ID NO: 1) | GFTFRTY (residues 50-56 of SEQ ID NO: 1) | AASGFTF RTYAMS (residues 47-59 of SEQ ID NO: 1) | GFTFR TYA (residues 50-57 of SEQ ID NO: 1) | GFTFRTY (residues 50-56 of SEQ ID NO: 1) | GFTFRT YA (residues 50-57 of SEQ ID NO: 1) | GFTFRT Y (residues 50-56 of SEQ ID NO: 1) |
| | CDR2 | TIGSDRR HTY (residues 74-83 of SEQ ID NO: 1) | IGSDR RHT (residues 75-82 of SEQ ID NO: 1) | GSDRRH (residues 76-81 of SEQ ID NO: 1) | TIGSDRR HTY (residues 74-83 of SEQ ID NO: 1) | IGSDR RHT (residues 75-82 of SEQ ID NO: 1) | GSDRRH (residues 76-81 of SEQ ID NO: 1) | IGSDRR HT (residues 75-82 of SEQ ID NO: 1) | GSDRR H (residues 76-81 of SEQ ID NO: 1) |

-continued

| SEQ | | | 1 | 2 | 3 | 4 | 5 | 6 | 7 | 8 |
|---|---|---|---|---|---|---|---|---|---|---|
| | | CDR3 | Not determined | Not determined | Not determined | Not determined | Not determined | Not determined | VGPYDGYYGEFDY (residues 121-133 of SEQ ID NO: 1) | VGPYDGYYGEFDY (residues 121-133 of SEQ ID NO: 1) |
| 2 | VH2 | CDR1 | AASGFTFRTYAMS (residues 47-59 of SEQ ID NO: 2) | GFTFRTYA (residues 50-57 of SEQ ID NO: 2) | GFTFRTY (residues 50-56 of SEQ ID NO: 2) | AASGFTFRTYAMS (residues 47-59 of SEQ ID NO: 2) | GFTFRTYA (residues 50-57 of SEQ ID NO: 2) | GFTFRTY (residues 50-56 of SEQ ID NO: 2) | GFTFRTYA (residues 50-57 of SEQ ID NO: 2) | GFTFRTY (residues 50-56 of SEQ ID NO: 2) |
| | | CDR2 | TIGSDRRHTY (residues 74-83 of SEQ ID NO: 2) | IGSDRRHT (residues 75-82 of SEQ ID NO: 2) | GSDRRH (residues 76-81 of SEQ ID NO: 2) | TIGSDRRHTY (residues 74-83 of SEQ ID NO: 2) | IGSDRRHT (residues 75-82 of SEQ ID NO: 2) | GSDRRH (residues 76-81 of SEQ ID NO: 2) | IGSDRRHT (residues 75-82 of SEQ ID NO: 2) | GSDRRH (residues 76-81 of SEQ ID NO: 2) |
| | | CDR3 | Not determined | Not determined | Not determined | Not determined | Not determined | Not determined | VGPYDGYYGEFDY (residues 121-133 of SEQ ID NO: 2) | VGPYDGYYGEFDY (residues 121-133 of SEQ ID NO: 2) |
| 3 | VH3 | CDR1 | KASGFTFRTYAMS (residues 47-59 of SEQ ID NO: 3) | GFTFRTYA (residues 50-57 of SEQ ID NO: 3) | GFTFRTY (residues 50-56 of SEQ ID NO: 3) | KASGFTFRTYAMS (residues 47-59 of SEQ ID NO: 3) | GFTFRTYA (residues 50-57 of SEQ ID NO: 3) | GFTFRTY (residues 50-56 of SEQ ID NO: 3) | GFTFRTYA (residues 50-57 of SEQ ID NO: 3) | GFTFRTY (residues 50-56 of SEQ ID NO: 3) |
| | | CDR2 | TIGSDRRHTY (residues 74-83 of SEQ ID NO: 3) | IGSDRRHT (residues 75-82 of SEQ ID NO: 3) | GSDRRH (residues 76-81 of SEQ ID NO: 3) | TIGSDRRHTY (residues 74-83 of SEQ ID NO: 3) | IGSDRRHT (residues 75-82 of SEQ ID NO: 3) | GSDRRH (residues 76-81 of SEQ ID NO: 3) | IGSDRRHTY (residues 75-83 of SEQ ID NO: 3) | GSDRRH (residues 76-81 of SEQ ID NO: 3) |
| | | CDR3 | Not determined | Not determined | Not determined | Not determined | Not determined | Not determined | VGPYDGYYGEFDY (residues 121-133 of SEQ ID NO: 3) | VGPYDGYYGEFDY (residues 121-133 of SEQ ID NO: 3) |
| 7 | VL1 | CDR1 | RSSQSLLDSDGKTFLN (residues 44-59 of SEQ ID NO: 7) | QSLLDSDGKTF (residues 47-57 of SEQ ID NO: 7) | RSSQSLLDSDGKTFLN (residues 44-59 of SEQ ID NO: 7) | RSSQSLLDSDGKTFLN (residues 44-59 of SEQ ID NO: 7) | QSLLDSDGKTF (residues 47-57 of SEQ ID NO: 7) | RSSQSLLDSDGKTFLN (residues 44-59 of SEQ ID NO: 7) | QSLLDSDGKTF (residues 47-57 of SEQ ID NO: 7) | QSLLDSDGKTF (residues 47-57 of SEQ ID NO: 7) |
| | | CDR2 | YLVSKLDS (residues 74-81 of SEQ ID NO: 7) | LVS (residues 75-77 of SEQ ID NO: 7) | LVSKLDS (residues 75-81 of SEQ ID NO: 7) | YLVSKLDS (residues 74-81 of SEQ ID NO: 7) | LVS (residues 75-77 of SEQ ID NO: 7) | LVSKLDS (residues 75-81 of SEQ ID NO: 7) | LVS (residues 75-77 of SEQ ID NO: 7) | LVS (residues 75-77 of SEQ ID NO: 7) |
| | | CDR3 | WQGTHFPYT (residues 114-122 of SEQ ID NO: 7) | WQGTHFPYT (residues 114-122 of SEQ ID NO: 7) | WQGTHFPYT (residues 114-122 of SEQ ID NO: 7) | WQGTHFPYT (residues 114-122 of SEQ ID NO: 7) | WQGTHFPYT (residues 114-122 of SEQ ID NO: 7) | WQGTHFPYT (residues 114-122 of SEQ ID NO: 7) | WQGTHFPYT (residues 114-122 of SEQ ID NO: 7) | WQGTHFPYT (residues 114-122 of SEQ ID NO: 7) |
| 8 | VL2 | CDR1 | RSSQSLLDSDGKT | QSLLDSDG | RSSQSLLDSDGKT | RSSQSLLDSDGKT | QSLLDSDG | RSSQSLLDSDGKT | QSLLDSDGKTF | QSLLDSDGKTF |

-continued

| SEQ | 1 | 2 | 3 | 4 | 5 | 6 | 7 | 8 |
|---|---|---|---|---|---|---|---|---|
| | FLN (residues 44-59 of SEQ ID NO: 8) | KTF (residues 47-57 of SEQ ID NO: 8) | FLN (residues 44-59 of SEQ ID NO: 8) | FLN (residues 44-59 of SEQ ID NO: 8) | KTF (residues 47-57 of SEQ ID NO: 8) | FLN (residues 44-59 of SEQ ID NO: 8) | (residues 47-57 of SEQ ID NO: 8) | (residues 47-57 of SEQ ID NO: 8) |
| CDR2 | YLVSKR DS (residues 74-81 of SEQ ID NO: 8) | LVS (residues 75-77 of SEQ ID NO: 8) | LVSKRD S (residues 75-81 of SEQ ID NO: 8) | YLVSKR DS (residues 74-81 of SEQ ID NO: 8) | LVS (residues 75-77 of SEQ ID NO: 8) | LVSKRD S (residues 75-81 of SEQ ID NO: 8) | LVS (residues 75-77 of SEQ ID NO: 8) | LVS (residues 75-77 of SEQ ID NO: 8) |
| CDR3 | WQGTHF PYT (residues 114-122 of SEQ ID NO: 8) | WQGT HFPYT (residues 114-122 of SEQ ID NO: 8) | WQGTHF PYT (residues 114-122 of SEQ ID NO: 8) | WQGTHF PYT (residues 114-122 of SEQ ID NO: 8) | WQGT HFPYT (residues 114-122 of SEQ ID NO: 8) | WQGTHF PYT (residues 114-122 of SEQ ID NO: 8) | WQGTH FPYT (residues 114-122 of SEQ ID NO: 8) | WQGTH FPYT (residues 114-122 of SEQ ID NO: 8) |
| 9 VL3 CDR1 | KSSQSLL DSDGKT FLN (residues 44-59 of SEQ ID NO: 9) | QSLL DSDG KTF (residues 47-57 of SEQ ID NO: 9) | KSSQSLL DSDGKT FLN (residues 44-59 of SEQ ID NO: 9) | KSSQSLL DSDGKT FLN (residues 44-59 of SEQ ID NO: 9) | QSLL DSDG KTF (residues 47-57 of SEQ ID NO: 9) | KSSQSLL DSDGKT FLN (residues 44-59 of SEQ ID NO: 9) | QSLLDS DGKTF (residues 47-57 of SEQ ID NO: 9) | QSLLDS DGKTF (residues 47-57 of SEQ ID NO: 9) |
| CDR2 | YLVSKL DS (residues 74-81 of SEQ ID NO: 9) | LVS (residues 75-77 of SEQ ID NO: 9) | LVSKLDS (residues 75-81 of SEQ ID NO: 9) | YLVSKL DS (residues 74-81 of SEQ ID NO: 9) | LVS (residues 75-77 of SEQ ID NO: 9) | LVSKLDS (residues 75-81 of SEQ ID NO: 9) | LVS (residues 75-77 of SEQ ID NO: 9) | LVS (residues 75-77 of SEQ ID NO: 9) |
| CDR3 | WQGTHF PYT (residues 114-122 of SEQ ID NO: 9) | WQGT HFPY T (residues 114-122 of SEQ ID NO: 9) | WQGTHF PYT (residues 114-122 of SEQ ID NO: 9) | WQGTHF PYT (residues 114-122 of SEQ ID NO: 9) | WQGT HFPY T (residues 114-122 of SEQ ID NO: 9) | WQGTHF PYT (residues 114-122 of SEQ ID NO: 9) | WQGTH FPYT (residues 114-122 of SEQ ID NO: 9) | WQGTH FPYT (residues 114-122 of SEQ ID NO: 9) |

SEQ: SEQ ID NO

| SEQ | 1 | 2 | 3 | 4 | 5 | 6 | 7 | 8 |
|---|---|---|---|---|---|---|---|---|
| 4 VH1 CDR1 | AASGFTF SRYGMS (residues 47-59 of SEQ ID NO: 4) | GFTF SRYG (residues 50-57 of SEQ ID NO: 4) | GFTFSR Y (residues 50-56 of SEQ ID NO: 4) | AASGFTF SRYGMS (residues 47-59 of SEQ ID NO: 4) | GFTF SRYG (residues 50-57 of SEQ ID NO: 4) | GFTFSR Y (residues 50-56 of SEQ ID NO: 4) | GFTFSRY G (residues 50-57 of SEQ ID NO: 4) | GFTFSRY (residues 50-56 of SEQ ID NO: 4) |
| CDR2 | TISSGGS YTY (residues 74-83 of SEQ ID NO: 4) | ISSG GSYT (residues 75-82 of SEQ ID NO: 4) | SSGGS Y (residues 76-81 of SEQ ID NO: 4) | TISSGGS YTY (residues 74-83 of SEQ ID NO: 4) | ISSG GSYT (residues 75-82 of SEQ ID NO: 4) | SSGGS Y (residues 76-81 of SEQ ID NO: 4) | ISSGGSYT (residues 75-82 of SEQ ID NO: 4) | SSGGSY (residues 76-81 of SEQ ID NO: 4) |
| CDR3 | Not determined | Not determined | Not determined | Not determined | Not determined | Not determined | ERHGGDG YWYFDV (residues 121-133 of SEQ ID NO: 4) | ERHGGDG YWYFDV (residues 121-133 of SEQ ID NO: 4) |

-continued

| SEQ | | 1 | 2 | 3 | 4 | 5 | 6 | 7 | 8 |
|---|---|---|---|---|---|---|---|---|---|
| 5 VH2 | CDR1 | AASGFTFSRYGMS (residues 47-59 of SEQ ID NO: 5) | GFTF SRYG (residues 50-57 of SEQ ID NO: 5) | GFTFSRY (residues 50-56 of SEQ ID NO: 5) | AASGFTFSRYGMS (residues 47-59 of SEQ ID NO: 5) | GFTF SRYG (residues 50-57 of SEQ ID NO: 5) | GFTFSRY (residues 50-56 of SEQ ID NO: 5) | GFTFSRYG (residues 50-57 of SEQ ID NO: 5) | GFTFSRY (residues 50-56 of SEQ ID NO: 5) |
| | CDR2 | TISSGGSYTY (residues 74-83 of SEQ ID NO: 5) | ISSGGSYT (residues 75-82 of SEQ ID NO: 5) | SSGGSY (residues 76-81 of SEQ ID NO: 5) | TISSGGSYTY (residues 74-83 of SEQ ID NO: 5) | ISSGGSYT (residues 75-82 of SEQ ID NO: 5) | SSGGSY (residues 76-81 of SEQ ID NO: 5) | ISSGGSYT (residues 75-82 of SEQ ID NO: 5) | SSGGSY (residues 76-81 of SEQ ID NO: 5) |
| | CDR3 | Not determined | Not determined | Not determined | Not determined | Not determined | Not determined | ERHGGDGYWYFDV (residues 121-133 of SEQ ID NO: 5) | ERHGGDGYWYFDV (residues 121-133 of SEQ ID NO: 5) |
| 6 VH3 | CDR1 | TASGFTFSRYGMS (residues 47-59 of SEQ ID NO: 6) | GFTF SRYG (residues 50-57 of SEQ ID NO: 6) | GFTFSRY (residues 50-56 of SEQ ID NO: 6) | TASGFTFSRYGMS (residues 47-59 of SEQ ID NO: 6) | GFTF SRYG (residues 50-57 of SEQ ID NO: 6) | GFTFSRY (residues 50-56 of SEQ ID NO: 6) | GFTFSRYG (residues 50-57 of SEQ ID NO: 6) | GFTFSRY (residues 50-56 of SEQ ID NO: 6) |
| | CDR2 | TISSGGSYTY (residues 74-83 of SEQ ID NO: 6) | ISSGGSYT (residues 75-82 of SEQ ID NO: 6) | SSGGSY (residues 76-81 of SEQ ID NO: 6) | TISSGGSYTY (residues 74-83 of SEQ ID NO: 6) | ISSGGSYT (residues 75-82 of SEQ ID NO: 6) | SSGGSY (residues 76-81 of SEQ ID NO: 6) | ISSGGSYT (residues 75-82 of SEQ ID NO: 6) | SSGGSY (residues 76-81 of SEQ ID NO: 6) |
| | CDR3 | Not determined | Not determined | Not determined | Not determined | Not determined | Not determined | ERHGGDGYWYFDV (residues 121-133 of SEQ ID NO: 6) | ERHGGDGYWYFDV (residues 121-133 of SEQ ID NO: 6) |
| 10 VL1 | CDR1 | RASQDISNYLN (residues 44-54 of SEQ ID NO: 10) | QDISNY (residues 47-52 of SEQ ID NO: 10) | RASQDISNYLN (residues 44-54 of SEQ ID NO: 10) | RASQDISNYLN (residues 44-54 of SEQ ID NO: 10) | QDISNY (residues 47-52 of SEQ ID NO: 10) | RASQDISNYLN (residues 44-54 of SEQ ID NO: 10) | QDISNY (residues 47-52 of SEQ ID NO: 10) | QDISNY (residues 47-52 of SEQ ID NO: 10) |
| | CDR2 | YYTSRLHS (residues 69-76 of SEQ ID NO: 10) | YTS (residues 70-72 of SEQ ID NO: 10) | YYTSRLHS (residues 70-76 of SEQ ID NO: 10) | YYTSRLHS (residues 69-76 of SEQ ID NO: 10) | YTS (residues 70-72 of SEQ ID NO: 10) | YYTSRLHS (residues 70-76 of SEQ ID NO: 10) | YTS (residues 70-72 of SEQ ID NO: 10) | YTS (residues 70-72 of SEQ ID NO: 10) |
| | CDR3 | QQGNPLRT (residues 109-116 of SEQ ID NO: 10) | QQGNPLRT (residues 109-116 of SEQ ID NO: 10) | QQGNPLRT (residues 109-116 of SEQ ID NO: 10) | QQGNPLRT (residues 109-116 of SEQ ID NO: 10) | QQGNPLRT (residues 109-116 of SEQ ID NO: 10) | QQGNPLRT (residues 109-116 of SEQ ID NO: 10) | QQGNPLRT (residues 109-116 of SEQ ID NO: 10) | QQGNPLRT (residues 109-116 of SEQ ID NO: 10) |
| 11 VL2 | CDR1 | RASQDISNYLN (residues 44-54 of SEQ ID NO: 11) | QDISNY (residues 47-52 of SEQ ID NO: 11) | RASQDISNYLN (residues 44-54 of SEQ ID NO: 11) | RASQDISNYLN (residues 44-54 of SEQ ID NO: 11) | QDISNY (residues 47-52 of SEQ ID NO: 11) | RASQDISNYLN (residues 44-54 of SEQ ID NO: 11) | QDISNY (residues 47-52 of SEQ ID NO: 11) | QDISNY (residues 47-52 of SEQ ID NO: 11) |

| SEQ | 1 | 2 | 3 | 4 | 5 | 6 | 7 | 8 |
|---|---|---|---|---|---|---|---|---|
| CDR2 | YYTSRLHS (residues 69-76 of SEQ ID NO: 11) | YTS (residues 70-72 of SEQ ID NO: 11) | YTSRLHS (residues 70-76 of SEQ ID NO: 11) | YYTSRLHS (residues 69-76 of SEQ ID NO: 11) | YTS (residues 70-72 of SEQ ID NO: 11) | YTSRLHS (residues 70-76 of SEQ ID NO: 11) | YTS (residues 70-72 of SEQ ID NO: 11) | YTS (residues 70-72 of SEQ ID NO: 11) |
| CDR3 | QQGNPLRT (residues 109-116 of SEQ ID NO: 11) | QQGNPLRT (residues 109-116 of SEQ ID NO: 11) | QQGNPLRT (residues 109-116 of SEQ ID NO: 11) | QQGNPLRT (residues 109-116 of SEQ ID NO: 11) | QQGNPLRT (residues 109-116 of SEQ ID NO: 11) | QQGNPLRT (residues 109-116 of SEQ ID NO: 11) | QQGNPLRT (residues 109-116 of SEQ ID NO: 11) | QQGNPLRT (residues 109-116 of SEQ ID NO: 11) |
| 12 VL3 CDR1 | RASQDISNYLN (residues 44-54 of SEQ ID NO: 12) | QDISNY (residues 47-52 of SEQ ID NO: 12) | RASQDISNYLN (residues 44-54 of SEQ ID NO: 12) | RASQDISNYLN (residues 44-54 of SEQ ID NO: 12) | QDISNY (residues 47-52 of SEQ ID NO: 12) | RASQDISNYLN (residues 44-54 of SEQ ID NO: 12) | QDISNY (residues 47-52 of SEQ ID NO: 12) | QDISNY (residues 47-52 of SEQ ID NO: 12) |
| CDR2 | YYTSRLHS (residues 69-76 of SEQ ID NO: 12) | YTS (residues 70-72 of SEQ ID NO: 12) | YTSRLHS (residues 70-76 of SEQ ID NO: 12) | YYTSRLHS (residues 69-76 of SEQ ID NO: 12) | YTS (residues 70-72 of SEQ ID NO: 12) | YTSRLHS (residues 70-76 of SEQ ID NO: 12) | YTS (residues 70-72 of SEQ ID NO: 12) | YTS (residues 70-72 of SEQ ID NO: 12) |
| CDR3 | QQGNPLRT (residues 109-116 of SEQ ID NO: 12) | QQGNPLRT (residues 109-116 of SEQ ID NO: 12) | QQGNPLRT (residues 109-116 of SEQ ID NO: 12) | QQGNPLRT (residues 109-116 of SEQ ID NO: 12) | QQGNPLRT (residues 109-116 of SEQ ID NO: 12) | QQGNPLRT (residues 109-116 of SEQ ID NO: 12) | QQGNPLRT (residues 109-116 of SEQ ID NO: 12) | QQGNPLRT (residues 109-116 of SEQ ID NO: 12) |

SEQ: SEQ ID NO

In certain embodiments, provided is an alternative CDR that is a CDR as identified herein further comprising an additional 1 amino acid, or alternatively 2 amino acids, or alternatively 3 amino acids, or alternatively 4 amino acids, or alternatively 5 amino acids, or alternatively 6 amino acids, or alternatively 7 amino acids, or alternatively 8 amino acids at its amino terminus, or carboxyl terminus or both in the corresponding variable region sequence. Additionally or alternatively, provided is an alternative CDR that is a CDR as indentified herein having 1 amino acid, or alternatively 2 amino acids, or alternatively 3 amino acids, or alternatively 4 amino acids, or alternatively 5 amino acids, or alternatively 6 amino acids, or alternatively 7 amino acids, or alternatively 8 amino acids truncated at its amino terminus, or carboxyl terminus or both in the corresponding variable region sequence. For example, CDR1 of SEQ ID NO: 1 may be amino acid 50 to amino acid 57 of SEQ ID NO: 1. However, the CDR1 of SEQ ID NO: 1 can also start from amino acid 42, or 43, or 44, or 45, or 46, or 47, or 48, or 49, or 50, or 51, or 52, or 53, or 54, or 55, or 56, or 57, or 58 of SED ID NO: 1. Further, CDR1 of SEQ ID NO: 1 can end at amino acid 49, or 50, or 51, or 52, or 53, or 54, or 55, or 56, or 57, or 58, or 59, or 60, or 61, or 62, or 63, or 64, or 65 of SEQ ID NO: 1 with proviso that the CDR1 ends after its start. Additionally or alternatively, the CDR is about 1, or alternatively about 2, or alternatively about 3, or alternatively about 4, or alternatively about 5, or alternatively about 6, or alternatively about 7, or alternatively about 8, or alternatively about 9, or alternatively about 10, or alternatively about 11, or alternatively about 12, or alternatively about 13, or alternatively about 14, or alternatively about 15 amino acids long.

In certain embodiments, CDR2 of any one of SEQ ID NOs: 1-6 comprises or consists essentially of, or yet further consists of amino acid 71 to amino acid 85 of each of SEQ ID NOs: 1-6, respectively. In certain embodiments, CDR3 of any one of SEQ ID NOs: 1-6 comprises or consists essentially of, or yet further consists of amino acid 121 to amino acid 133 of each of SEQ ID NOs: 1-6, respectively. In certain embodiments, CDR2 of any one of SEQ ID NOs: 7-9 comprises or consists essentially of, or yet further consists of amino acid 71 to amino acid 81 of each of SEQ ID NOs: 7-9, respectively. In certain embodiments, CDR3 of any one of SEQ ID NOs: 7-9 comprises or consists essentially of, or yet further consists of amino acid 114 to amino acid 121 of each of SEQ ID NOs: 7-9, respectively. In certain embodiments, CDR2 of any one of SEQ ID NOs: 10-12 comprises or consists essentially of, or yet further consists of amino acid 66 to amino acid 76 of each of SEQ ID NOs: 10-12, respectively. In certain embodiments, CDR3 of any one of SEQ ID NOs: 10-12 comprises or consists essentially of, or yet further consists of amino acid 109 to amino acid 115 of each of SEQ ID NOs: 10-12, respectively.

In certain embodiments, CDR1 of any one of SEQ ID NOs: 1-6 comprises or consists essentially of, or yet further consists of amino acid 50 to amino acid 57 of each of SEQ ID NOs: 1-6, respectively. In certain embodiments, CDR2 of any one of SEQ ID NOs: 1-6 comprises or consists essentially of, or yet further consists of amino acid 75 to amino acid 82 of each of SEQ ID NOs: 1-6, respectively. In certain embodiments, CDR3 of any one of SEQ ID NOs: 1-6 comprises or consists essentially of, or yet further consists of amino acids 121 and 122 of each of SEQ ID NOs: 1-6, respectively. In certain embodiments, CDR1 of any one of SEQ ID NOs: 7-9 comprises or consists essentially of, or yet further consists of amino acid 47 to amino acid 57 of each of SEQ ID NOs: 7-9, respectively. In certain embodiments, CDR2 of any one of SEQ ID NOs: 7-9 comprises or consists essentially of, or yet further consists of amino acid 75 to amino acid 77 of each of SEQ ID NOs: 7-9, respectively. In certain embodiments, CDR3 of any one of SEQ ID NOs: 7-9 comprises or consists essentially of, or yet further consists of amino acids 114 and 120 of each of SEQ ID NOs: 7-9, respectively. In certain embodiments, CDR1 of any one of SEQ ID NOs: 10-12 comprises or consists essentially of, or yet further consists of amino acid 47 to amino acid 52 of each of SEQ ID NOs: 10-12, respectively. In certain embodiments, CDR2 of any one of SEQ ID NOs: 10-12 comprises or consists essentially of, or yet further consists of amino acid 70 to amino acid 72 of each of SEQ ID NOs: 10-12, respectively. In certain embodiments, CDR3 of any one of SEQ ID NOs: 10-12 comprises or consists essentially of, or yet further consists of amino acids 109 and 110 of each of SEQ ID NOs: 10-12, respectively.

In certain embodiments, CDR1 of any one of SEQ ID NOs: 1-6 comprises or consists essentially of, or yet further consists of amino acid 47 to amino acid 59 of each of SEQ ID NOs: 1-6, respectively. In certain embodiments, CDR2 of any one of SEQ ID NOs: 1-6 comprises or consists essentially of, or yet further consists of amino acid 74 to amino acid 83 of each of SEQ ID NOs: 1-6, respectively. In certain embodiments, CDR1 of any one of SEQ ID NOs: 7-9 comprises or consists essentially of, or yet further consists of amino acid 44 to amino acid 59 of each of SEQ ID NOs: 7-9, respectively. In certain embodiments, CDR2 of any one of SEQ ID NOs: 7-9 comprises or consists essentially of, or yet further consists of amino acid 74 to amino acid 81 of each of SEQ ID NOs: 7-9, respectively. In certain embodiments, CDR3 of any one of SEQ ID NOs: 7-9 comprises or consists essentially of, or yet further consists of amino acids 114 and 122 of each of SEQ ID NOs: 7-9, respectively. In certain embodiments, CDR1 of any one of SEQ ID NOs: 10-12 comprises or consists essentially of, or yet further consists of amino acid 44 to amino acid 54 of each of SEQ ID NOs: 10-12, respectively. In certain embodiments, CDR2 of any one of SEQ ID NOs: 10-12 comprises or consists essentially of, or yet further consists of amino acid 79 to amino acid 76 of each of SEQ ID NOs: 10-12, respectively. In certain embodiments, CDR3 of any one of SEQ ID NOs: 10-12 comprises or consists essentially of, or yet further consists of amino acids 109 and 116 of each of SEQ ID NOs: 10-12, respectively.

In one aspect, provided is one or more of variable region(s) of an antibody or fragment thereof as disclosed herein, and/or one or more of equivalent(s) of the variable regions(s). In a further embodiment, provided is an antibody, a fragment thereof, or an equivalent of each thereof, comprising, or alternatively consisting essentially of, or yet further consisting of any one or any two or more of: the variable regions as disclosed herein and/or one or more of equivalent(s) of the variable regions(s). Additionally or alternatively, the one or more of variable region(s) specifically binds to a DNABII peptide (such as the tip region and/or the tail region, including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$). In certain embodiments, the variable region is selected from the following: amino acid (aa) 25 to aa 144 of SEQ ID NOs: 1-6, 13, 24 and 26; aa 21 to aa 132 of SEQ ID NOs: 7-9, 14, and 25; aa 21 to aa 126 of SEQ ID NOs: 10-12 or 27; amino acid 24 to amino acid 144 of SEQ ID NOs: 1-6, 13, 24 and 26; amino acid 20 to amino acid 132 of SEQ ID NOs: 7-12, 14, 25 and 27; amino acid 20 to amino acid 126 of SEQ ID NOs: 7-12, 14, 25 and 27.

In a further embodiment, the variable region or an equivalent thereof is a variable region as disclosed herein further comprising an additional 1 amino acid, or alternatively 2 amino acids, or alternatively 3 amino acids, or alternatively 4 amino acids, or alternatively 5 amino acids, or alternatively 6 amino acids, or alternatively 7 amino acids, or alternatively 8 amino acids at its amino terminus, or carboxyl terminus or both in the corresponding sequence provided herein with a SEQ ID NO. Additionally or alternatively, the variable region or an equivalent thereof is a variable region as disclosed herein having 1 amino acid, or alternatively 2 amino acids, or alternatively 3 amino acids, or alternatively 4 amino acids, or alternatively 5 amino acids, or alternatively 6 amino acids, or alternatively 7 amino acids, or alternatively 8 amino acids truncated at its amino terminus, or carboxyl terminus or both in the corresponding sequence provided herein with a SEQ ID NO. For example, of SEQ ID NO: 1 may be amino acid 50 to amino acid 57 of SEQ ID NO: 1. However, the variable region or an equivalent thereof relating to the variable region consisting of amino acid 24 to amino acid 144 of SEQ ID NO: 1 can also start from amino acid 16, or 17, or 18, or 19, or 20, or 21, or 22, or 23, or 24, or 25, or 26, or 27, or 28, or 29, or 30, or 31, or 32 of SED ID NO: 1. Further, the variable region or an equivalent thereof relating to the variable region consisting of amino acid 24 to amino acid 144 of SEQ ID NO: 1 can end at amino acid 136, or 137, or 138, or 139, or 140, or 141, or 142, or 143, or 144, or 145, or 146, or 147, or 148, or 149, or 150, or 151, or 152 of SEQ ID NO: 1 with proviso that the variable region ends after its start. Additionally or alternatively, the variable region is about 90 amino acids long to about 200 amino acids long, for example, about 100 amino acid long, or alternatively about 110 amino acid long, or alternatively about 120 amino acid long, or alternatively about 130 amino acid long, or alternatively about 140 amino acid long, or alternatively about 150 amino acid long, or alternatively about 160 amino acid long, or alternatively about 170 amino acid long, or alternatively about 180 amino acid long, or alternatively about 190 amino acid long, or alternatively about 200 amino acid long.

Additionally or alternatively, the equivalent to an antibody or a fragment thereof comprises one or more of (for example but not limited to 1, 2, 3, 4, 5, 6, 7, 8, 9, 10, 11, 12, 13, 14, 15, 16, 17, 18, 19, 20, 21, 22, 23, 24 or 25) amino acid differences compared to the antibody or a fragment thereof in the regions other than the variable domain(s) (referred to herein as non-VH regions). Such non-VH regions include, but are not limited to, a constant region, a Fc region, a pFc' region, a constant heavy chain (CH) domain (such as CH1, CH2, CH3 or CH4), a constant light chain (CL) domain, or a hinge region. It would be understood by one of skill in the art that an antibody, a fragment thereof, or an equivalent of each thereof as disclosed herein, may be further modified in the non-VH regions (such as for increasing the assembly of a heavy chain with a light chain, conjugating directly or indirectly to a detectable or purification marker or a drug, increasing or decreasing activation of complement, enhancing or reducing antibody-dependent cellular cytotoxicity (ADCC), or increasing or decreasing activation and recruitment of an immune cell), providing a further equivalent.

In certain embodiments, the equivalent further comprises up to 50, or alternatively up to 30, or alternatively up to 25, or alternatively up to 20, or alternatively up to 15, or alternatively up to 10, or alternatively up to 5 random amino acids on either the amino or carboxyl termini or on both. In certain embodiments, the equivalent to an amino acid sequence comprises or consists essentially of, or yet further consists of the amino acid sequence truncated at the amino or carboxyl termini or both, for example, by 1, 2, 3, 4, 5, 6, 7, 8, 9, 10, 11, 12, 13, 14, 15, 20 or 25 amino acids. Such addition or truncation may not change the three-dimensional arrangement of the CDR(s) and/or the three-dimensional arrangement of the antibody, fragment thereof, CDR thereof, or the CDR-containing polypeptide.

In certain embodiments, an antibody or a fragment thereof comprises a signal peptide at the amino terminus of VH and/or the amino terminus of VL. In one embodiment, the VH signal peptide is different to the VL signal peptide. In another embodiment, the VH signal peptide is the same compared to the VL signal peptide. In a further embodiment, the signal peptide comprises or consists essentially of, or yet further consists of an amino acid sequence of amino acids 1-24 of SEQ ID NO: 1. In yet a further embodiment, the signal peptide comprises or consists essentially of, or yet further consists of an amino acid sequence of amino acids 1-20 of SEQ ID NO: 7. In certain embodiments, the equivalent to an antibody or a fragment thereof comprises a signal peptide which is different from the signal peptide(s) of the antibody with the proviso that the signal peptide of the equivalent directs VH and/or VL to the same cellular location as the signal peptide(s) of the antibody.

In certain embodiments, the equivalent to an antibody or a fragment thereof retains at least 50% (such as at least 60%, at least 70%, at least 80%, at least 90%, at least 95%, or at least 99%) of or improves one or more of functional activities of the antibody or fragment. Such functional activities include but are not limited to binding specificity, binding avidity and/or affinity to a DNABII peptide (such as the tip region and/or the tail region, including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$), preventing formation of a biofilm in vivo or in vitro, or disrupting a biofilm in vivo or in vitro. Methods of quantifying such functional activities are illustrated in the examples.

In a further aspect, provided is an antibody or a fragment thereof that competes for binding to an epitope with an antibody or a fragment thereof as disclosed herein. The antibody or fragment thereof may be a polyclonal, a monoclonal and/or a humanized antibody.

In one aspect, the antibody is a bispecific antibody or a trispecific, tetraspecific or pentaspecific antibody. In a further aspect, the antibody is an IgA, an IgD, an IgE, an IgG or an IgM antibody. In another aspect, the antibodies further comprise a constant region selected from an IgA, an IgD, an IgE, an IgG or an IgM constant region. In a specific aspect, the constant region is an IgG1 constant region. In another aspect, provided herein are antibodies that compete for binding to an epitope with an antibody as disclosed herein. These can be identified using conventional techniques, e.g. a competitive ELISA.

The antibodies as disclosed herein can be polyclonal, monoclonal or humanized. In one aspect, the antibodies bind the "tip" region of a DNABII polypeptide, e.g., HU or IHF (such as IhfA and IhfB). In a further aspect, the antibodies bind the "tail" region of a DNABII polypeptide, e.g., HU or IHF (such as IhfA and IhfB). As noted above, this disclosure provides antigen binding fragments. The antigen binding fragments are any one of Fab, F(ab')$_2$, Fab', scFv, or Fv, that can be prepared using conventional techniques known to those of skill in the art. In some of the aspects of the antibodies provided herein, the antibody is soluble Fab. In another aspect, this disclosure provides a Fab fragment of the antibody as disclosed herein, wherein the antibody specifically binds the tip region of a DNABII peptide (including but not limited to: a tip region of IHF or HU, a tip region of IHFA or IHFB, and/or the tip-chimeric peptide IhfA5-mIhfB4$_{NTHI}$). In one aspect of the disclosure the DNABII is an IHF or an HU peptide. In a specific aspect, the DNABII is an IHF peptide.

As noted above, this disclosure provides equivalents to antibodies and antigen binding fragments. An equivalent can comprise a polypeptide having at least 80% amino acid identity to polypeptide, or a polypeptide that is encoded by a polynucleotide that hybridizes under conditions of high stringency to the complement of a polynucleotide encoding the polypeptide.

In some of the aspects of the antibodies provided herein, the antibody, fragment thereof, polypeptide or CDR binds a DNABII protein (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$) at a half maximal effective concentration (EC$_{50}$) of less than 500 ng/mL, or alternatively less than 250 ng/mL, or alternatively less than 200 ng/mL, or alternatively less than 150 ng/mL, or alternatively less than 100 ng/mL, or alternatively less than 90 ng/mL, or alternatively less than 80 ng/mL, or alternatively less than 70 ng/mL, or alternatively less than 65 ng/mL, or alternatively less than 60 ng/mL, or alternatively less than 55 ng/mL, or alternatively less than 50 ng/mL, or alternatively less than 45 ng/mL, or alternatively less than 40 ng/mL, or alternatively less than 35 ng/mL, or alternatively less than 30 ng/mL. In a further embodiment, such EC$_{50}$ is determined using the ELISA methods shown in the Examples.

In some of the aspects of the antibodies provided herein, the antibody, fragment thereof, polypeptide or CDR binds a DNABII protein (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$) with an equilibrium constant $K_D$ of less than $10^{-4}$M, $10^{-5}$M, $10^{-6}$ M, $10^{-7}$M, $10^{-8}$ M, $10^{-9}$M, $10^{-10}$ M, $10^{-11}$ M, or $10^{-12}$M. In one embodiment, the antibody, fragment thereof, polypeptide or CDR binds a DNABII protein with a $K_D$ of less than 1000 nM, or alternatively less than 900 nM, or alternatively less than 800 nM, or alternatively less than 700 nM, or alternatively less than 600 nM, or alternatively less than 500 nM, or alternatively less than 400 nM, or alternatively less than 300 nM, or alternatively less than 200 nM, or alternatively less than 100 nM, or alternatively less than 90 nM, or alternatively less than 80 nM, or alternatively less than 70 nM, or alternatively less than 60 nM, or alternatively less than 50 nM, or alternatively less than 40 nM, or alternatively less than 30 nM, or alternatively less than 20 nM, or alternatively less than 15 nM, or alternatively less than 10 nM, or alternatively less than 9 nM, or alternatively less than 8 nM, or alternatively less than 7 nM, or alternatively less than 6 nM, or alternatively less than 5 nM, or alternatively less than 4 nM, or alternatively less than 3 nM, or alternatively less than 2 nM, or alternatively less than 1 nM. In one embodiment, such $K_D$ is determined using the surface plasmon resonance (SPR) methods shown in the Examples. In some of the aspects of the antibodies provided herein, the antigen binding site specifically binds to a DNABII protein.

In some of the aspects of the antibodies provided herein, the antibody, fragment thereof, polypeptide or CDR binds a DNABII protein (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$) with a $K_{off}$ of less than 1.0E-02 s$^{-1}$, or alternatively less than 9.0E-03 s$^{-1}$, or alternatively less than 8.0E-03 s$^{-1}$, or alternatively less than 7.0E-03 s$^{-1}$, or alternatively less than 6.0E-03 s$^{-1}$, or alternatively less than 5.0E-03 s$^{-1}$, or alternatively less than 4.0E-03 s$^{-1}$, or alternatively less than 3.0E-03 s$^{-1}$, or alternatively less than 2.0E-03 s$^{-1}$ or alternatively less than 1.0E-03 s$^{-1}$, or alternatively less than 9.0E-04 s$^{-1}$, or alternatively less than 8.0E-04 s$^{-1}$, or alternatively less than 7.0E-04 s$^{-1}$, or alternatively less than 6.0E-04 s$^{-1}$, or alternatively less than 5.0E-04 s$^{-1}$, or alternatively less than 4.0E-04 s$^{-1}$, or alternatively less than 3.0E-04 s$^{-1}$, or alternatively less than 2.0E-04 s$^{-1}$ or alternatively less than 1.0E-04 s$^{-1}$, or alternatively less than 9.0E-05 s$^{-1}$, or alternatively less than 8.0E-05 s$^{-1}$, or alternatively less than 7.0E-05 s$^{-1}$, or alternatively less than 6.0E-05 s$^{-1}$, or alternatively less than 5.0E-05 s$^{-1}$, or alternatively less than 4.0E-05 s$^{-1}$, or alternatively less than 3.0E-05 s$^{-1}$, or alternatively less than 2.0E-05 s$^{-1}$ or alternatively less than 1.0E-05 s$^{-1}$. In one embodiment, such $K_{off}$ is determined using the surface plasmon resonance (SPR) methods shown in the Examples.

In some of the aspects of the antibodies provided herein, the antibody, fragment thereof, polypeptide or CDR binds a DNABII protein (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$) with a $K_{on}$ of less than 9.0E-02 M$^{-1}$ s$^{-1}$, or alternatively less than 8.0E-02 M$^{-1}$ s$^{-1}$, or alternatively less than 7.0E-02 M$^{-1}$ s$^{-1}$, or alternatively less than 6.0E-02 M$^{-1}$ s$^{-1}$, or alternatively less than 5.0E-02 M$^{-1}$ s$^{-1}$, or alternatively less than 4.0E-02 M$^{-1}$ s$^{-1}$, or alternatively less than 3.0E-02 M$^{-1}$ s$^{-1}$, or alternatively less than 2.0E-02 M$^{-1}$ s$^{-1}$ or alternatively less than 1.0E-02 M$^{-1}$ s$^{-1}$, or alternatively less than 9.0E-03 M$^{-1}$ s$^{-1}$, or alternatively less than 8.0E-03 M$^{-1}$ s$^{-1}$, or alternatively less than 7.0E-03 M$^{-1}$ s$^{-1}$, or alternatively less than 6.0E-03 M$^{-1}$ s$^{-1}$, or alternatively less than 5.0E-03 M$^{-1}$ s$^{-1}$, or alternatively less than 4.0E-03 M$^{-1}$ s$^{-1}$, or alternatively less than 3.0E-03 M$^{-1}$ s$^{-1}$, or alternatively less than 2.0E-03 M$^{-1}$ s$^{-1}$ or alternatively less than 1.0E-03 M$^{-1}$ s$^{-1}$, or alternatively less than 9.0E-04 M$^{-1}$ s$^{-1}$, or alternatively less than 8.0E-04 M$^{-1}$ s$^{-1}$, or alternatively less than 7.0E-04 M$^{-1}$ s$^{-1}$, or alternatively less than 6.0E-04 M$^{-1}$ s$^{-1}$, or alternatively less than 5.0E-04 M$^{-1}$ s$^{-1}$, or alternatively less than 4.0E-04 M$^{-1}$ s$^{-1}$, or alternatively less than 3.0E-04 M$^{-1}$ s$^{-1}$, or alternatively less than 2.0E-04 M$^{-1}$ s$^{-1}$ or alternatively less than 1.0E-04 M$^{-1}$ s$^{-1}$, or alternatively less than 9.0E-05 M$^{-1}$ s$^{-1}$, or alternatively less than 8.0E-05 M$^{-1}$ s$^{-1}$, or alternatively less than 7.0E-05 M$^{-1}$ s$^{-1}$, or alternatively less than 6.0E-05 M$^{-1}$ s$^{-1}$, or alternatively less than 5.0E-05 M$^{-1}$ s$^{-1}$, or alternatively less than 4.0E-05 M$^{-1}$ s$^{-1}$, or alternatively less than 3.0E-05 M$^{-1}$ s$^{-1}$, or alternatively less than 2.0E-05 M$^{-1}$ s$^{-1}$ or alternatively less than 1.0E-05 M$^{-1}$ s$^{-1}$. In one embodiment, such $K_{on}$ is determined using the surface plasmon resonance (SPR) methods shown in the Examples.

In some aspects of this invention, the association constant $K_A$ for the IhfA5-mIhfB4$_{NTHI}$ Tip chimeric peptide (in 1/M) is about 3E+05 to about 2E+08. In another aspect, the $K_A$ is about 3E+05 to about 1E+08, or alternatively about 2E+05 to about 1E+08, or alternatively about 1E+05 to about 1E+08, or alternatively about 1E+06 to about 1E+08, or alternatively about 1E+07 to about 1E+08, or alternatively about 1E+04 to about 1E+09, alternatively about 1E+05 to about 1E+09, alternatively about 1E+06 to about 1E+09, alternatively about 1E+07 to about 1E+09, alternatively about 1E+08 to about 1E+09, alternatively about 1E+04 to about 1E+09, or alternatively about 1E+03 to about 1E+10.

In another aspect, the dissociation constant $K_D$ for the IhfA5-mIhfB4$_{NTHI}$ Tip chimeric peptide (in M) is about 5E-09 to about 3E-06, or alternatively about 1E-09 to about 1E-06, or alternatively about 1E-08 to about 1E-05, or alternatively about 1E-07 to about 1E-05, or alternatively about 1E-06 to about 1E-05, or alternatively about 1E-09 to about 1E-08, or alternatively about 1E-08 to about 1E-07, or alternatively about 1E-9 to about 1E-08, or alternatively about 1E-10 to about 1E-09, or alternatively about 1E-11 to about 1E-10.

In one aspect, the $K_A$ for the IhfA3-IhfB2$_{NTHI}$ Tail chimeric peptide (in 1/M) is from about 7E+06 to about 2E+09, or alternatively about 1E+05 to about 1E+08, or alternatively about 1E+06 to about 1E+08, or alternatively about 1E+07 to about 1E+08, or alternatively about 1E+04 to about 1E+09, alternatively about 1E+05 to about 1E+09, alternatively about 1E+06 to about 1E+09, alternatively about 1E+07 to about 1E+09, alternatively about 1E+08 to about 1E+09, alternatively about 1E+04 to about 1E+09, or alternatively about 1E+03 to about 1E+10, or alternatively about 1E+03 to about 1E+11, or alternatively about 1E+03 to about 1E+12, or alternatively about 1E+09 to about 1E+10, or alternatively about 1E+10 to about 1E+11, or alternatively about 1E+11 to about 1E+12.

In another aspect, the $K_D$ for the IhfA3-IhfB2$_{NTHI}$ Tail chimeric peptide (in M) is about 6E-10 to about 2E-07, or alternatively about 1E-09 to about 1E-06, or alternatively about 1E-08 to about 1E-05, or alternatively about 1E-07 to about 1E-05, or alternatively about 1E-06 to about 1E-05, or alternatively about 1E-09 to about 1E-08, or alternatively about 1E-08 to about 1E-07, or alternatively about 1E-9 to about 1E-08, or alternatively about 1E-10 to about 1E-09, or alternatively about 1E-11 to about 1E-10, or alternatively about 1E-11 to about 1E-12.

In some of the aspects of the antibodies provided herein, the antibody, fragment thereof, polypeptide or CDR that binds the tip region of a DNABII protein (including but not limited to: a tip region of IHF or HU, a tip region of IHFA or IHFB, and/or the tip-chimeric peptide IhfA5-mIhfB4$_{NTHI}$) reduces biomass of a biofilm in vitro by at least about 10%, or alternatively at least about 15%, or alternatively at least about 20%, or alternatively at least about 25%, or alternatively at least about 30%, or alternatively at least about 35%, or alternatively at least about 40%, or alternatively at least about 45%, or alternatively at least about 50%, or alternatively at least about 55%, or alternatively at least about 60%, or alternatively at least about 65%, or alternatively at least about 70%, or alternatively at least about 75%, or alternatively at least about 80%, or alternatively at least about 85%, or alternatively at least about 90%, or alternatively at least about 95%. In some of the aspects of the antibodies provided herein, the antibody, fragment thereof, polypeptide or CDR that binds the tail region of a DNABII protein (including but not limited to: a tail region of IHF or HU, a tail region of IHFA or IHFB, and/or the tail-chimeric peptide IhfA3-IhfB2$_{NTHI}$) reduces biomass of a biofilm in vitro by less than about 1%, or alternatively less than about 2%, or alternatively less than about 3%, or alternatively less than about 4%, or alternatively less than about 5%, or alternatively less than about 6%, or alternatively less than about 7%, or alternatively less than about 8%, or alternatively less than about 9%, or alternatively less than about 10%, or alternatively less than about 12%, or alternatively less than about 15%, or alternatively less than about 20%, or alternatively less than about 25%, or alternatively less than about 30%, or alternatively less than about 35%, or alternatively less than about 40%, or alternatively less than about 45%, or alternatively less than about 50%. In one embodiment, such biomass change is determined using the methods shown in Example 3 or 4.

In some of the aspects of the antibodies provided herein, the antibody, fragment thereof, polypeptide or CDR that binds the tip region of a DNABII protein (including but not limited to: a tip region of IHF or HU, a tip region of IHFA or IHFB, and/or the tip-chimeric peptide IhfA5-mIhfB4$_{NTHI}$) reduces bacterial load in a subject by at least about 10%, or alternatively at least about 15%, or alternatively at least about 20%, or alternatively at least about 25%, or alternatively at least about 30%, or alternatively at least about 35%, or alternatively at least about 40%, or alternatively at least about 45%, or alternatively at least about 50%, or alternatively at least about 55%, or alternatively at least about 60%, or alternatively at least about 65%, or alternatively at least about 70%, or alternatively at least about 75%, or alternatively at least about 80%, or alternatively at least about 85%, or alternatively at least about 90%, or alternatively at least about 91%, or alternatively at least about 92%, or alternatively at least about 93%, or alternatively at least about 94%, or alternatively at least about 95%, or alternatively at least about 96%, or alternatively at least about 97%, or alternatively at least about 98%, or alternatively at least about 99%. In some of the aspects of the antibodies provided herein, the antibody, fragment thereof, polypeptide or CDR that binds the tail region of a DNABII protein (including but not limited to: a tail region of IHF or HU, a tail region of IHFA or IHFB, and/or the tail-chimeric peptide IhfA3-IhfB2$_{NTHI}$) reduces bacterial load in a subject by less than about 1%, or alternatively less than about 2%, or alternatively less than about 3%, or alternatively less than about 4%, or alternatively less than about 5%, or alternatively less than about 6%, or alternatively less than about 7%, or alternatively less than about 8%, or alternatively less than about 9%, or alternatively less than about 10%, or alternatively less than about 12%, or alternatively less than about 15%, or alternatively less than about 20%, or alternatively less than about 25%, or alternatively less than about 30%, or alternatively less than about 35%, or alternatively less than about 40%, or alternatively less than about 45%, or alternatively less than about 50%. In one embodiment, such change in the bacterial load is determined using the methods shown in the Examples.

In some of the aspects of the antibodies provided herein, the antibody, fragment thereof, polypeptide or CDR that binds the tip region of a DNABII protein (including but not limited to: a tip region of IHF or HU, a tip region of IHFA or IHFB, and/or the tip-chimeric peptide IhfA5-mIhfB4$_{NTHI}$) reduces middle ear occlusion in a subject having otitis media (OM) by at least about 10%, or alternatively at least about 15%, or alternatively at least about 20%, or alternatively at least about 25%, or alternatively at least about 30%, or alternatively at least about 35%, or alternatively at least about 40%, or alternatively at least about 45%, or alternatively at least about 50%, or alternatively at least about 55%, or alternatively at least about 60%, or alternatively at least about 65%, or alternatively at least about 70%, or alternatively at least about 75%, or alternatively at least about 80%, or alternatively at least about 85%, or alternatively at least about 90%, or alternatively at least about 91%, or alternatively at least about 92%, or alternatively at least about 93%, or alternatively at least about 94%, or alternatively at least about 95%, or alternatively at least about 96%, or alternatively at least about 97%, or alternatively at least about 98%, or alternatively at least about 99%. In some of the aspects of the antibodies provided herein, the antibody, fragment thereof, polypeptide or CDR that binds the tail region of a DNABII protein (including but not limited to: a tail region of IHF or HU, a tail region of IHFA or IHFB, and/or the tail-chimeric peptide IhfA3-IhfB2$_{NTHI}$) reduces middle ear occlusion in a subject having otitis media (OM) by less than about 1%, or alternatively less than about 2%, or alternatively less than about 3%, or alternatively less than about 4%, or alternatively less than about 5%, or alternatively less than about 6%, or alternatively less than about 7%, or alternatively less than about 8%, or alternatively less than about 9%, or alternatively less than about 10%, or alternatively less than about 12%, or alternatively less than about 15%, or alternatively less than about 20%, or alternatively less than about 25%, or alternatively less than about 30%, or alternatively less than about 35%, or alternatively less than about 40%, or alternatively less than about 45%, or alternatively less than about 50%. In one embodiment, such change in middle ear occlusion is determined using the methods shown in the Examples in an experimental OM model.

In some of the aspects of the antibodies provided herein, the antibody, fragment thereof, polypeptide or CDR that binds the tip region of a DNABII protein (including but not limited to: a tip region of IHF or HU, a tip region of IHFA or IHFB, and/or the tip-chimeric peptide IhfA5-mIhfB4$_{NTHI}$) reduces the relative mucosal biofilm score and/or biomass score in a subject having a mucosal biofilm (such as having OM) by at least about 10%, or alternatively at least about 15%, or alternatively at least about 20%, or alternatively at least about 25%, or alternatively at least about 30%, or alternatively at least about 35%, or alternatively at least about 40%, or alternatively at least about 45%, or alternatively at least about 50%, or alternatively at least about 55%, or alternatively at least about 60%, or alternatively at least about 65%, or alternatively at least about 70%, or alternatively at least about 75%, or alternatively at least about 80%, or alternatively at least about 85%, or alternatively at least about 90%, or alternatively at least about 91%, or alternatively at least about 92%, or alternatively at least about 93%, or alternatively at least about 94%, or alternatively at least about 95%, or alternatively at least about 96%, or alternatively at least about 97%, or alternatively at least about 98%, or alternatively at least about 99%. In one embodiment, the antibody, fragment thereof, polypeptide or CDR that binds the tip region of a DNABII protein (including but not limited to: a tip region of IHF or HU, a tip region of IHFA or IHFB, and/or the tip-chimeric peptide IhfA5-mIhfB4$_{NTHI}$) reduces the relative mucosal biofilm score and/or biomass score in a subject having a mucosal biofilm (such as having OM) by at least about 0.5, or alternatively at least about 1, or alternatively at least about 1.5, or alternatively at least about 2, or alternatively at least about 2.5, or alternatively at least about 3, or alternatively at least about 3.5, or alternatively at least about 4. In some of the aspects of the antibodies provided herein, the antibody, fragment thereof, polypeptide or CDR that binds the tail region of a DNABII protein (including but not limited to: a tail region of IHF or HU, a tail region of IHFA or IHFB, and/or the tail-chimeric peptide IhfA3-IhfB2$_{NTHI}$) reduces the relative mucosal biofilm score and/or biomass score in a subject having a mucosal biofilm (such as having OM) by less than about 1%, or alternatively less than about 2%, or alternatively less than about 3%, or alternatively less than about 4%, or alternatively less than about 5%, or alternatively less than about 6%, or alternatively less than about 7%, or alternatively less than about 8%, or alternatively less than about 9%, or alternatively less than about 10%, or alternatively less than about 12%, or alternatively less than about 15%, or alternatively less than about 20%, or alternatively less than about 25%, or alternatively less than about 30%, or alternatively less than about 35%, or alternatively less than about 40%, or alternatively less than about 45%, or alternatively less than about 50%. In some of the aspects of the antibodies provided herein, the antibody, fragment thereof, polypeptide or CDR that binds the tail region of a DNABII protein (including but not limited to: a tail region of IHF or HU, a tail region of IHFA or IHFB, and/or the tail-chimeric peptide IhfA3-IhfB2$_{NTHI}$) reduces the relative mucosal biofilm score and/or biomass score in a subject having a mucosal biofilm (such as having OM) by less than about 0.1, or alternatively less than about 0.2, or alternatively less than about 0.3, or alternatively less than about 0.4, or alternatively less than about 0.5, or alternatively less than about 0.6, or alternatively less than about 0.7, or alternatively less than about 0.8, or alternatively less than about 0.9, or alternatively less than about 1, or alternatively less than about 1.5, or alternatively less than about 2, or alternatively less than about 2.5. In one embodiment, such score is determined using the methods shown in the Examples.

In certain embodiments, the DNABII protein is an HU or an IHF. In a further embodiment, the DNABII protein is an IhfA, an IhfB or both. In yet a further embodiment, the antibody, fragment thereof, polypeptide or CDR binds the tip region or the tail region of the DNABII protein (including but not limited to: a tip region of IHF or HU, a tip region of IHFA or IHFB, the tip-chimeric peptide IhfA5-mIhfB4$_{NTHI}$, a tail region of IHF or HU, a tail region of IHFA or IHFB, and/or the tail-chimeric peptide IhfA3-IhfB2$_{NTHI}$). In one embodiment, the antibody, fragment thereof, polypeptide or CDR binds the IhfA5-mIhfB4$_{NTHI}$ Tip chimeric peptide. In another embodiment, the antibody, fragment thereof, polypeptide or CDR binds the IhfA3-IhfB2$_{NTHI}$ Tail chimeric peptide.

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some of the aspects of the antibodies provided herein, the antibody is a full-length antibody.

In some of the aspects of the antibodies provided herein, the antibody is chimeric or humanized.

In some of the aspects of the antibodies provided herein, the antibody comprises an Fc domain. In some of the aspects of the antibodies provided herein, the antibody is a non-human animal such as a rat, sheep, bovine, canine, feline or rabbit antibody. In some of the aspects of the antibodies provided herein, the antibody is a human or humanized antibody or is non-immunogenic in a human.

In some of the aspects of the antibodies provided herein, the antibody comprises a human antibody framework region. Examples of framework regions that can be fused to the LC and HC sequences are known in the art, examples of such are provided in SEQ ID NOs: 15-23, or equivalents of each thereof.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families.

1) Amino acids with basic side chains: lysine, arginine, histidine.

2) Amino acids with acidic side chains: aspartic acid, glutamic acid

3) Amino acids with uncharged polar side chains: asparagine, glutamine, serine, threonine, tyrosine.

4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising such varied CDR sequences still bind a DNABII protein with similar specificity and sensitivity profiles as the disclosed antibodies. This may be tested by way of the binding assays, such as ELISA or SPR.

In a further aspect, the antibodies are characterized by being both immunodominant and immunoprotective, as determined using appropriate assays and screens.

In another aspect, the antibodies can be modified by conventional techniques, that may in one aspect increase the half-life of the antibody, e.g., PEGylation, a PEG mimetic, polysialyation, HESylation or glycosylation.

The antibodies and antigen binding fragments can further comprise a detectable marker or a purification marker.

Antibodies and Derivatives Thereof

This disclosure also provides an antibody that binds and/or specifically recognizes and binds an isolated polypeptide for use in the methods disclosed herein. The antibody can be any of the various antibodies described herein, non-limiting, examples of such include a polyclonal antibody, a monoclonal antibody, a chimeric antibody, a human antibody, a veneered antibody, a diabody, a humanized antibody, an antibody derivative, a recombinant humanized antibody, or an equivalent (such as a derivative) or fragment of each thereof. In one aspect, the fragment comprises, or alternatively consists essentially of, or yet further consists of the CDR of the antibody. In one aspect, the antibody is detectably labeled or further comprises a detectable label conjugated to it.

Also provided is a hybridoma cell line that produces a monoclonal antibody disclosed herein. Compositions comprising or alternatively consisting essentially of or yet further, consisting of one or more of the above embodiments are further provided herein. Further provided are polynucleotides that encode the amino acid sequence of the antibodies and fragments as well as methods to produce recombinantly or chemically synthesize the antibody polypeptides and fragments thereof. The antibody polypeptides can be produced in a eukaryotic or prokaryotic cell, or by other methods known in the art and described herein.

Examples of CDR sequences include without limitation comprise, consist essentially of, or yet further consist of, the following: the heavy chain variable region of the antibody or a fragment thereof comprises, or alternatively consists essentially of, or yet further consists of, the polypeptide encoded by the below polynucleotide sequence:

Antibodies can be generated using conventional techniques known in the art and are well-described in the literature. Several methodologies exist for production of polyclonal antibodies. For example, polyclonal antibodies are typically produced by immunization of a suitable mammal such as, but not limited to, chickens, goats, guinea pigs, hamsters, horses, mice, rats, and rabbits. An antigen is injected into the mammal, induces the B-lymphocytes to produce immunoglobulins specific for the antigen. Immunoglobulins may be purified from the mammal's serum.

Variations of this methodology include modification of adjuvants, routes and site of administration, injection volumes per site and the number of sites per animal for optimal production and humane treatment of the animal. For example, adjuvants typically are used to improve or enhance an immune response to antigens. Most adjuvants provide for an injection site antigen depot, which allows for a stow release of antigen into draining lymph nodes. Other adjuvants include surfactants which promote concentration of protein antigen molecules over a large surface area and immunostimulatory molecules. Non-limiting examples of adjuvants for polyclonal antibody generation include Freund's adjuvants, Ribi adjuvant system, and Titermax. Polyclonal antibodies can be generated using methods known in the art some of which are described in U.S. Pat. Nos. 7,279,559; 7,119,179; 7,060,800; 6,709,659; 6,656,746; 6,322,788; 5,686,073; and 5,670,153.

Monoclonal antibodies can be generated using conventional hybridoma techniques known in the art and well described in the literature. For example, a hybridoma is produced by fusing a suitable immortal cell line (e.g., a myeloma cell line such as, but not limited to, Sp2/0, Sp2/0-AG14, NSO, NS1, NS2, AE-1, L.5, P3X63Ag8,653, Sp2 SA3, Sp2 MAI, Sp2 SS1, Sp2 SA5, U397, MIA 144, ACT IV, MOLT4, DA-1, JURKAT, WEHI, K-562, COS, RAJI, NIH 313, HL-60, MLA 144, NAMAIWA, NEURO 2A, CHO, PerC.6, YB2/O) or the like, or heteromyelomas, fusion products thereof, or any cell or fusion cell derived there from, or any other suitable cell line as known in the art (see, those at the following web addresses, e.g., atcc.org, lifetech.com, last accessed on Nov. 26, 2007), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. Antibody producing cells can also be obtained from the peripheral blood or, in particular embodiments, the spleen or lymph nodes, of humans or other suitable animals that have been immunized with the antigen of interest and then screened for the activity of interest. Any other suitable host cell can also be used for expressing-heterologous or endogenous nucleic acid encoding an antibody, specified fragment or variant thereof, of the present disclosure. The fused cells (hybridomas) or recombinant cells can be isolated using selective culture conditions or other suitable known methods, and cloned by limiting dilution or cell sorting, or other known methods.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, cDNA, or the like, display library; e.g., as available from various commercial vendors such as MorphoSys (Martinsreid/Planegg, Del.), BioInvent (Lund, Sweden), Affitech (Oslo, Norway) using methods known in the art. Art known methods are described in the patent literature some of which include U.S. Pat. Nos. 4,704,692; 5,723,323; 5,763,192; 5,814,476; 5,817,483; 5,824,514; and 5,976,862. Alternative methods rely upon immunization of transgenic animals (e.g., SCID mice, Nguyen et al. (1977) Microbiol. Immunol. 41:901-907 (1997); Sandhu et al. (1996) Crit, Rev. Biotechnol. 16:95-118; Eren et al. (1998) Mumma 93:154-161 that are capable of producing a repertoire of human antibodies, as known in the art and/or as described herein. Such techniques, include, but are not limited to, ribosome display Wanes et al. (1997) Proc. Natl. Acad. Sci. USA 94:4937-4942; Hanes et al. (1998) Proc. Natl. Acad. Sci. USA 95:14130-14135); single cell antibody producing technologies (e.g., selected lymphocyte antibody method ("SLAM") (U.S. Pat. No. 5,627,052; Wen et al. (1987) J. Immunol 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.); Gray et al. (1995) J. Imm. Meth. 182:155-163; and Kenny et al. (1995) Bio. Technol. 13:787-790); B-cell selection (Steenbakkers et al. (1994) Molec. Biol. Reports 19:125-134).

Antibody derivatives of the present disclosure can also be prepared by delivering a polynucleotide encoding an antibody disclosed herein to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873, 316; 5,849,992; 5,994,616; 5,565,362; and 5,304,489.

The term "antibody derivative" includes post-translational modification to linear polypeptide sequence of the antibody or fragment. For example, U.S. Pat. No. 6,602,684 B1 describes a method for the generation of modified glycol-forms of antibodies, including whole antibody molecules, antibody fragments, or fusion proteins that include a region equivalent to the Fc region of an immunoglobulin, having enhanced Fe-mediated cellular toxicity, and glycoproteins so generated.

The antibodies disclosed herein also include derivatives that are modified by the covalent attachment of any type of molecule to the antibody such that covalent attachment does not prevent the antibody from generating an anti-idiotypic response. Antibody derivatives include, but are not limited to, antibodies that have been modified by glycosylation, acetylation, pegylation, phosphorylation, amidation, derivatization by known protecting/blocking groups, proteolytic cleavage, linkage to a cellular ligand or other protein, etc. Additionally, the derivatives may contain one or more non-classical amino acids.

Antibody derivatives also can be prepared by delivering a polynucleotide disclosed herein to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize has been used to express mammalian proteins at commercial production levels, with biological activities equivalent to those produced in other recombinant systems or purified from natural sources. See, e.g., Hood et al. (1999) Adv. Exp. Med. Biol. 464:127-147 and references cited therein. Antibody derivatives have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and references cited therein. Thus, antibodies can also be produced using transgenic plants, according to know methods.

Antibody derivatives also can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids or variable or constant regions from other isotypes.

In general, the CDR residues are directly and most substantially involved in influencing antigen binding. Humanization or engineering of antibodies can be performed using any known method such as, but not limited to, those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

Chimeric, humanized or primatized antibodies of the present disclosure can be prepared based on the sequence of a reference monoclonal antibody prepared using standard molecular biology techniques. DNA encoding the heavy and light chain immunoglobulins can be obtained from the hybridoma of interest and engineered to contain non-reference (e.g., human) immunoglobulin sequences using standard molecular biology techniques. For example, to create a chimeric antibody, the murine variable regions can be linked to human constant regions using methods known in the art (U.S. Pat. No. 4,816,567). To create a humanized antibody, the murine CDR regions can be inserted into a human framework using methods known in the art (U.S. Pat. Nos. 5,225,539 and 5,530,101; 5,585,089; 5,693,762; and 6,180, 370). Similarly, to create a primatized antibody the murine CDR regions can be inserted into a primate framework using methods known in the art (WO 93/02108 and WO 99/55369).

Techniques for making partially to fully human antibodies are known in the art and any such techniques can be used. According to one embodiment, fully human antibody sequences are made in a transgenic mouse which has been engineered to express human heavy and light chain antibody genes. Multiple strains of such transgenic mice have been made which can produce different classes of antibodies. B cells from transgenic mice which are producing a desirable antibody can be fused to make hybridoma cell lines for continuous production of the desired antibody. (See for example, Russel et al. (2000) Infection and Immunity April 2000:1820-1826; Gallo et al. (2000) European J. of Immun. 30:534-540; Green (1999) J. of Immun. Methods 231:11-23; Yang et al. (1999A) J. of Leukocyte Biology 66:401-410; Yang (1999B) Cancer Research 59(6):1236-1243; Jakobovits (1998) Advanced Drug Reviews 31:33-42; Green and Jakobovits (1998) J. Exp. Med. 188(3):483-495; Jakobovits (1998) Exp. Opin. Invest. Drugs 7(4):607-614; Tsuda et al. (1997) Genomics 42:413-421; Sherman-Gold (1997) Genetic Engineering News 17(14); Mendez et al. (1997) Nature Genetics 15:146-156; Jakobovits (1996) Weir's Handbook of Experimental Immunology, The Integrated Immune System Vol. IV, 194.1-194.7; Jakobovits (1995) Current Opinion in Biotechnology 6:561-566; Mendez et al. (1995) Genomics 26:294-307; Jakobovits (1994) Current Biology 4(8):761-763; Arbones et al. (1994) Immunity 1(4):247-260; Jakobovits (1993) Nature 362(6417):255-258; Jakobovits et al. (1993) Proc. Natl. Acad. Sci. USA 90(6):2551-2555; and U.S. Pat. No. 6,075,181.)

The antibodies disclosed herein also can be modified to create chimeric antibodies. Chimeric antibodies are those in which the various domains of the antibodies' heavy and light chains are coded for by DNA from more than one species. See, e.g., U.S. Pat. No. 4,816,567.

Alternatively, the antibodies disclosed herein can also be modified to create veneered antibodies. Veneered antibodies are those in which the exterior amino acid residues of the antibody of one species are judiciously replaced or "veneered" with those of a second species so that the antibodies of the first species will not be immunogenic in the second species thereby reducing the immunogenicity of the antibody. Since the antigenicity of a protein is primarily dependent on the nature of its surface, the immunogenicity of an antibody could be reduced by replacing the exposed residues which differ from those usually found in another mammalian species. This judicious replacement of exterior residues should have little, or no, effect on the interior domains, or on the interdomain contacts. Thus, ligand binding properties should be unaffected as a consequence of alterations which are limited to the variable region framework residues. The process is referred to as "veneering" since only the outer surface or skin of the antibody is altered, the supporting residues remain undisturbed.

The procedure for "veneering" makes use of the available sequence data for human antibody variable domains compiled by Kabat et al. (1987) Sequences of Proteins of Immunological interest, 4th ed., Bethesda, Md., National Institutes of Health, updates to this database, and other accessible U.S. and foreign databases (both nucleic acid and protein). Non-limiting examples of the methods used to generate veneered antibodies include EP 519596; U.S. Pat. No. 6,797,492; and described in Padlan et al. (1991) Mol. Immunol. 28(4-5):489-498.

The term "antibody derivative" also includes "diabodies" which are small antibody fragments with two antigen-binding sites, wherein fragments comprise a heavy chain variable domain (VH) connected to a light chain variable domain (VL) in the same polypeptide chain. (See for example, EP 404,097; WO 93/11161; and Hollinger et al. (1993) Proc. Natl. Acad. Sci. USA 90:6444-6448.) By using a linker that is too short to allow pairing between the two domains on the same chain, the domains are forced to pair with the complementary domains of another chain and create two antigen-binding sites. (See also, U.S. Pat. No. 6,632,926 to Chen et al., which discloses antibody variants that have one or more amino acids inserted into a hypervariable region of the parent antibody and a binding affinity for a target antigen which is at least about two fold stronger than the binding affinity of the parent antibody for the antigen).

The term "antibody derivative" further includes engineered antibody molecules, fragments and single domains such as scFv, dAbs, nanobodies, minibodies, Unibodies, and Affibodies & Hudson (2005) Nature Biotech 23(9):1126-36; U.S. Pat. Application Publication No. 2006/0211088; PCT International Application Publication No. WO 2007/059782; U.S. Pat. No. 5,831,012).

The term "antibody derivative" further includes "linear antibodies". The procedure for making linear antibodies is known in the art and described in Zapata et al. (1995) Protein Eng. 8(10):1057-1062. Briefly, these antibodies comprise a pair of tandem Ed segments ($V_H$-$C_H$1-$V_H$-$C_H$1) which form a pair of antigen binding regions. Linear antibodies can be bispecific or monospecific.

The antibodies disclosed herein can be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Antibodies of the present disclosure include naturally purified products, products of chemical synthetic procedures, and products produced by recombinant techniques from a eukaryotic host, including, for example, yeast, higher plant, insect and mammalian cells, or alternatively from a prokaryotic host as described above. A number of antibody production systems are described in Birch & Radner (2006) Adv. Drug Delivery Rev. 58: 671-685.

If an antibody being tested binds with protein or polypeptide, then the antibody being tested and the antibodies provided by this disclosure are equivalent. It also is possible to determine without undue experimentation, whether an antibody has the same specificity as the antibody disclosed herein by determining whether the antibody being tested prevents an antibody disclosed herein from binding the protein or polypeptide with which the antibody is normally reactive. If the antibody being tested competes with the antibody disclosed herein as shown by a decrease in binding by the monoclonal antibody disclosed herein, then it is likely that the two antibodies bind to the same or a closely related epitope. Alternatively, one can pre-incubate the antibody disclosed herein with a protein with which it is normally reactive, and determine if the antibody being tested is inhibited in its ability to bind the antigen. If the antibody being tested is inhibited then, in all likelihood, it has the same, or a closely related, epitopic specificity as the antibody disclosed herein.

The term "antibody" also is intended to include antibodies of all immunoglobulin isotypes and subclasses. Particular isotypes of a monoclonal antibody can be prepared either directly by selecting from an initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. USA 82:8653 or Spira et al. (1984) J. Immunol. Methods 74:307. Alternatively, recombinant DNA techniques may be used.

The isolation of other monoclonal antibodies with the specificity of the monoclonal antibodies described herein can also be accomplished by one of ordinary skill in the art by producing anti-idiotypic antibodies. Herlyn et al. (1986) Science 232:100. An anti-idiotypic antibody is an antibody which recognizes unique determinants present on the monoclonal antibody of interest.

In some aspects disclosed herein, it will be useful to detectably or therapeutically label the antibody. Suitable labels are described supra. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample.

The coupling of antibodies to low molecular weight haptens can increase the sensitivity of the antibody in an assay. The haptens can then be specifically detected by means of a second reaction. For example, it is common to use haptens such as biotin, which reacts avidin, or dinitrophenol, pyridoxal, and fluorescein, which can react with specific anti-hapten antibodies. See, Harlow and Lane (1988) supra.

The variable region of the antibodies of the present disclosure can be modified by mutating amino acid residues within the VH and/or VL CDR 1, CDR 2 and/or CDR 3 regions to improve one or more binding properties (e.g., affinity) of the antibody. Mutations may be introduced by site-directed mutagenesis or PCR-mediated mutagenesis and the effect on antibody binding, or other functional property of interest, can be evaluated in appropriate in vitro or in vivo assays. In certain embodiments, conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

In addition, the antibodies disclosed herein may be engineered to include modifications within the Fc region to alter one or more functional properties of the antibody, such as serum half-fife, complement fixation, Fc receptor binding, and/or antigen-dependent cellular cytotoxicity. Such modifications include, but are not limited to, alterations of the number of cysteine residues in the hinge region to facilitate assembly of the light and heavy chains or to increase or decrease the stability of the antibody (U.S. Pat. No. 5,677,425) and amino acid mutations in the Fc hinge region to decrease the biological half-life of the antibody (U.S. Pat. No. 6,165,745).

Additionally, the antibodies disclosed herein may be chemically modified. Glycosylation of an antibody can be altered, for example, by modifying one or more sites of glycosylation within the antibody sequence to increase the affinity of the antibody for antigen (U.S. Pat. Nos. 5,714,350 and 6,350,861). Alternatively, to increase antibody-dependent cell-mediated cytotoxicity, a hypofucosylated antibody having reduced amounts of fucosyl residues or an antibody having increased bisecting GlcNac structures can be obtained by expressing the antibody in a host cell with altered glycosylation mechanism (Shields, R. L. et al. (2002) J. Biol. Chem. 277:26733-26740; Umana et al. (1999) Nat. Biotech. 17:176-180).

The antibodies disclosed herein can be pegylated to increase biological half-life by reacting the antibody or fragment thereof with polyethylene glycol (PEG) or a reactive ester or aldehyde derivative of PEG, under conditions in which one or more PEG groups become attached to the antibody or antibody fragment. Antibody pegylation may be carried out by an acylation reaction or an alkylation reaction with a reactive PEG molecule (or an analogous reactive water soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to the antibodies disclosed herein (EP 0154316 and EP 0401384).

Additionally, antibodies may be chemically modified by conjugating or fusing the antigen-binding region of the antibody to serum protein, such as human serum albumin, to increase half-life of the resulting molecule. Such approach is for example described in EP 0322094 and EP 0486525.

The antibodies or fragments thereof of the present disclosure may be conjugated to a diagnostic agent and used diagnostically, for example, to monitor the development or progression of a disease and determine the efficacy of a given treatment regimen. Examples of diagnostic agents include enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or fragment thereof, or indirectly, through a linker using techniques known in the art. Examples of suitable enzymes include horseradish peroxidase, alkaline phosphatase, beta-galactosidase, or acetylcholinesterase. Examples of suitable prosthetic group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of bioluminescent materials include luciferase, luciferin, and aequorin. Examples of suitable radioactive material include $^{125}$I, $^{131}$I, Indium-111, Lutetium-171, Bismuth-212, Bismuth-213, Astatine-211, Copper-62, Copper-64, Copper-67, Yttrium-90, Iodine-125, Iodine-131, Phosphorus-32, Phosphorus-33, Scandium-47, Silver-111, Gallium-67, Praseodymium-142, Samarium-153, Terbium-161, Dysprosium-166, Holmium-166, Rhenium-186, Rhenium-188, Rhenium-189, Lead-212, Radium-223, Actinium-225, Iron-59, Selenium-75, Arsenic-77, Strontium-89, Molybdenum-99, Rhodium-1105, Palladium-109, Praseodymium-143, Promethium-149, Erbium-169, Iridium-194, Gold-198, Gold-199, and Lead-211. Monoclonal antibodies may be indirectly conjugated with radiometal ions through the use of bifunctional chelating agents that are covalently linked to the antibodies. Chelating agents may be attached through amities (Meares et al. (1984) Anal. Biochem. 142:68-78); sulfhydral groups (Koyama (1994) Chem. Abstr. 120:217-262) of amino acid residues and carbohydrate groups (Rodwell et al. (1986) PNAS USA 83:2632-2636; Quadri et al. (1993) Nucl. Med. Biol. 20:559-570).

Further, the antibodies or fragments thereof of the present disclosure may be conjugated to a therapeutic agent. Suitable therapeutic agents include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin, antimetabolites (such as methotrexate, 6-mercaptopurine, 6-thioguanine, cytarabine, fludarabin, 5-fluorouracil, decarbazine, hydroxyurea, asparaginase, gemcitabinc, cladribine), alkylating agents (such as mechlorethamine, thioepa, chloramhucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), diphtheria toxin and related molecules (such as diphtheria A chain and active fragments thereof and hybrid molecules), ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alpha-sarcin, *Aleurites fordii* proteins, dianthin proteins, *Phytolacca* americanaproteins (PAPI, PAPII, and PAP-S), *Momordica charantia* inhibitor, curcin, crotin, *Sapaonaria officinalis* inhibitor, gelonin, mitogellin, restrietocin, phenomycin, enomycin toxins and mixed toxins.

Additional suitable conjugated molecules include ribonuclease (RNase), DNase I, an antisense nucleic acid, an inhibitory RNA molecule such as a siRNA molecule, an immunostimulatory nucleic acid, aptamers, ribozymes, triplex forming molecules, and external guide sequences. Aptamers are small nucleic acids ranging from 15-50 bases in length that fold into defined secondary and tertiary structures, such as stem-loops or G-quartets, and can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Ribozymes are nucleic acid molecules that are capable of catalyzing a chemical reaction, either intramolecularly or intermolecularly. Ribozymes typically cleave nucleic acid substrates through recognition and binding of the target substrate with subsequent cleavage. Triplex forming function nucleic acid molecules can interact with double-stranded or single-stranded nucleic acid by forming a triplex, in which three strands of DNA form a complex dependent on both Watson-Crick and Hoogsteen base-pairing. Triplex molecules can bind target regions with high affinity and specificity.

The functional nucleic acid molecules may act as effectors, inhibitors, modulators, and stimulators of a specific activity possessed by a target molecule, or the functional nucleic acid molecules may possess a de novo activity independent of any other molecules.

The therapeutic agents can be linked to the antibody directly or indirectly, using any of a large number of available methods. For example, an agent can be attached at the hinge region of the reduced antibody component via disulfide bond formation, using cross-linkers such as N-succinyl 3-(2-pyridyldithio)proprionate (SPDP), or via a carbohydrate moiety in the Fc region of the antibody (Yu et al. 1994 Int. J. Cancer 56: 244; Upeslacis et al., "Modification of Antibodies by Chemical Methods," in Monoclonal antibodies: principles and applications, Birch et al. (eds.), pages 187-230 (Wiley-Liss, Inc. 1995); Price, "Production and Characterization of Synthetic Peptide-Derived Antibodies," in Monoclonal antibodies: Production, engineering and clinical application, Ritter et al. (eds.), pages 60-84 (Cambridge University Press 1995)).

Techniques for conjugating therapeutic agents to antibodies are well known (Amon et al. "Monoclonal Antibodies For Immunotargeting Of Drugs In Cancer Therapy," in Monoclonal Antibodies And Cancer Therapy; Reisfeld et al. (eds.), pp. 243-56 (Alan R. Liss, Inc. 1985); Hellstrom et al. "Antibodies For Drug Delivery," in Controlled Drug Delivery (2nd Ed.); Robinson et al. (eds.), pp. 623-53 (Marcel Dekker, Inc. 1987); Thorpe "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy," in Monoclonal Antibodies For Cancer Detection And Therapy, Baldwin et al. (eds.), pp. 303-16 (Academic Press 1985), and Thorpe et al. "The Preparation And Cytotoxic Properties Of Antibody-Toxin Conjugates," (1982) Immunol. Rev. 62:119-58).

The antibodies disclosed herein or antigen-binding regions thereof can be linked to another functional molecule such as another antibody or ligand for a receptor to generate a bi-specific or multi-specific molecule that binds to at least two or more different binding sites or target molecules. Linking of the antibody to one or more other binding molecules, such as another antibody, antibody fragment, peptide or binding mimetic, can be done, for example, by chemical coupling, genetic fusion, or noncovalent association. Multi-specific molecules can further include a third binding specificity, in addition to the first and second target epitope.

Bi-specific and multi-specific molecules can be prepared using methods known in the art. For example, each binding unit of the bi-specific molecule can be generated separately and then conjugated to one another. When the binding molecules are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitroberizoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-I-carboxylate (sulfo-SMCC) (Karpovsky et al. (1984) J. Exp. Med. 160:1686; Liu et al. (1985) Proc. Natl. Acad. Sci. USA 82:8648). When the binding molecules are antibodies, they can be conjugated by sulfhydryl bonding of the C-terminus hinge regions of the two heavy chains.

The antibodies or fragments thereof of the present disclosure may be linked to a moiety that is toxic to a cell to which the antibody is bound to form "depleting" antibodies. These antibodies are particularly useful in applications where it is desired to deplete an NK cell.

The antibodies disclosed herein may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

The antibodies also can be bound to many different carriers. Thus, this disclosure also provides compositions containing the antibodies and another substance, active or inert. Examples of well-known carriers include glass, polystyrene, polypropylene, polyethylene, dextran, nylon, amylase, natural and modified cellulose, polyacrylamide, agarose, and magnetite. The nature of the carrier can be either soluble or insoluble for purposes disclosed herein. Those skilled in the art will know of other suitable carriers for binding monoclonal antibodies, or will be able to ascertain such, using routine experimentation.

In certain aspects, the disclosure relates to an antibody or antigen binding fragment that specifically recognizes or binds a tip or tail domain of a DNABII protein or fragment thereof, the tail fragment or tip fragment. The DNABII protein or fragment thereof can be an IHF or an HU polypeptide.

Functional Analysis with Antibodies

Antibodies disclosed herein can be used to purify the polypeptides disclosed herein and to identify biological equivalent polypeptide and/or polynucleotides. They also can be used to identify agents that modify the function of the polypeptides disclosed herein. These antibodies include polyclonal antisera, monoclonal antibodies, and various reagents derived from these preparations that are familiar to those practiced in the art and described above.

Antibodies that neutralize the activities of proteins encoded by identified genes can also be used in vivo and in vitro to demonstrate function by adding such neutralizing antibodies into in vivo and in vitro test systems. They also are useful as pharmaceutical agents to modulate the activity of polypeptides disclosed herein.

Various antibody preparations can also be used in analytical methods such as ELISA assays or Western blots to demonstrate the expression of proteins encoded by the identified genes by test cells in vitro or in vivo. Fragments of such proteins generated by protease degradation during metabolism can also be identified by using appropriate polyclonal antisera with samples derived from experimental samples.

The antibodies disclosed herein may be used for vaccination or to boost vaccination, alone or in combination with peptides or protein-based vaccines or dendritic-cell based vaccines.

Diagnostic and Therapeutic Methods

A method is provided for preventing, or inhibiting, or competing with the binding of a DNABII polypeptide or protein to a microbial DNA, by contacting the DNABII polypeptide or protein or the microbial DNA with an effective amount of one or more of agents as described above, e.g., an antibody or antigen binding fragment thereof, a polypeptide or CDR as disclosed herein, thereby preventing or inhibiting or competing with the binding of the DNABII protein or polypeptide to the microbial DNA. The DNABII polypeptide can be an IHF or HU peptide. In one aspect, the antibody or antigen binding fragment thereof selectively binds to a tip region of the DNABII polypeptide (including but not limited to: a tip region of IHF or HU, a tip region of IHFA or IHFB, and/or the tip-chimeric peptide IhfA5-mIhfB4$_{NTHI}$). In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 24 or an equivalent thereof, and/or a light chain (LC) immunoglobulin variable domain sequence comprising, or consisting essentially of, or yet further consisting of an amino acid sequence of SEQ ID NO: 25 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 1, 2 or 3, or an equivalent of each thereof, and/or a light chain (LC) immunoglobulin variable domain sequence comprising, or consisting essentially of, or yet further consisting of an amino acid sequence selected from the group of SEQ ID NOs: 7, 8 or 9, or an equivalent of each thereof. In yet a further embodiment, the contacting is in vivo or in vitro.

In another aspect, the antibody or an antigen binding fragment thereof for use in a method as disclosed herein, comprises or consists essentially of, or yet further consists of: a heavy chain (HC) immunoglobulin variable domain sequence comprising a sequence selected from the group of SEQ ID NO: 13, 24, or 26, or an equivalent of each thereof; and/or a light chain (LC) immunoglobulin variable domain sequence comprising a sequence selected from the group of SEQ ID NO: 14, 25,or 27, or an equivalent of each thereof.

In a further aspect, one or more of the DNABII polypeptide and/or the microbial DNA and/or the antibody or antigen binding fragment thereof and/or the polypeptide or CDRs as disclosed herein are detectably labeled, for example with a radioisotope or luminescent molecules that will emit a signal when brought into close contact with each other. The contacting can be performed in vitro or in vivo. These methods can be combined with diagnostic methods to detect and/or monitor biofilm formation and/or disruption, for example, using one or more of the DNABII polypeptide and/or the microbial DNA and/or the antibody or antigen binding fragment thereof and/or the polypeptide or CDRs as disclosed herein. In one aspect, the diagnostic methods comprise the use of an antibody or antigen binding fragment as disclosed herein that in one aspect, specifically binds to a tail region or fragment of a DNABII polypeptide (including but not limited to: a tail region of IHF or HU, a tail region of IHFA or IHFB, and/or the tail-chimeric peptide IhfA3-IhfB2$_{NTHI}$). In a further aspect, the antibody or antigen binding fragment are detectably labeled. In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 26 or an equivalent thereof, and/or a light chain (LC) immunoglobulin variable domain sequence comprising, or consisting essentially of, or yet further consisting of an amino acid sequence of SEQ ID NO: 27 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 4, 5 or 6, or an equivalent of each thereof, and/or a light chain (LC) immunoglobulin variable domain sequence comprising, or consisting essentially of, or yet further consisting of an amino acid sequence selected from the group of SEQ ID NOs: 10, 11 or 12, or an equivalent of each thereof.

In another aspect, a method for disrupting a microbial biofilm is provided by contacting the biofilm with an effective amount of one or more of agent as described above, e.g., an antibody or antigen binding fragment thereof, a polypeptide, or a CDR, thereby disrupting the microbial biofilm. In one aspect, the antibody or antigen binding fragment thereof selectively binds to a tip region of the DNABII polypeptide (including but not limited to: a tip region of IHF or HU, a tip region of IHFA or IHFB, and/or the tip-chimeric peptide IhfA5-mIhfB4$_{NTHI}$). The DNABII polypeptide can be an IHF or HU peptide. In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 24 or an equivalent thereof, and/or a light chain (LC) immunoglobulin variable domain sequence comprising, or consisting essentially of, or yet further consisting of an amino acid sequence of SEQ ID NO: 25 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 1, 2 or 3, or an equivalent of each thereof, and/or a light chain (LC) immunoglobulin variable domain sequence comprising, or consisting essentially of, or yet further consisting of an amino acid sequence selected from the group of SEQ ID NOs: 7, 8 or 9, or an equivalent of each thereof. In yet a further embodiment, the contacting is in vivo or in vitro.

In one aspect, the microbial biofilm is produced by a microorganism that exports a DNABII polypeptide. The DNABII polypeptide can be an IHF or HU peptide. In a further aspect, one or more of the antibody, antibody fragment, DNABII polypeptide and the microbial DNA are detectably labeled, for example with a radioisotope or luminescent molecules that will emit a signal when brought into close contact with each other. The contacting can be performed in vitro or in vivo. In one aspect, the agent is one or more antibodies and/or antigen binding fragments that are the same or different from each other. In some embodiments, such antibodies or antigen binding fragments are administered alone or in combination with each other, or an agent other than the antibody, or yet a further pharmaceutically effective agent, alone or in combination with a pharmaceutically acceptable carrier. These methods can be combined with diagnostic methods to detect and/or monitor biofilm formation and/or disruption. In one aspect, the diagnostic methods comprise the use of an antibody or antigen binding fragment as disclosed herein that in one aspect, specifically binds to a tail region or tail fragment of a DNABII polypeptide (including but not limited to: a tail region of IHF or HU, a tail region of IHFA or IHFB, and/or the tail-chimeric peptide IhfA3-IhfB2$_{NTHI}$). In a further aspect, the antibody or antigen binding fragment are detectably labeled.

Also provided are methods to prevent formation of or to disrupt a biofilm on a surface comprising, or consisting essentially of, or yet further consisting of, treating the surface susceptible to or containing a biofilm with an effective amount of one or more of an antibody or antigen binding fragment thereof, polypeptide, or CDR as described herein, wherein the antibody or the antigen binding fragment thereof, binds a tip region of a DNABII peptide (including but not limited to: a tip region of IHF or HU, a tip region of IHFA or IHFB, and/or the tip-chimeric peptide IhfA5-mIhfB4$_{NTHI}$). The DNABII polypeptide can be an IHF or HU peptide. In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 26 or an equivalent thereof, and/or a light chain (LC) immunoglobulin variable domain sequence comprising, or consisting essentially of, or yet further consisting of an amino acid sequence of SEQ ID NO: 27 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 4, 5 or 6, or an equivalent of each thereof, and/or a light chain (LC) immunoglobulin variable domain sequence comprising, or consisting essentially of, or yet further consisting of an amino acid sequence selected from the group of SEQ ID NOs: 10, 11 or 12, or an equivalent of each thereof.

In one aspect, the antibody or antigen binding fragment comprises a detectable label. These methods can be combined with diagnostic methods to detect and/or monitor biofilm formation and/or disruption. In one aspect, the diagnostic methods comprise the use of an antibody or antigen binding fragment as disclosed herein that in one aspect, specifically binds to a tail region or fragment of a DNABII polypeptide (including but not limited to: a tail region of IHF or HU, a tail region of IHFA or IHFB, and/or the tail-chimeric peptide IhfA3-IhfB2$_{NTHI}$). In a further aspect, the antibody or antigen binding fragment are detectably labeled. In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 26 or an equivalent thereof, and/or a light chain (LC) immunoglobulin variable domain sequence comprising, or consisting essentially of, or yet further consisting of an amino acid sequence of SEQ ID NO: 27 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 4, 5 or 6, or an equivalent of each thereof, and/or a light chain (LC) immunoglobulin variable domain sequence comprising, or consisting essentially of, or yet further consisting of an amino acid sequence selected from the group of SEQ ID NOs: 10, 11 or 12, or an equivalent of each thereof.

Further provided herein are methods to detect a biofilm in a subject, comprising, or consisting essentially of, or consisting of, administering to the subject an effective amount of one or more of an antibody or the fragment thereof, a polypeptide, or a CDR as disclosed herein to the subject. In one aspect, the diagnostic methods comprise the use of an antibody or antigen binding fragment as disclosed herein that in one aspect, specifically binds to a tail region or fragment of a DNABII polypeptide (including but not limited to: a tail region of IHF or HU, a tail region of IHFA or IHFB, and/or the tail-chimeric peptide IhfA3-IhfB2$_{NTHI}$). The DNABII polypeptide can be an IHF or HU peptide. In a further aspect, the antibody or antigen binding fragment are detectably labeled. In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 26 or an equivalent thereof, and/or a light chain (LC) immunoglobulin variable domain sequence comprising, or consisting essentially of, or yet further consisting of an amino acid sequence of SEQ ID NO: 27 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 4, 5 or 6, or an equivalent of each thereof, and/or a light chain (LC) immunoglobulin variable domain sequence comprising, or consisting essentially of, or yet further consisting of an amino acid sequence selected from the group of SEQ ID NOs: 10, 11 or 12, or an equivalent of each thereof.

Methods to prevent or disrupt a biofilm in a subject are provided. The methods, comprise, or consist essentially of, or consist of, administering to the subject an antibody or the fragment thereof as disclosed herein that binds to a tip region of a DNABII peptide (including but not limited to: a tip region of IHF or HU, a tip region of IHFA or IHFB, and/or the tip-chimeric peptide IhfA5-mIhfB4$_{NTHI}$). In one aspect, methods to prevent or disrupt a biofilm in a subject are provided, comprising, or alternatively consisting of, or yet further consisting of, administering to the subject an effective amount of one or more of the antibody, fragment thereof, polypeptide, or CDR as disclosed herein, and/or an effective amount of one or more of a polynucleotide or a vector encoding the antibody, fragment thereof, polypeptide or CDR. The DNABII peptide can be an IHF or HU peptide. In one aspect, the antibody or antigen binding fragment thereof selectively binds to a tip region of the DNABII polypeptide (including but not limited to: a tip region of IHF or HU, a tip region of IHFA or IHFB, and/or the tip-chimeric peptide IhfA5-mIhfB4$_{NTHI}$). In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 24 or an equivalent thereof, and/or a light chain (LC) immunoglobulin variable domain sequence comprising, or consisting essentially of, or yet further consisting of an amino acid sequence of SEQ ID NO: 25 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 1, 2 or 3, or an equivalent of each thereof, and/or a light chain (LC) immunoglobulin variable domain sequence comprising, or consisting essentially of, or yet further consisting of an amino acid sequence selected from the group of SEQ ID NOs: 7, 8 or 9, or an equivalent of each thereof. In yet a further embodiment, the contacting is in vivo or in vitro. The antibody or antigen binding fragment thereof can be detectably labeled. These methods can be combined with diagnostic methods to detect and/or monitor biofilm formation and/or disruption. In one aspect, the diagnostic methods comprise the use of an antibody or antigen binding fragment as disclosed herein that in one aspect, specifically binds to a tail region or fragment of a DNABII polypeptide (including but not limited to: a tail region of IHF or HU, a tail region of IHFA or IHFB, and/or the tail-chimeric peptide IhfA3-IhfB2$_{NTHI}$). In a further aspect, the antibody or antigen binding fragment are detectably labeled.

Methods to treat a condition characterized by the formation of biofilm in a subject are provided, the methods, comprising, or consisting essentially of, or consisting of, administering to the subject an antibody or the fragment thereof as disclosed herein that binds to a tip region of a DNABII polypeptide (including but not limited to: a tip region of IHF or HU, a tip region of IHFA or IHFB, and/or the tip-chimeric peptide IhfA5-mIhfB4$_{NTHI}$). In one aspect, methods to prevent or treat a condition characterized by the formation of biofilm in a subject are provided by administering to the subject an effective amount of one or more of the antibody, the fragment thereof, polypeptide, or CDR as disclosed herein, and/or an effective amount of one or more of a polynucleotide or a vector encoding the antibody, fragment thereof, polypeptide or CDR. In another aspect, methods for inhibiting, preventing or treating a microbial infection that produces a biofilm in a subject are provided, comprising, or alternatively consisting of, or yet further consisting of, administering to the subject an effective amount of one or more of the antibody, fragment thereof, polypeptide, or CDR as disclosed herein, and/or an effective amount of one or more of a polynucleotide or a vector encoding the antibody, fragment thereof, polypeptide or CDR. The DNABII polypeptide can be an IHF or HU peptide. In one aspect, the antibody or antigen binding fragment thereof selectively binds to a tip region of the DNABII polypeptide (including but not limited to: a tip region of IHF or HU, a tip region of IHFA or IHFB, and/or the tip-chimeric peptide IhfA5-mIhfB4$_{NTHI}$). In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 24 or an equivalent thereof, and/or a light chain (LC) immunoglobulin variable domain sequence comprising, or consisting essentially of, or yet further consisting of an amino acid sequence of SEQ ID NO: 25 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 1, 2 or 3, or an equivalent of each thereof, and/or a light chain (LC) immunoglobulin variable domain sequence comprising, or consisting essentially of, or yet further consisting of an amino acid sequence selected from the group of SEQ ID NOs: 7, 8 or 9, or an equivalent of each thereof. In yet a further embodiment, the contacting is in vivo or in vitro. These methods can be combined with diagnostic methods to detect and/or monitor biofilm formation and/or disruption. In one aspect, the diagnostic methods comprise the use of an antibody or antigen binding fragment as disclosed herein that in one aspect, specifically binds to a tail region or tail fragment of a DNABII polypeptide (including but not limited to: a tail region of IHF or HU, a tail region of IHFA or IHFB, and/or the tail-chimeric peptide IhfA3-IhfB2$_{NTHI}$). In a further aspect, the antibody or antigen binding fragment are detectably labeled.

In the above methods, the biofilm is derived from a gram negative or a gram positive biofilm producing bacteria. Non-limiting examples of conditions are selected from the group of: chronic non-healing wounds, including venous ulcers and diabetic foot ulcers, ear infections, sinus infections, urinary tract infections, gastrointestinal tract ailments, pulmonary infections, respiratory tract infections, cystic fibrosis, chronic obstructive pulmonary disease, catheter-associated infections, indwelling devices associated infections, infections associated with implanted prostheses, osteomyelitis, cellulitis, abscesses, and periodontal disease.

In certain embodiments of a method disclosed herein, administration of one or more of the antibody, fragment thereof, polypeptide, or CDR reduces one or more of pro-inflammatory cytokines in the subject. Non-limiting examples of the pro-inflammatory cytokines includes: IL-10, IL6, IL8, IL12p70, IL17A, Interferon (IFN) and tumor necrosis factor (TNF). Additionally or alternatively, administration of an effective amount of one or more of the antibody, fragment thereof, polypeptide, or CDR increases one or more of anti-inflammatory cytokines in the subject. In one embodiment, the anti-inflammatory cytokines include, but are not limited to, IL10, IL13, IL-1ra, IL-4, IL-11, and transforming growth factor-β (TGF-β).

Also provided are methods for one or more of: inducing a pro-inflammatory response or treating a condition mediated by a reduced inflammatory response in a subject in need thereof, the method comprising, or alternatively consisting essentially of, or yet further consisting of, administering to the subject an effective amount of an antibody that binds to a tail region of a DNABII polypeptide (including but not limited to: a tail region of IHF or HU, a tail region of IHFA or IHFB, and/or the tail-chimeric peptide IhfA3-IhfB2$_{NTHI}$). The DNABII polypeptide can be an IHF or HU peptide. These methods can be combined with diagnostic methods to detect and/or monitor cytokine release or levels in a tissue or the subject. In one aspect, the diagnostic methods comprise the use of an antibody or antigen binding fragment as disclosed herein that in one aspect, specifically binds to a tail region or tail fragment of a DNABII polypeptide (including but not limited to: a tail region of IHF or HU, a tail region of IHFA or IHFB, and/or the tail-chimeric peptide IhfA3-IhfB2$_{NTHI}$). In a further aspect, the antibody or antigen binding fragment is detectably labeled. Non-limiting cytokines include, e.g., IL1beta, IL6, IL8, IL12p70, IL10, IL13 and IFN.

Also provided are methods for one of more of inhibiting a pro-inflammatory response or treating a condition mediated by an enhanced inflammatory response in a subject in need thereof, the method comprising, or alternatively consisting essentially of, or yet further consisting of, administering to the subject an effective amount of an antibody or antigen binding fragment thereof binds to a tip region of a DNABII polypeptide (including but not limited to: a tip region of IHF or HU, a tip region of IHFA or IHFB, and/or the tip-chimeric peptide IhfA5-mIhfB4$_{NTHI}$). The DNABII polypeptide can be an IHF or HU peptide. These methods can be combined with diagnostic methods to detect and/or monitor cytokine release or levels in a tissue or the subject. In one aspect, the diagnostic methods comprise the use of an antibody or antigen binding fragment as disclosed herein that in one aspect, specifically binds to a tail region or tail fragment of a DNABII polypeptide (including but not limited to: a tail region of IHF or HU, a tail region of IHFA or IHFB, and/or the tail-chimeric peptide IhfA3-IhfB2$_{NTHI}$). In a further aspect, the antibody or antigen binding fragment is detectably labeled. Non-limiting cytokines include, e.g., IL1beta, IL6, IL8, IL12p70, IL10, IL13 and IFN.

Additionally or alternatively provided are methods to detect a biofilm on a surface comprising, or alternatively consisting of, or yet further consisting of, contacting the surface (in one aspect susceptible to or containing a biofilm) with an effective amount of one or more of the antibody, antigen binding fragment, polypeptide or CDR as described herein, wherein the antibody, fragment thereof, polypeptide or CDR binds a tail or tip region of a DNABII peptide (including but not limited to: a tip region of IHF or HU, a tip region of IHFA or IHFB, the tip-chimeric peptide IhfA5-mIhfB4$_{NTHi}$, tail region of IHF or HU, a tail region of IHFA or IHFB, and/or or the tail-chimeric peptide IhfA3-IhfB2$_{NTHi}$). In one embodiment, the contacting is in vivo or in vitro. In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 26 or an equivalent thereof, and/or a light chain (LC) immunoglobulin variable domain sequence comprising, or consisting essentially of, or yet further consisting of an amino acid sequence of SEQ ID NO: 27 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 4, 5 or 6, or an equivalent of each thereof, and/or a light chain (LC) immunoglobulin variable domain sequence comprising, or consisting essentially of, or yet further consisting of an amino acid sequence selected from the group of SEQ ID NOs: 10, 11 or 12, or an equivalent of each thereof. In a further aspect, the antibody or antigen binding fragment are detectably labeled.

Additionally or alternatively provided is a method for detecting a microbial infection that produces a biofilm in a subject. The method comprises, or alternatively consists of, or yet further consists of, contacting an effective amount of one or more of the antibody, fragment thereof, polypeptide, or CDR as disclosed herein with a biological sample suspected of comprising the biofilm and isolated from the subject and detecting the binding of the antibody, fragment thereof, polypeptide, or CDR to any biofilm in the sample. In one embodiment, the antibody, fragment thereof, polypeptide or CDR binds a tail or tip region of a DNABII peptide (including but not limited to: a tip region of IHF or HU, a tip region of IHFA or IHFB, the tip-chimeric peptide IhfA5-mIhfB4$_{NTHi}$, tail region of IHF or HU, a tail region of IHFA or IHFB, and/or or the tail-chimeric peptide IhfA3-IhfB2$_{NTHi}$). In a further embodiment, the contacting is in vivo or in vitro. In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 26 or an equivalent thereof, and/or a light chain (LC) immunoglobulin variable domain sequence comprising, or consisting essentially of, or yet further consisting of an amino acid sequence of SEQ ID NO: 27 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 4, 5 or 6, or an equivalent of each thereof, and/or a light chain (LC) immunoglobulin variable domain sequence comprising, or consisting essentially of, or yet further consisting of an amino acid sequence selected from the group of SEQ ID NOs: 10, 11 or 12, or an equivalent of each thereof. In a further aspect, the antibody or antigen binding fragment are detectably labeled.

Additionally or alternatively provided is a method for screening subjects having a biofilm, comprising, or alternatively consisting of, or yet further consisting of, contacting an effective amount of one or more of an antibody, a fragment thereof, a polypeptide, or a CDR as disclosed herein with a biological sample comprising the biofilm and isolated from the subject, and detecting the binding of the antibody, fragment thereof, polypeptide, or CDR to any biofilm in the sample. In one embodiment, the antibody, fragment thereof, polypeptide or CDR binds a tail or tip region of a DNABII peptide (including but not limited to: a tip region of IHF or HU, a tip region of IHFA or IHFB, the tip-chimeric peptide IhfA5-mIhfB4$_{NTHi}$, tail region of IHF or HU, a tail region of IHFA or IHFB, and/or or the tail-chimeric peptide IhfA3-IhfB2$_{NTHi}$). In a further embodiment, a subject detected with the binding is selected for administration with an effective amount of one or more of an antibody, a fragment thereof, a polypeptide, or a CDR as disclosed herein, and/or an effective amount of one or more of a polynucleotide or a vector encoding the antibody, fragment thereof, polypeptide or CDR, wherein the antibody, fragment thereof, polypeptide, or CDR binds a tip region of a DNABII peptide (including but not limited to: a tip region of IHF or HU, a tip region of IHFA or IHFB, or the tip-chimeric peptide IhfA5-mIhfB4$_{NTHi}$). In yet a further embodiment, the contacting is in vivo or in vitro. In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 26 or an equivalent thereof, and/or a light chain (LC) immunoglobulin variable domain sequence comprising, or consisting essentially of, or yet further consisting of an amino acid sequence of SEQ ID NO: 27 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 4, 5 or 6, or an equivalent of each thereof, and/or a light chain (LC) immunoglobulin variable domain sequence comprising, or consisting essentially of, or yet further consisting of an amino acid sequence selected from the group of SEQ ID NOs: 10, 11 or 12, or an equivalent of each thereof. In a further aspect, the antibody or antigen binding fragment are detectably labeled.

Further provided are method to prepare an interfering nucleic acid comprising preparing a nucleic acid consisting of about 10-20 nucleotides that specifically binds a specific binding partner to the antibody or fragment thereof as disclosed herein and optionally isolating the interfering nucleic acid prepared by the method.

When practiced in vitro, the several of the disclosed methods are useful to screen for or confirm agents (e.g., antibodies, fragments and mimics thereof) having the same, similar or opposite ability as the polypeptides, polynucleotides, antibodies, host cells, small molecules and compositions disclosed herein. Alternatively, they can be used to identify which agent is best suited to treat a microbial infection or if the treatment has been effective. For example, one can screen for new agents or combination therapies by having two samples containing for example, the DNABII polypeptide and microbial DNA and the agent to be tested. The DNABII polypeptide can be an IHF or HU peptide. The second sample contains the DNABII polypeptide and microbial DNA and an agent known to active, e.g., an agent as described above, e.g., an antibody or antigen binding fragment thereof, to serve as a positive control. In a further aspect, several samples are provided and the agents are added to the system in increasing dilutions to determine the optimal dose that would likely be effective in treating a subject in the clinical setting. As is apparent to those of skill in the art, a negative control containing the DNABII polypeptide and the microbial DNA can be provided. In a further aspect, the DNABII polypeptide and the microbial DNA are detectably labeled, for example with luminescent molecules that will emit a signal when brought into close contact with each other. The samples are contained under similar conditions for an effective amount of time for the agent to inhibit, compete or titrate the interaction between the DNABII polypeptide and microbial DNA and then the sample is assayed for emission of signal from the luminescent molecules. If the sample emits a signal, then the agent is not effective to inhibit binding.

In another aspect, the in vitro method is practiced in a miniaturized chamber slide system wherein the microbial (such as a bacterial) isolate causing an infection could be isolated from the human/animal then cultured to allow it to grow as a biofilm in vitro. The agent (e.g., an antibody or antigen binding fragment thereof) or potential agent biofilm is added alone or in combination with another agent to the culture with or without increasing dilutions of the potential compound or agent such as an antibody or antigen binding fragment thereof, to find the optimal dose that would likely be effective at treating that patient when delivered to the subject where the infection existed. As apparent to those of skill in the art, a positive and negative control can be performed simultaneously.

In a further aspect, the method is practiced in a high throughput platform with an agent as described above, e.g., an antibody or antigen binding fragment thereof, and/or potential agent (alone or in combination with another agent) in a flow cell. The agent as described above, e.g., an antibody or antigen binding fragment thereof, or potential agent is added alone or in combination with another agent to the culture with or without increasing dilutions of the potential agent or the agent as described above, e.g., an antibody or antigen binding fragment thereof, (or other antibody, small molecule, agent, etc.) to find the optimal dose that would likely be effective at treating that patient when delivered to the subject where the infection existed. Biofilm isolates are sonicated to separate biofilm bacteria from DNABII polypeptide such as IHF bound to microbial DNA. The DNABII polypeptide-DNA complexes are isolated by virtue of the anti-DNABII or IHF antibody on the platform. The microbial DNA is then released with e.g., a salt wash, and used to identify the biofilm bacteria added. The freed DNA is then identified, e.g., by PCR sequenced. If DNA is not freed, then the agent(s) successfully performed or bound the microbial DNA. If DNA is found in the sample, then the agent did not interfere with DNABII polypeptide-microbial DNA binding. As is apparent to those of skill in the art, a positive and/or negative control can be simultaneously performed.

The above methods also can be used as a diagnostic test since it is possible that a given bacterial species will respond better to reversal of its biofilm by one agent more than another, this rapid high throughput assay system could allow one skilled the art to assay a panel of possible anti-DNABII or IHF-like agents to identify the most efficacious of the group.

The advantage of these methods is that most clinical microbiology labs in hospitals are already equipped to perform these sorts of assays (i.e., determination of MIC, MBC values) using bacteria that are growing in liquid culture (or planktonically). As is apparent to those of skill in the art, bacteria generally do not grow planktonic ally when they are causing diseases. Instead they are growing as a stable biofilm and these biofilms are significantly more resistant to treatment by antibiotics, antibodies or other therapeutics. This resistance is why most MIC/MBC values fail to accurately predict efficacy in vivo. Thus, by determining what "dose" of agent could reverse a bacterial biofilm in vitro (as described above) Applicants' pre-clinical assay would be a more reliable predictor of clinical efficacy, even as an application of personalized medicine.

In addition to the clinical setting, the methods can be used to identify the microbe causing the infection and/or confirm effective treatments and agents in an industrial setting. Thus, the agents can be used to treat, inhibit or disrupt a biofilm in an industrial setting.

In a further aspect of the above methods, an antibiotic or antimicrobial known to inhibit growth of the underlying infection is added sequentially or concurrently, to determine if the infection can be inhibited. It is also possible to add the interfering agent to the microbial DNA or DNABII polypeptide before adding the missing complex to assay for biofilm inhibition. In one aspect, DNase treatment is excluded from the method of use.

When practiced in vivo in non-human animal such as a chinchilla, the method provides a pre-clinical screen to identify agents that can be used alone or in combination with other agents to disrupt biofilms.

In another aspect, provided herein is a method of inhibiting, preventing or disrupting a biofilm in a subject by administering to the subject an effective amount of an agent as described above, e.g., an antibody or antigen binding fragment thereof, thereby inhibiting, preventing or disputing the microbial biofilm. The methods, comprise, or consist essentially of, or consist of, administering to the subject an antibody or the fragment thereof as disclosed herein that binds to a tip region of a DNABII peptide (including but not limited to: a tip region of IHF or HU, a tip region of IHFA or IHFB, and/or the tip-chimeric peptide IhfA5-mIhfB4$_{NTHi}$). The DNABII peptide can be an IHF or HU peptide. The antibody or antigen binding fragment thereof can be detectably labeled. These methods can be combined with diagnostic methods to detect and/or monitor biofilm formation and/or disruption. In one aspect, the diagnostic methods comprise the use of an antibody or antigen binding fragment as disclosed herein that in one aspect, specifically binds to a tail region or fragment of a DNABII polypeptide (including but not limited to: a tail region of IHF or HU, a tail region of IHFA or IHFB, or the tail-chimeric peptide IhfA3-IhfB2$_{NTHi}$). In a further aspect, the antibody or antigen binding fragment are detectably labeled.

In one aspect, the agent is one or more antibodies and/or antigen binding fragments that are the same or different from each other. In some embodiments, such antibodies or antigen binding fragments are administered alone or in combination with each other, or an agent other than the antibody, or yet a further pharmaceutically effective agent, alone or in combination with a pharmaceutically acceptable carrier. Non-limiting examples of such subjects include mammals, e.g., pets, and human patients.

Also provided herein is a method for inducing an immune response in or conferring passive immunity in a subject in need thereof, comprising, or alternatively consisting essentially of or yet further consisting of, administering to the subject an effective amount of one or more of the antibodies or antigen binding fragments thereof as described therein that bind to a tip region of a DNABII peptide, e.g., IHF or HU peptide. Such tip region of a DNABII peptide includes, but is not limited to: a tip region of IHF or HU, a tip region of IHFA or IHFB, or the tip-chimeric peptide IhfA5-mIhfB4$_{NTHI}$. In one aspect, provided is a method for conferring passive immunity in a subject, comprising, or alternatively consisting essentially of, or yet further consisting of administering to the subject an effective amount of one or more of an antibody, fragment thereof of, polypeptide, or CDR as disclosed herein, and/or an effective amount of one or more of a polynucleotide or a vector encoding the antibody, fragment thereof, polypeptide or CDR, wherein the antibody, fragment, polypeptide or CDR binds to a tip region of a DNABII peptide (including but not limited to: a tip region of IHF or HU, a tip region of IHFA or IHFB, or the tip-chimeric peptide IhfA5-mIhfB4$_{NTHI}$). In one embodiment, provided is an antibody or a fragment thereof, that comprises or consists essentially of, or yet further consists of: a heavy chain (HC) immunoglobulin variable domain sequence comprising, or consisting essentially of, or yet further consisting of an amino acid sequence of SEQ ID NO: 24 or an equivalent thereof, and/or a light chain (LC) immunoglobulin variable domain sequence comprising, or consisting essentially of, or yet further consisting of an amino acid sequence of SEQ ID NO: 25 or an equivalent thereof. In a further embodiment, the antibody or fragment thereof comprises or consists essentially of, or yet further consists of: a heavy chain (HC) immunoglobulin variable domain sequence comprising, or consisting essentially of, or yet further consisting of an amino acid sequence selected from the group of SEQ ID NOs: 1, 2 or 3, or an equivalent of each thereof, and/or a light chain (LC) immunoglobulin variable domain sequence comprising, or consisting essentially of, or yet further consisting of an amino acid sequence selected from the group of SEQ ID NOs: 7, 8 or 9, or an equivalent of each thereof. The antibody or antigen binding fragment thereof can be detectably labeled. These methods can be combined with diagnostic methods to detect and/or monitor biofilm formation and/or disruption. In one aspect, the diagnostic methods comprise the use of an antibody or antigen binding fragment as disclosed herein that in one aspect, specifically binds to a tail region or tail fragment of a DNABII polypeptide (including but not limited to: a tail region of IHF or HU, a tail region of IHFA or IHFB, or the tail-chimeric peptide IhfA3-IhfB2$_{NTHI}$). In a further aspect, the antibody or antigen binding fragment are detectably labeled.

In one aspect, the agent is one or more antibodies and/or antigen binding fragments that are the same or different from each other. In some embodiments, such antibodies or antigen binding fragments are administered alone or in combination with each other, or an agent other than the antibody, or yet a further pharmaceutically effective agent, alone or in combination with a pharmaceutically acceptable carrier.

In a further aspect, the methods further comprise, or alternatively consist essentially of, or yet further consist of administering to the subject an effective amount of one or more of an antimicrobial, an antigenic peptide or an adjuvant.

A non-limiting example of an antimicrobial agent is another vaccine component such as a surface antigen, e.g., an OMP P5, rsPilA, OMP 26, OMP P2, or Type IV Pilin protein (see Jurcisek and Bakaletz (2007) J. Bacteriology 189(10):3868-3875; Murphy, T. F. et al. (2009) The Pediatric Infectious Disease Journal 28: S121-S126).

The agents and compositions disclosed herein can be concurrently or sequentially administered with other antimicrobial agents and/or surface antigens. In one particular aspect, administration is locally to the site of the infection by direct injection or by inhalation for example. Other non-limiting examples of administration include by one or more method comprising transdermally, urethrally, sublingually, rectally, vaginally, ocularly, subcutaneously, intramuscularly, intraperitoneally, intranasally, by inhalation or orally.

Microbial infections and disease that can be treated by the methods disclosed herein include infection by a gram-positive or gram-negative organism that produces a biofilm, e.g., *Streptococcus agalactiae*, *Neisseria meningitidis*, *Treponemes, denticola, pallidum*, *Burkholderia cepacia*, or *Burkholderia pseudomallei*. In one aspect, the microbial infection is one or more of *Haemophilus influenzae* (non-typeable), *Moraxella catarrhalis*, *Streptococcus pneumoniae*, *Streptococcus pyogenes*, *Pseudomonas aeruginosa*, *Mycobacterium tuberculosis*. These microbial infections may be present in the upper, mid and lower airway (otitis, sinusitis, bronchitis but also exacerbations of chronic obstructive pulmonary disease (COPD), chronic cough, complications of and/or primary cause of cystic fibrosis (CF) and community acquired pneumonia (CAP). Thus, by practicing the in vivo methods disclosed herein, these diseases and complications from these infections can also be prevented or treated.

Infections might also occur in the oral cavity (caries, periodontitis) and caused by *Streptococcus mutans*, *Porphyromonas gingivalis*, *Aggregatibacter actinomvctemcomitans*. Infections might also be localized to the skin (abscesses, 'staph' infections, impetigo, secondary infection of burns, Lyme disease) and caused by *Staphylococcus aureus*, *Staphylococcus epidermidis*, *Pseudomonas aeruginosa* and *Borrelia burdorferi*. Infections of the urinary tract (UTI) can also be treated and are typically caused by *Escherichia coli*. Infections of the gastrointestinal tract (GI) (diarrhea, cholera, gall stones, gastric ulcers) are typically caused by *Salmonella enterica serovar*, *Vibrio cholerae* and *Helicobacter pylori*. Infections of the genital tract include and are typically caused by *Neisseria gonorrhoeae*. Infections can be of the bladder or of an indwelling device caused by *Enterococcus faecalis*. Infections associated with implanted prosthetic devices, such as artificial hip or knee replacements, or dental implants, or medical devices such as pumps, catheters, stents, or monitoring systems, typically caused by a variety of bacteria, can be treated by the methods disclosed herein. These devices can be coated or conjugated to an agent as described herein. Thus, by practicing the in vivo methods disclosed herein, these diseases and complications from these infections can also be prevented or treated.

Infections caused by *Streptococcus agalactiae* can also be treated by the methods disclosed herein and it is the major cause of bacterial septicemia in newborns. Infections caused by *Neisseria meningitidis* which can cause meningitis can also be treated.

Thus, routes of administration applicable to the methods disclosed herein include intranasal, intramuscular, urethrally, intratracheal, subcutaneous, intradermal, transdermal, topical application, intravenous, rectal, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery include systemic or localized routes. In general, routes of administration suitable for the methods disclosed herein include, but are not limited to, direct injection, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The agents disclosed herein can also be delivered to the subject by enteral administration. Enteral routes of administration include, but are not limited to, oral and rectal (e.g., using a suppository) delivery.

Methods of administration of the active through the skin or mucosa include, but are not limited to, topical application of a suitable pharmaceutical preparation, transcutaneous transmission, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

In various embodiments of the methods disclosed herein, the interfering agent will be administered by inhalation, injection or orally on a continuous, daily basis, at least once per day (QD), and in various embodiments two (BID), three (TID), or even four times a day. Typically, the therapeutically effective daily dose will be at least about 1 mg, or at least about 10 mg, or at least about 100 mg, or about 200 to about 500 mg, and sometimes, depending on the compound, up to as much as about 1 g to about 2.5 g.

Dosing of can be accomplished in accordance with the methods disclosed herein using capsules, tablets, oral suspension, suspension for intra-muscular injection, suspension for intravenous infusion, get or cream for topical application, or suspension for intra-articular injection.

Dosage, toxicity and therapeutic efficacy of compositions described herein can be determined by standard pharmaceutical procedures in cell cultures or experimental animals, for example, to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In certain embodiments, compositions exhibit high therapeutic indices. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies (in certain embodiments, within a range of circulating concentrations that include the ED50 with little or no toxicity. The dosage may vary within this range depending upon the dosage form employed and the route of administration utilized. For any compound used in the methods, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In some embodiments, an effective amount of a composition sufficient for achieving a therapeutic or prophylactic effect, ranges from about 0.000001 mg per kilogram body weight per administration to about 10,000 mg per kilogram body weight per administration. Suitably, the dosage ranges are from about 0.0001 mg per kilogram body weight per administration to about 100 mg per kilogram body weight per administration. Administration can be provided as an initial dose, followed by one or more "booster" doses. Booster doses can be provided a day, two days, three days, a week, two weeks, three weeks, one, two, three, six or twelve months after an initial dose. In some embodiments, a booster dose is administered after an evaluation of the subject's response to prior administrations.

The skilled artisan will appreciate that certain factors may influence the dosage and timing required to effectively treat a subject, including but not limited to, the severity of the disease or disorder, previous treatments, the general health and/or age of the subject, and other diseases present. Moreover, treatment of a subject with a therapeutically effective amount of the therapeutic compositions described herein can include a single treatment or a series of treatments.

Polypeptides

Also provided herein are isolated polypeptides comprising the heavy and light chains of the antibodies, antigen binding fragments thereof, CDRs and equivalents of each thereof with the addition of up to 25, or alternatively 20, or alternatively 15, or alternatively up to 10, or alternatively up to 5 random amino acids on either the amino or carboxyl termini (or on both).

In one aspect, provided herein are isolated polypeptides comprising, or consisting essentially of, or yet further consisting of, an amino acid sequence of the group of SEQ ID NOs: 1-14, or 24-27, or an equivalent of each thereof. The polypeptides can further comprise a detectable or purification marker.

This disclosure also provides isolated or recombinant polypeptides comprising or alternatively consisting essentially of, or yet further consisting of, two or more, or three or more, four or more, five or more, six or more, seven or more, eight or more, nine or more, ten or more, eleven or more, twelve or more, thirteen or more of all fourteen of the isolated polypeptides or a fragment or an equivalent of each thereof.

In any of the above embodiments, a peptide linker can be added to the N-terminus or C-terminus of the polypeptide. A "linker" or "peptide linker" refers to a peptide sequence linked to either the N-terminus or the C-terminus of a polypeptide sequence. In one aspect, the linker is from about 1 to about 20 amino acid residues long or alternatively 2 to about 10, about 3 to about 5 amino acid residues long. An example of a peptide linker is Gly-Pro-Ser-Leu-Lys-Leu (SEQ ID NO: 33). Other examples include Gly-Gly-Gly; Gly-Pro-Ser-Leu (SEQ ID NO: 34); Gly-Pro-Ser; Pro-Ser-Leu-Lys (SEQ ID NO: 35); Gly-Pro-Ser-Leu-Lys (SEQ ID NO: 36) and Ser-Leu-Lys-Leu (SEQ ID NO: 37).

The isolated polypeptides disclosed herein are intended to include recombinantly produced polypeptides and proteins from prokaryotic and eukaryotic host cells, as well as muteins, analogs and fragments thereof, examples of such cells are described above. In some embodiments, the term also includes antibodies and anti-idiotypic antibodies as described herein. Such polypeptides can be isolated or produced using the methods known in the art and briefly described herein.

It is understood that functional equivalents or variants of the wild type polypeptide or protein also are within the scope of this disclosure, for example, those having conservative amino acid substitutions of the amino acids.

In a further aspect, the polypeptides are conjugated or linked to a detectable label or an agent to increase the half-life of the polypeptide, e.g., PEGylation a PEG mimetic, polysialyation, HESylation or glycosylation. Suitable labels are known in the art and described herein.

In a yet further aspect, the polypeptides with or without a detectable label can be contained or expressed on the surface of a host prokaryotic or eukaryotic host cell, such as a dendritic cell.

The proteins and polypeptides are obtainable by a number of processes known to those of skill in the art, which include purification, chemical synthesis and recombinant methods. Polypeptides can be isolated from preparations such as host cell systems by methods such as immunoprecipitation with antibody, and standard techniques such as gel filtration, ion-exchange, reversed-phase, and affinity chromatography. For such methodology, see for example Deutscher et al. (1999) Guide To Protein Purification: Methods In Enzymology (Vol. 182, Academic Press). Accordingly, this disclosure also provides the processes for obtaining these polypeptides as well as the products obtainable and obtained by these processes.

The polypeptides also can be obtained by chemical synthesis using a commercially available automated peptide synthesizer such as those manufactured by Perkin/Elmer/Applied Biosystems, Inc., Model 430A or 431A, Foster City, Calif., USA. The synthesized polypeptide can be precipitated and further purified, for example by high performance liquid chromatography (HPLC). Accordingly, this disclosure also provides a process for chemically synthesizing the proteins disclosed herein by providing the sequence of the protein and reagents, such as amino acids and enzymes and linking together the amino acids in the proper orientation and linear sequence.

Alternatively, the proteins and polypeptides can be obtained by well-known recombinant methods as described, for example, in Sambrook et al. (1989) supra, using a host cell and vector systems described herein.

Also provided by this application are the polypeptides described herein conjugated to a detectable agent for use in the diagnostic methods. For example, detectably labeled polypeptides can be bound to a column and used for the detection and purification of antibodies. They also are useful as immunogens for the production of antibodies. The polypeptides disclosed herein are useful in an in vitro assay system to screen for agents or drugs, which modulate cellular processes. In another aspect, antibodies that are specific for the tail regions of the DNABII polypeptides (including but not limited to: a tail region of IHF or HU, a tail region of IHFA or IHFB, and/or the tail-chimeric peptide IhfA3-IhfB2$_{NTHI}$) are particularly useful in diagnostic assays for the detection of biofilms and can be used alone or in combination of one or more antibodies as described herein. In one aspect, antibodies specific for the tail regions are used as a companion diagnostic for an antibody that is specific for a tip region of the DNABII polypeptide (including but not limited to: a tip region of IHF or HU, a tip region of IHFA or IHFB, and/or the tip-chimeric peptide IhfA5-mIhfB4$_{NTHI}$). The DNABII polypeptide can be an IFH or an HU polypeptide.

It is well known to those skilled in the art that modifications can be made to the peptides disclosed herein to provide them with altered properties. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

Peptides disclosed herein can be modified to include unnatural amino acids. Thus, the peptides may comprise D-amino acids, a combination of and L-amino acids, and various "designer" amino acids (e.g., beta-methyl amino acids, C-alpha-methyl amino acids, and N-alpha-methyl amino acids, etc.) to convey special properties to peptides. Additionally, by assigning specific amino acids at specific coupling steps, peptides with alpha-helices, beta. turns, beta. sheets, gamma-turns, and cyclic peptides can be generated. Generally, it is believed that alpha-helical secondary structure or random secondary structure may be of particular use.

The polypeptides disclosed herein also can be combined with various solid phase carriers, such as an implant, a stent, a paste, a gel, a dental implant, or a medical implant or liquid phase carriers, such as beads, sterile or aqueous solutions, pharmaceutically acceptable carriers, pharmaceutically acceptable polymers, liposomes, micelles, suspensions and emulsions. Examples of non-aqueous solvents include propyl ethylene glycol, polyethylene glycol and vegetable oils. When used to prepare antibodies or induce an immune response in vivo, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides. Other suitable adjuvants include monophosphoryl lipid A (MPL), mutant derivatives of the heat labile enterotoxin of E. coli, mutant derivatives of cholera toxin, CPG oligonucleotides, and adjuvants derived from squalene.

This disclosure also provides a pharmaceutical composition comprising or alternatively consisting essentially of, or yet further consisting of, any of a polypeptide, analog, mutein, or fragment disclosed herein, alone or in combination with each other or other agents, such an antibiotic and an acceptable carrier or solid support. These compositions are useful for various diagnostic and therapeutic methods as described herein.

Polynucleotides

This disclosure also provides isolated or recombinant polynucleotides encoding one or more of the above-identified antibodies, fragments thereof, CDRs, isolated or recombinant polypeptides and their respective complementary strands. Vectors comprising the isolated or recombinant polynucleotides are further provided examples of which are known in the art and briefly described herein. In one aspect where more than one isolated or recombinant polynucleotide is to be expressed as a single unit, the isolated or recombinant polynucleotides can be contained within a polycistronic vector. The polynucleotides can be DNA, RNA, mRNA or interfering RNA, such as siRNA, miRNA or dsRNA.

In another aspect, this disclosure provides an interfering agent that is a polynucleotide that interferes with the binding of the DNA to a polypeptide or protein in a microbial biofilm, or a four-way junction polynucleotide resembling a Holliday junction, a 3 way junction polynucleotide resembling a replication fork, a polynucleotide that has inherent flexibility or bent polynucleotide which can treat or inhibit DNABII polynucleotide (HU or IHF) from binding to microbial DNA as well treat, prevent or inhibit biofilm formation and associated infections and disorders. One of skill in the art can make such polynucleotides using the information provided herein and knowledge of those of skill in the art. See Goodman and Kay (1999) J. Biological Chem. 274(52):37004-37011 and Kamashev and Rouviere-Yaniv (2000) EMBO J. 19(23):6527-6535.

The disclosure further provides the isolated or recombinant polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are known in the art and commercially available. For general methodology and cloning strategies, see Gene Expression Technology (Goeddel ed., Academic Press, Inc. (1991)) and references cited therein and Vectors: Essential Data Series (Gacesa and Ramji, eds., John Wiley & Sons, N.Y. (1994)) which contains maps, functional properties, commercial suppliers and a reference to GenEMBL accession numbers for various suitable vectors.

In one embodiment, polynucleotides derived from the polynucleotides disclosed herein encode polypeptides or proteins having diagnostic and therapeutic utilities as described herein as well as probes to identify transcripts of the protein that may or may not be present. These nucleic acid fragments can by prepared, for example, by restriction enzyme digestion of larger polynucleotides and then labeled with a detectable marker. Alternatively, random fragments can be generated using nick translation of the molecule. For methodology for the preparation and labeling of such fragments, see, Sambrook et al. (1989) supra.

Expression vectors containing these nucleic acids are useful to obtain host vector systems to produce proteins and polypeptides. It is implied that these expression vectors must be replicable in the host organisms either as episomes or as an integral part of the chromosomal DNA. Non-limiting examples of suitable expression vectors include plasmids, yeast vectors, viral vectors and liposomes. Adenoviral vectors are particularly useful for introducing genes into tissues in vivo because of their high levels of expression and efficient transformation of cells both in vitro and in vivo. When a nucleic acid is inserted into a suitable host cell, e.g., a prokaryotic or a eukaryotic cell and the host cell replicates, the protein can be recombinantly produced. Suitable host cells will depend on the vector and can include mammalian cells, animal cells, human cells, simian cells, insect cells, yeast cells, and bacterial cells constructed using known methods. See, Sambrook et al. (1989) supra. In addition to the use of viral vector for insertion of exogenous nucleic acid into cells, the nucleic acid can be inserted into the host cell by methods known in the art such as transformation for bacterial cells; transfection using calcium phosphate precipitation for mammalian cells; or DEAE-dextran; electroporation; or microinjection. See, Sambrook et al. (1989) supra, for methodology. Thus, this disclosure also provides a host cell, e.g., a mammalian cell, an animal cell (rat or mouse), a human cell, or a prokaryotic cell such as a bacterial cell, containing a polynucleotide encoding a protein or polypeptide or antibody.

A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment disclosed herein that is a polynucleotide encompasses both the double-stranded form and each of two complementary single-stranded forms known or predicted to make up the double-stranded form.

When the vectors are used in an method as disclosed herein as gene therapy in vivo or ex vivo, a pharmaceutically acceptable vector, such as a replication-incompetent retroviral or adenoviral vector, are exemplary (but non-limiting) and may be of particular use. Pharmaceutically acceptable vectors containing the nucleic acids disclosed herein can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication-incompetent" vector defined by its inability to produce viral proteins, precluding spread of the vector in the infected host cell. An example of a replication-incompetent retroviral vector is LNL6 (Miller et al. (1989) BioTechniques 7:980-990). The methodology of using replication-incompetent retroviruses for retroviral-mediated gene transfer of gene markers has been established. (Bordignon (1989) PNAS USA 86:8912-8952; Culver (1991) PNAS USA 88:3155; and Rill (1991) Blood 79(10):2694-2700).

This disclosure also provides genetically modified cells that contain and/or express the polynucleotides disclosed herein. The genetically modified cells can be produced by insertion of upstream regulatory sequences such as promoters or gene activators (see, U.S. Pat. No. 5,733,761). In one embodiment, the modified cells are eukaryotic cells or prokaryotic cells.

The polynucleotides can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. In one aspect, one will likely desire to employ a fluorescent label or an enzyme tag, such as urease, alkaline phosphatase or peroxidase, instead of radioactive or other environmentally undesirable reagents. In the case of enzyme tags, calorimetric indicator substrates can be employed to provide a means visible to the human eye or spectrophotometrically, to identify specific hybridization with complementary nucleic acid-containing samples. Thus, this disclosure further provides a method for detecting a single-stranded polynucleotide or its complement, by contacting target single-stranded polynucleotide with a labeled, single-stranded polynucleotide (a probe) which is a portion of the polynucleotide disclosed herein under conditions permitting hybridization (optionally moderately stringent hybridization conditions) of complementary single-stranded polynucleotides, or optionally, under highly stringent hybridization conditions. Hybridized polynucleotide pairs are separated from un-hybridized, single-stranded polynucleotides. The hybridized polynucleotide pairs are detected using methods known to those of skill in the art and set forth, for example, in Sambrook et al. (1989) supra.

The polynucleotide embodied in this disclosure can be obtained using chemical synthesis, recombinant cloning methods, PCR, or any combination thereof. Methods of chemical polynucleotide synthesis are known in the art and need not be described in detail herein. One of skill in the art can use the sequence data provided herein to obtain a desired polynucleotide by employing a DNA synthesizer or ordering from a commercial service.

The polynucleotides disclosed herein can be isolated or replicated using PCR. The PCR technology is the subject matter of U.S. Pat. Nos. 4,683,195; 4,800,159; 4,754,065; and 4,683,202 and described in PCR: The Polymerase Chain Reaction (Mullis et al. eds., Birkhauser Press, Boston (199.4)) or MacPherson et al. (1991) and (1995) supra, and references cited therein. Alternatively, one of skill in the art can use the sequences provided herein and a commercial DNA synthesizer to replicate the DNA. Accordingly, this disclosure also provides a process for obtaining the polynucleotides disclosed herein by providing the linear sequence of the polynucleotide, nucleotides, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the poly-nucleotide into a suitable replication vector and insert the vector into a suitable host cell (prokaryotic or eukaryotic) for replication and amplification. The DNA so amplified can be isolated from the cell by methods known to those of skill in the art. A process for obtaining polynucleotides by this method is further provided herein as well as the polynucleotides so obtained.

RNA can be obtained by first inserting a DNA polynucleotide into a suitable host cell. The DNA can be delivered by any appropriate method, e.g., by the use of an appropriate gene delivery vehicle (e.g., liposome, plasmid or vector) or by electroporation. When the cell replicates and the DNA is transcribed into RNA; the RNA can then be isolated using methods known to those of skill in the art, for example, as set forth in Sambrook et al. (1989) supra. For instance, mRNA can be isolated using various lytic enzymes or chemical solutions according to the procedures set forth in Sambrook et al. (1989) supra, or extracted by nucleic-acid-binding resins following the accompanying instructions provided by manufactures.

Polynucleotides exhibiting sequence complementarity or homology to a polynucleotide disclosed herein are useful as hybridization probes or as an equivalent of the specific polynucleotides identified herein. Since the full coding sequence of the transcript is known, any portion of this sequence or homologous sequences can be used in the methods disclosed herein.

It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. In some embodiments, a probe useful for detecting the aforementioned mRNA is at least about 80% identical to the homologous region. In some embodiments, the probe is 85% identical to the corresponding gene sequence after alignment of the homologous region; in some embodiments, it exhibits 90% identity.

These probes can be used in radioassays (e.g., Southern and Northern blot analysis) to detect, prognose, diagnose or monitor various cells or tissues containing these cells. The probes also can be attached to a solid support or an array such as a chip for use in high throughput screening assays for the detection of expression of the gene corresponding a polynucleotide disclosed herein. Accordingly, this disclosure also provides a probe comprising or corresponding to a polynucleotide disclosed herein, or its equivalent, or its complement, or a fragment thereof, attached to a solid support for use in high throughput screens.

The total size of fragment, as well as the size of the complementary stretches, will depend on the intended use or application of the particular nucleic acid segment. Smaller fragments will generally find use in hybridization embodiments, wherein the length of the complementary region may be varied, such as between at least 5 to 10 to about 100 nucleotides, or even full length according to the complementary sequences one wishes to detect.

Nucleotide probes having complementary sequences over stretches greater than 5 to 10 nucleotides in length are generally well suited, so as to increase stability and selectivity of the hybrid, and thereby improving the specificity of particular hybrid molecules obtained. In certain embodiments, one can design polynucleotides having gene-complementary stretches of 10 or more or more than 50 nucleotides in length, or even longer where desired. Such fragments may be readily prepared by, for example, directly synthesizing the fragment by chemical means, by application of nucleic acid reproduction technology, such as the PCR technology with two priming oligonucleotides as described in U.S. Pat. No. 4,603,102 or by introducing selected sequences into recombinant vectors for recombinant production. In one aspect, a probe is about 50-75 or more alternatively, 50-100, nucleotides in length.

The polynucleotides of the present disclosure can serve as primers for the detection of genes or gene transcripts that are expressed in cells described herein. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of E. coli DNA polymerase, and reverse transcriptase. For illustration purposes only, a primer is the same length as that identified for probes.

One method to amplify polynucleotides is PCR and kits for PCR amplification are commercially available. After amplification, the resulting DNA fragments can be detected by any appropriate method known in the art, e.g., by agarose gel electrophoresis followed by visualization with ethidium bromide staining and ultraviolet illumination.

Methods for administering an effective amount of a gene delivery vector or vehicle to a cell have been developed and are known to those skilled in the art and described herein. Methods for detecting gene expression in a cell are known in the art and include techniques such as in hybridization to DNA microarrays, in situ hybridization, PCR, RNase protection assays and Northern blot analysis. Such methods are useful to detect and quantify expression of the gene in a cell. Alternatively, expression of the encoded polypeptide can be detected by various methods. In particular, it is useful to prepare polyclonal or monoclonal antibodies that are specifically reactive with the target polypeptide. Such antibodies are useful for visualizing cells that express the polypeptide using techniques such as immunohistology, ELISA, and Western blotting. These techniques can be used to determine expression level of the expressed polynucleotide.

Production Methods

Also provided are methods to produce the antibodies, fragments, CDRs, or polypeptides comprising, or alternatively consisting of, or yet further consisting of, culturing a host cell comprising a polynucleotide encoding the antibody, antigen binding fragment, polypeptide, or CDR under conditions for expression of the polynucleotide, and optionally isolating the antibody, fragment, CDR and/or polypeptide from the cell and/or culture. Additionally provided is a host cell comprising a polynucleotide encoding the antibody, antigen binding fragment, polypeptide, or CDR under conditions for expression of the polynucleotide. In one embodiment, the host cell is a eukaryotic cell or a prokaryotic cell. In a further embodiment, the host cell is a mammalian cell.

Compositions

Compositions are further provided. The compositions comprise a carrier and one or more of an isolated polypeptide disclosed herein, an isolated polynucleotide disclosed herein, a vector disclosed herein, an isolated host cell disclosed herein, a small molecule or an antibody, and/or an antigen binding fragment disclosed herein. The carriers can be one or more of a solid support or a pharmaceutically acceptable carrier. The compositions can further comprise an adjuvant or other components suitable for administrations as vaccines. In one aspect, the compositions are formulated with one or more pharmaceutically acceptable excipients, diluents, carriers and/or adjuvants. In addition, embodiments of the compositions of the present disclosure include one or more of an isolated polypeptide disclosed herein, an isolated polynucleotide disclosed herein, a vector disclosed herein, a small molecule, an isolated host cell disclosed herein, or an antibody of the disclosure, formulated with one or more pharmaceutically acceptable substances.

For oral preparations, any one or more of an isolated or recombinant polypeptide as described herein, an isolated or recombinant polynucleotide as described herein, a vector as described herein, an isolated host cell as described herein, a small molecule or an antibody or fragment thereof as described herein can be used alone or in pharmaceutical formulations disclosed herein comprising, or consisting essentially of, the compound in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical formulations and unit dose forms suitable for oral administration are particularly useful in the treatment of chronic conditions, infections, and therapies in which the patient self-administers the drug. In one aspect, the formulation is specific for pediatric administration.

The disclosure provides pharmaceutical formulations in which the one or more of an isolated polypeptide disclosed herein, an isolated polynucleotide disclosed herein, a vector disclosed herein, an isolated host cell disclosed herein, or an antibody disclosed herein can be formulated into preparations for injection in accordance with the disclosure by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives or other antimicrobial agents. A non-limiting example of such is a antimicrobial agent such as other vaccine components such as surface antigens, e.g., an OMP P5, OMP 26, OMP P2, or Type IV Pilin protein (see Jurcisek and Bakaletz (2007) J. of Bacteriology 189(10):3868-3875 and Murphy, T F, Bakaletz, L O and Smeesters, P R (2009) The Pediatric Infectious Disease Journal, 28:S121-S126) and antibacterial agents. For intravenous administration, suitable carriers include physiological bacteriostatic water, Cremophor EL™ (BASF, Parsippany, N.J.), or phosphate buffered saline (PBS). In all cases, a composition for parenteral administration must be sterile and should be fluid to the extent that easy syringability exists.

Aerosol formulations provided by the disclosure can be administered via inhalation and can be propellant or non-propellant based. For example, embodiments of the pharmaceutical formulations disclosed herein comprise a compound disclosed herein formulated into pressurized acceptable propellants such as dichlorodifluoromethane, propane, nitrogen and the like. For administration by inhalation, the compounds can be delivered in the form of an aerosol spray from a pressurized container or dispenser which contains a suitable propellant, e.g., a gas such as carbon dioxide, or a nebulizer. A non-limiting example of a non-propellant is a pump spray that is ejected from a closed container by means of mechanical force (i.e., pushing down a piston with one's finger or by compression of the container, such as by a compressive force applied to the container wall or an elastic force exerted by the wall itself, e.g., by an elastic bladder).

Suppositories disclosed herein can be prepared by mixing a compound disclosed herein with any of a variety of bases such as emulsifying bases or water-soluble bases. Embodiments of this pharmaceutical formulation of a compound disclosed herein can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more compounds disclosed herein. Similarly, unit dosage forms for injection or intravenous administration may comprise a compound disclosed herein in a composition as a solution in sterile water, normal saline or another pharmaceutically acceptable carrier.

Embodiments of the pharmaceutical formulations disclosed herein include those in which one or more of an isolated polypeptide disclosed herein, an isolated polynucleotide disclosed herein, a vector disclosed herein, a small molecule for use in the disclosure, an isolated host cell disclosed herein, or an antibody or fragment thereof as disclosed herein is formulated in an injectable composition. Injectable pharmaceutical formulations disclosed herein are prepared as liquid solutions or suspensions; or as solid forms suitable for solution in, or suspension in, liquid vehicles prior to injection. The preparation may also be emulsified or the active ingredient encapsulated in liposome vehicles in accordance with other embodiments of the pharmaceutical formulations disclosed herein.

In an embodiment, one or more of an isolated polypeptide disclosed herein, an isolated polynucleotide disclosed herein, a vector disclosed herein, an isolated host cell disclosed herein, or an antibody disclosed herein is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of a compound disclosed herein can be accomplished using any of a variety of refillable, pump systems. Pumps provide consistent, controlled release over time. In some embodiments, a compound disclosed herein is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation, polymers such as for example poly(glycolide-co-lactide) (PGLA) that is commercially available from a number of vendors, e.g., BioDegmer and Sigma-Aldrich. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer (e.g., PGLA) and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852; and the like. In general, a subject treatment method can be accomplished using any of a variety of refillable, non-exchangeable pump systems. Pumps and other convective systems may be utilized due to their generally more consistent, controlled release over time. Osmotic pumps are used in some embodiments due to their combined advantages of more consistent controlled release and relatively small size (see, e.g., PCT International Application Publication No. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like. A further exemplary device that can be adapted for the present disclosure is the Synchromed infusion pump (Medtronic).

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

Suitable excipient vehicles for a compound disclosed herein are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the compound adequate to achieve the desired state in the subject being treated.

Compositions of the present disclosure include those that comprise a sustained-release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylatanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

In another embodiment, the polypeptide, antibody or fragment thereof (as well as combination compositions) is delivered in a controlled release system. For example, a compound disclosed herein may be administered using intravenous infusion, an implantable osmotic pump, a transdermal patch, liposomes, or other modes of administration. In one embodiment, a pump may be used (Sefton (1987) CRC Crit. Ref. Biomed. Eng. 14:201; Buchwald et al. (1980) Surgery 88:507; Saudek et al. (1989) N. Engl. J. Med. 321:574). In another embodiment, polymeric materials are used. In yet another embodiment a controlled release system is placed in proximity of the therapeutic target, i.e., the liver, thus requiring only a fraction of the systemic dose. In yet another embodiment, a controlled release system is placed in proximity of the therapeutic target, thus requiring only a fraction of the systemic. Other controlled release systems are discussed in the review by Langer (1990) Science 249:1527-1533.

In another embodiment, the compositions of the present disclosure (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The present disclosure provides methods and compositions for the administration of a one or more of an interfering agent to a host (e.g., a human) for the treatment of a microbial infection. In various embodiments, these methods disclosed herein span almost any available method and route suitable for drug delivery, including in vivo and ex vivo methods, as well as systemic and localized routes of administration.

Screening Assays

The present disclosure provides methods for screening for equivalent agents, such as equivalent monoclonal antibodies to a polyclonal antibody as described herein and various agents that modulate the activity of the active agents and pharmaceutical compositions disclosed herein or the function of a polypeptide or peptide product encoded by the polynucleotide disclosed herein. For the purposes of this disclosure, an "agent" is intended to include, but not be limited to a biological or chemical compound such as a simple or complex organic or inorganic molecule (referred to herein as a small molecule, such as a nucleic acid), a peptide, a protein (e.g., antibody), a polynucleotide antisense) or a ribozyme. A vast array of compounds can be synthesized, for example polymers, such as polypeptides and polynucleotides, and synthetic organic compounds based on various core structures, and these are also included in the term "agent." In addition, various natural sources can provide compounds for screening, such as plant or animal extracts, and the like. It should be understood, although not always explicitly stated that the agent is used alone or in combination with another agent, having the same or different biological activity as the agents identified by the inventive screen.

One embodiment is a method for screening agents capable of interacting with, binding to, or inhibiting the DNA-DNABII (e.g., IHF or HU) interaction. Accordingly, the disclosure permits the use of virtual design techniques, also known as computer-aided, in silico design or modeling, to design, select, and synthesize agents capable of interacting with, binding to, or inhibiting the DNA-DNABII (e.g., IHF or HU) interaction. In turn, the candidate agents may be effective in the treatment of biofilms and associated diseases or conditions (medical, industrial or veterinary) as described herein. Thus, the present disclosure also provides agents identified or designed by the in silico methods.

A candidate agent is found to be able to bind to DNA and/or DNABII protein if a desired interaction between the candidate agent and either or both is found. The interaction can be quantitative, e.g., strength of interaction and/or number of interaction sites, or qualitative, e.g., interaction or lack of interaction. The output of the method, accordingly, can be quantitative or qualitative. In one aspect, therefore, the present disclosure also provides a method for identifying an agent that does not inhibit the interaction or alternatively, strengthens the interaction between the DNA and protein.

The potential inhibitory or binding effect (i.e., interaction or association) of an agent such as a small molecule compound may be analyzed prior to its actual synthesis and testing by the use of computer modeling techniques. If the theoretical structure of the given compound suggests insufficient interaction and association between it and microbial DNA in the biofilm and/or DNABII protein, synthesis and testing of the agent can be obviated. However, if computer modeling indicates a strong interaction, the agent can then be synthesized and tested for its ability to bind to or inhibit the interaction using various methods such as in vitro or in vivo experiments. Methods of testing an agent's ability to inhibit or titrate a biofilm, alone or in connection with another agent, are disclosed herein. In this manner, synthesis of inoperative agents and compounds can be avoided.

One skilled in the art may use any of several methods to screen chemical or biological entities or fragments for their ability to associate with DNABII or microbial DNA and more particularly with the specific binding sites. Selected fragments or chemical entities may then be positioned in a variety of orientations, or docked, within an individual binding site of DNA or DNABII polypeptide. Docking may be accomplished using software such as QUANTA, SYBYL, followed by energy minimization and molecular dynamics with standard molecular mechanical force fields, such as CHARMM and AMBER.

Commercial computer programs are also available for in silico design. Examples include, without limitation, GRID (Oxford University, Oxford, UK), MCSS (Molecular Simulations, Burlington, Mass.), AUTODOCK (Scripps Research Institute, La Jolla, Calif.), DOCK (University of California, San Francisco, Calif.), GLIDE (Schrodinger Inc.), FlexX (Tripos Inc.) and GOLD (Cambridge Crystallographic Data Centre).

Once an agent or compound has been designed or selected by the above methods, the efficiency with which that agent or compound may bind to each other can be tested and optimized by computational evaluation. For example, an effective DNABII fragment or may demonstrate a relatively small difference in energy between its bound and free states (i.e., a small deformation energy of binding).

A compound designed or selected can be further computationally optimized so that in its bound state it may optionally lack repulsive electrostatic interaction with the target protein. Such non-complementary (e.g., electrostatic) interactions include repulsive charge-charge, dipole-dipole, and charge-dipole interactions. Specifically, the sum of all electrostatic interactions between the agent and DNABII and/or microbial DNA in the biofilm when the agent or compound is bound to either agent, optionally making a neutral or favorable contribution to the enthalpy of binding.

Computer softwares are also available in the art to evaluate compound deformation energy and electrostatic interaction. Examples include, without limitation, Gaussian 92 [Gaussian, Inc., Pittsburgh, Pa.]; AMBER [University of California at San Francisco]; QUANTA/CHARMM [Molecular Simulations, Inc., Burlington, Mass.]; and Insight II/Discover [Biosysm Technologies Inc., San Diego, Calif.].

Once a binding agent has been optimally selected or designed, as described above, substitutions may then be made in some of its atoms or side groups in order to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analyzed for efficiency of fit to the DNABII protein and/or microbial DNA in the biofilm by the same computer methods described in detail, above.

Certain embodiments relate to a method for screening small molecules capable of interacting with the protein or polynucleotide disclosed herein. For the purpose of this disclosure, "small molecules" are molecules having low molecular weights (MW) that are, in one embodiment, capable of binding to a protein of interest thereby altering the function of the protein. In some embodiments, the MW of a small molecule is no more than 1,000. Methods for screening small molecules capable of altering protein function are known in the art. For example, a miniaturized arrayed assay for detecting small molecule-protein interactions in cells is discussed by You et al. (1997) Chem. Biol. 4:961-968.

To practice the screening method in vitro, suitable cell culture or tissue infected with the microbial to be treated are first provided. The cells are cultured under conditions (temperature, growth or culture medium and gas ($CO_2$)) and for an appropriate amount of time to attain exponential proliferation without density dependent constraints. It also is desirable to maintain an additional separate cell culture that is not infected as a control.

As is apparent to one of skill in the art, suitable cells can be cultured in micro-titer plates and several agents can be assayed at the same time by noting genotypic changes, phenotypic changes or a reduction in microbial titer.

When the agent is a composition other than a DNA or RNA, such as a small molecule as described above, the agent can be directly added to the cell culture or added to culture medium for addition. As is apparent to those skilled in the art, an "effective" a mount must be added which can be empirically determined, When the agent is an antibody or antigen binding fragment, the agent can be contacted or incubated with the target antigen and polyclonal antibody as described herein under conditions to perform a competitive ELISA. Such methods are known to the skilled artisan.

The assays also can be performed in a subject. When the subject is an animal such as a rat, chinchilla, mouse or simian, the method provides a convenient animal model system that can be used prior to clinical testing of an agent in a human patient. In this system, a candidate agent is a potential drug if symptoms of the disease or microbial infection is reduced or eliminated, each as compared to untreated, animal having the same infection. It also can be useful to have a separate negative control group of cells or animals that are healthy and not treated, which provides a basis for comparison.

The agents and compositions can be used in the manufacture of medicaments and for the treatment of humans and other animals by administration in accordance with conventional procedures, such as an active ingredient in pharmaceutical compositions.

Combination Therapy

The compositions and related methods of the present disclosure may be used in combination with the administration of other therapies. These include, but are not limited to, the administration of DNase enzymes, antibiotics, antimicrobials, anti-infectives, anti-fungals, anti-parasitics, anti-virals, or other antibodies.

In some embodiments, the methods and compositions include a deoxyribonuclease (DNase) enzyme that acts synergistically with the anti-DNABII antibody. A DNase is any enzyme that catalyzes the cleavage of phosphodiester linkages in the DNA backbone. Three non-limiting examples of DNase enzymes that are known to target not only cruciform structures, but also a variety of secondary structure of DNA include DNAse I, T4 EndoVII, T7 Endo I, RuvABC, and RusA. In certain embodiments, the effective amount of anti-DNABII antibody needed to destabilize the biofilm is reduced when combined with a DNase. When administered in vitro, the DNase can be added directly to the assay or in a suitable buffer known to stabilize the enzyme. The effective Unit dose of DNase and the assay conditions may vary, and can be optimized according to procedures known in the art.

In other embodiments, the methods and compositions can be combined with antibiotics and/or antimicrobials. Antimicrobials are substances that kill or inhibit the growth of microorganisms such as bacteria, fungi, or protozoans. Although biofilms are generally resistant to the actions of antibiotics, compositions and methods described herein can be used to sensitize the infection involving a biofilm to traditional therapeutic methods for treating infections. In other embodiments, the use of antibiotics or antimicrobials in combination with methods and compositions described herein allow for the reduction of the effective amount of the antimicrobial and/or biofilm reducing agent. Some non-limiting examples of antimicrobials and antibiotics useful in combination with methods of the current disclosure include amoxicillin, amoxicillin-clavulanate, cefdinir, azithromycin, and sulfamethoxazole-trimethoprim. The therapeutically effective dose of the antimicrobial and/or antibiotic in combination with the biofilm reducing agent can be readily determined by traditional methods. In some embodiments the dose of the antimicrobial agent in combination with the biofilm reducing agent is the average effective dose which has been shown to be effective in other bacterial infections, for example, bacterial infections wherein the etiology of the infection does not include a biofilm. In other embodiments, the dose is 0.1, 0.15, 0.2, 0.25, 0.30, 0.35, 0.40, 0.45, 0.50, 0.55, 0.60, 0.65, 0.70, 0.75, 0.8, 0.85, 0.9, 0.95, 1.1, 1.2, 1.3, 1.4, 1.5, 1.6, 1.7, 1.8, 1.9, 2.0, 2.5, 3.0 or 5 times the average effective dose. The antibiotic or antimicrobial can be added prior to, concurrent with, or subsequent to the addition of the anti-DNABII antibody.

In other embodiments, the methods and compositions can be combined with antibodies that treat the bacterial infection. One example of an antibody useful in combination with the methods and compositions described herein is an antibody directed against an unrelated outer membrane protein (i.e., OMP P5). Treatment with this antibody alone does not debulk a biofilm in vitro. Combined therapy with this antibody and a biofilm reducing agent results in a greater effect than that which could be achieved by either reagent used alone at the same concentration. Other antibodies that may produce a synergistic effect when combined with a biofilm reducing agent or methods to reduce a biofilm include anti-rsPilA anti-OMP26, anti-OMP P2, and anti-whole OMP preparations.

The compositions and methods described herein can be used to sensitize the bacterial infection involving a biofilm to common therapeutic modalities effective in treating bacterial infections without a biofilm but are otherwise ineffective in treating bacterial infections involving a biofilm. In other embodiments, the compositions and methods described herein can be used in combination with therapeutic modalities that are effective in treating bacterial infections involving a biofilm, but the combination of such additional therapy and biofilm reducing agent or method produces a synergistic effect such that the effective dose of either the biofilm reducing agent or the additional therapeutic agent can be reduced. In other instances, the combination of such additional therapy and biofilm reducing agent or method produces a synergistic effect such that the treatment is enhanced. An enhancement of treatment can be evidenced by a shorter amount of time required to treat the infection.

The additional therapeutic treatment can be added prior to, concurrent with, or subsequent to methods or compositions used to reduce the biofilm, and can be contained within the same formation/composition or as a separate formulation/composition.

Kits

Kits containing the agents and instructions necessary to perform the in vitro and in vivo methods as described herein also are claimed. Accordingly, the disclosure provides kits for performing these methods which may include an antibody, antibody fragment, polypeptide, polynucleotide, vector or host cell, as well as instructions for carrying out the methods disclosed herein such as collecting tissue and/or performing the screen, and/or analyzing the results, and/or administration of an effective amount of an antibody, antibody fragment, polypeptide, polynucleotide, vector or host cell, as defined herein. These can be used alone or in combination with other suitable antimicrobial agents.

For example, a kit can comprise, or alternatively consist essentially of, or yet further consist of any one or more of agents identified above, e.g., antibody, antibody fragment, polypeptide, polynucleotide, vector or host cell, and instructions for use. The kit can further comprise one or more of an adjuvant, an antigenic peptide or an antimicrobial. Examples of carriers include a liquid carrier, a pharmaceutically acceptable carrier, a solid phase carrier, a pharmaceutically acceptable carrier, a pharmaceutically acceptable polymer, a liposome, a micelle, an implant, a stent, a paste, a gel, a dental implant, or a medical implant.

The following examples are intended to illustrate, and not limit the embodiments disclosed herein.

Experimental

Experiment No. 1

Antibodies were generated from 2 IHF(NTHI) tip chimeric peptide and IHF(NTHI) tail chimeric peptide in addition to two murine hybridoma cells lines IHF(NTHI) tip chimeric peptide clone and IHF(NTHI) tail chimeric peptide clone. Heavy and light chains were sequenced. A chimeric parenteral antibody comprised of the murine variable region sequences for two separate antibodies were fused to the backbone of the constant region for human IgG1. Specificity of each clone to the respective synthetic peptide confirmed by ELISA. A fully human antibody was completed and 9 antibody variants to the tip chimeric peptide and 9 antibody variants to the tail chimeric peptide was completed and specificity of each clone to its respective target was confirmed by ELISA (see Experiment No. 2). Avidity and affinity of each antibody was determined.

Experiment No. 2

A direct binding ELISA was performed to assess the binding of the humanized variants against the corresponding peptides. Tip or tail chimeric peptide was coated onto a 96-well plate at 2 μg/mL and an 8-point dilution series of the antibodies were added (starting concentration of 50 ug/mL, 1:3 dilution). An anti-human IgG Fc HRP conjugated antibody (1:7000, Jackson Immuno Research, 109-035-098) was used as the secondary detection antibody. A standard direct ELISA protocol was followed and the read the absorbance at 450 nm using a microplate reader. $EC_{50}$ values were calculated, and the humanized variants were determined to have comparable binding. See FIGS. 2A through 2D as well as Tables 1 and 2 below.

TABLE 1

ELISA results using humanized anti-tip antibodies.

| Heavy chain | Light chain | ELISA #1: peptide as target (titration curves not reaching equilibrium) $EC_{50}$ (ng/ml) | ELISA #2: peptide as target (titration curves reaching equilibrium) $EC_{50}$ (ng/ml) |
|---|---|---|---|
| SEQ ID NO: 1 | SEQ ID NO: 7 | 60.0 | 70.4 |
| SEQ ID NO: 1 | SEQ ID NO: 8 | 66.0 | 64.4 |
| SEQ ID NO: 1 | SEQ ID NO: 9 | 32.0 | 55.0 |
| SEQ ID NO: 2 | SEQ ID NO: 7 | 49.0 | 62.0 |
| SEQ ID NO: 2 | SEQ ID NO: 8 | 55.0 | 40.2 |
| SEQ ID NO: 2 | SEQ ID NO: 9 | 27.0 | 45.3 |
| SEQ ID NO: 3 | SEQ ID NO: 7 | 75.0 | 85.8 |
| SEQ ID NO: 3 | SEQ ID NO: 8 | 66.0 | 93.4 |
| SEQ ID NO: 3 | SEQ ID NO: 9 | 35.0 | 111.1 |

TABLE 2

ELISA results using humanized anti-tail antibodies.

| Heavy chain | Light chain | ELISA #1: peptide as target (titration curves not reaching equilibrium) $EC_{50}$ (ng/ml) | ELISA #2: peptide as target (titration curves reaching equilibrium) $EC_{50}$ (ng/ml) |
|---|---|---|---|
| SEQ ID NO: 4 | SEQ ID NO: 10 | 10.0 | 42.7 |
| SEQ ID NO: 4 | SEQ ID NO: 11 | 11.0 | 40.8 |
| SEQ ID NO: 4 | SEQ ID NO: 12 | 12.0 | 40.4 |
| SEQ ID NO: 5 | SEQ ID NO: 10 | 7.0 | 36.7 |
| SEQ ID NO: 5 | SEQ ID NO: 11 | 14.0 | 33.9 |
| SEQ ID NO: 5 | SEQ ID NO: 12 | 15.0 | 42.9 |
| SEQ ID NO: 6 | SEQ ID NO: 10 | 13.0 | 27.4 |
| SEQ ID NO: 6 | SEQ ID NO: 11 | 11.0 | 28.0 |
| SEQ ID NO: 6 | SEQ ID NO: 12 | 8.0 | 29.4 |

Surface plasmon resonance (SPR) was also used to determine the affinity of the humanized Mabs to the tip or tail chimeric peptide (i.e., target peptide) and to native $IHF_{NTHI}$. SPR using a Biacore 3000 instrument (GE Healthcare Life Sciences) was performed. All experiments were conducted at 25° C. and 10 mM HEPES (pH 7.4)-150 mM NaCl-3 mM EDTA-0.005% Surfactant P20 (HBS-EP; GE Healthcare) served as the running buffer.

In one experimental setting, surface plasmon resonance (SPR) was performed as indicated below: A CM5 reagent grade sensor chip was used to immobilize $IHF_{NTHI}$ tip or $IHF_{NTHI}$ tail chimeric peptide to individual flow cells via amine coupling chemistry. Each monoclonal antibody was diluted two-fold from 100 nM to 3.1 nM in HBS-EP buffer+NSB and injected across the sensor chip surface at a flow rate 30 μl/min, 2 min injection cycle, 2 min dissociation cycle. A buffer-only negative control injection cycle was also included to reveal non-specific binding. Association and dissociation constants were determined using BiaEvaluation In one experimental setting, via amine couple chemistry and at a flow rate of 5 μl/min, humanized monoclonal antibody was immobilized to flow cells of a CM5 sensor chip to 4000 resonance units (RU) to assay binding of the target peptide or 2000 RU to assess binding of native $IHF_{NTHI}$. Next, the target peptide or native $IHF_{NTHI}$ was suspended in HBS-EP plus NSB reducer and serial two-fold dilutions from 100 nM to 3.1 nM, including a buffer-only sample, were injected across the antibody-bound surface at a flow rate of 30 μl/min, 5 min injection time, 5 min dissociation time using the KINJECT command. BiaEvaluation software was used align sensorgram curves, subtract buffer-only injection cycle and determine $K_D$ values. The results are shown in Tables 3 and 4 below.

TABLE 3

SPR results using humanized anti-tip antibodies.

| Heavy chain | Light chain | SPR: Peptide immobilized, HuMab as analyte ||| SPR: IHF$_{NTHI}$ immobilized, HuMab as analyte |||
|---|---|---|---|---|---|---|---|
| | | $k_{on}$ (M$^{-1}$s$^{-1}$) | $k_{off}$ (s$^{-1}$) | $K_D$ (nM) | $k_{on}$ (M$^{-1}$s$^{-1}$) | $k_{off}$ (s$^{-1}$) | $K_D$ (nM) |
| SEQ ID NO: 1 | SEQ ID NO: 7 | 3.1E+04 | 2.2E−04 | 7.0 | 5.4E+03 | 9.0E−05 | 17.0 |
| SEQ ID NO: 1 | SEQ ID NO: 8 | 4.2E+04 | 1.1E−05 | 0.3 | 1.5E+05 | 6.0E−03 | 40.0 |
| SEQ ID NO: 1 | SEQ ID NO: 9 | 4.0E+04 | 1.3E−05 | 0.3 | 6.5E+06 | 1.6E−01 | 24.0 |
| SEQ ID NO: 2 | SEQ ID NO: 7 | 1.8E+04 | 2.6E−03 | 144.0 | 3.1E+01 | 1.4E−03 | 4400.0 |
| SEQ ID NO: 2 | SEQ ID NO: 8 | 2.2E+04 | 2.8E−04 | 13.0 | 4.2E+02 | 1.5E−04 | 354.0 |
| SEQ ID NO: 2 | SEQ ID NO: 9 | 3.7E+03 | 1.2E−05 | 4.0 | 4.6E+00 | 1.7E−03 | 125.0 |
| SEQ ID NO: 3 | SEQ ID NO: 7 | 4.8E+04 | 4.0E−04 | 8.0 | 1.4E+02 | 1.1E−04 | 825.0 |
| SEQ ID NO: 3 | SEQ ID NO: 8 | 5.1E+04 | 3.5E−04 | 7.0 | 1.8E+03 | 2.1E−04 | 115.0 |
| SEQ ID NO: 3 | SEQ ID NO: 9 | 7.9E+04 | 2.1E−04 | 3.0 | 4.6E+03 | 1.6E−02 | 3400.0 |

TABLE 4

SPR results using humanized anti-tail antibodies.

| Heavy chain | Light chain | SPR: Peptide immobilized, HuMab as analyte |||
|---|---|---|---|---|
| | | kon (M$^{-1}$s$^{-1}$) | koff (s$^{-1}$) | KD (nM) |
| SEQ ID NO: 4 | SEQ ID NO: 10 | 1.5E+05 | 6.4E−04 | 4.3 |
| SEQ ID NO: 4 | SEQ ID NO: 11 | 1.4E+05 | 6.8E−04 | 4.9 |
| SEQ ID NO: 4 | SEQ ID NO: 12 | 1.1E+05 | 5.6E−04 | 5.1 |
| SEQ ID NO: 5 | SEQ ID NO: 10 | 1.3E+05 | 8.2E−04 | 6.1 |
| SEQ ID NO: 5 | SEQ ID NO: 11 | 1.2E+05 | 7.6E−04 | 6.2 |
| SEQ ID NO: 5 | SEQ ID NO: 12 | 8.5E+04 | 7.7E−04 | 9.1 |
| SEQ ID NO: 6 | SEQ ID NO: 10 | 1.8E+05 | 4.6E−04 | 2.5 |
| SEQ ID NO: 6 | SEQ ID NO: 11 | 1.6E+05 | 1.6E−04 | 1.0 |
| SEQ ID NO: 6 | SEQ ID NO: 12 | 2.5E+05 | 6.0E−04 | 2.4 |

In another experimental setting, via amine couple chemistry and at a flow rate of 5 μl/min, the target peptide or native IHF$_{NTHI}$ was immobilized to flow cells of a CM5 sensor chip to 4000 resonance units (RU) or 2000 RU respectively to assay binding of the humanized monoclonal antibodies. Next, the humanized monoclonal antibodies were as suspended in HBS-EP plus NSB reducer and serial two-fold dilutions from 100 nM to 3.1 nM, including a buffer-only sample, were injected across the peptide/IHF$_{NTHI}$-bound surface at a flow rate of 30 μl/min, 5 min injection time, 5 min dissociation time using the KINJECT command. BiaEvaluation software was used align sensorgram curves, subtract buffer-only injection cycle and determine $K_D$ values. The results are shown in Tables 5 and 6 below.

TABLE 5

SPR results using humanized anti-tip antibodies.

| Heavy chain | Light chain | SPR: HuMab immobilized, peptide as analyte ||| SPR: HuMab immobilized, IHF$_{NTHI}$ as analyte |||
|---|---|---|---|---|---|---|---|
| | | $k_{on}$ (M$^{-1}$s$^{-1}$) | $k_{off}$ (s$^{-1}$) | $K_D$ (nM) | $k_{on}$ (M$^{-1}$s$^{-1}$) | $k_{off}$ (s$^{-1}$) | $K_D$ (nM) |
| SEQ ID NO: 1 | SEQ ID NO: 7 | 4.5E+03 | 3.4E−04 | 76.0 | 1.4E+03 | 1.4E−05 | 10.0 |
| SEQ ID NO: 1 | SEQ ID NO: 8 | 1.7E+04 | 3.7E−04 | 21.0 | 1.4E+06 | 3.2E−04 | 0.2 |
| SEQ ID NO: 1 | SEQ ID NO: 9 | 2.5E+03 | 3.8E−04 | 152.0 | 6.3E+05 | 3.7E−04 | 0.6 |
| SEQ ID NO: 2 | SEQ ID NO: 7 | 2.8E+02 | 1.5E−04 | 527.0 | 6.4E+05 | 4.0E−04 | 0.6 |
| SEQ ID NO: 2 | SEQ ID NO: 8 | 3.0E+02 | 7.7E−05 | 257.0 | 7.0E+04 | 5.9E−04 | 9.0 |
| SEQ ID NO: 2 | SEQ ID NO: 9 | 3.5E+03 | 7.4E−05 | 23.0 | 7.2E+03 | 4.5E−04 | 62.0 |
| SEQ ID NO: 3 | SEQ ID NO: 7 | 5.4E+04 | 1.6E−03 | 29.0 | 6.6E+04 | 4.0E−04 | 6.0 |

TABLE 5-continued

SPR results using humanized anti-tip antibodies.

| Heavy chain | Light chain | SPR: HuMab immobilized, peptide as analyte | | | SPR: HuMab immobilized, IHF$_{NTHI}$ as analyte | | |
|---|---|---|---|---|---|---|---|
| | | $k_{on}$ (M$^{-1}$s$^{-1}$) | $k_{off}$ (s$^{-1}$) | $K_D$ (nM) | $k_{on}$ (M$^{-1}$s$^{-1}$) | $k_{off}$ (s$^{-1}$) | $K_D$ (nM) |
| SEQ ID NO: 3 | SEQ ID NO: 8 | 9.5E+04 | 1.9E−03 | 20.0 | 7.5E+03 | 1.8E−03 | 245.0 |
| SEQ ID NO: 3 | SEQ ID NO: 9 | 9.5E+03 | 1.9E−03 | 200.0 | 1.7E+03 | 2.7E−03 | 1600.0 |

TABLE 6

SPR results using humanized anti-tail antibodies.

| Heavy chain | Light chain | SPR: HuMab immobilized, peptide as analyte | | | SPR: HuMab immobilized, IHF$_{NTHI}$ as analyte | | |
|---|---|---|---|---|---|---|---|
| | | $k_{on}$ (M$^{-1}$s$^{-1}$) | $k_{off}$ (s$^{-1}$) | $K_D$ (nM) | $k_{on}$ (M$^{-1}$s$^{-1}$) | $k_{off}$ (s$^{-1}$) | $K_D$ (nM) |
| SEQ ID NO: 4 | SEQ ID NO: 10 | 1.1E+04 | 3.3E−04 | 29.6 | 7.7E+04 | 4.3E−04 | 33.1 |
| SEQ ID NO: 4 | SEQ ID NO: 11 | 4.3E+02 | 2.7E−04 | 62.2 | 1.0E+05 | 5.3E−04 | 53.0 |
| SEQ ID NO: 4 | SEQ ID NO: 12 | ND | ND | ND | ND | ND | ND |
| SEQ ID NO: 5 | SEQ ID NO: 10 | 4.8E+03 | 2.9E−04 | 60.0 | 1.6E+05 | 5.7E−04 | 93.4 |
| SEQ ID NO: 5 | SEQ ID NO: 11 | 5.7E+03 | 2.7E−04 | 47.0 | 1.4E+05 | 6.1E−04 | 82.4 |
| SEQ ID NO: 5 | SEQ ID NO: 12 | 2.0E+04 | 4.4E−04 | 23.0 | 3.3E+04 | 1.2E−03 | 39.0 |
| SEQ ID NO: 6 | SEQ ID NO: 10 | 1.8E+04 | 1.3E−03 | 72.0 | 2.5E+04 | 7.3E−04 | 18.0 |
| SEQ ID NO: 6 | SEQ ID NO: 11 | 3.3E+04 | 1.3E−03 | 67.0 | 4.6E+04 | 6.8E−04 | 31.0 |
| SEQ ID NO: 6 | SEQ ID NO: 12 | 1.6E+05 | 2.1E−03 | 13.0 | 7.7E+03 | 1.1E−03 | 8.5 |

* ND = not done

Experiment No. 3

This experiment describes an in vitro model for reversal of an established biofilm in 8-well chamber slide. The materials used in this experiment are: Chocolate Agar; sBHI (BHI with 2 mg heme/mL and 2 mg b-NAD/mL); 8-well Chamber slides (Nunc* Lab-Tek* Fisher catalog #12-565-18); Sterile 0.9% saline; LIVE/DEAD BacLight Bacterial Viability Kit (Fisher catalog #NC9439023) and Formalin.

NTHI 86-028NP colonies were collected from overnight culture on chocolate agar and suspended in brain heart infusion broth supplemented with 2 µg β-NAD and heme per ml medium (sBHI). The optical density at 490 nm was then adjusted to 0.65 and the culture diluted 1:6 in sBHI prior to incubation at 37° C. with 5% CO2 for 3 hr, static. Next, the culture was diluted 1:2500 in fresh sBHI and 200 µl of the suspension aliquotted into each well of an 8-well chamber slide. The slide was then incubated at 37° C. with 5% CO2 for 3 hr, static. After 16 hr, 200 µl fresh sBHI was added to each well, and the slide incubated an additional 8 hr. At this time point, medium was aspirated from each well and monoclonal antibodies at 5 µg per well added. The biofilms were incubated an additional 16 hr. Biofilms were then washed and stained with FM1-43FX bacterial cell membrane stain (Invitrogen) and fixed overnight at 4° C. in 16% paraformaldehyde, 2.5% glutaraldehyde, 4.0% acetic acid in 0.1 M phosphate buffer (pH 7.4). Fixative was aspirated an 200 µl 0.9% Hank's Balanced Salt Solution was added to each well prior to viewing of biofilms on a Zeiss 800 Meta-laser scanning confocal microscope. Images were compiled with Zeiss Zen Blue software and biofilm biomass calculated with COMSTAT2 software. See FIG. 3 as well as Tables 7-8 below.

TABLE 7

In vitro biofilm disruption results using humanized anti-tip antibodies.

| Heavy chain | Light chain | Biofilm disruption in vitro (% change in biomass) |
|---|---|---|
| SEQ ID NO: 1 | SEQ ID NO: 7 | ↓87 |
| SEQ ID NO: 1 | SEQ ID NO: 8 | ↓80 |
| SEQ ID NO: 1 | SEQ ID NO: 9 | ↓90 |
| SEQ ID NO: 2 | SEQ ID NO: 7 | ↓50 |
| SEQ ID NO: 2 | SEQ ID NO: 8 | ↓60 |
| SEQ ID NO: 2 | SEQ ID NO: 9 | ↓70 |
| SEQ ID NO: 3 | SEQ ID NO: 7 | ↓87 |
| SEQ ID NO: 3 | SEQ ID NO: 8 | ↓80 |
| SEQ ID NO: 3 | SEQ ID NO: 9 | ↓67 |

↓ indicates decrease in biomass;
while ↑ indicates increase in biomass.

TABLE 8

In vitro biofilm disruption using humanized anti-tail antibodies.

| Heavy chain | Light chain | Biofilm disruption in vitro (% change in biomass) |
|---|---|---|
| SEQ ID NO: 4 | SEQ ID NO: 10 | ↓6 |
| SEQ ID NO: 4 | SEQ ID NO: 11 | ↑7 |
| SEQ ID NO: 4 | SEQ ID NO: 12 | ↑8 |
| SEQ ID NO: 5 | SEQ ID NO: 10 | ↓4 |
| SEQ ID NO: 5 | SEQ ID NO: 11 | ↑4 |
| SEQ ID NO: 5 | SEQ ID NO: 12 | 0 |
| SEQ ID NO: 6 | SEQ ID NO: 10 | ↓6 |

TABLE 8-continued

In vitro biofilm disruption using humanized anti-tail antibodies.

| Heavy chain | Light chain | Biofilm disruption in vitro (% change in biomass) |
|---|---|---|
| SEQ ID NO: 6 | SEQ ID NO: 11 | ↓3 |
| SEQ ID NO: 6 | SEQ ID NO: 12 | ↑3 |

↓ indicates decrease in biomass;
while ↑ indicates increase in biomass.

Experiment No. 4

In a follow up study to Experiments 1 to 3, above, the following study is described, showing targeting a bacterial DNABII protein with a chimeric peptide immunogen or humanized monoclonal antibody to prevent or treat recalcitrant biofilm-mediated infections Study Overview First, as a therapeutic approach, Applicant used intact IgG or Fab fragments against a chimeric peptide immunogen designed to target protective epitopes within the DNA-binding tip domains of integration host factor to disrupt established biofilms in vitro and to mediate resolution of existing disease in vivo. Second, Applicant performed preventative active immunization with the chimeric peptide to induce the formation of antibody that blocks biofilm formation and disease development in a model of viral-bacterial superinfection. Further, toward the path for clinical use, Applicant humanized a monoclonal antibody against the chimeric peptide immunogen, then characterised and validated that it maintained therapeutic efficacy.

Applicant demonstrated efficacy of each approach in two well-established pre-clinical models of otitis media induced by the prevalent respiratory tract pathogen nontypeable *Haemophilus influenzae*, a common biofilm disease. Collectively, Applicant's data revealed two approaches with substantive efficacy and potential for broad application to combat diseases with a biofilm component.

The aims of Experiment No. 4 were to (1) test the pre-clinical therapeutic potential of the antigen binding domains of IgG (Fab fragments) of a monoclonal antibody directed against a DNABII-directed tip-chimeric peptide to resolve a well-characterized biofilm disease, otitis media due to NTHI, and (2) test this same tip-chimeric peptide as an immunogen for its ability to induce antibodies that would prevent biofilm formation and disease when used as a vaccine antigen in active immunization regimens as a complementary preventative strategy. Applicant first evaluated Fabs- or intact IgG against the tip-chimeric peptide mediated disruption of bacterial biofilms in vitro. Applicant then used two well-established chinchilla models of a common biofilm disease, otitis media due to NTHI (one based on direct bacterial challenge of the middle ear and the other, a viral-bacterial superinfection model of ascending OM), and demonstrated the pre-clinical efficacy of both Applicant's DNABII-directed therapeutic and prevention strategies, respectively. Lastly, Applicant humanized one DNABII-directed monoclonal antibody and validated its activity in vitro as well as its therapeutic efficacy pre-clinically.

In vitro biofilm disruption assays were repeated three times on separate days. For in vivo experiments, chinchillas were randomly divided into cohorts based on body weight; both male and female animals were enrolled. To examine disruption of NTHI biofilms from the middle ear as induced by murine β-tip, Fabs, β-tail Fabs or isotype control Fabs, 3 or 4 animals were enrolled into each cohort. To test biofilm disruption induced by Fabs from rabbit polyclonal anti-tip chimeric peptide serum IgG, anti-tail chimeric peptide serum IgG or IgG from naive rabbit serum, cohorts of six chinchillas each were established. Efficacy of HuTipMabs, compared to HuTailMabs or saline was evaluated with six animals per cohort. Neither animals nor samples were excluded from the study. Evaluation of relative mucosal biofilm that remained in the middle ear after treatment was performed by 6-8 individuals not involved in the study and who were blinded to therapy delivered. For each study assessment, each middle ear was considered independent.

Murine Monoclonal Antibodies, Polyclonal Rabbit Antibodies and Humanized Monoclonal Antibodies Murine monoclonal antibodies against β-tip (clone 12E6.F8.D12.D5, mIhfB4$_{NTHI}$) or β-tail (clone 7A4.E4.G11, IhfB2$_{NTHI}$) domains of IHF$_{NTHI}$ were purified from cell culture supernatants as described in (L. A. Novotny et al. (2016) EBioMedicine 10: 33-44). Mouse IgG1κ isotype control antibody (clone P3.6.2.8.1; eBioscience cat #16-4714-82, RRID: AB_470161) served as a negative control. Fab fragments were then generated by papain digestion with Mouse IgG1 Fab and F(ab')$_2$ preparation kit (Pierce) according to instructions. Polyclonal rabbit anti-tip chimeric peptide and anti-tail chimeric peptide were generated at Rockland Immunochemical, Inc. (L. A. Novotny et al. (2014) Mol. Microbiol 93:1246-1258). Naive rabbit serum served as a negative control. IgG was enriched from each rabbit serum by passage through rProtein A Protein G GraviTrap columns (GE Healthcare) according to manufacturer's instructions. Fab fragments (Fabs) were then generated via Pierce Fab Preparation kit. Digestion of intact murine or rabbit IgG to Fabs was confirmed by SDS-PAGE with Coomassie Fluor™ Orange Protein Gel stain (ThermoFisher). Humanized monoclonal antibodies against the tip chimeric peptide (HuTipMab) or tail chimeric peptide (HuTailMab) were generated at LakePharma, Inc. and described briefly above. The antigen-binding domains were derived from a murine monoclonal antibody directed against the tip chimeric peptide (clone 1F8.C3.D11.F1) or tail chimeric peptide (clone 11E7.G11.C7). Humanized monoclonal antibody clones TP-21949 (tip chimeric peptide-directed; HuTipMab) and TP-21958 (tail chimeric peptide-directed; HuTailMab) were used for the work herein. Bacterial endotoxin test via ToxinSensor Chromogenic LAL endotoxin kit (Genscript) was performed on all antibody lots prior to use.

In Vitro Biofilm Disruption

Biofilms formed by NTHI strain 86-028NP (a minimally passaged clinical isolate from the nasopharynx of a child with chronic OM, see for example, Bakaletz L O et al. (1988) Infect Immun 1988; 56: 331-5), *M. catarrhalis* strain 7169 (a minimally passaged clinical isolate from the middle ear of a child with chronic OM, see for example, Luke N R et al (1999) Infect Immun 1999; 67: 681-7), *P. aeruginosa* strain 27853, *B. cenocepacia* strain K56 (isolated from the sputum of a patient with cystic fibrosis, see, for example, Mahenthiralingam E et al (2000) J Clin Microbiol 2000; 38: 910-3) and *S. aureus* strain 29213 were first established in 8-well chambered coverglass (CellVis) for 24 h prior to incubation with 170 nM intact IgG or Fab fragments for an additional 16 h (S. D. Goodman et al. (2011) Mucosal Immunol 4:625-637; J. A. Jurcisek et al. (2011) J Vis Exp). In one embodiment, NTHI strain 86-028NP was kept no more than passage #4 since it came out of a child in 1986. Additionally or alternatively, the Mcat strain has similarly been kept at a very low passage number since its isolation. In a further embodiment, the *Burkholderia* was isolated from the sputum of a cystic fibrosis (CF) patient. In yet a further embodiment, the *Staphylococcus aureus* isolate was from the ATCC. A concentration of 170 nM was based on prior studies wherein 5 μg intact IgG per 0.2 ml volume was applied to in vitro biofilms (Goodman S D et al (2011) Mucosal Immunol 2011; 4: 625-37; Brockson M E et al (2014) Mol Microbiol 2014; 93: 1246-58; Novotny L A et al (2019) NPJ Vaccines 2019; 4: 43; Novotny L A et al (2013) PLoS One 2013; 8: e67629; and Novotny L A et al (2016) EBioMedicine 2016; 10: 33-44) to permit direct comparison between IgG-versus Fabs-mediated disruption. Bacteria within the biofilms were then stained with FM1-43FX (ThermoFisher), fixed overnight in a solution of 16% paraformaldehyde-4% acetic acid-2.5% glutaraldehyde in 0.1 M phosphate buffer (pH 7.4) then washed with 10 mM phosphate buffered saline (pH 7.4). Biofilms were viewed with a Zeiss 800 scanning confocal laser microscope, images rendered in Zeiss Zen Pro software and biomass determined with COMSTAT2 software (A. Heydorn et al. (2000) Microbiology 146 (pt 10): 2395-2407). In vitro biofilm disruption assays were repeated three times on separate days.

Animals

Chinchilla work was performed in accordance with the NIH Guide for the Care and Use of Laboratory Animals and under protocol #01304AR approved by Abigail Wexner Research Institute at Nationwide Children's Hospital Animal Care and Use Committee. Juvenile or adult chinchillas (*Chinchilla lanigera*; juvenile animals were 250-499 g in body mass; adult animals were 500-850 g in body mass) were obtained from Rauscher's Chinchilla Ranch, LLC. These outbred, non-specific pathogen-free animals were housed in individual cages with autoclaved corncob bedding and sterile water provided ad libitum. Animals were randomly divided into cohorts based on body weight (as an indication of juvenile or adult status) and both male and female animals were used. Experimental groups were as follows: to examine disruption of NTHI biofilms from the middle ear as induced by murine β-tip Fabs, β-tail Fabs or isotype control Fabs, three or four animals were enrolled into each cohort (mean body mass per cohort, 625 g). To test biofilm disruption induced by Fabs from rabbit polyclonal anti-tip chimeric peptide serum IgG, anti-tail chimeric peptide serum IgG or IgG from naive rabbit serum, cohorts of three chinchillas each were established (mean body mass per cohort, 505 g). Efficacy of HuTipMab, compared to HuTailMab or saline was evaluated with three animals per cohort (mean body mass per cohort, 580 g). To evaluate the ability of the tip chimeric peptide to induce production of antibodies that prevented the development of NTHI-induced OM, eight juvenile animals were used per cohort (mean body mass per cohort, 430 g).

Disruption of NTHI Biofilms Formed in the Middle Ears of Chinchillas in Experimental OM Both middle ears of each animal were challenged with 1000 CFU NTHI strain 86-028NP by direct injection to induce experimental OM. Four days later, NTHI mucosal biofilms fill >50% of the middle ear (L. A. Novonty et al. (2011) Mucosal Immunol 4: 456-467). At this time, 342 nM Fabs or humanized monoclonal antibody was injected into each middle ear (0.1 ml delivered per bulla), with identical treatment delivered 24 h later. A concentration of 342 nM was based on prior studies wherein 5 μg intact IgG per 0.1 ml volume was injected into the middle ears of chinchillas (Goodman S D et al 92011) Mucosal Immunol 2011; 4: 625-37; Novotny L A et al (2019) NPJ Vaccines 2019; 4: 43; and Novotny L A et al (2016) EBioMedicine 2016; 10: 33-44) 11, 13, 21 and to permit direct comparison between IgG-versus Fabs-mediated disruption in vivo. To determine the immediate outcome of treatment, animals were sacrificed one day after completion of antibody therapy, images of mucosal biofilms captured with a Zeiss SV6 dissecting microscope, then mucosal biofilms and middle ear mucosa collected, homogenized and plated on to chocolate agar to quantitate the bacterial load within the middle ear (S. D. Goodman et al. (2011) Mucosal Immunol 4: 625-637). In two of the studies described herein (assessment of biofilms disruption by polyclonal rabbit IgG Fab fragments and efficacy of humanized monoclonal antibody to disrupt mucosal biofilms, and cytokine profile of HuMabs treated animals), a subset of animals in each cohort was monitored an extra seven days without additional treatment to examine whether NTHI biofilms would re-form upon cessation of antibody therapy as well as determine how the cytokine profile might change over time. Mucosal biofilms were collected and processed as described (S. D. Goodman et al. (2011) Mucosal Immunol 4: 625-637).

Quantitative Assessment of Amount of Mucosal Biofilm

As an additional assessment, the amount of biofilm in each middle ear was qualitatively determined. Images of each middle ear were captured, randomized and ranked by six reviewers blinded to treatment delivered using an established rubric wherein 0=no mucosal biofilm visible, 1=<25% of middle ear occluded by mucosal biofilm, 2=≥25-50% occluded, 3=≥50-75% occluded, 4=≥75-100% occluded (L. A. Novotny et al. (2011) Mucosal Immunol 4: 456-467). For both quantitation of bacterial load and qualitative assessment of mucosal biofilm, each middle ear was considered independent.

Quantitation of Cytokines in Middle Ear Fluids

To quantitate cytokines in middle ear fluids (MEF) a BD™ Cytometric Bead Array was performed with fluids collected at the time of animal sacrifice. With BD™ human-specific Flex Sets each MEF was individually examined for quantity of IL-1β (cat #558279), IL-6 (cat #558276), IL-8 (cat #558277), IL-10 (cat #558274), IL12-p70 (cat #558283), IL-17A (cat #560383) and TNF (cat #560112) using according to manufacturer's instructions. The cytokine IL-13 (cat #558450) was added to the panel used to assay MEF collected in the HuMabs study. MEF from each animal were assayed individually. Data were captured on a BD Accuri™ C6 cytometer (BD Biosciences) and analyzed with FlowJo software (FlowJo, LLC). The concentration of cytokines in each MEF was determined using a standard curve and calculated using GraphPad Prism software.

Surface Plasmon Resonance

To determine the affinity of the humanized tip chimeric peptide directed monoclonal antibody to the tip chimeric peptide and to native $IHF_{NTHI}$, surface plasmon resonance using a Biacore 3000 instrument (GE Healthcare Life Sciences) was performed. All experiments were conducted at 25° C. and 10 mM HEPES (pH 7.4)-150 mM NaCl-3 mM EDTA-0.005% Surfactant P20 (HBS-EP; GE Healthcare, cat #BR100188) served as the running buffer. Via amine couple chemistry and at a flow rate of 5 μl/min, humanized tip chimeric peptide-specific monoclonal antibody was immobilized to flow cells of a CM5 sensor chip (GE Healthcare, cat #BR100012) to 4000 resonance units (RU) to assay binding of tip chimeric peptide or 2000 RU to assess binding of native $IHF_{NTHI}$. Next, tip chimeric peptide or native IHF$_{NTHI}$ was suspended in HBS-EP plus NSB reducer (GE Healthcare, cat #BR100691) and serial two-fold dilutions from 100 nM to 3.1 nM, including a buffer-only sample, were injected across the antibody-bound surface at a flow rate of 30 µl/min, 5 min injection time, 5 min dissociation time using the KINJECT command. BiaEvaluation software was used align sensorgram curves, subtract buffer-only injection cycle and determine $K_D$ values.

Viral-Bacterial Co-Infection Model of Experimental NTHI-Induced OM

An established adenovirus-NTHI polymicrobial challenge model (K. Suzuki et al. (1994) Infect Immun 62: 1710-1718) was employed to assess efficacy of the tip chimeric peptide when delivered as a pre-clinical vaccine antigen and/or to evaluate the ability of the tip chimeric peptide to induce production of antibodies that prevented the development of NTHI-induced OM. Chinchillas were randomly divided into three cohorts of eight animals each based on body weight and immunized by rubbing vaccine formulations on to the unabraded skin behind each pinna (post-auricular region) (L. A. Novotny et al. (2017) Clin Vaccine Immunol 24). Formulations consisted of 10 µg tip chimeric peptide or 10 µg tail chimeric peptide, each admixed with 10 µg of the adjuvant LT(R192G/L211A), a double mutant of E. coli heat labile enterotoxin (dmLT; a generous gift from Dr. John Clements) (J. D. Clements et al. (2018) dmLT. mSphere 3). As a negative control, one cohort received 10 µg dmLT only. A second identical dose was delivered one week later. Two days after receipt of the second dose, the time when the maximal immune response is observed for this immunization regimen (L. A. Novotny et al. (2013) Vaccine 31: 3417-3426), all chinchillas were inoculated with $1.9 \times 10^7$ TCID$_{50}$ of adenovirus serotype 1 by passive inhalation of droplets. Seven days later, when adenovirus-induced compromise of the airway occurs (K. Suzuki et al. (1994) Infect Immun 62: 1710-1718), all animals were challenged with $10^8$ CFU NTHI strain 86-028NP by passive droplet inhalation. To confirm that all cohorts were equivalently colonized by NTHI (now resident within the nasopharynx) and thereby available to ascend the virus-compromised Eustachian tube, a nasopharyngeal lavage was performed one day after bacterial challenge. Nasopharyngeal lavage fluids were serially diluted and plated on to chocolate agar plus 15 µg ampicillin/ml medium to limit growth of normal chinchilla flora (L. A. Novotny et al. (2017) Clin Vaccine Immunol 24: e00563-16. This concentration of ampicillin has no effect on growth of NTHI strain 86-028NP.). NTHI colonies were enumerated after incubation for 24 h at 37° C.

Video Otoscopy

Video otoscopy was performed on all animals using a Welch Allyn MacroView™ otoscope and Welch Allyn Viewer software. Each tympanic membrane was blindly ranked on a on an established scale of 0 to 4, and middle ears with a score of ≥2.0 were considered positive for OM as inflammation (erythema) and MEF were visible (L. A. Novotny et al. (2006) Vaccine 24: 4804-4811). If one middle ear was ranked ≥2.0, but the contralateral ear was ranked <2.0, the animal was considered positive for OM. To calculate vaccine efficacy, the number of observations of OM during the 20-day study period was first determined and converted to a percentage relative to the total number of observations for each cohort. This value was then subtracted from the percentage computed for the cohort given dmLT only. Video otoscopy was performed by an individual blinded to formulation delivered.

Statistical Analyses

Graphical results and statistical tests were performed with GraphPad Prism 8. Differences in biomass for in vitro biofilm disruption assays were determined by one-way ANOVA with multiple comparisons. Differences in quantity of cytokines in middle ear fluids among cohorts was determined by determined by one-way ANOVA with multiple comparisons. Differences in bacterial load and mean mucosal biomass score were determined by one-way ANOVA with multiple comparisons. Delay to onset of OM and time to resolution of disease was determined by Mantel-Cox test.

Results

β-Tip Fab Fragments from a Murine Monoclonal Antibody Disrupted Bacterial Biofilms In Vitro Applicant first performed an in vitro chambered covergalss assay wherein biofilms formed by five diverse bacterial species were allowed to form for 24 h prior to incubation with Fab fragments to validate their potential activity. Fab fragments were derived from a murine monoclonal antibody directed against a 15-mer previously defined immunoprotective domain within the DNA-binding 'tip' region of the β-subunit of NTHI IHF (IHF$_{NTHI}$, herein referred to as 'β-tip Fabs') (M. E. Brockson et al. (2014) Mol Microbiol 93: 1246-1258) and compared the outcome to that induced by use of the respective intact IgG molecule. As negative controls, Fab fragments derived from a murine monoclonal antibody against a 15-mer non-protective domain within the 'tail' region of the β-subunit of IHF$_{NTHI}$ Fabs'), which does not disrupt bacterial biofilms (L. A. Novotny et al. (2016) EBioMedicine 10: 33-44) or nonspecific murine IgG1 isotype antibody ('isotype control Fabs') were used.

Figures 8A, 8B:
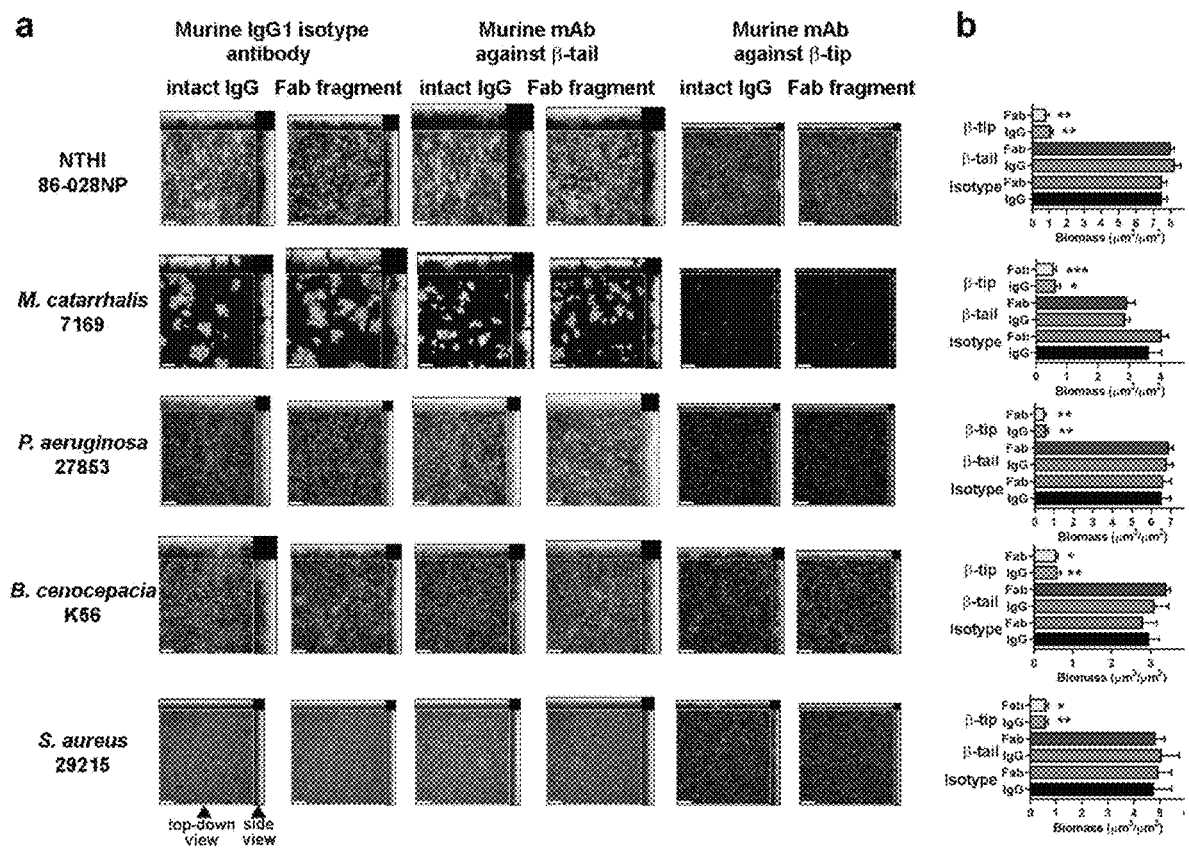
FIGS. 8A to 8B show that murine monoclonal antibody-derived Fab fragments directed against the β-tip disrupted biofilms formed by five human pathogens in vitro.

Representative images revealed that each of the five diverse bacterial species tested formed biofilms of varied architecture within 24 h (FIG. 8A). β-tail Fabs or isotype control Fabs had no disruptive effect, similar to the outcome with intact IgG from which these negative control fragments were derived. In contrast, incubation with β-tip Fabs was significantly disruptive of the biofilms formed by all bacterial species tested. Quantitation of biofilm biomass revealed that biofilm disruption by this concentration of β-tip Fabs was comparable to that achieved with an equimolar concentration of the respective intact β-tip IgG (P≤0.05; one-way ANOVA with multiple comparisons) (FIG. 8B). Thus, the minimal antigen-binding domain of the β-tip-directed antibody molecule was sufficient to bind to, and sequester DNABII protein, then disrupt the biofilm as effectively as the intact antibody from which the Fab fragments were generated.

Figures 9A, 9B, 9C, 9D:
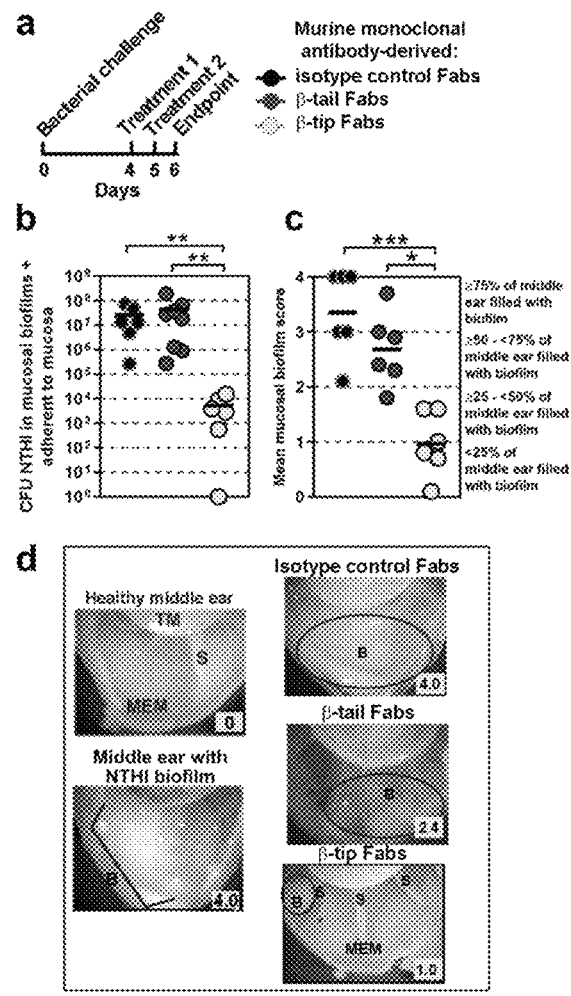
FIGS. 9A to 9D show murine monoclonal antibody β-tip Fabs mediated eradication of biofilm-resident NTHI and resolution of mucosal biofilms from the middle ear.

Murine β-Tip Fabs Eradicated NTHI from Biofilms and Resolved Biofilms During Experimental OM With biofilm-disruptive function of the β-tip Fabs demonstrated in vitro, Applicant addressed the first question: in the context of experimental disease, is antibody-mediated DNABII protein sequestration via only the Fab domains sufficient to induce biofilm collapse with subsequent clearance of released bacteria? To answer this query, Applicant employed a well-established chinchilla model of OM due to the predominant pathogen of chronic and recurrent disease, NTHI. Experimental OM was first induced by direct challenge of the middle ear. After four-days, NTHI biofilms fill the middle ear (Novotny L A et al (2011) Mucosal Immunol 2011; 4: 456-67). Murine monoclonal antibody-derived β-tip Fabs, β-tail Fabs or isotype control Fabs were then injected into both middle ears, with a second identical treatment given 24 h later (FIG. 9A). One day after receipt of the second dose of Fabs, all animals were sacrificed to assess relative immediate treatment efficacy.

Applicant first quantitated the number of NTHI resident within mucosal biofilms and/or adherent to the middle ear mucosa by plate count. There was no difference in the bacterial load in animals that received β-tail Fabs compared to isotype control Fabs (FIG. 9B). Conversely, a significant 4-log fewer NTHI were detected within mucosal biofilms recovered from animals treated with β-tip Fabs and in one of the six middle ears in this cohort, all NTHI had been eradicated ($P \leq 0.01$; one-way ANOVA with multiple comparisons) (FIG. 9B). Thus, delivery of β-tip Fabs induced augmented eradication of NTHI from chinchilla middle ears.

To next discern whether any of the three treatments induced rapid resolution of the established NTHI biofilms, one day after completion of Fab fragment therapy images of each middle ear were captured, randomized and ranked by six blinded reviewers. Reviewers used an established rubric wherein a score of 0 equated to no mucosal biofilm observed, and a score of 4+ indicated that ≥75% of the middle ear remained filled with mucosal biofilm. Accordingly, β-tail Fabs induced a slight but non-significant reduction in amount of mucosal biofilm when compared to delivery of isotype control Fab fragments. Importantly, ≥50% of the middle ears in the isotype control Fab and β-tail Fabs cohorts remained filled with mucosal biofilm with mean biomass scores of 3.4 and 2.7, respectively (FIG. 9C). Conversely, β-tip Fabs induced a significant reduction in mucosal biofilm ($P \leq 0.05$; one-way ANOVA with multiple comparisons) and a majority (4 of 6, 67%) of middle ears in this latter cohort were assigned a score ≤1.0 which indicated that ≤25% of the middle ear contained any residual visible biofilm. Thus, delivery of β-tip Fabs both significantly reduced the bacterial load in the middle ears and induced effective eradication of already established mucosal biofilms.

Representative images of a middle ear from each cohort are presented in FIG. 9D with both a healthy chinchilla middle ear and one filled with an NTHI biofilm shown for reference. In naive animals, the middle ear mucosa and full length of the natural bony septae are visible (score 0). In contrast, four days after NTHI challenge, neither the thin mucosal lining of the middle ear nor the bony septae are visible as these anatomical features are now occluded by a large mucosal biofilm (score 4). In this study, after delivery of β-tail Fabs or isotype control Fabs, mucosal biofilms still filled 50%-100% of the middle ears, with a representative assigned score of 4.0 or 2.4, respectively (FIG. 9D). However, β-tip Fabs largely eradicated these structures as evidenced by the fact that both the middle ear mucosal lining and the bony septae were fully visible (assigned score of 1.0). Also of note, whereas extensive inflammation was observed in the middle ear mucosae and tympanic membranes of animals that received β-tail Fabs (FIG. 9D, middle image, right side), there was only limited fine capillary dilatation within the middle ear mucosae of animals treated with β-tip Fabs (FIG. 9D, bottom image, right side) despite the fact that just 2-days earlier these ears were filled with a biofilm formed by NTHI.

Figures 10A, 10B:
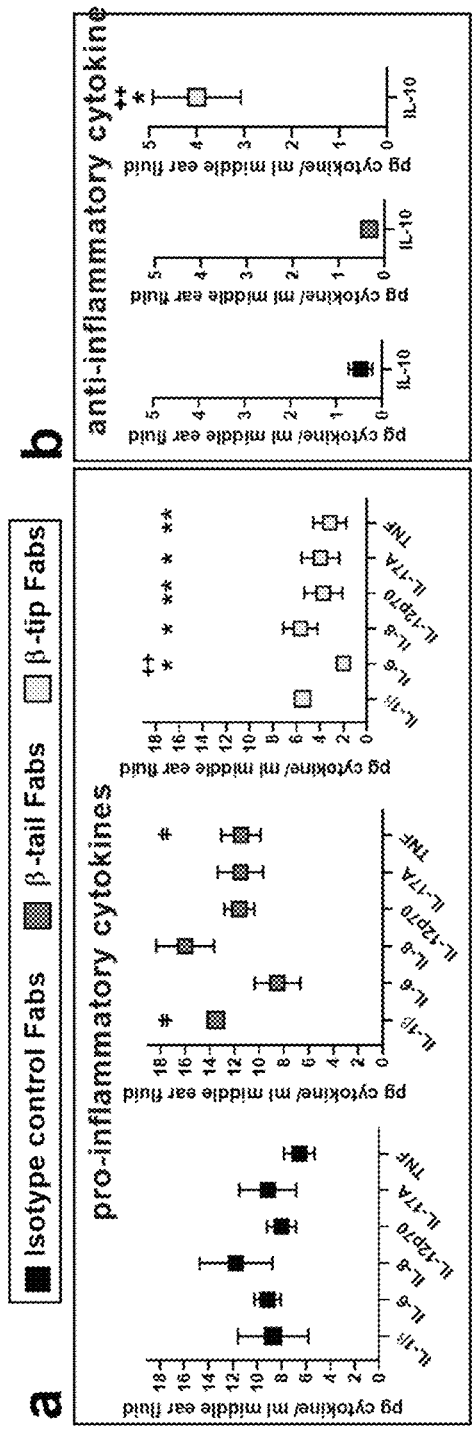
FIGS. 10A to 10B show pro-inflammatory cytokines predominated in middle ear fluids from animals treated with 342 nM murine monoclonal antibody-derived β-tail Fabs.

To begin to understand why the middle ears of animals that received β-tail Fabs consistently appeared to be overtly inflamed (FIG. 9D, middle image, right side), whereas β-tip Fabs-treated ears were not (FIG. 9D, bottom image, right side), Applicant determined a focused cytokine profile within middle ear fluids collected from animals at the time of sacrifice. Via cytometric bead assay, a significantly greater quantity of each of a panel of six pro-inflammatory cytokines was detected in the middle ears of animals that received β-tail Fabs, compared to animals treated with β-tip Fabs ($P \leq 0.05$) (FIG. 10A). Conversely, significantly more of the anti-inflammatory cytokine IL-10 was detected in middle ear fluids of animals that received β-tip Fabs ($P \leq 0.05$; one-way ANOVA with multiple comparisons) (FIG. 10B). Moreover, compared to animals that received isotype control Fabs, significantly more of the pro-inflammatory cytokines IL-1β and TNF were detected in middle ear fluids from animals treated with β-tip Fabs (FIG. 10B), which likely contributed to the inflammation consistently observed within the mucosae in the latter cohort (see FIG. 9D). These data suggested that in the context of active experimental OM, biofilm collapse and clearance of NTHI induced by β-tip Fabs also mediated resolution of disease-associated inflammation. Collectively, and central to the original question, to this point the data showed that β-tip Fabs effectively disrupted bacterial biofilms in vivo, thus the Fc portion of the anti-DNABII-directed antibody was not required to induce biofilm collapse. This result added support to the model wherein biofilm structural collapse, with release of resident bacteria, is the result of a DNABII protein targeted antibody-mediated equilibrium shift that subsequently tips the balance in favor of the host to now effectively eradicate newly released pathogens via engagement of multiple host immune effectors.

Rabbit IgG Fabs Against Domains within Both IHF Subunits Rapidly Disrupted Biofilm In Vivo Thus far, Applicant examined Fab fragments directed against the β-subunit, one of two heterologous subunits that comprise $IHF_{NTHI}$. While this approach was effective, in previous work Applicant demonstrate that a cocktail of murine monoclonal antibodies against tip domains within the α-subunit plus those against the β-subunit of $IHF_{NTHI}$ induces significantly greater biofilm disruption compared to antibody against either subunit individually, including those bacterial species that only possess an HU allele (L. A. Novotny et al. (2016) EBioMedicine 10: 33-44). Although 74.7% similar in amino acid sequence, there is only 47.3% identity within each 94 amino acid subunit of $IHF_{NTHI}$, thus the cocktail of α-subunit-plus β-subunit-directed antibodies afforded broader coverage of the complete diversity within IHF and its orthologue, HU. With that information, Applicant then designed an epitope-targeted, chimeric peptide immunogen to first induce antibody in a rabbit against both protective domains concurrently. Designated 'tip chimeric peptide', slightly larger (e.g. 20-mer) segments from within the DNA-binding tip domains of both the α-subunit and β-subunit of $IHF_{NTHI}$ were incorporated and joined by a 4-residue linker peptide to permit flexibility between these two protective epitopes (L. A. Novotny et al. (2019) NPJ Vaccines 4: 43). As a negative control, a 'tail chimeric peptide' immunogen was also developed that incorporated 20-mer segments from non-protective domains within the tail region of the α-subunit and β-subunit of $IHF_{NTHI}$ and joined by the same 4-residue linker. Applicant previously shown that polyclonal rabbit IgG against this tip chimeric peptide disrupts biofilms formed by multiple bacterial species in vitro and resolves mucosal biofilms within the middle ears of chinchillas during experimental NTHI-induced OM (L. A. Novotny et al. (2019) NPJ Vaccines 4: 43).

To now merge the chimeric peptide design strategy with determination of potential Fab fragment-mediated therapeutic biofilm disruption, herein, Applicant tested the ability of polyclonal rabbit anti-tip chimeric peptide Fabs to disrupt NTHI biofilms already present in the middle ear of chinchillas with experimental OM. Applicant also evaluated the endurance of any resultant biofilm resolution, i.e. would NTHI biofilms re-establish once antibody therapy ceased?

Figures 11A, 11B, 11C, 11D:
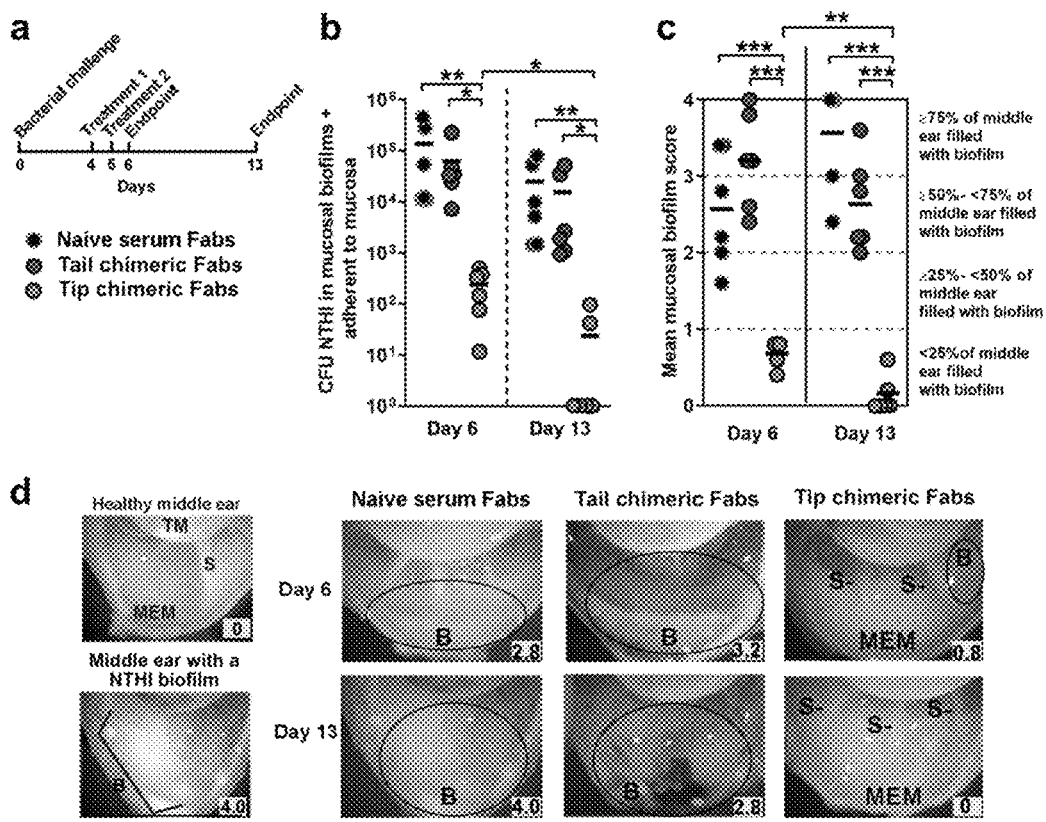
FIGS. 11A to 11D provide that tip chimeric Fabs from polyclonal rabbit IgG mediated clearance of biofilm resident NTHI, eradication of established mucosal biofilms and resolution of experimental disease.

Accordingly, NTHI was allowed to establish large biofilms in the chinchilla middle ear before Applicant delivered treatment with either Fabs derived from polyclonal rabbit IgG against 1) tip chimeric peptide; 2) tail chimeric peptide or 3) naive serum (FIG. 11A). One day after delivery of the second therapeutic dose, a subset of animals in each cohort was sacrificed to examine the immediate effect of treatment. The remaining animals were monitored an additional seven days, without further treatment, to assess the durability of this therapeutic approach.

One day after receiving two doses of tip chimeric peptide Fabs, there were >2-log fewer NTHI within mucosal biofilms and/or adherent to the middle ear mucosa, compared to either of the two negative control cohorts (P≤0.05; one-way ANOVA with multiple comparisons) (FIG. 11B). After an additional week without further treatment, there was only a slight decrease in NTHI load within middle ear mucosal biofilms/adherent to the mucosa of animals given tail chimeric peptide Fabs or naive serum Fabs. Conversely, at this latter time point, in animals given tip chimeric peptide Fabs there was an added 10-fold decrease in bacterial load (P≤0.05; one-way ANOVA with multiple comparisons). Notably, in 4 of 6 (67%) middle ears, these homogenized tissues were culture negative for NTHI. These data suggested that NTHI released from the biofilm by tip chimeric peptide Fabs were subsequently cleared by host immune effectors without any additional intervention or treatment.

Applicant next qualitatively evaluated whether treatment with these chimeric peptide directed Fabs was able to eradicate NTHI biofilms already present in the chinchilla middle ear. To do so, blinded evaluators were asked to rank the relative amount of mucosal biofilm that remained within the middle ears after treatment on a 0-4+ scale. Receipt of tail chimeric peptide Fabs was not effective. One day after treatment in animals that received tail chimeric peptide Fabs, the remaining biofilms were actually slightly larger than those in the middle ears of animals treated with naïve serum Fabs, with mean biomass scores of 3.2 and 2.6, respectively (FIG. 11C). In both of these negative control cohorts, >50% of the middle ear remained filled with mucosal biofilm. Conversely, in the cohort given tip chimeric peptide Fabs, all six middle ears were ranked ≤1.0 which indicated only minimal remaining mucosal biofilm was observed (P≤0.001; one-way ANOVA with multiple comparisons), with a mean biomass score of 0.7. Thus, the immediate outcome of tip chimeric peptide Fab therapy was significant reduction of bacterial load and significant disruption of established NTHI biofilms.

To assay the durability of the observed treatment effect, middle ears were evaluated in a subset of each cohort after an additional week, without any further treatment. In the cohort given Fabs from naive rabbit serum, mucosal biofilms actually increased, whereas they only slightly decreased in those given tail chimeric peptide Fabs (e.g. >50% of the middle ears remained filled with an NTHI biofilm), with mean biomass scores of 3.6 and 2.6, respectively (FIG. 11C). Importantly, animals treated with tip chimeric peptide Fabs, continued to clear NTHI biofilms, as evidenced by an additional significant reduction in mucosal biofilm (P≤0.01; one-way ANOVA with multiple comparisons) and a mean biomass score of 0.2. Notably, there was no visible evidence of a biofilm in 4 of 6 (67%) middle ears. These qualitative assessments correlated well with bacterial load data as shown in FIG. 11B.

To demonstrate what blinded evaluators ranked in terms of remaining mucosal biofilms observed, examples of a healthy middle ear and one with a four-day NTHI biofilm as well as representative images of middle ears from each cohort on day 13 are depicted in FIG. 11D. As anticipated, one day after completion of treatment, substantial mucosal biofilm remained in animals that received naive serum or tail chimeric peptide Fabs, as evidenced by the fact that these biofilms occluded visibility of the middle ear mucosa and bony septae, with representative assigned scores of 2.8 or 3.2 respectively (FIG. 11D). These scores did not decrease significantly by seven days after treatment completion and in fact that for the cohort treated with naive serum Fabs increased notably, with representative assigned scores of 4.0 and 2.8, respectively. Conversely, in the middle ears of animals treated with tip chimeric peptide Fabs, the normal anatomical landmarks were fully visible one day after treatment completion and remained so, with no evidence of biofilm regrowth in the seven-days that followed. Representative assigned scores were 0.8 (day 6) and 0 (day 13) for this latter cohort. Collectively, these data provided additional strong support for the potential to deliver tip chimeric peptide Fabs to eradicate existing NTHI biofilms within the middle ear, and further that this eradication was likely enduring.

Figures 12A, 12B:
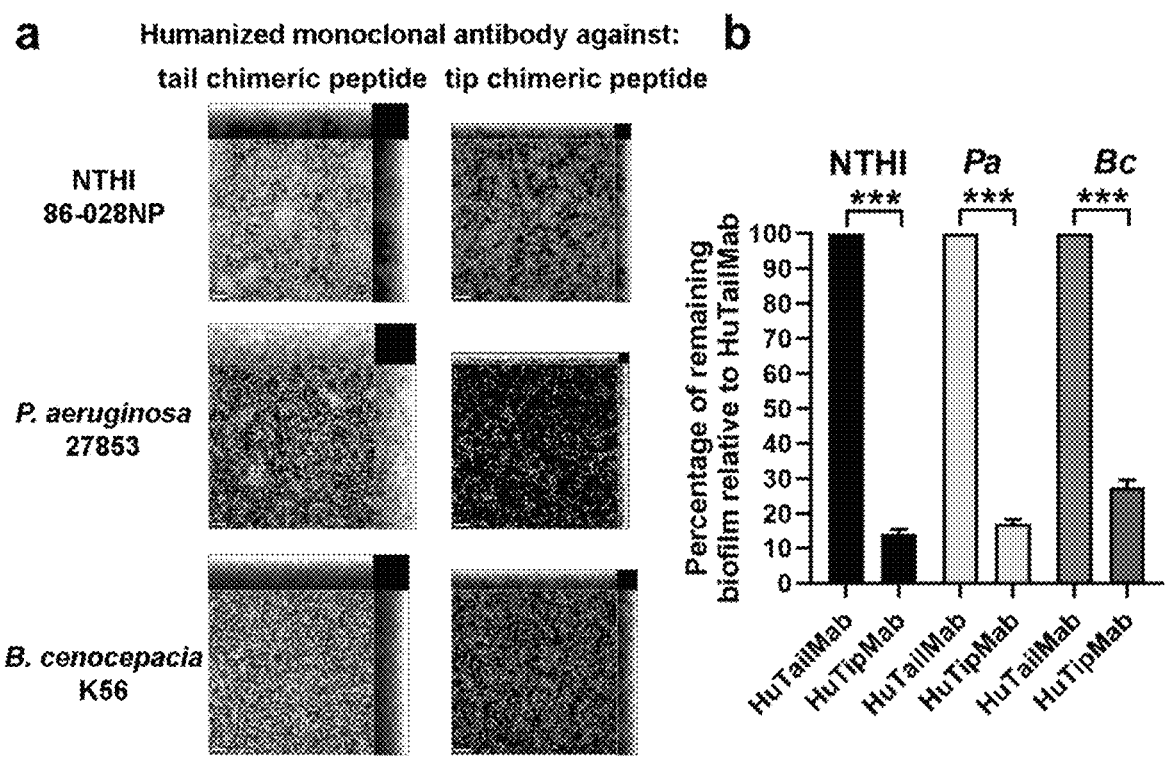
FIGS. 12A to 12B show that humanized tip-chimeric peptide monoclonal antibody disrupted bacterial biofilms in vitro.

Development and Validation of a Humanized Version of the Tip Chimeric Peptide Monoclonal Antibody With data in support of use of anti-tip chimeric peptide Fabs to disrupt diverse bacterial biofilms in vitro, and to also eradicate mucosal NTHI biofilms in vivo, Applicant now wanted to move toward use of these novel therapeutic agents in clinical trials. To do so, Applicant generated a panel of humanized tip chimeric peptide-directed monoclonal antibodies (herein called 'HuTipMAb') designed after a murine monoclonal antibody against the tip chimeric peptide. Here, Applicant presents data in support of the functional in vitro activity of one of the HuTipMabs as evidence of the effectiveness of humanization. As a measure of humanness, Applicant determined the T20 score for the variable regions within the heavy and light chains individually (S. H. Gao et al. (2013) BMC Biotechnol 13: 55). These values were 82 for the heavy chain variable region and 97 for the light chain variable region, which indicated a high degree of humanness for each antibody domain. By surface plasmon resonance, the HuTipMab had a $K_D$ of 76 nM to the tip chimeric peptide and a $K_D$ of 10 nM to native $IHF_{NTHI}$, thus strong affinity to the target peptide, and even greater affinity to the native protein as would be needed for disease resolution was shown. In vitro, HuTipMab significantly disrupted biofilms formed by NTHI, *P. aeruginosa* or *B. cenocepacia* (P≤0.001; unpaired t-test) (FIG. 12A) and only 13-26% biofilm biomass remained after a 16 h exposure to the selected concentration of humanized Mab used, compared to biofilms incubated with an equivalent concentration of humanized anti-tail chimeric peptide antibody (called 'HuTailMab') (FIG. 12B). Thus, humanization of a murine tip chimeric peptide-specific monoclonal antibody yielded a therapeutic candidate with strong affinity to its protein target and proven ability to disrupt biofilms formed by three human respiratory tract pathogens in vitro.

Figures 13A, 13B, 13C, 13D:
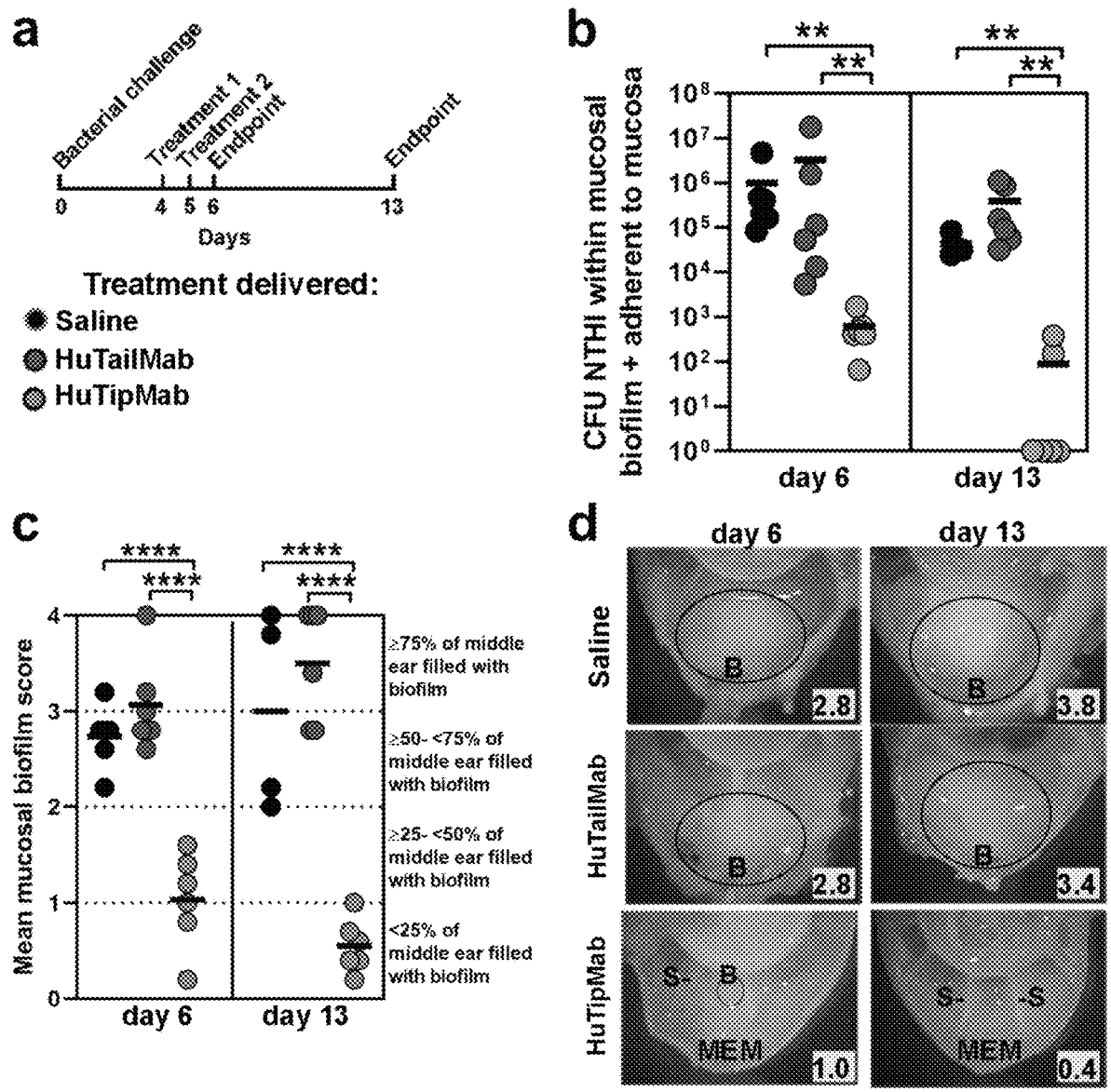
FIGS. 13A to 13D show that a humanized monoclonal antibody against the tip chimeric peptide (HuTipMab) resolved pre-existing NTHI biofilms present in the middle ears during experimental NTHI-induced OM.

To next confirm that the humanized monoclonal also functioned in vivo, Applicant used the chinchilla model of NTHI-induced experimental OM wherein biofilms were already resident within the middle ears prior to treatment. Either HuTipMab, HuTailMab or an equivalent volume of sterile saline (diluent used with humanized antibodies) was delivered to both middle ears, followed 24 h later by a second identical treatment (FIG. 13A). As before, a subset of animals from each cohort was sacrificed one day after therapy was completed to examine the immediate outcome, and a second subset of animals were followed for another week without additional treatment to determine if the effect of therapy endured.

One day after therapy, HuTipMab induced a significant >3.5 log reduction in the number of NTHI, compared to HuTailMab or saline (P≤0.01; one-way ANOVA with multiple comparisons) (FIG. 13B). One week later, whereas either HuTailMab or saline induced only a slight additional decrease in NTHI load, that in middle ears treated with HuTipMab decreased another 7-fold. Notably, a week after treatment with HuTipMab, homogenates of 4 of 6 middle ear mucosae (67%) were culture-negative (P≤0.05; one-way ANOVA with multiple comparisons). Thus, treatment with HuTipMab induced rapid eradication of NTHI within mucosal biofilms from the middle ear.

To qualitatively assess how much mucosal biofilm remained in the middle ear after treatment, middle ears were once again blindly evaluated on a 0-4+ scale. Animals that received saline or HuTailMab remained filled with mucosal biofilm that occupied >50% of the middle ear, and mean biomass scores were 2.7 and 3.1, respectively (FIG. 13C & FIG. 13D; representative scores appear within the box at the bottom right corner of each panel within FIG. 13D, first row). Conversely, in those middle ears treated with HuTipMab, minimal remaining mucosal biofilm was observed (<25%) and the mean biomass score for the cohort was 1.0 (FIG. 13C & FIG. 13D). Seven days later, whereas the mucosal biofilm actually increased in cohorts treated with either saline (mean score, 3.0) or HuTailMab (mean score, 3.5), in those treated with the HuTipMab minimal biofilm was observed (mean score, 0.6) (FIG. 13C & FIG. 13D; representative scores appear within the box at the bottom right corner of each panel within FIG. 13D, second row). Representative images for each cohort are shown in FIG. 13D and correlated well with data presented in FIG. 13C.

Figures 14A, 14B:
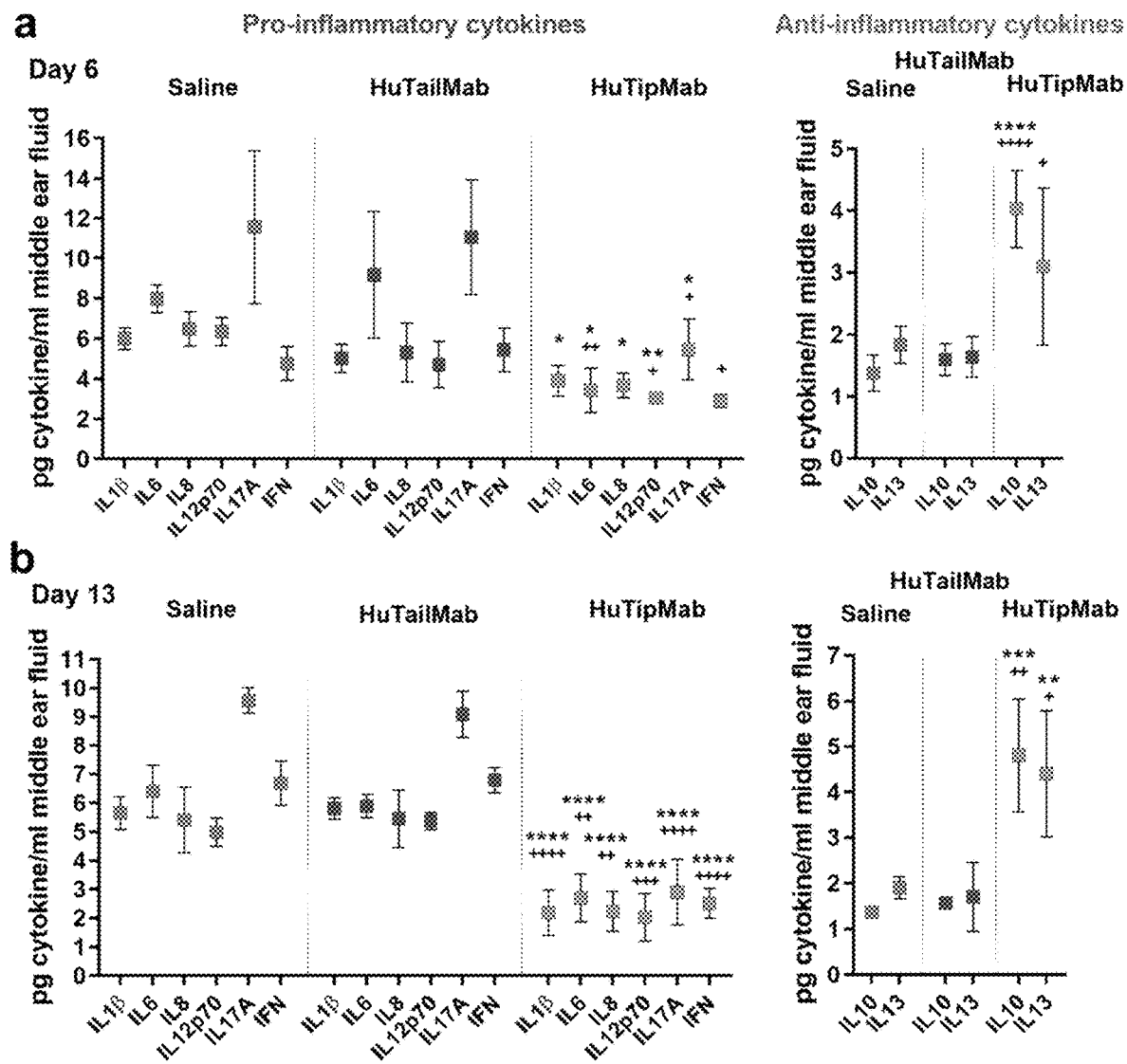
FIGS. 14A to 14B show that pro-inflammatory cytokines were significantly less abundant in middle ear fluids from animals treated with HuTipMabs. Relative quantity of pro-inflammatory and anti-inflammatory cytokines in chinchilla middle ear fluids after NTHI challenge and treatment with humanised monoclonal antibodies (FIG. 14A) six days after NTHI challenge (one day after completion of therapy) and (FIG. 14B) 13 days after NTHI challenge (seven days after completion of therapy) as determined by cytometric bead array. *P≤0.05 vs. saline, P≤0.01 vs. saline, *P≤0.001 vs. saline, ****P≤0.0001 vs. saline, +P≤0.05 vs. HuTailMab, ++P≤0.01 vs. HuTailMab, +++P≤0.001 vs. HuTailMab, ++++P≤0.0001 vs. HuTailMab (one-way ANOVA with multiple comparisons). 3 to 5 middle ear fluids tested per cohort. Mean cytokine concentration ±SD shown. The pro-inflammatory cytokine levels in animals that received HuTailMab were now equivalent to those that received saline provides support for the absence of association of receipt of this now humanized monoclonal compared to the murine monoclonal antibodies.

Unlike in FIG. 9D, wherein inflammation was visible in the middle ears of animals that received murine monoclonal antibody fragments directed exclusively at the β-tip of one of the IHF subunits, treatment with the HuTipMab did not result in overt inflammation (see FIG. 13D). To begin to explain this observation, Applicant again performed a cytometric bead assay to determine a focused but now slightly expanded cytokine profile within middle ear fluids collected from these animals at the time of sacrifice. One day after completion of antibody therapy, a comparable quantity of six proinflammatory cytokines was detected in middle ear fluids from animals that received saline or HuTailMab, whereas significantly less were present in fluids from HuTipMab-treated animals (FIG. 14A). Moreover, significantly more of two anti-inflammatory cytokines were detected in middle ear fluids recovered from animals that received HuTipMab. This pattern was maintained and further enhanced within fluids collected on day 13 (7 days after completion of therapy) (FIG. 14B). As pro-inflammatory cytokine concentrations were similar between saline and HuTailMab-treated animals, and without wishing to be bound by the theory, Applicants theorize that humanization of the murine monoclonal antibody abrogated the inflammation seen in animals in this latter cohort (see FIG. 13D). Collectively, these data demonstrated that humanization of the murine monoclonal directed against the tip chimeric peptide did not diminish its effectiveness either in vitro or in vivo. The HuTipMab induced rapid and enduring clearance of NTHI-induced mucosal biofilms from the middle ear during experimental OM, thus fostering resolution of disease.

The biofilm disruption effects of the HuTipMab and HuTailMab are summarized in the Table below.

TABLE 9

In vivo biofilm disruption results.

| | | | Biofilm disruption in vivo | | | |
|---|---|---|---|---|---|---|
| | | | % change in bacterial load post treatment | | % middle ear occluded post treatment | |
| Antibody | Heavy Chain | Light Chain | day 1 | day 8 | day 1 | day 8 |
| HuTipMab | SEQ ID NO: 1 | SEQ ID NO: 7 | ↓99 | ↓99 | <25% | <25% |
| HuTailMab | SEQ ID NO: 4 | SEQ ID NO: 10 | ↑222 | ↑796 | 50-<75% | 50-<75 |

↓ indicates decrease in bacterial load; while ↑ indicates increase in bacterial load.

Additionally, Applicant determined a limited cytokine profile within middle ear fluids collected from animals at the time of sacrifice. As shown in FIG. 14, significantly less pro-inflammatory cytokines were observed in HuTipMab treated middle ears, while significantly more anti-inflammatory cytokines were found in HuTipMab treated middle ears. However, HuTailMab-treated middle ears were comparable to saline-treated middle ears in terms of pro-inflammatory cytokines. This suggests that humanization of the murine mAbs abrogated some type of rodent-specific inflammation observed in the mAb Fab study. This is a positive outcome for use of a HuTailMab as a diagnostic tool.

Pre-Clinical Efficacy of the Tip Chimeric Peptide after Active Transcutaneous Immunization Thus far, Applicant reported development of an effective DNABII-targeted therapeutic (e.g., delivery of a humanized monoclonal antibody that targets the immunoprotective tip regions of both IHF subunits to disrupt biofilms/resolve ongoing disease), however prevention of biofilm formation and disease induction by active immunization is also an important goal. Toward this end, Applicant used a unique chinchilla viral-bacterial co-infection model of experimental OM wherein prior adenovirus infection predisposes the middle ear to invasion by NTHI that colonize the nasopharynx which now ascend the virus-compromised Eustachian tube (K. Suzuki et al. (1994) Infect Immun 62: 1710-1718). This superinfection model is designed to mimic "My child gets a cold, then a week later has an ear infection". Thus, animals were first actively immunized with the tip or tail chimeric peptide to induce the appropriate immune response (L. A. Novotny et al. (2015) Clin Vaccine Immunol 22: 867-874; L. A. Novotny et al. (2013) Vaccine 31: 3417-3426; L. A. Novotny et al. (2011) Mucosal Immunol 4: 456-467; L. A. Novotny et al. (2017) Clin Vaccine Immunol 24). Subsequently, chinchillas were challenged first with adenovirus, then 4 days later with NTHI, after which they were monitored for relative development of ascending OM.

Figures 15A, 15B, 15C, 15D:
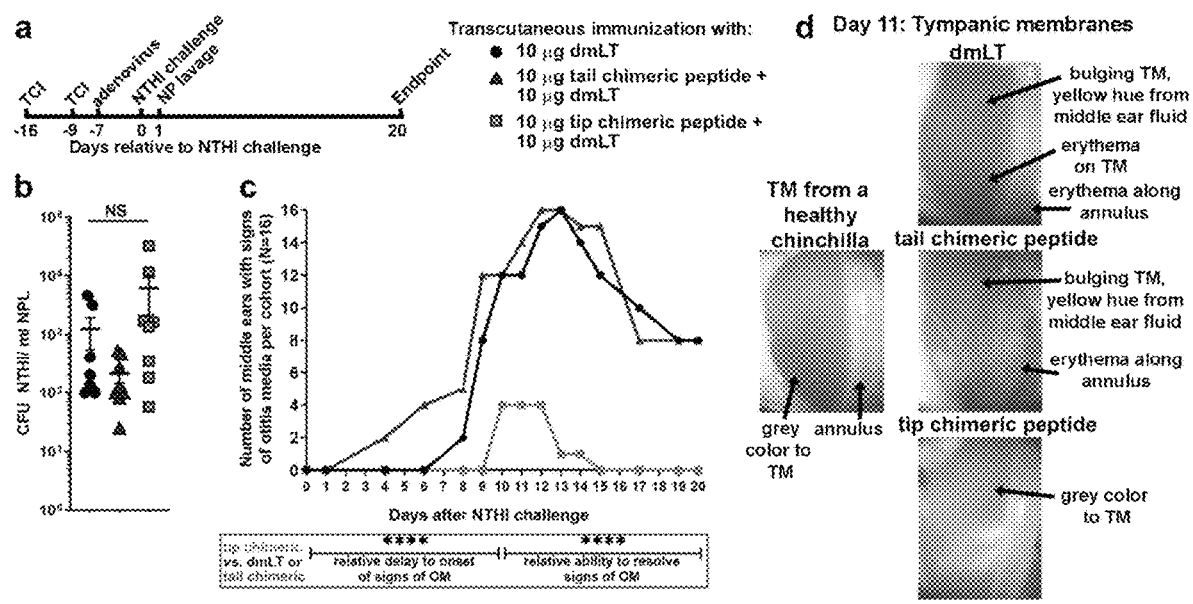
FIGS. 15A to 15D shows immunization with tip chimeric peptide prevented ascending experimental OM in a viral-bacterial co-infection model.

Three cohorts of naive chinchillas were immunized by rubbing vaccine formulations on to the skin just behind both ears (e.g. post-auricular region), a procedure repeated one week later (FIG. 15A). Formulations used were: tip chimeric peptide admixed with the adjuvant LT(R192G/L211A) (dmLT), a double mutant of E. coli heat labile enterotoxin (J. D. Clements et al. (2018) mSphere 2018 July-August; 3(4): e00215-18.); tail chimeric peptide plus dmLT or dmLT alone. Two days after the second immunization, all animals were inoculated intranasally (IN) with adenovirus, followed one week later by IN challenge with NTHI. Nasopharyngeal lavage was performed one day after NTHI challenge to confirm that all animals were equivalently colonized (FIG. 15B). This result ensured that each animal had the potential to develop experimental OM, with the only discriminating factor being resultant induced immunity due to immunogen received.

The primary readout for vaccine efficacy was video otoscopy, wherein each tympanic membrane (TM) was blindly viewed to determine whether overt inflammation and middle ear fluid were visible as signs of OM (L. A. Novotny et al. (2006) Vaccine 24: 4804-4811). Within 8 days of NTHI challenge of virus-infected chinchillas, there were signs of that NTHI had ascended the compromised Eustachian tube and induced OM in 2 of 16 middle ears (13%) in the adjuvant-only cohort, with a peak incidence of 100% on day 13 (FIG. 15C). Experimental OM began to decrease after day 13, but persisted in 8 of 16 middle ears (50%) on day 20. As anticipated, immunization with tail chimeric peptide did not provide a benefit. Signs of OM were present in two middle ears (13%) four days after NTHI challenge, peaked at 100% on days 12 and 13 before beginning to decline however 8 of 16 middle ears (50%) maintained signs of OM at study conclusion. In sharp contrast, there was a significant delay to onset of signs of OM in the tip chimeric peptide-immunized cohort (P≤0.0001; Mantel-Cox test) until day 10. Maximum incidence of OM on days 10 to 12 occurred in only 4 of 18 middle ears (25%) in this latter cohort with complete resolution by day 14, which was significantly earlier than controls (P≤0.0001; Mantel-Cox test). Further, over the 20-day observation period, the proportion of animals with signs of experimental OM was significantly less in those immunized with the tip chimeric peptide (4 ears; 2 animals; P≤0.0001; Mantel-Cox test) compared to the other two cohorts (16 ears; 8 animals).

Images of the chinchilla TM shown in FIG. 15D are representative of that observed by blinded otoscopy on day 11. Whereas a healthy chinchilla TM is grey in color, those of animals immunized with dmLT or the tail chimeric peptide were slightly bulging, erythematous and yellow middle ear fluid was visible behind the TM. Conversely, TMs of the majority of animals in the tip chimeric peptide immunized cohort (12 of 16; 75%) showed minimal, if any, signs of inflammation. Overall, vaccine efficacy afforded by immunization with the tip chimeric peptide was 85%, compared to either negative control cohort. Collectively, these data supported the design and use of the tip chimeric peptide as an effective vaccine candidate antigen to prevent development of experimental OM due to NTHI and complemented Applicant's development of a therapeutic humanized monoclonal.

Experimental Discussion

Biofilms are involved in the majority of chronic and recurrent bacterial diseases of the respiratory tract (L. O. Bakaletz et al. (2012) Paediatr Respir 13: 154-159; J. H. Fastenberg et al. (2016) World J Otorhinolaryngol Head Neck Surg 2: 219-229; J. W. Costerton (2001) Trends Microbiol 9: 50-52), oral cavity (W. H. Bowen et al. (2018) Trends Microbiol 26: 229-242; P. E. Petersen et al. (2005) J Periodontol 76: 2187-2193), gastrointestinal tract (E. C. von Rosenvinge et al. (2013) Pathog Dis 67: 25-38; S. Macfarlane et al. (2007) J Appl Microbiol 102: 1187-1196) and urogenital tract (A. L. Flores-Mireles et al. (2016) J Urol 196: 416-421; P. Tenke et al. (2012) World J Urol 30: 51-57). The formation and persistence of these often polymicrobial communities contributes significantly to the pathogenesis of these diseases, largely due to a characteristic recalcitrance to clearance by host immune effectors and antibiotics. Thus, recognition of the role of biofilms in disease pathogenesis and persistence requires novel approaches to either prevent their formation or eradicate those already present.

As such, many laboratories have developed a variety of approaches for biofilm mitigation which has been the subject of many excellent reviews (Verderosa A D et al. (2019) Front Chem 2019; 7: 824; Koo H et al. (2017) Nat Rev Microbiol 2017; 15: 740-55; Fleming D et al. (2017) Microorganisms 2017; 5: 15; Worthington R J (2012) Org Biomol Chem 2012; 10: 7457-74; Reza A et al. (2019) Antibiotics (Basel) 2019; 8: 229). A broad area of research is focused on biofilm eradication via agents that induce dispersal of biofilm-resident bacteria, e.g. treatment of biofilms with enzymes, molecules that interfere with processes such as quorum sensing, signaling via cyclic di-GMP or delivery of small molecule inhibitors or analogues (Verderosa A D et al. (2019) Front Chem 2019; 7: 824; Koo H et al. (2017) Nat Rev Microbiol 2017; 15: 740-55; Fleming D et al. (2017) Microorganisms 2017; 5: 15; Worthington R J (2012) Org Biomol Chem 2012; 10: 7457-74; Reza A et al. (2019) Antibiotics (Basel) 2019; 8: 229). Alternatively, prevention of biofilm formation is an approach that could also restrict disease-induced inflammation, which is often more damaging to the host compared to the presence of the biofilm itself (Vestby L K et al. (2020) Antibiotics (Basel) 2020; 9: 59). Modification of implantable devices or incorporation of inhibitors within biomaterials, use of antimicrobial peptides or blockade of adhesive proteins expressed by microorganisms are shown to limit biofilm formation (Bazaka K et al. (2012) Appl Microbiol Biotechnol 2012; 95: 299-311; Qvortrup K et al (2019) Front Chem 2019; 7: 742; Rabin N et al (2015) Future Med Chem 2015; 7: 647-71; Chung P Y et al (2017) J Microbiol Immunol Infect 2017; 50: 405-10).

Over the past 10+ years, since Applicant identified the structural eDNA-DNABII lattice within biofilms formed by NTHI in the chinchilla middle ear (S. D. Goodman et al. (2011) Mucosal Immunol 4: 625-637), this observation was expanded to demonstrate the presence of this bacterial-permissive, but host-restrictive lattice in biofilms formed by many diverse bacterial species, including the high priority ESKAPE pathogens (A. Abu Khweek et al. (2013) Front Cell Infect Microbiol 3: 18; A. Devaraj et al. (2015) Mol Microbiol 96: 1119-1135; M. O. Freire et al. (2017) Mol Oral Microbiol 32: 74-88; J. E. Gustave et al. (2013) J Cyst Fibros 12: 384-389; L. A. Novotny et al. (2013) PLoS One 8: e67629; L. A. Novotny et al. (2016) EBioMedicine 10: 33-44; C. J. Rocco et al. (2018) J Bacteriol 200; K. M. Rood et al. (2018) Sci Rep 8: 8756). Collectively, this observation initially made in vitro, then expanded to testing in multiple pre-clinical models (Goodman S D et al (2011) Mucosal Immunol 2011; 4: 625-37; Brockson M E et al (2014) Mol Microbiol 2014; 93: 1246-58; Novotny L A et al (2019) NPJ Vaccines 2019; 4: 43; Freire M O et al (2017) Mol Oral Microbiol 2017; 32: 74-88; and Novotny L A et al (2016) EBioMedicine 2016; 10: 33-44) supported the development of a novel DNABII-focused approach to mediate biofilm diseases that would target this seemingly species-independent 'Achilles heel'.

As such, a two-pronged approach against bacterial biofilms was designed and presented, both of which target the eDNA+DNABII scaffold of the bacterial biofilm. The First approach is a preventative active immunisation strategy wherein the tip-chimeric peptide is used as an immunogen to induce the formation of antibody that blocks biofilm formation by NTHI in the middle ear and thereby, development of experimental OM. Applicant designed an epitope-specific DNABII chimeric protein vaccine candidate antigen to induce the formation of antibodies that would prevent biofilm formation after active immunization. The second is a therapeutic strategy wherein IgG or Fab fragments of antibodies directed against the tip-chimeric peptide immunogen (and ultimately, a humanised monoclonal antibody), are delivered directly into the middle ear to disrupt established NTHI biofilms and mediate resolution of experimental OM. Applicant humanized a murine monoclonal antibody against this immunogen for use, either intact or as Fab fragments, as a broadly effective therapeutic wherein bacteria released from biofilm residence that could then be killed by host immune effectors and/or antibiotics, although now able to be used at a greatly reduced dose (M. Shigeta et al. (1997) Chemotherapy 43: 137-141; D. M. Lewis (2005) J Theor Biol 234: 565-591; S. Singh et al. (2017) Open Microbiol J 11: 53-62). Here Applicant presented promising preclinical evidence from four studies, using two distinct models of OM, which consistently showed how effective these approaches can be in terms of biofilm and disease prevention and/or marked and significant reduction of existing mucosal biofilms with rapid disease resolution.

Applicant employed two pre-clinical models of a highly prevalent pediatric disease whose chronicity and recurrence are due to biofilms in the middle ear to assess preventative and therapeutic efficacy of Applicant's DNABII-targeted strategies. These models faithfully recapitulate the natural disease course of OM observed in children (G. S. Giebink (1999) Microb Drug Resists 5: 57-72; L. O. Bakaletz (2009) Expert Rev Vaccines 8: 1063-1082; J. T. Poolman et al. (2000) Vaccine 19 Suppl 1: S108-115) and have accurately predicted clinical trial outcomes (L. A. Novotny et al. (2006) Vaccine 24: 4804-4811; R. Prymula et al. (2006) Lancet 367: 740-748). Important for work presented here, the chinchilla model is a well-established host in which to study mono- and polymicrobial biofilm formation, persistence and interventions (L. O. Bakaletz (2012) Paediatr Respir Rev 13: 154-159; G. D. Ehrlich et al. (2002) JAMA 287: 1710-1715; M. A. Apicella (2009) J Infect Dis 199: 774-775).

Applicant provide answers to several previously unanswered questions. Applicant found that Fab fragments were as effective as intact antibody to disrupt biofilms in vitro and in vivo and could thus serve as a therapeutic when repeated dosing might be required (due to a resulted concern about inducing an anti-antibody response). Applicant also determined that the Fc portion of a DNABII-directed antibody was not required for biofilm disruption in vitro or for biofilm resolution in vivo. This outcome suggested that release of bacteria from the protective biofilm would be sufficient to promote clearance and disease resolution by innate host immune effectors and/or antibiotics. Applicant learned that incorporating protective domains from both of the heterogeneous subunits of $IHF_{NTHI}$ did result in an increased efficacy. Further, active immunization with the tip chimeric peptide induced the formation of antibody that prevented development of experimental OM and promoted rapid disease resolution. Humanization of the tip chimeric peptide monoclonal antibody yielded a highly promising therapeutic with nanomolar affinity to both the immunogen and native protein.

Collectively, these data added to the understanding of the eDNA+DNABII-directed strategy and were highly supportive of entry into both preventative and therapeutic clinical trials of both the tip chimeric peptide immunogen and the humanized monoclonal antibody against it, respectively. Given the species-independent nature of Applicant's DNABII targeted approach and without to be bound by the theory, provided is a therapeutic product for improved clinical management of a multitude of diseases wherein pathogenesis, enduring chronicity and/or cyclical recurrence is due to a recalcitrant biofilm.

Experiment No. 5

A number of oral bacteria (e.g., *Aggregatibacter actinomycetemcomitans, Porphyromonas gingivalis*) have been implicated in the pathogenesis of inflammatory diseases such as periodontitis and peri-implantitis, which destroy alveolar bone and gingiva. Investigations of the pathogenesis of these bacteria are hampered by lack of effective animal models. One of the challenges of investigating the pathogenicity of specific bacteria is the difficulty of establishing a biofilm when exogenous bacteria are introduced into the oral cavity of animals. Though animal models of periodontitis have been developed, cultivable bacteria are rarely recovered from the oral cavity of inoculated animals. Developing an effective animal model which can assess the pathogenicity of specific bacteria wilt greatly aid in elucidating their pathogenic mechanisms.

Applicants established a rat model of peri-implantitis where bacterial biofilms (e.g. *A. actinomycetemcomitans, P. gingivalis*) are grown on the heads of titanium screw implants (Freire, M. O., (2011) J. Periodontology 82(5):778-89 and Freire, M. O., (2017) Molecular Oral Microbiology 32(1):74-88). The biofilm laden screws are then surgically implanted into the rat maxilla aveolar bone and monitored over time. Micro computed tomography can be used to measure bone loss surrounding the screws, and DNA extracted from the screws as well as the tissue and bone surrounding the screws can be utilized for qPCR or microbiome analyses to reveal the species present. This established animal model revealed the presence of bone loss surrounding the screw implant and the detection of the inoculated bacterial pathogens at least 2 weeks post implantation.

Experiment No. 6

This experiment provides a mouse model for pre-clinical testing of interfering agents to treat lyme disease. See Dresser et al. Pathogens 5(12)e1000680, Epub 2009 Dec. 4. Lyme disease is the most common tick-borne disease in the United States. Reported cases have more than doubled between 1992 and 2006, with approximately 29,000 new cases confirmed in 2008. Estimates are that the actual number of cases of Lyme disease may exceed that reported by a factor of 6-12 in endemic areas. By definition, these endemic areas are expanding as populations continue to move from cities to suburban and rural areas and whitetail deer (which carry the tick species *Ixodes*) increasingly roam these areas. Lyme disease is caused by the microorganism *Borrelia burgdorferi*, a spirochete. *B. burgdorferi* is transmitted via the bite of the *Ixodes* tick and subsequently disseminates, via the bloodstream, to other tissues and organs.

In this animal model, C3H/HeN mice are injected with spirochetes via dorsal subcutaneous and intraperitoneal injection, or via intravenous injection. Blood and biopsy specimens are recovered at approximately 7 days post infection for evaluation of microbial burden and assessment of pathology in tissues and organs. The methods and compositions disclosed herein are contemplated to develop both therapeutic as well as preventative strategies for reduction and/or elimination of the resulting *B. burgdorferi* biofilms which form subsequent to challenge and are believed to contribute to both the pathogenesis and chronic nature of the disease.

Experiment No. 7

This experiment provides a porcine model for pre-clinical testing of interfering agents to treat cystic fibrosis. See Stoltz et al. (2010) Science Translational Medicine 2(29):29-31. Cystic fibrosis is an autosomal recessive disease due to mutations in a gene that encodes the CF transmembrane conductance regulator (called CFTR) anion channel. In this model, pigs which have been specifically bred to carry a defect in the genes called "CFTR" and called CF pigs spontaneously develop hallmark features of CF lung disease that includes infection of the lower airway by multiple bacterial species. The pigs can be immunized with the interfering agents to either 1) immunize these CF pigs with a polypeptide or other immunogenic agent thereby inducing the formation of antibodies which will eradicate bacterial biofilms in the lungs to deliver antibodies, or fragments or derivatives thereof to the lungs of these animals by nebulization to assess the amelioration of the signs of disease and associated pathologies.

Experiment No. 8

Applicants also provide a pre-clinical model for tuberculosis (TB). See Ordway et al. (2010) Anti. Agents and Chemotherapy 54:1820. The microorganism *Mycobacterium tuberculosis* is responsible for a growing global epidemic. Current figures suggest that there are approximately 8 million new cases of TB and about 2.7 million deaths due to TB annually. In addition to the role of this microbe as a co-infection of individuals with HIV (of the ~45 million infected with HIV, estimates are that ~⅓ are also co-infected with *M. tuberculosis*), its particularly troublesome that isolates have become highly resistant to multiple drugs and no new drug for TB has been introduced in over a quarter of a century. In this animal model, SPF guinea pigs are maintained in a barrier colony and infected via aerosolized spray to deliver ~20 cfu of *M. tuberculosis* strain Erdman K01 bacilli into their lungs. Animals are sacrificed with determination of bacterial load and recovery of tissues for histopathological assessment on days 25, 50, 75, 100, 125 and 150 days post-challenge. Unlike mice which do not develop classic signs of TB, guinea pigs challenged in this manner develop well-organized granulomas with central necrosis, a hallmark of human disease. Further, like humans, guinea pigs develop severe pyogranulomatous and necrotizing lymphadenitis of the draining lymph nodes as part of the primary lesion complex. Use of this model will provide a pre-clinical screen to confirm and identify therapeutic as well as preventative strategies for reduction and/or elimination of the resulting *M. tuberculosis* biofilms which have been observed to form in the lungs of these animals subsequent to challenge and are believed to contribute to both the pathogenesis and chronicity of the disease.

Experiment No. 9

Multiple animal models of catheter/indwelling device biofilm infections are known. See Otto (2009) Nature Reviews Microbiology 7:555. While typically considered normal skin flora, the microbe *Staphylococcus epidermidis* has become what many regard as a key opportunistic pathogen, ranking first among causative agents of nosocomial infections. Primarily, this bacterium is responsible for the majority of infections that develop on indwelling medical devices which are contaminated by this common skin colonizer during device insertion. While not typically life-threatening, the difficulty associated with treatment of these biofilm infections, combined with their frequency, makes them a serious public health burden. Current costs associated with treatment of vascular catheter associated bloodstream infections alone that are due to *S. epidermidis* amount to $2 billion annually in the United States. In addition to *S. epidermidis, E. faecalis* and *S. aureus* are also contaminations found on indwelling medical devices. There are several animal models of catheter-associated *S. epidermidis* infections including rabbits, mice, guinea pigs and rats all of which are used to study the molecular mechanisms of pathogenesis and which lend themselves to studies of prevention and/or therapeutics. Rat jugular vein catheters have been used to evaluate therapies that interfere with *E. faecalis, S. aureus* and *S. epidermidis* biofilm formation. Biofilm reduction is often measured three ways—(i) sonicate catheter and calculate CFUs, (ii) cut slices of catheter or simply lay on a plate and score, or (iii) the biofilm can be stained with crystal violet or another dye, eluted, and OD measured as a proxy for CFUs.

Experiment No. 10

Methods described herein may be used to elicit immune responses in humans and animals. Immunogenic compositions may be administered to human and animal subjects in the presence of adjuvants such as but not limited to aluminum salts and liposomes. Those skilled in the art will understand that any number of pharmaceutically acceptable adjuvants can also be used. Immunogenic compositions may be administered to a human or animal subjects intramuscularly, subdermally, intranasally, or through any other suitable route. Immunogenic compositions may be prepared in a manner consistent with the selected mode of administration. Immunogenic compositions may take the form of polypeptides, nucleic acids, or a combination thereof, and may comprise full-length or partial antigens. Additionally, or alternatively, immunogenic compositions may take the form of APCs pulsed with a particular antigen, or APCs transfected with one or more polynucleotides encoding a particular antigen. Administration may comprise a single dose of an immunogenic composition, or an initial administration, followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

Experiment No. 11

Methods described herein may be used to confer passive immunity on a non-immune subject. Passive immunity against a given antigen may be conferred through the transfer of antibodies or antigen binding fragments that specifically recognize or bind to a particular antigen. Antibody donors and recipients may be human or non-human subjects. Additionally, or alternatively, the antibody composition may comprise an isolated or recombinant polynucleotide encoding an antibody or antigen binding fragment that specifically recognizes or binds to a particular antigen.

Passive immunity may be conferred in cases where the administration of immunogenic compositions poses a risk for the recipient subject, the recipient subject is immunocompromised, or the recipient subject requires immediate immunity. Immunogenic compositions may be prepared in a manner consistent with the selected mode of administration. Compositions may comprise whole antibodies, antigen binding fragments, polyclonal antibodies, monoclonal antibodies, antibodies generated in vivo, antibodies generated in vitro, purified or partially purified antibodies, or whole serum. Administration may comprise a single dose of an antibody composition, or an initial administration followed by one or more booster doses. Booster doses may be provided a day, two days, three days, a week, two weeks, three weeks, one, two, three, six or twelve months, or at any other time point after an initial dose. A booster dose may be administered after an evaluation of the subject's antibody titer.

Equivalents

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

Unless otherwise defined, all technical and scientific terms used herein have the same meaning as commonly understood by one of ordinary skill in the art to which this disclosure belongs. All nucleotide sequences provided herein are presented in the 5' to 3' direction.

The embodiments illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

Thus, it should be understood that although the present disclosure has been specifically disclosed by specific embodiments and optional features, modification, improvement and variation of the embodiments therein herein disclosed may be resorted to by those skilled in the art, and that such modifications, improvements and variations are considered to be within the scope of this disclosure. The materials, methods, and examples provided here are representative of particular embodiments, are exemplary, and are not intended as limitations on the scope of the disclosure.

The scoped of the disclosure has been described broadly and generically herein. Each of the narrower species and subgeneric groupings falling within the generic disclosure also form part of the disclosure. This includes the generic description with a proviso or negative limitation removing any subject matter from the genus, regardless of whether or not the excised material is specifically recited herein.

In addition, where features or aspects of the disclosure are described in terms of Markush groups, those skilled in the art will recognize that embodiments of the disclosure may also thereby be described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Non-Limiting Embodiments of the Disclosure

Embodiment 1

An antibody or a fragment thereof comprising, or alternatively consisting essentially of, or yet further consisting of:
(i) a heavy chain (HC) immunoglobulin variable domain sequence comprising, or alternatively consisting essentially of, or yet further consisting of a sequence selected from the group of: amino acid (aa) 25 to aa 144 of SEQ ID NOs: 13, 24 or 26 or an equivalent of each thereof; and/or
(ii) a light chain (LC) immunoglobulin variable domain sequence comprising, or alternatively consisting essentially of, or yet further consisting of a sequence selected from the group of: aa 21 to aa 132 of SEQ ID NOs: 14 or 25, aa 21 to aa 126 of SEQ ID NO: 27 or an equivalent of each thereof.

Embodiment 2

The antibody or a fragment thereof of embodiment 1, wherein the antibody comprises, or consists essentially of, or yet further consists of:
(i) a heavy chain (HC) immunoglobulin variable domain sequence comprising, or alternatively consisting essentially of, or yet further consisting of a sequence of aa 25 to aa 144 of SEQ ID NO: 24 or an equivalent thereof; and/or
(ii) a light chain (LC) immunoglobulin variable domain sequence comprising, or alternatively consisting essentially of, or yet further consisting of a sequence of aa 21 to aa 132 of SEQ ID NO: 25 or an equivalent thereof.

Embodiment 3

The antibody or a fragment thereof of embodiment 1, wherein the antibody comprises, or consists essentially of, or yet further consists of:
(i) a heavy chain (HC) immunoglobulin variable domain sequence comprising, or alternatively consisting essentially of, or yet further consisting of a sequence selected from the group of: aa 25 to aa 144 of SEQ ID NOs: 1-6, 13, 24 or 26 or an equivalent of each thereof; and/or
(ii) a light chain (LC) immunoglobulin variable domain sequence comprising, or alternatively consisting essentially of, or yet further consisting of a sequence selected from the group of: aa 21 to aa 132 of SEQ ID NOs: 7-9, 14 or 25, aa 21 to aa 126 of SEQ ID NOs: 10-12 or 27, or an equivalent of each thereof.

Embodiment 4

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 1 or an equivalent thereof, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27, or an equivalent of each thereof.

Embodiment 5

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 2 or an equivalent thereof, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27, or an equivalent of each thereof.

Embodiment 6

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 3 or an equivalent thereof, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27, or an equivalent of each thereof.

Embodiment 7

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 4 or an equivalent thereof, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27, or an equivalent of each thereof.

Embodiment 8

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 5 or an equivalent thereof, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27, or an equivalent of each thereof.

Embodiment 9

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 6 or an equivalent thereof, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27, or an equivalent of each thereof.

Embodiment 10

The antibody or a fragment thereof of embodiment 1, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26 or an equivalent of each thereof, and/or wherein the light chain (LC) immunoglobulin variable domain sequence comprises, or consists essentially of, or yet further consists of an amino acid sequence of aa 21 to aa 132 of SEQ ID NO: 7 or an equivalent thereof.

Embodiment 11

The antibody or a fragment thereof of embodiment 1, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26 or an equivalent of each thereof, and/or wherein the light chain (LC) immunoglobulin variable domain sequence comprises, or consists essentially of, or yet further consists of an amino acid sequence of aa 21 to aa 132 of SEQ ID NO: 8 or an equivalent thereof.

Embodiment 12

The antibody or a fragment thereof of embodiment 1, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26 or an equivalent of each thereof, and/or wherein the light chain (LC) immunoglobulin variable domain sequence comprises, or consists essentially of, or yet further consists of an amino acid sequence of aa 21 to aa 132 of SEQ ID NO: 9 or an equivalent thereof.

Embodiment 13

The antibody or a fragment thereof of embodiment 1, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26 or an equivalent of each thereof, and/or wherein the light chain (LC) immunoglobulin variable domain sequence comprises, or consists essentially of, or yet further consists of an amino acid sequence of aa 21 to aa 126 of SEQ ID NO: 10 or an equivalent thereof.

Embodiment 14

The antibody or a fragment thereof of embodiment 1, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26 or an equivalent of each thereof, and/or wherein the light chain (LC) immunoglobulin variable domain sequence comprises, or consists essentially of, or yet further consists of an amino acid sequence of aa 21 to aa 126 of SEQ ID NO: 11 or an equivalent thereof.

Embodiment 15

The antibody or a fragment thereof of embodiment 1, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26 or an equivalent of each thereof, and/or wherein the light chain (LC) immunoglobulin variable domain sequence comprises, or consists essentially of, or yet further consists of an amino acid sequence of aa 21 to aa 126 of SEQ ID NO: 12 or an equivalent thereof.

Embodiment 16

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 1 or an equivalent thereof, and/or wherein the light chain (LC) immunoglobulin variable domain sequence comprises, or consists essentially of, or yet further consists of an amino acid sequence of aa 21 to aa 132 of SEQ ID NO: 7 or an equivalent thereof.

Embodiment 17

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 1 or an equivalent thereof, and/or wherein the light chain (LC) immunoglobulin variable domain sequence comprises, or consists essentially of, or yet further consists of an amino acid sequence of aa 21 to aa 132 of SEQ ID NO: 8 or an equivalent thereof.

Embodiment 18

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 1 or an equivalent thereof, and/or wherein the light chain (LC) immunoglobulin variable domain sequence comprises, or consists essentially of, or yet further consists of an amino acid sequence of aa 21 to aa 132 of SEQ ID NO: 9 or an equivalent thereof.

Embodiment 19

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 2 or an equivalent thereof, and/or wherein the light chain (LC) immunoglobulin variable domain sequence comprises, or consists essentially of, or yet further consists of an amino acid sequence aa 21 to aa 132 of SEQ ID of NO: 7 or an equivalent thereof.

Embodiment 20

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 2 or an equivalent thereof, and/or wherein the light chain (LC) immunoglobulin variable domain sequence comprises, or consists essentially of, or yet further consists of an amino acid sequence of aa 21 to aa 132 of SEQ ID NO: 8 or an equivalent thereof.

Embodiment 21

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 2 or an equivalent thereof, and/or wherein the light chain (LC) immunoglobulin variable domain sequence comprises, or consists essentially of, or yet further consists of an amino acid sequence of aa 21 to aa 132 of SEQ ID NO: 9 or an equivalent thereof.

Embodiment 22

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 3 or an equivalent thereof, and/or wherein the light chain (LC) immunoglobulin variable domain sequence comprises, or consists essentially of, or yet further consists of an amino acid sequence of aa 21 to aa 132 of SEQ ID NO: 7 or an equivalent thereof.

Embodiment 23

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 3 or an equivalent thereof, and/or wherein the light chain (LC) immunoglobulin variable domain sequence comprises, or consists essentially of, or yet further consists of an amino acid sequence of aa 21 to aa 132 of SEQ ID NO: 8 or an equivalent thereof.

Embodiment 24

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 3 or an equivalent thereof, and/or wherein the light chain (LC) immunoglobulin variable domain sequence comprises, or consists essentially of, or yet further consists of an amino acid sequence of aa 21 to aa 132 of SEQ ID NO: 9 or an equivalent thereof.

Embodiment 25

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 4 or an equivalent thereof, and/or wherein the light chain (LC) immunoglobulin variable domain sequence comprises, or consists essentially of, or yet further consists of an amino acid sequence of aa 21 to aa 126 of SEQ ID NO: 10 or an equivalent thereof.

Embodiment 26

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 4 or an equivalent thereof, and/or wherein the light chain (LC) immunoglobulin variable domain sequence comprises, or consists essentially of, or yet further consists of an amino acid sequence of aa 21 to aa 126 of SEQ ID NO: 11 or an equivalent thereof.

Embodiment 27

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 4 or an equivalent thereof, and/or wherein the light chain (LC) immunoglobulin variable domain sequence comprises, or consists essentially of, or yet further consists of an amino acid sequence of aa 21 to aa 126 of SEQ ID NO: 12 or an equivalent thereof.

Embodiment 28

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 5 or an equivalent thereof, and/or wherein the light chain (LC) immunoglobulin variable domain sequence comprises, or consists essentially of, or yet further consists of an amino acid sequence of aa 21 to aa 126 of SEQ ID NO: 10 or an equivalent thereof.

Embodiment 29

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 5 or an equivalent thereof, and/or wherein the light chain (LC) immunoglobulin variable domain sequence comprises, or consists essentially of, or yet further consists of an amino acid sequence of aa 21 to aa 126 of SEQ ID NO: 11 or an equivalent thereof.

Embodiment 30

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 5 or an equivalent thereof, and/or wherein the light chain (LC) immunoglobulin variable domain sequence comprises, or consists essentially of, or yet further consists of an amino acid sequence of aa 21 to aa 126 of SEQ ID NO: 12 or an equivalent thereof.

Embodiment 31

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 6 or an equivalent thereof, and/or wherein the light chain (LC) immunoglobulin variable domain sequence comprises, or consists essentially of, or yet further consists of an amino acid sequence of aa 21 to aa 126 of SEQ ID NO: 10 or an equivalent thereof.

Embodiment 32

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 6 or an equivalent thereof, and/or wherein the light chain (LC) immunoglobulin variable domain sequence comprises, or consists essentially of, or yet further consists of an amino acid sequence of aa 21 to aa 126 of SEQ ID NO: 11 or an equivalent thereof.

Embodiment 33

The antibody or a fragment thereof of embodiment 1, wherein the heavy chain (HC) immunoglobulin variable domain sequence comprises, or consists essentially of, or yet further consists of an amino acid sequence of aa 25 to aa 144 of SEQ ID NO: 6 or an equivalent thereof, and/or wherein the light chain (LC) immunoglobulin variable domain sequence comprises, or consists essentially of, or yet further consists of an amino acid sequence of aa 21 to aa 126 of SEQ ID NO: 12 or an equivalent thereof.

Embodiment 34

An antibody or a fragment thereof comprising, or alternatively consisting essentially of, or yet further consisting of:
(i) a heavy chain (HC) immunoglobulin variable domain sequence comprising, or alternatively consisting essentially of, or yet further consisting of a sequence selected from the group of: amino acid (aa) 25 to aa 144 of SEQ ID NOs: 13, 24 or 26; and/or
(ii) a light chain (LC) immunoglobulin variable domain sequence comprising, or alternatively consisting essentially of, or yet further consisting of a sequence selected from the group of: aa 21 to aa 132 of SEQ ID NOs: 14 or 25, aa 21 to aa 126 of SEQ ID NO: 27.

Embodiment 35

The antibody or a fragment thereof of embodiment 34, wherein the antibody comprises, or consists essentially of, or yet further consists of:
(i) a heavy chain (HC) immunoglobulin variable domain sequence comprising, or alternatively consisting essentially of, or yet further consisting of a sequence of aa 25 to aa 144 of SEQ ID NO: 24; and/or
(ii) a light chain (LC) immunoglobulin variable domain sequence comprising, or alternatively consisting essentially of, or yet further consisting of a sequence of aa 21 to aa 132 of SEQ ID NO: 25.

Embodiment 36

The antibody or a fragment thereof of embodiment 34, wherein the antibody comprises, or consists essentially of, or yet further consists of:

(i) a heavy chain (HC) immunoglobulin variable domain sequence comprising, or alternatively consisting essentially of, or yet further consisting of a sequence selected from the group of: aa 25 to aa 144 of SEQ ID NOs: 1-6, 13, 24 or 26; and/or (ii) a light chain (LC) immunoglobulin variable domain sequence comprising, or alternatively consisting essentially of, or yet further consisting of a sequence selected from the group of: aa 21 to aa 132 of SEQ ID NOs: 7-9, 14 or 25, aa 21 to aa 126 of SEQ ID NOs: 10-12 or 27.

Embodiment 37

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 1, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27.

Embodiment 38

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 2, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27.

Embodiment 39

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 3, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27.

Embodiment 40

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 4, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27.

Embodiment 41

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 5, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27.

Embodiment 42

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 6, and/or wherein the light chain (LC) immunoglobulin variable domain sequence comprises, or consists essentially of, or yet further consists of an amino acid sequence selected from the group of: aa 21 to aa 132 of SEQ ID NOs: 7-9, 14 or 25, aa 21 to aa 126 of SEQ ID NOs: 10-12 or 27.

Embodiment 43

The antibody or a fragment thereof of embodiment 34, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26, and/or wherein the light chain (LC) immunoglobulin variable domain sequence comprises, or consists essentially of, or yet further consists of an amino acid sequence of aa 21 to aa 132 of SEQ ID NO: 7.

Embodiment 44

The antibody or a fragment thereof of embodiment 34, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26, and/or wherein the light chain (LC) immunoglobulin variable domain sequence comprises, or consists essentially of, or yet further consists of an amino acid sequence of aa 21 to aa 132 of SEQ ID NO: 8.

Embodiment 45

The antibody or a fragment thereof of embodiment 34, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26, and/or wherein the light chain (LC) immunoglobulin variable domain sequence comprises, or consists essentially of, or yet further consists of an amino acid sequence of aa 21 to aa 132 of SEQ ID NO: 9.

Embodiment 46

The antibody or a fragment thereof of embodiment 34, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26, and/or wherein the light chain (LC) immunoglobulin variable domain sequence comprises, or consists essentially of, or yet further consists of an amino acid sequence of aa 21 to aa 126 of SEQ ID NO: 10.

Embodiment 47

The antibody or a fragment thereof of embodiment 34, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26, and/or wherein the light chain (LC) immunoglobulin variable domain sequence comprises, or consists essentially of, or yet further consists of an amino acid sequence of aa 21 to aa 126 of SEQ ID NO: 11.

Embodiment 48

The antibody or a fragment thereof of embodiment 34, wherein the heavy chain (HC) immunoglobulin variable domain sequence comprises, or consists essentially of, or yet further consists of an amino acid sequence selected from the group of: aa 25 to aa 144 of SEQ ID NOs: 1-6, 13, 24, or 26, and/or wherein the light chain (LC) immunoglobulin variable domain sequence comprises, or consists essentially of, or yet further consists of an amino acid sequence of aa 21 to aa 126 of SEQ ID NO: 12.

Embodiment 49

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 1, and/or wherein the light chain (LC) immunoglobulin variable domain sequence comprises, or consists essentially of, or yet further consists of an amino acid sequence of aa 21 to aa 132 of SEQ ID NO: 7.

Embodiment 50

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 1, and/or wherein the light chain (LC) immunoglobulin variable domain sequence comprises, or consists essentially of, or yet further consists of an amino acid sequence of aa 21 to aa 132 of SEQ ID NO: 8.

Embodiment 51

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 1, and/or wherein the light chain (LC) immunoglobulin variable domain sequence comprises, or consists essentially of, or yet further consists of an amino acid sequence of aa 21 to aa 132 of SEQ ID NO: 9.

Embodiment 52

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 2, and/or wherein the light chain (LC) immunoglobulin variable domain sequence comprises, or consists essentially of, or yet further consists of an amino acid sequence aa 21 to aa 132 of SEQ ID of NO: 7.

Embodiment 53

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 2, and/or wherein the light chain (LC) immunoglobulin variable domain sequence comprises, or consists essentially of, or yet further consists of an amino acid sequence of aa 21 to aa 132 of SEQ ID NO: 8.

Embodiment 54

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 2, and/or wherein the light chain (LC) immunoglobulin variable domain sequence comprises, or consists essentially of, or yet further consists of an amino acid sequence of aa 21 to aa 132 of SEQ ID NO: 9.

Embodiment 55

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 3, and/or wherein the light chain (LC) immunoglobulin variable domain sequence comprises, or consists essentially of, or yet further consists of an amino acid sequence of aa 21 to aa 132 of SEQ ID NO: 7.

Embodiment 56

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 3, and/or wherein the light chain (LC) immunoglobulin variable domain sequence comprises, or consists essentially of, or yet further consists of an amino acid sequence of aa 21 to aa 132 of SEQ ID NO: 8.

Embodiment 57

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 3, and/or wherein the light chain (LC) immunoglobulin variable domain sequence comprises, or consists essentially of, or yet further consists of an amino acid sequence of aa 21 to aa 132 of SEQ ID NO: 9.

Embodiment 58

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 4, and/or wherein the light chain (LC)

immunoglobulin variable domain sequence comprises, or consists essentially of, or yet further consists of an amino acid sequence of aa 21 to aa 126 of SEQ ID NO: 10.

Embodiment 59

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 4, and/or wherein the light chain (LC) immunoglobulin variable domain sequence comprises, or consists essentially of, or yet further consists of an amino acid sequence of aa 21 to aa 126 of SEQ ID NO: 11.

Embodiment 60

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 4, and/or wherein the light chain (LC) immunoglobulin variable domain sequence comprises, or consists essentially of, or yet further consists of an amino acid sequence of aa 21 to aa 126 of SEQ ID NO: 12.

Embodiment 61

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 5, and/or wherein the light chain (LC) immunoglobulin variable domain sequence comprises, or consists essentially of, or yet further consists of an amino acid sequence of aa 21 to aa 126 of SEQ ID NO: 10.

Embodiment 62

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 5, and/or wherein the light chain (LC) immunoglobulin variable domain sequence comprises, or consists essentially of, or yet further consists of an amino acid sequence of aa 21 to aa 126 of SEQ ID NO: 11.

Embodiment 63

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 5, and/or wherein the light chain (LC) immunoglobulin variable domain sequence comprises, or consists essentially of, or yet further consists of an amino acid sequence of aa 21 to aa 126 of SEQ ID NO: 12.

Embodiment 64

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 6, and/or wherein the light chain (LC) immunoglobulin variable domain sequence comprises, or consists essentially of, or yet further consists of an amino acid sequence of aa 21 to aa 126 of SEQ ID NO: 10.

Embodiment 65

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 6, and/or wherein the light chain (LC) immunoglobulin variable domain sequence comprises, or consists essentially of, or yet further consists of an amino acid sequence of aa 21 to aa 126 of SEQ ID NO: 11.

Embodiment 66

The antibody or a fragment thereof of embodiment 34, wherein the heavy chain (HC) immunoglobulin variable domain sequence comprises, or consists essentially of, or yet further consists of an amino acid sequence of aa 25 to aa 144 of SEQ ID NO: 6, and/or wherein the light chain (LC) immunoglobulin variable domain sequence comprises, or consists essentially of, or yet further consists of an amino acid sequence of aa 21 to aa 126 of SEQ ID NO: 12.

Embodiment 67

An antibody or a fragment thereof comprising, or alternatively consisting essentially of, or yet further consisting of:
(i) a heavy chain (HC) comprising, or alternatively consisting essentially of, or yet further consisting of a sequence selected from the group of: amino acid (aa) 25 to aa 473 of SEQ ID NOs: 13, 24 or 26 or an equivalent of each thereof; and/or
(ii) a light chain (LC) comprising, or alternatively consisting essentially of, or yet further consisting of a sequence selected from the group of: aa 21 to aa 239 of SEQ ID NOs: 14 or 25, aa 21 to aa 233 of SEQ ID NO: 27 or an equivalent of each thereof.

Embodiment 68

The antibody or a fragment thereof of embodiment 67, wherein the antibody comprises, or consists essentially of, or yet further consists of:
(i) a heavy chain (HC) comprising, or alternatively consisting essentially of, or yet further consisting of a sequence of aa 25 to aa 473 of SEQ ID NO: 24 or an equivalent thereof and/or
(ii) a light chain (LC) comprising, or alternatively consisting essentially of, or yet further consisting of a sequence of aa 21 to aa 239 of SEQ ID NO: 25 or an equivalent thereof.

Embodiment 69

The antibody or a fragment thereof of embodiment 67, wherein the antibody comprises, or consists essentially of, or yet further consists of:
(i) a heavy chain (HC) comprising, or alternatively consisting essentially of, or yet further consisting of a sequence selected from the group of: aa 25 to aa 473 of SEQ ID NOs: 1-6, 13, 24 or 26 or an equivalent of each thereof; and/or
(ii) a light chain (LC) comprising, or alternatively consisting essentially of, or yet further consisting of a sequence selected from the group of: aa 21 to aa 239 of SEQ ID NOs: 7-9, 14 or 25, aa 21 to aa 233 of SEQ ID NOs: 10-12 or 27, or an equivalent of each thereof.

Embodiment 70

The antibody or a fragment thereof of embodiment 67, wherein the heavy chain (HC) comprises, or consists essentially of, or yet further consists of an amino acid sequence of aa 25 to aa 473 of SEQ ID NO: 1 or an equivalent thereof, and/or wherein the light chain (LC) comprises, or consists essentially of, or yet further consists of an amino acid sequence selected from the group of: aa 21 to aa 239 of SEQ ID NOs: 7-9, 14 or 25, aa 21 to aa 233 of SEQ ID NOs: 10-12 or 27, or an equivalent of each thereof.

Embodiment 71

The antibody or a fragment thereof of embodiment 67, wherein the heavy chain (HC) comprises, or consists essentially of, or yet further consists of an amino acid sequence of aa 25 to aa 473 of SEQ ID NO: 2 or an equivalent thereof, and/or wherein the light chain (LC) comprises, or consists essentially of, or yet further consists of an amino acid sequence selected from the group of: aa 21 to aa 239 of SEQ ID NOs: 7-9, 14 or 25, aa 21 to aa 233 of SEQ ID NOs: 10-12 or 27, or an equivalent of each thereof.

Embodiment 72

The antibody or a fragment thereof of embodiment 67, wherein the heavy chain (HC) comprises, or consists essentially of, or yet further consists of an amino acid sequence of aa 25 to aa 473 of SEQ ID NO: 3 or an equivalent thereof, and/or wherein the light chain (LC) comprises, or consists essentially of, or yet further consists of an amino acid sequence selected from the group of: aa 21 to aa 239 of SEQ ID NOs: 7-9, 14 or 25, aa 21 to aa 233 of SEQ ID NOs: 10-12 or 27, or an equivalent of each thereof.

Embodiment 73

The antibody or a fragment thereof of embodiment 67, wherein the heavy chain (HC) comprises, or consists essentially of, or yet further consists of an amino acid sequence of aa 25 to aa 473 of SEQ ID NO: 4 or an equivalent thereof, and/or wherein the light chain (LC) comprises, or consists essentially of, or yet further consists of an amino acid sequence selected from the group of: aa 21 to aa 239 of SEQ ID NOs: 7-9, 14 or 25, aa 21 to aa 233 of SEQ ID NOs: 10-12 or 27, or an equivalent of each thereof.

Embodiment 74

The antibody or a fragment thereof of embodiment 67, wherein the heavy chain (HC) comprises, or consists essentially of, or yet further consists of an amino acid sequence of aa 25 to aa 473 of SEQ ID NO: 5 or an equivalent thereof, and/or wherein the light chain (LC) comprises, or consists essentially of, or yet further consists of an amino acid sequence selected from the group of: aa 21 to aa 239 of SEQ ID NOs: 7-9, 14 or 25, aa 21 to aa 233 of SEQ ID NOs: 10-12 or 27, or an equivalent of each thereof.

Embodiment 75

The antibody or a fragment thereof of embodiment 67, wherein the heavy chain (HC) comprises, or consists essentially of, or yet further consists of an amino acid sequence of aa 25 to aa 473 of SEQ ID NO: 6 or an equivalent thereof, and/or wherein the light chain (LC) comprises, or consists essentially of, or yet further consists of an amino acid sequence selected from the group of: aa 21 to aa 239 of SEQ ID NOs: 7-9, 14 or 25, aa 21 to aa 233 of SEQ ID NOs: 10-12 or 27, or an equivalent of each thereof.

Embodiment 76

The antibody or a fragment thereof of embodiment 67, wherein the heavy chain (HC) comprises, or consists essentially of, or yet further consists of an amino acid sequence selected from the group of: aa 25 to aa 473 of SEQ ID NOs: 1-6, 13, 24, or 26 or an equivalent of each thereof, and/or wherein the light chain (LC) comprises, or consists essentially of, or yet further consists of an amino acid sequence of aa 21 to aa 239 of SEQ ID NO: 7 or an equivalent thereof.

Embodiment 77

The antibody or a fragment thereof of embodiment 67, wherein the heavy chain (HC) comprises, or consists essentially of, or yet further consists of an amino acid sequence selected from the group of: aa 25 to aa 473 of SEQ ID NOs: 1-6, 13, 24, or 26 or an equivalent of each thereof, and/or wherein the light chain (LC) comprises, or consists essentially of, or yet further consists of an amino acid sequence of aa 21 to aa 239 of SEQ ID NO: 8 or an equivalent thereof.

Embodiment 78

The antibody or a fragment thereof of embodiment 67, wherein the heavy chain (HC) comprises, or consists essentially of, or yet further consists of an amino acid sequence selected from the group of: aa 25 to aa 473 of SEQ ID NOs: 1-6, 13, 24, or 26 or an equivalent of each thereof, and/or wherein the light chain (LC) comprises, or consists essentially of, or yet further consists of an amino acid sequence of aa 21 to aa 239 of SEQ ID NO: 9 or an equivalent thereof.

Embodiment 79

The antibody or a fragment thereof of embodiment 67, wherein the heavy chain (HC) comprises, or consists essentially of, or yet further consists of an amino acid sequence selected from the group of: aa 25 to aa 473 of SEQ ID NOs: 1-6, 13, 24, or 26 or an equivalent of each thereof, and/or wherein the light chain (LC) comprises, or consists essentially of, or yet further consists of an amino acid sequence of aa 21 to aa 233 of SEQ ID NO: 10 or an equivalent thereof.

Embodiment 80

The antibody or a fragment thereof of embodiment 67, wherein the heavy chain (HC) comprises, or consists essentially of, or yet further consists of an amino acid sequence selected from the group of: aa 25 to aa 473 of SEQ ID NOs: 1-6, 13, 24, or 26 or an equivalent of each thereof, and/or wherein the light chain (LC) comprises, or consists essentially of, or yet further consists of an amino acid sequence of aa 21 to aa 233 of SEQ ID NO: 11 or an equivalent thereof.

Embodiment 81

The antibody or a fragment thereof of embodiment 67, wherein the heavy chain (HC) comprises, or consists essentially of, or yet further consists of an amino acid sequence selected from the group of: aa 25 to aa 473 of SEQ ID NOs: 1-6, 13, 24, or 26 or an equivalent of each thereof, and/or wherein the light chain (LC) comprises, or consists essentially of, or yet further consists of an amino acid sequence of aa 21 to aa 233 of SEQ ID NO: 12 or an equivalent thereof.

Embodiment 82

The antibody or a fragment thereof of embodiment 67, wherein the heavy chain (HC) comprises, or consists essentially of, or yet further consists of an amino acid sequence of aa 25 to aa 473 of SEQ ID NO: 1 or an equivalent thereof, and/or wherein the light chain (LC) comprises, or consists essentially of, or yet further consists of an amino acid sequence of aa 21 to aa 239 of SEQ ID NO: 7 or an equivalent thereof.

Embodiment 83

The antibody or a fragment thereof of embodiment 67, wherein the heavy chain (HC) comprises, or consists essentially of, or yet further consists of an amino acid sequence of aa 25 to aa 473 of SEQ ID NO: 1 or an equivalent thereof, and/or wherein the light chain (LC) comprises, or consists essentially of, or yet further consists of an amino acid sequence of aa 21 to aa 239 of SEQ ID NO: 8 or an equivalent thereof.

Embodiment 84

The antibody or a fragment thereof of embodiment 67, wherein the heavy chain (HC) comprises, or consists essentially of, or yet further consists of an amino acid sequence of aa 25 to aa 473 of SEQ ID NO: 1 or an equivalent thereof, and/or wherein the light chain (LC) comprises, or consists essentially of, or yet further consists of an amino acid sequence of aa 21 to aa 239 of SEQ ID NO: 9 or an equivalent thereof.

Embodiment 85

The antibody or a fragment thereof of embodiment 67, wherein the heavy chain (HC) comprises, or consists essentially of, or yet further consists of an amino acid sequence of aa 25 to aa 473 of SEQ ID NO: 2 or an equivalent thereof, and/or wherein the light chain (LC) comprises, or consists essentially of, or yet further consists of an amino acid sequence aa 21 to aa 239 of SEQ ID of NO: 7 or an equivalent thereof.

Embodiment 86

The antibody or a fragment thereof of embodiment 67, wherein the heavy chain (HC) comprises, or consists essentially of, or yet further consists of an amino acid sequence of aa 25 to aa 473 of SEQ ID NO: 2 or an equivalent thereof, and/or wherein the light chain (LC) comprises, or consists essentially of, or yet further consists of an amino acid sequence of aa 21 to aa 239 of SEQ ID NO: 8 or an equivalent thereof.

Embodiment 87

The antibody or a fragment thereof of embodiment 67, wherein the heavy chain (HC) comprises, or consists essentially of, or yet further consists of an amino acid sequence of aa 25 to aa 473 of SEQ ID NO: 2 or an equivalent thereof, and/or wherein the light chain (LC) comprises, or consists essentially of, or yet further consists of an amino acid sequence of aa 21 to aa 239 of SEQ ID NO: 9 or an equivalent thereof.

Embodiment 88

The antibody or a fragment thereof of embodiment 67, wherein the heavy chain (HC) comprises, or consists essentially of, or yet further consists of an amino acid sequence of aa 25 to aa 473 of SEQ ID NO: 3 or an equivalent thereof, and/or wherein the light chain (LC) comprises, or consists essentially of, or yet further consists of an amino acid sequence of aa 21 to aa 239 of SEQ ID NO: 7 or an equivalent thereof.

Embodiment 89

The antibody or a fragment thereof of embodiment 67, wherein the heavy chain (HC) comprises, or consists essentially of, or yet further consists of an amino acid sequence of aa 25 to aa 473 of SEQ ID NO: 3 or an equivalent thereof, and/or wherein the light chain (LC) comprises, or consists essentially of, or yet further consists of an amino acid sequence of aa 21 to aa 239 of SEQ ID NO: 8 or an equivalent thereof.

Embodiment 90

The antibody or a fragment thereof of embodiment 67, wherein the heavy chain (HC) comprises, or consists essentially of, or yet further consists of an amino acid sequence of aa 25 to aa 473 of SEQ ID NO: 3 or an equivalent thereof, and/or wherein the light chain (LC) comprises, or consists essentially of, or yet further consists of an amino acid sequence of aa 21 to aa 239 of SEQ ID NO: 9 or an equivalent thereof.

Embodiment 91

The antibody or a fragment thereof of embodiment 67, wherein the heavy chain (HC) comprises, or consists essentially of, or yet further consists of an amino acid sequence of aa 25 to aa 473 of SEQ ID NO: 4 or an equivalent thereof, and/or wherein the light chain (LC) comprises, or consists essentially of, or yet further consists of an amino acid sequence of aa 21 to aa 233 of SEQ ID NO: 10 or an equivalent thereof.

Embodiment 92

The antibody or a fragment thereof of embodiment 67, wherein the heavy chain (HC) comprises, or consists essentially of, or yet further consists of an amino acid sequence of aa 25 to aa 473 of SEQ ID NO: 4 or an equivalent thereof, and/or wherein the light chain (LC) comprises, or consists essentially of, or yet further consists of an amino acid sequence of aa 21 to aa 233 of SEQ ID NO: 11 or an equivalent thereof.

Embodiment 93

The antibody or a fragment thereof of embodiment 67, wherein the heavy chain (HC) comprises, or consists essentially of, or yet further consists of an amino acid sequence of aa 25 to aa 473 of SEQ ID NO: 4 or an equivalent thereof, and/or wherein the light chain (LC) comprises, or consists essentially of, or yet further consists of an amino acid sequence of aa 21 to aa 233 of SEQ ID NO: 12 or an equivalent thereof.

Embodiment 94

The antibody or a fragment thereof of embodiment 67, wherein the heavy chain (HC) comprises, or consists essentially of, or yet further consists of an amino acid sequence of aa 25 to aa 473 of SEQ ID NO: 5 or an equivalent thereof, and/or wherein the light chain (LC) comprises, or consists essentially of, or yet further consists of an amino acid sequence of aa 21 to aa 233 of SEQ ID NO: 10 or an equivalent thereof.

Embodiment 95

The antibody or a fragment thereof of embodiment 67, wherein the heavy chain (HC) comprises, or consists essentially of, or yet further consists of an amino acid sequence of aa 25 to aa 473 of SEQ ID NO: 5 or an equivalent thereof, and/or wherein the light chain (LC) comprises, or consists essentially of, or yet further consists of an amino acid sequence of aa 21 to aa 233 of SEQ ID NO: 11 or an equivalent thereof.

Embodiment 96

The antibody or a fragment thereof of embodiment 67, wherein the heavy chain (HC) comprises, or consists essentially of, or yet further consists of an amino acid sequence of aa 25 to aa 473 of SEQ ID NO: 5 or an equivalent thereof, and/or wherein the light chain (LC) comprises, or consists essentially of, or yet further consists of an amino acid sequence of aa 21 to aa 233 of SEQ ID NO: 12 or an equivalent thereof.

Embodiment 97

The antibody or a fragment thereof of embodiment 67, wherein the heavy chain (HC) comprises, or consists essentially of, or yet further consists of an amino acid sequence of aa 25 to aa 473 of SEQ ID NO: 6 or an equivalent thereof, and/or wherein the light chain (LC) comprises, or consists essentially of, or yet further consists of an amino acid sequence of aa 21 to aa 233 of SEQ ID NO: 10 or an equivalent thereof.

Embodiment 98

The antibody or a fragment thereof of embodiment 67, wherein the heavy chain (HC) comprises, or consists essentially of, or yet further consists of an amino acid sequence of aa 25 to aa 473 of SEQ ID NO: 6 or an equivalent thereof, and/or wherein the light chain (LC) comprises, or consists essentially of, or yet further consists of an amino acid sequence of aa 21 to aa 233 of SEQ ID NO: 11 or an equivalent thereof.

Embodiment 99

The antibody or a fragment thereof of embodiment 67, wherein the heavy chain (HC) comprises, or consists essentially of, or yet further consists of an amino acid sequence of aa 25 to aa 473 of SEQ ID NO: 6 or an equivalent thereof, and/or wherein the light chain (LC) comprises, or consists essentially of, or yet further consists of an amino acid sequence of aa 21 to aa 233 of SEQ ID NO: 12 or an equivalent thereof.

Embodiment 100

An antibody or a fragment thereof comprising, or alternatively consisting essentially of, or yet further consisting of:
  (i) a heavy chain (HC) comprising, or alternatively consisting essentially of, or yet further consisting of a sequence selected from the group of: SEQ ID NOs: 13, 24 or 26 or an equivalent of each thereof; and/or
  (ii) a light chain (LC) comprising, or alternatively consisting essentially of, or yet further consisting of a sequence selected from the group of: SEQ ID NOs: 14, 25, or 27 or an equivalent of each thereof.

Embodiment 101

The antibody or a fragment thereof of embodiment 100, wherein the antibody comprises, or consists essentially of, or yet further consists of:
  (i) a heavy chain (HC) comprising, or alternatively consisting essentially of, or yet further consisting of a sequence of SEQ ID NO: 24 or an equivalent thereof; and/or
  (ii) a light chain (LC) comprising, or alternatively consisting essentially of, or yet further consisting of a sequence of SEQ ID NO: 25 or an equivalent thereof.

Embodiment 102

The antibody or a fragment thereof of embodiment 100, wherein the antibody comprises, or consists essentially of, or yet further consists of:
  (i) a heavy chain (HC) comprising, or alternatively consisting essentially of, or yet further consisting of a sequence selected from the group of: SEQ ID NOs: 1-6, 13, 24 or 26 or an equivalent of each thereof; and/or
  (ii) a light chain (LC) comprising, or alternatively consisting essentially of, or yet further consisting of a sequence selected from the group of: SEQ ID NOs: 7-12, 14, 25, or 27, or an equivalent of each thereof.

Embodiment 103

The antibody or a fragment thereof of embodiment 100, wherein the heavy chain (HC) comprises, or consists essentially of, or yet further consists of an amino acid sequence of SEQ ID NO: 1 or an equivalent thereof, and/or wherein the light chain (LC) comprises, or consists essentially of, or yet further consists of an amino acid sequence selected from the group of: SEQ ID NOs: 7-12, 14, 25, or 27, or an equivalent of each thereof.

Embodiment 104

The antibody or a fragment thereof of embodiment 100, wherein the heavy chain (HC) comprises, or consists essentially of, or yet further consists of an amino acid sequence of SEQ ID NO: 2 or an equivalent thereof, and/or wherein the light chain (LC) comprises, or consists essentially of, or yet further consists of an amino acid sequence selected from the group of: SEQ ID NOs: 7-12, 14, 25, or 27, or an equivalent of each thereof.

Embodiment 105

The antibody or a fragment thereof of embodiment 100, wherein the heavy chain (HC) comprises, or consists essentially of, or yet further consists of an amino acid sequence of SEQ ID NO: 3 or an equivalent thereof, and/or wherein the light chain (LC) comprises, or consists essentially of, or yet further consists of an amino acid sequence selected from the group of: SEQ ID NOs: 7-12, 14, 25, or 27, or an equivalent of each thereof.

Embodiment 106

The antibody or a fragment thereof of embodiment 100, wherein the heavy chain (HC) comprises, or consists essentially of, or yet further consists of an amino acid sequence of SEQ ID NO: 4 or an equivalent thereof, and/or wherein the light chain (LC) comprises, or consists essentially of, or yet further consists of an amino acid sequence selected from the group of: SEQ ID NOs: 7-12, 14, 25, or 27, or an equivalent of each thereof.

Embodiment 107

The antibody or a fragment thereof of embodiment 100, wherein the heavy chain (HC) comprises, or consists essentially of, or yet further consists of an amino acid sequence of SEQ ID NO: 5 or an equivalent thereof, and/or wherein the light chain (LC) comprises, or consists essentially of, or yet further consists of an amino acid sequence selected from the group of: SEQ ID NOs: 7-12, 14, 25, or 27, or an equivalent of each thereof.

Embodiment 108

The antibody or a fragment thereof of embodiment 100, wherein the heavy chain (HC) comprises, or consists essentially of, or yet further consists of an amino acid sequence of SEQ ID NO: 6 or an equivalent thereof, and/or wherein the light chain (LC) comprises, or consists essentially of, or yet further consists of an amino acid sequence selected from the group of: SEQ ID NOs: 7-12, 14, 25, or 27, or an equivalent of each thereof.

Embodiment 109

The antibody or a fragment thereof of embodiment 100, wherein the heavy chain (HC) comprises, or consists essentially of, or yet further consists of an amino acid sequence selected from the group of: SEQ ID NOs: 1-6, 13, 24, or 26 or an equivalent of each thereof, and/or wherein the light chain (LC) comprises, or consists essentially of, or yet further consists of an amino acid sequence of SEQ ID NO: 7 or an equivalent thereof.

Embodiment 110

The antibody or a fragment thereof of embodiment 100, wherein the heavy chain (HC) comprises, or consists essentially of, or yet further consists of an amino acid sequence selected from the group of: SEQ ID NOs: 1-6, 13, 24, or 26 or an equivalent of each thereof, and/or wherein the light chain (LC) comprises, or consists essentially of, or yet further consists of an amino acid sequence of SEQ ID NO: 8 or an equivalent thereof.

Embodiment 111

The antibody or a fragment thereof of embodiment 100, wherein the heavy chain (HC) comprises, or consists essentially of, or yet further consists of an amino acid sequence selected from the group of: SEQ ID NOs: 1-6, 13, 24, or 26 or an equivalent of each thereof, and/or wherein the light chain (LC) comprises, or consists essentially of, or yet further consists of an amino acid sequence of SEQ ID NO: 9 or an equivalent thereof.

Embodiment 112

The antibody or a fragment thereof of embodiment 100, wherein the heavy chain (HC) comprises, or consists essentially of, or yet further consists of an amino acid sequence selected from the group of: SEQ ID NOs: 1-6, 13, 24, or 26 or an equivalent of each thereof, and/or wherein the light chain (LC) comprises, or consists essentially of, or yet further consists of an amino acid sequence of SEQ ID NO: 10 or an equivalent thereof.

Embodiment 113

The antibody or a fragment thereof of embodiment 100, wherein the heavy chain (HC) comprises, or consists essentially of, or yet further consists of an amino acid sequence selected from the group of: SEQ ID NOs: 1-6, 13, 24, or 26 or an equivalent of each thereof, and/or wherein the light chain (LC) comprises, or consists essentially of, or yet further consists of an amino acid sequence of SEQ ID NO: 11 or an equivalent thereof.

Embodiment 114

The antibody or a fragment thereof of embodiment 100, wherein the heavy chain (HC) comprises, or consists essentially of, or yet further consists of an amino acid sequence selected from the group of: SEQ ID NOs: 1-6, 13, 24, or 26 or an equivalent of each thereof, and/or wherein the light chain (LC) comprises, or consists essentially of, or yet further consists of an amino acid sequence of SEQ ID NO: 12 or an equivalent thereof.

Embodiment 115

The antibody or a fragment thereof of embodiment 100, wherein the heavy chain (HC) comprises, or consists essentially of, or yet further consists of an amino acid sequence of SEQ ID NO: 1 or an equivalent thereof, and/or wherein the light chain (LC) comprises, or consists essentially of, or yet further consists of an amino acid sequence of SEQ ID NO: 7 or an equivalent thereof.

Embodiment 116

The antibody or a fragment thereof of embodiment 100, wherein the heavy chain (HC) comprises, or consists essentially of, or yet further consists of an amino acid sequence of SEQ ID NO: 1 or an equivalent thereof, and/or wherein the light chain (LC) comprises, or consists essentially of, or yet further consists of an amino acid sequence of SEQ ID NO: 8 or an equivalent thereof.

Embodiment 117

The antibody or a fragment thereof of embodiment 100, wherein the heavy chain (HC) comprises, or consists essentially of, or yet further consists of an amino acid sequence of SEQ ID NO: 1 or an equivalent thereof, and/or wherein the light chain (LC) comprises, or consists essentially of, or yet further consists of an amino acid sequence of SEQ ID NO: 9 or an equivalent thereof.

Embodiment 118

The antibody or a fragment thereof of embodiment 100, wherein the heavy chain (HC) comprises, or consists essentially of, or yet further consists of an amino acid sequence of SEQ ID NO: 2 or an equivalent thereof, and/or wherein the light chain (LC) comprises, or consists essentially of, or yet further consists of an amino acid sequence of SEQ ID NO: 7 or an equivalent thereof.

Embodiment 119

The antibody or a fragment thereof of embodiment 100, wherein the heavy chain (HC) comprises, or consists essentially of, or yet further consists of an amino acid sequence of SEQ ID NO: 2 or an equivalent thereof, and/or wherein the light chain (LC) comprises, or consists essentially of, or yet further consists of an amino acid sequence of SEQ ID NO: 8 or an equivalent thereof.

Embodiment 120

The antibody or a fragment thereof of embodiment 100, wherein the heavy chain (HC) comprises, or consists essentially of, or yet further consists of an amino acid sequence of SEQ ID NO: 2 or an equivalent thereof, and/or wherein the light chain (LC) comprises, or consists essentially of, or yet further consists of an amino acid sequence of SEQ ID NO: 9 or an equivalent thereof.

Embodiment 121

The antibody or a fragment thereof of embodiment 100, wherein the heavy chain (HC) comprises, or consists essentially of, or yet further consists of an amino acid sequence of SEQ ID NO: 3 or an equivalent thereof, and/or wherein the light chain (LC) comprises, or consists essentially of, or yet further consists of an amino acid sequence of SEQ ID NO: 7 or an equivalent thereof.

Embodiment 122

The antibody or a fragment thereof of embodiment 100, wherein the heavy chain (HC) comprises, or consists essentially of, or yet further consists of an amino acid sequence of SEQ ID NO: 3 or an equivalent thereof, and/or wherein the light chain (LC) comprises, or consists essentially of, or yet further consists of an amino acid sequence of SEQ ID NO: 8 or an equivalent thereof.

Embodiment 123

The antibody or a fragment thereof of embodiment 100, wherein the heavy chain (HC) comprises, or consists essentially of, or yet further consists of an amino acid sequence of SEQ ID NO: 3 or an equivalent thereof, and/or wherein the light chain (LC) comprises, or consists essentially of, or yet further consists of an amino acid sequence of SEQ ID NO: 9 or an equivalent thereof.

Embodiment 124

The antibody or a fragment thereof of embodiment 100, wherein the heavy chain (HC) comprises, or consists essentially of, or yet further consists of an amino acid sequence of SEQ ID NO: 4 or an equivalent thereof, and/or wherein the light chain (LC) comprises, or consists essentially of, or yet further consists of an amino acid sequence of SEQ ID NO: 10 or an equivalent thereof.

Embodiment 125

The antibody or a fragment thereof of embodiment 100, wherein the heavy chain (HC) comprises, or consists essentially of, or yet further consists of an amino acid sequence of SEQ ID NO: 4 or an equivalent thereof, and/or wherein the light chain (LC) comprises, or consists essentially of, or yet further consists of an amino acid sequence of SEQ ID NO: 11 or an equivalent thereof.

Embodiment 126

The antibody or a fragment thereof of embodiment 100, wherein the heavy chain (HC) comprises, or consists essentially of, or yet further consists of an amino acid sequence of SEQ ID NO: 4 or an equivalent thereof, and/or wherein the light chain (LC) comprises, or consists essentially of, or yet further consists of an amino acid sequence of SEQ ID NO: 12 or an equivalent thereof.

Embodiment 127

The antibody or a fragment thereof of embodiment 100, wherein the heavy chain (HC) comprises, or consists essentially of, or yet further consists of an amino acid sequence of SEQ ID NO: 5 or an equivalent thereof, and/or wherein the light chain (LC) comprises, or consists essentially of, or yet further consists of an amino acid sequence of SEQ ID NO: 10 or an equivalent thereof.

Embodiment 128

The antibody or a fragment thereof of embodiment 100, wherein the heavy chain (HC) comprises, or consists essentially of, or yet further consists of an amino acid sequence of SEQ ID NO: 5 or an equivalent thereof, and/or wherein the light chain (LC) comprises, or consists essentially of, or yet further consists of an amino acid sequence of SEQ ID NO: 11 or an equivalent thereof.

Embodiment 129

The antibody or a fragment thereof of embodiment 100, wherein the heavy chain (HC) comprises, or consists essentially of, or yet further consists of an amino acid sequence of SEQ ID NO: 5 or an equivalent thereof, and/or wherein the light chain (LC) comprises, or consists essentially of, or yet further consists of an amino acid sequence of SEQ ID NO: 12 or an equivalent thereof.

Embodiment 130

The antibody or a fragment thereof of embodiment 100, wherein the heavy chain (HC) comprises, or consists essentially of, or yet further consists of an amino acid sequence of SEQ ID NO: 6 or an equivalent thereof, and/or wherein the light chain (LC) comprises, or consists essentially of, or yet further consists of an amino acid sequence of SEQ ID NO: 10 or an equivalent thereof.

Embodiment 131

The antibody or a fragment thereof of embodiment 100, wherein the heavy chain (HC) comprises, or consists essen-

161 tially of, or yet further consists of an amino acid sequence of SEQ ID NO: 6 or an equivalent thereof, and/or wherein the light chain (LC) comprises, or consists essentially of, or yet further consists of an amino acid sequence of SEQ ID NO: 11 or an equivalent thereof.

Embodiment 132

The antibody or a fragment thereof of embodiment 100, wherein the heavy chain (HC) comprises, or consists essentially of, or yet further consists of an amino acid sequence of SEQ ID NO: 6 or an equivalent thereof, and/or wherein the light chain (LC) comprises, or consists essentially of, or yet further consists of an amino acid sequence of SEQ ID NO: 12 or an equivalent thereof.

Embodiment 133

An antibody or a fragment thereof comprising, or alternatively consisting essentially of, or yet further consisting of one or two or three or four or five or all six of the following (i) to (vi):
- (i) a heavy chain complementarity-determining region 1 (CDRH1) comprising, or alternatively consisting essentially of, or yet further consisting of a sequence selected from the group of: GFTFXXY (amino acid (aa) 50 to aa 56 of SEQ ID NO: 13), GFTFRTY (aa 50 to aa 56 of SEQ ID NO: 1 or 2 or 3 or 24), or GFTFSRY (aa 50 to aa 56 of SEQ ID NO: 4 or 5 or 6 or 26), wherein X is any amino acid or an amino acid at the aligned aa position of a sequence selected from SEQ ID NOs: 1-6;
- (ii) a heavy chain complementarity-determining region 2 (CDRH2) comprising, or alternatively consisting essentially of, or yet further consisting of a sequence selected from the group of: XSXXXX (amino acid (aa) 76 to aa 81 of SEQ ID NO: 13), GSDRRH (aa 76 to aa 81 of SEQ ID NO: 1 or 2 or 3 or 24), or SSGGSY (aa 76 to aa 81 of SEQ ID NO: 4 or 5 or 6 or 26), wherein X is any amino acid or an amino acid at the aligned aa position of a sequence selected from SEQ ID NOs: 1-6;
- (iii) a heavy chain complementarity-determining region 3 (CDRH3) comprising, or alternatively consisting essentially of, or yet further consisting of a sequence selected from the group of: XXXXXXXXYXXFDX (amino acid (aa) 121 to aa 133 of SEQ ID NO: 13), VGPYDGYYGEFDY (aa 121 to aa 133 of SEQ ID NO: 1 or 2 or 3 or 24), or ERHGGDGYWYFDV (aa 121 to aa 133 of SEQ ID NO: 4 or 5 or 6 or 26), wherein X is any amino acid or an amino acid at the aligned aa position of a sequence selected from SEQ ID NOs: 1-6;
- (iv) a light chain complementarity-determining region 1 (CDRL1) comprising, or alternatively consisting essentially of, or yet further consisting of a sequence selected from the group of: QXXXXXXXXXX (aa 47 to aa 57 of SEQ ID NO: 14), QXXXXX (aa 47 to aa 52 of SEQ ID NO: 14), QSLLDSDGKTF (aa 47 to aa 57 of SEQ ID NO: 7 or 8 or 9 or 25), or QDISNY (aa 47 to aa 52 of SEQ ID NO: 10 or 11 or 12 or 27), wherein X is any amino acid or an amino acid at the aligned aa position of a sequence selected from SEQ ID NOs: 7-12;
- (v) a light chain complementarity-determining region 2 (CDRL2) comprising, or alternatively consisting essentially of, or yet further consisting of a sequence selected from the group of: XXS (aa 75 to aa 77 of SEQ ID NO: 14), LVS (aa 75 to aa 77 of SEQ ID NO: 7 or 8 or 9 or 25), or YTS (aa 70 to aa 72 of SEQ ID NO: 10 or 11 or 12 or 27), wherein X is any amino acid or an amino acid at the aligned aa position of a sequence selected from SEQ ID NOs: 7-12; and
- (vi) a light chain complementarity-determining region 3 (CDRL3) comprising, or alternatively consisting essentially of, or yet further consisting of a sequence selected from the group of: XQGXXXXXT (aa 114 to aa 122 of SEQ ID NO: 14), WQGTHFPYT (aa 114 to aa 122 of SEQ ID NO: 7 or 8 or 9 or 25), or QQGNPLRT (aa 109 to aa 116 of SEQ ID NO: 10 or 11 or 12 or 27), wherein X is any amino acid or an amino acid at the aligned aa position of a sequence selected from SEQ ID NOs: 7-12, optionally wherein the antibody or fragment thereof comprises, or alternatively consists essentially of, or yet further consists of a light chain and a heavy chain, further optionally wherein the light chain is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identical to an amino acid sequence of any one or more of SEQ ID NOs: 7-12, 14, 25 or 27 or optionally a SEQ ID NO selected therefrom whose sequence comprises one or two or three CDR(s) of the antibody or a fragment thereof, and further optionally wherein the heavy chain is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identical to an amino acid sequence of any one or more of SEQ ID NOs: 7-12, 14, 25 or 27 or optionally a SEQ ID NO selected therefrom whose sequence comprises one or two or three CDR(s) of the antibody or a fragment thereof.

Embodiment 134

An antibody or a fragment thereof comprising, or alternatively consisting essentially of, or yet further consisting of one or two or three or four or five or all six of the following (i) to (vi):
- (i) a heavy chain complementarity-determining region 1 (CDRH1) comprising, or alternatively consisting essentially of, or yet further consisting of a sequence of GFTFRTY (aa 50 to aa 56 of SEQ ID NO: 1 or 2 or 3 or 24);
- (ii) a heavy chain complementarity-determining region 2 (CDRH2) comprising, or alternatively consisting essentially of, or yet further consisting of a sequence of GSDRRH (aa 76 to aa 81 of SEQ ID NO: 1 or 2 or 3 or 24);
- (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
- (iv) a light chain complementarity-determining region 1 (CDRL1) comprising, or alternatively consisting essentially of, or yet further consisting of a sequence of QSLLDSDGKTF (aa 47 to aa 57 of SEQ ID NO: 7 or 8 or 9 or 25);
- (v) a light chain complementarity-determining region 2 (CDRL2) comprising, or alternatively consisting essentially of, or yet further consisting of a sequence of LVS (aa 75 to aa 77 of SEQ ID NO: 7 or 8 or 9 or 25); and (vi) a light chain complementarity-determining region 3 (CDRL3) comprising, or alternatively consisting essentially of, or yet further consisting of a sequence of WQGTHFP (aa 114 to aa 120 of SEQ ID NO: 7 or 8 or 9 or 25), optionally wherein the antibody or fragment thereof comprises, or alternatively consists essentially of, or yet further consists of a light chain and a heavy chain, further optionally wherein the light chain is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identical to an amino acid sequence of any one or more of SEQ ID NOs: 7-12, 14, 25 or 27 or optionally a SEQ ID NO selected therefrom whose sequence comprises one or two or three CDR(s) of the antibody or a fragment thereof, and further optionally wherein the heavy chain is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identical to an amino acid sequence of any one or more of SEQ ID NOs: 7-12, 14, 25 or 27 or optionally a SEQ ID NO selected therefrom whose sequence comprises one or two or three CDR(s) of the antibody or a fragment thereof.

Embodiment 135

The antibody or a fragment thereof of any one of embodiments 133-134, wherein the CDRH1 comprises, or consists essentially of, or yet further consists of a sequence of GFTFRTYA (aa 50 to aa 57 of SEQ ID NO: 1 or 2 or 3 or 24).

Embodiment 136

The antibody or a fragment thereof of any one of embodiments 133-135, wherein the CDRH1 comprises, or consists essentially of, or yet further consists of a sequence of aASGFTFRTYAMS (aa 47 to aa 59 of SEQ ID NO: 24), wherein the small letter a is A (aa 47 to aa 59 of SEQ ID NO: 1 or 2) or wherein the small letter a is K (aa 47 to aa 59 of SEQ ID NO: 3).

Embodiment 137

The antibody or a fragment thereof of any one of embodiments 133-136, wherein the CDRH2 comprises, or consists essentially of, or yet further consists of a sequence of IGSDRRHT (aa 75 to aa 82 of SEQ ID NO: 1 or 2 or 3 or 24).

Embodiment 138

The antibody or a fragment thereof of any one of embodiments 133-137, wherein the CDRH2 comprises, or consists essentially of, or yet further consists of a sequence of IGSDRRHTY (aa 75 to aa 83 of SEQ ID NO: 1 or 2 or 3 or 24).

Embodiment 139

The antibody or a fragment thereof of any one of embodiments 133-138, wherein the CDRH2 comprises, or consists essentially of, or yet further consists of a sequence of TIGSDRRHTY (aa 74 to aa 83 of SEQ ID NO: 1 or 2 or 3 or 24).

Embodiment 140

The antibody or a fragment thereof of any one of embodiments 133-139, wherein the CDRH2 comprises, or consists essentially of, or yet further consists of a sequence of WVATIGSDRRHTYW (aa 71 to aa 85 of SEQ ID NO: 1 or 2 or 3 or 24).

Embodiment 141

The antibody or a fragment thereof of any one of embodiments 133-140, wherein the CDRL1 comprises, or consists essentially of, or yet further consists of a sequence of rSSQSLLDSDGKTFLN (aa 44 to aa 59 of SEQ ID NO: 25), wherein the smaller letter r is R (aa 44 to aa 59 of SEQ ID NO: 7 or 8) or wherein the smaller letter r is K (aa 44 to aa 59 of SEQ ID NO: 9).

Embodiment 142

The antibody or a fragment thereof of any one of embodiments 133-141, wherein the CDRL2 comprises, or consists essentially of, or yet further consists of a sequence of LVSK1DS (aa 75 to aa 81 of SEQ ID NO: 25), wherein the smaller letter 1 is L (aa 75 to aa 81 of SEQ ID NO: 7 or 9) or wherein the smaller letter 1 is R (aa 75 to aa 81 of SEQ ID NO: 8).

Embodiment 143

The antibody or a fragment thereof of any one of embodiments 133-142, wherein the CDRL2 comprises, or consists essentially of, or yet further consists of a sequence of YLVSK1DS (aa 74 to aa 81 of SEQ ID NO: 25), wherein the smaller letter 1 is L (aa 74 to aa 81 of SEQ ID NO: 7 or 9) or wherein the smaller letter 1 is R (aa 74 to aa 81 of SEQ ID NO: 8).

Embodiment 144

The antibody or a fragment thereof of any one of embodiments 133-142, wherein the CDRL2 comprises, or consists essentially of, or yet further consists of a sequence of LVSK1DSG (aa 75 to aa 82 of SEQ ID NO: 25), wherein the smaller letter 1 is L (aa 75 to aa 82 of SEQ ID NO: 7 or 9) or wherein the smaller letter 1 is R (aa 75 to aa 82 of SEQ ID NO: 8).

Embodiment 145

The antibody or a fragment thereof of any one of embodiments 133-144, wherein the CDRL2 comprises, or consists essentially of, or yet further consists of a sequence of YLVSK1DSGV (aa 74 to aa 83 of SEQ ID NO: 25), wherein the smaller letter 1 is L (aa 74 to aa 83 of SEQ ID NO: 7 or 9) or wherein the smaller letter 1 is R (aa 74 to aa 83 of SEQ ID NO: 8).

Embodiment 146

The antibody or a fragment thereof of any one of embodiments 133-145, wherein the CDRL2 comprises, or consists essentially of, or yet further consists of a sequence of RLIYLVSK1DSGVPD (aa 71 to aa 85 of SEQ ID NO: 25), wherein the smaller letter 1 is L (aa 71 to aa 85 of SEQ ID NO: 7 or 9) or wherein the smaller letter 1 is R (aa 71 to aa 85 of SEQ ID NO: 8).

Embodiment 147

The antibody or a fragment thereof of any one of embodiments 134-146, wherein the CDRL3 comprises, or consists essentially of, or yet further consists of a sequence of WQGTHFPY (aa 114 to aa 121 of SEQ ID NO: 7 or 8 or 9 or 25).

Embodiment 148

The antibody or a fragment thereof of any one of embodiments 133-147, wherein the CDRL3 comprises, or consists essentially of, or yet further consists of a sequence of WQGTHFPYT (aa 114 to aa 122 of SEQ ID NO: 7 or 8 or 9 or 25).

Embodiment 149

The antibody or a fragment thereof of embodiment 133 or 134, wherein the antibody comprises, or consists essentially of, or yet further consists of one or two or three or four or five or all six of the following (i) to (vi):
  (i) a heavy chain complementarity-determining region 1 (CDRH1) comprising, or alternatively consisting essentially of, or yet further consisting of a sequence of GFTFRTY (aa 50 to aa 56 of SEQ ID NO: 1 or 2 or 3 or 24);
  (ii) a heavy chain complementarity-determining region 2 (CDRH2) comprising, or alternatively consisting essentially of, or yet further consisting of a sequence of GSDRRH (aa 76 to aa 81 of SEQ ID NO: 1 or 2 or 3 or 24);
  (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
  (iv) a light chain complementarity-determining region 1 (CDRL1) comprising, or alternatively consisting essentially of, or yet further consisting of a sequence of QSLLDSDGKTF (aa 47 to aa 57 of SEQ ID NO: 7 or 8 or 9 or 25);
  (v) a light chain complementarity-determining region 2 (CDRL2) comprising, or alternatively consisting essentially of, or yet further consisting of a sequence of LVS (aa 75 to aa 77 of SEQ ID NO: 7 or 8 or 9 or 25); and
  (vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 150

The antibody or a fragment thereof of any one of embodiments 133, 134, and 149, wherein the antibody comprises, or consists essentially of, or yet further consists of one or two or three or four or five or all six of the following (i) to (vi):
  (i) a heavy chain complementarity-determining region 1 (CDRH1) comprising, or alternatively consisting essentially of, or yet further consisting of a sequence of GFTFRTYA (aa 50 to aa 57 of SEQ ID NO: 1 or 2 or 3 or 24);
  (ii) a heavy chain complementarity-determining region 2 (CDRH2) comprising, or alternatively consisting essentially of, or yet further consisting of a sequence of IGSDRRHT (aa 75 to aa 82 of SEQ ID NO: 1 or 2 or 3 or 24);
  (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
  (iv) a light chain complementarity-determining region 1 (CDRL1) comprising, or alternatively consisting essentially of, or yet further consisting of a sequence of QSLLDSDGKTF (aa 47 to aa 57 of SEQ ID NO: 7 or 8 or 9 or 25);
  (v) a light chain complementarity-determining region 2 (CDRL2) comprising, or alternatively consisting essentially of, or yet further consisting of a sequence of LVS (aa 75 to aa 77 of SEQ ID NO: 7 or 8 or 9 or 25); and
  (vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 151

The antibody or a fragment thereof of any one of embodiments 133, 134, and 149, wherein the antibody comprises, or consists essentially of, or yet further consists of one or two or three or four or five or all six of the following (i) to (vi):
  (i) a heavy chain complementarity-determining region 1 (CDRH1) comprising, or alternatively consisting essentially of, or yet further consisting of a sequence of aASGFTFRTYAMS (aa 47 to aa 59 of SEQ ID NO: 24), wherein the small letter a is A (aa 47 to aa 59 of SEQ ID NO: 1 or 2) or wherein the small letter a is K (aa 47 to aa 59 of SEQ ID NO: 3);
  (ii) a heavy chain complementarity-determining region 2 (CDRH2) comprising, or alternatively consisting essentially of, or yet further consisting of a sequence of TIGSDRRHTY (aa 74 to aa 83 of SEQ ID NO: 1 or 2 or 3 or 24);
  (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
  (iv) a light chain complementarity-determining region 1 (CDRL1) comprising, or alternatively consisting essentially of, or yet further consisting of a sequence of rSSQSLLDSDGKTFLN (aa 44 to aa 59 of SEQ ID NO: 25), wherein the smaller letter r is R (aa 44 to aa 59 of SEQ ID NO: 7 or 8) or wherein the smaller letter r is K (aa 44 to aa 59 of SEQ ID NO: 9);
  (v) a light chain complementarity-determining region 2 (CDRL2) comprising, or alternatively consisting essentially of, or yet further consisting of a sequence of YLVSK1DS (aa 74 to aa 81 of SEQ ID NO: 25), wherein the smaller letter 1 is L (aa 74 to aa 81 of SEQ ID NO: 7 or 9) or wherein the smaller letter 1 is R (aa 74 to aa 81 of SEQ ID NO: 8); and
  (vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 152

The antibody or a fragment thereof of any one of embodiments 133, 134, 149 and 151, wherein the antibody comprises, or consists essentially of, or yet further consists of one or two or three or four or five or all six of the following (i) to (vi):
- (i) a heavy chain complementarity-determining region 1 (CDRH1) comprising, or alternatively consisting essentially of, or yet further consisting of a sequence of AASGFTFRTYAMS (aa 47 to aa 59 of SEQ ID NO: 1 or 2);
- (ii) a heavy chain complementarity-determining region 2 (CDRH2) comprising, or alternatively consisting essentially of, or yet further consisting of a sequence of TIGSDRRHTY (aa 74 to aa 83 of SEQ ID NO: 1 or 2 or 3 or 24);
- (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
- (iv) a light chain complementarity-determining region 1 (CDRL1) comprising, or alternatively consisting essentially of, or yet further consisting of a sequence of RSSQSLLDSDGKTFLN (aa 44 to aa 59 of SEQ ID NO: 7);
- (v) a light chain complementarity-determining region 2 (CDRL2) comprising, or alternatively consisting essentially of, or yet further consisting of a sequence of YLVSKLDS (aa 74 to aa 81 of SEQ ID NO: 7); and
- (vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 153

The antibody or a fragment thereof of any one of embodiments 133, 134, 149, and 151, wherein the antibody comprises, or consists essentially of, or yet further consists of one or two or three or four or five or all six of the following (i) to (vi):
- (i) a heavy chain complementarity-determining region 1 (CDRH1) comprising, or alternatively consisting essentially of, or yet further consisting of a sequence of AASGFTFRTYAMS (aa 47 to aa 59 of SEQ ID NO: 1 or 2);
- (ii) a heavy chain complementarity-determining region 2 (CDRH2) comprising, or alternatively consisting essentially of, or yet further consisting of a sequence of TIGSDRRHTY (aa 74 to aa 83 of SEQ ID NO: 1 or 2 or 3 or 24);
- (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
- (iv) a light chain complementarity-determining region 1 (CDRL1) comprising, or alternatively consisting essentially of, or yet further consisting of a sequence of RSSQSLLDSDGKTFLN (aa 44 to aa 59 of SEQ ID NO: 8);
- (v) a light chain complementarity-determining region 2 (CDRL2) comprising, or alternatively consisting essentially of, or yet further consisting of a sequence of YLVSKRDS (aa 74 to aa 81 of SEQ ID NO: 8); and
- (vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 154

The antibody or a fragment thereof of any one of embodiments 133, 134, 149, and 151, wherein the antibody comprises, or consists essentially of, or yet further consists of one or two or three or four or five or all six of the following (i) to (vi):
- (i) a heavy chain complementarity-determining region 1 (CDRH1) comprising, or alternatively consisting essentially of, or yet further consisting of a sequence of AASGFTFRTYAMS (aa 47 to aa 59 of SEQ ID NO: 1 or 2);
- (ii) a heavy chain complementarity-determining region 2 (CDRH2) comprising, or alternatively consisting essentially of, or yet further consisting of a sequence of TIGSDRRHTY (aa 74 to aa 83 of SEQ ID NO: 1 or 2 or 3 or 24);
- (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
- (iv) a light chain complementarity-determining region 1 (CDRL1) comprising, or alternatively consisting essentially of, or yet further consisting of a sequence of KSSQSLLDSDGKTFLN (aa 44 to aa 59 of SEQ ID NO: 9);
- (v) a light chain complementarity-determining region 2 (CDRL2) comprising, or alternatively consisting essentially of, or yet further consisting of a sequence of YLVSKLDS (aa 74 to aa 81 of SEQ ID NO: 9); and
- (vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 155

The antibody or a fragment thereof of any one of embodiments 133, 134, 149, and 151, wherein the antibody comprises, or consists essentially of, or yet further consists of one or two or three or four or five or all six of the following (i) to (vi):
- (i) a heavy chain complementarity-determining region 1 (CDRH1) comprising, or alternatively consisting essentially of, or yet further consisting of a sequence of KASGFTFRTYAMS (aa 47 to aa 59 of SEQ ID NO: 3);
- (ii) a heavy chain complementarity-determining region 2 (CDRH2) comprising, or alternatively consisting essentially of, or yet further consisting of a sequence of TIGSDRRHTY (aa 74 to aa 83 of SEQ ID NO: 1 or 2 or 3 or 24);

(iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
(iv) a light chain complementarity-determining region 1 (CDRL1) comprising, or alternatively consisting essentially of, or yet further consisting of a sequence of RSSQSLLDSDGKTFLN (aa 44 to aa 59 of SEQ ID NO: 7);
(v) a light chain complementarity-determining region 2 (CDRL2) comprising, or alternatively consisting essentially of, or yet further consisting of a sequence of YLVSKLDS (aa 74 to aa 81 of SEQ ID NO: 7); and
(vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 156

The antibody or a fragment thereof of any one of embodiments 133, 134, 149, and 151, wherein the antibody comprises, or consists essentially of, or yet further consists of one or two or three or four or five or all six of the following (i) to (vi):
(i) a heavy chain complementarity-determining region 1 (CDRH1) comprising, or alternatively consisting essentially of, or yet further consisting of a sequence of KASGFTFRTYAMS (aa 47 to aa 59 of SEQ ID NO: 3);
(ii) a heavy chain complementarity-determining region 2 (CDRH2) comprising, or alternatively consisting essentially of, or yet further consisting of a sequence of TIGSDRRHTY (aa 74 to aa 83 of SEQ ID NO: 1 or 2 or 3 or 24);
(iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
(iv) a light chain complementarity-determining region 1 (CDRL1) comprising, or alternatively consisting essentially of, or yet further consisting of a sequence of RSSQSLLDSDGKTFLN (aa 44 to aa 59 of SEQ ID NO: 8);
(v) a light chain complementarity-determining region 2 (CDRL2) comprising, or alternatively consisting essentially of, or yet further consisting of a sequence of YLVSKRDS (aa 74 to aa 81 of SEQ ID NO: 8); and
(vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 157

The antibody or a fragment thereof of any one of embodiments 133, 134, 149, an 151, wherein the antibody comprises, or consists essentially of, or yet further consists of one or two or three or four or five or all six of the following (i) to (vi):
(i) a heavy chain complementarity-determining region 1 (CDRH1) comprising, or alternatively consisting essentially of, or yet further consisting of a sequence of KASGFTFRTYAMS (aa 47 to aa 59 of SEQ ID NO: 3);
(ii) a heavy chain complementarity-determining region 2 (CDRH2) comprising, or alternatively consisting essentially of, or yet further consisting of a sequence of TIGSDRRHTY (aa 74 to aa 83 of SEQ ID NO: 1 or 2 or 3 or 24);
(iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
(iv) a light chain complementarity-determining region 1 (CDRL1) comprising, or alternatively consisting essentially of, or yet further consisting of a sequence of KSSQSLLDSDGKTFLN (aa 44 to aa 59 of SEQ ID NO: 9);
(v) a light chain complementarity-determining region 2 (CDRL2) comprising, or alternatively consisting essentially of, or yet further consisting of a sequence of YLVSKLDS (aa 74 to aa 81 of SEQ ID NO: 9); and
(vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 158

The antibody or a fragment thereof of any one of embodiments 133, 134, or 149, wherein the antibody comprises, or consists essentially of, or yet further consists of one or two or three or four or five or all six of the following (i) to (vi):
(i) a heavy chain complementarity-determining region 1 (CDRH1) comprising, or alternatively consisting essentially of, or yet further consisting of a sequence of GFTFRTY (aa 50 to aa 56 of SEQ ID NO: 1 or 2 or 3 or 24);
(ii) a heavy chain complementarity-determining region 2 (CDRH2) comprising, or alternatively consisting essentially of, or yet further consisting of a sequence of GSDRRH (aa 76 to aa 81 of SEQ ID NO: 1 or 2 or 3 or 24);
(iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
(iv) a light chain complementarity-determining region 1 (CDRL1) comprising, or alternatively consisting essentially of, or yet further consisting of a sequence of rSSQSLLDSDGKTFLN (aa 44 to aa 59 of SEQ ID NO: 25), wherein the smaller letter r is R (aa 44 to aa 59 of SEQ ID NO: 7 or 8) or wherein the smaller letter r is K (aa 44 to aa 59 of SEQ ID NO: 9);
(v) a light chain complementarity-determining region 2 (CDRL2) comprising, or alternatively consisting essentially of, or yet further consisting of a sequence of LVSK1DS (aa 75 to aa 81 of SEQ ID NO: 25), wherein the smaller letter 1 is L (aa 75 to aa 81 of SEQ ID NO: 7 or 9) or wherein the smaller letter 1 is R (aa 75 to aa 81 of SEQ ID NO: 8); and
(vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 159

The antibody or a fragment thereof of any one of embodiments 133, 134, 149, or 158, wherein the antibody comprises, or consists essentially of, or yet further consists of one or two or three or four or five or all six of the following (i) to (vi):
- (i) a heavy chain complementarity-determining region 1 (CDRH1) comprising, or alternatively consisting essentially of, or yet further consisting of a sequence of GFTFRTY (aa 50 to aa 56 of SEQ ID NO: 1 or 2 or 3 or 24);
- (ii) a heavy chain complementarity-determining region 2 (CDRH2) comprising, or alternatively consisting essentially of, or yet further consisting of a sequence of GSDRRH (aa 76 to aa 81 of SEQ ID NO: 1 or 2 or 3 or 24);
- (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
- (iv) a light chain complementarity-determining region 1 (CDRL1) comprising, or alternatively consisting essentially of, or yet further consisting of a sequence of RSSQSLLDSDGKTFLN (aa 44 to aa 59 of SEQ ID NO: 7);
- (v) a light chain complementarity-determining region 2 (CDRL2) comprising, or alternatively consisting essentially of, or yet further consisting of a sequence of LVSKLDS (aa 75 to aa 81 of SEQ ID NO: 7); and
- (vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 160

The antibody or a fragment thereof of any one of embodiments 133, 134, 149, or 158, wherein the antibody comprises, or consists essentially of, or yet further consists of one or two or three or four or five or all six of the following (i) to (vi):
- (i) a heavy chain complementarity-determining region 1 (CDRH1) comprising, or alternatively consisting essentially of, or yet further consisting of a sequence of GFTFRTY (aa 50 to aa 56 of SEQ ID NO: 1 or 2 or 3 or 24);
- (ii) a heavy chain complementarity-determining region 2 (CDRH2) comprising, or alternatively consisting essentially of, or yet further consisting of a sequence of GSDRRH (aa 76 to aa 81 of SEQ ID NO: 1 or 2 or 3 or 24);
- (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
- (iv) a light chain complementarity-determining region 1 (CDRL1) comprising, or alternatively consisting essentially of, or yet further consisting of a sequence of RSSQSLLDSDGKTFLN (aa 44 to aa 59 of SEQ ID NO: 8);
- (v) a light chain complementarity-determining region 2 (CDRL2) comprising, or alternatively consisting essentially of, or yet further consisting of a sequence of LVSKRDS (aa 75 to aa 81 of SEQ ID NO: 8); and
- (vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 161

The antibody or a fragment thereof of any one of embodiments 133, 134, 149, or 158, wherein the antibody comprises, or consists essentially of, or yet further consists of one or two or three or four or five or all six of the following (i) to (vi):
- (i) a heavy chain complementarity-determining region 1 (CDRH1) comprising, or alternatively consisting essentially of, or yet further consisting of a sequence of GFTFRTY (aa 50 to aa 56 of SEQ ID NO: 1 or 2 or 3 or 24);
- (ii) a heavy chain complementarity-determining region 2 (CDRH2) comprising, or alternatively consisting essentially of, or yet further consisting of a sequence of GSDRRH (aa 76 to aa 81 of SEQ ID NO: 1 or 2 or 3 or 24);
- (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
- (iv) a light chain complementarity-determining region 1 (CDRL1) comprising, or alternatively consisting essentially of, or yet further consisting of a sequence of KSSQSLLDSDGKTFLN (aa 44 to aa 59 of SEQ ID NO: 9);
- (v) a light chain complementarity-determining region 2 (CDRL2) comprising, or alternatively consisting essentially of, or yet further consisting of a sequence of LVSKLDS (aa 75 to aa 81 of SEQ ID NO: 9); and
- (vi) a light chain complementarity-determining region 3 (CDRL3) comprising, or alternatively consisting essentially of, or yet further consisting of a sequence of WQGTHFPYT (aa 114 to aa 122 of SEQ ID NO: 7 or 8 or 9 or 25).

Embodiment 162

The antibody or a fragment thereof of embodiment 133 or 134, wherein the antibody comprises, or consists essentially of, or yet further consists of one or two or three or four or five or all six of the following (i) to (vi):
- (i) a heavy chain complementarity-determining region 1 (CDRH1) comprising, or alternatively consisting essentially of, or yet further consisting of a sequence of GFTFRTYA (aa 50 to aa 57 of SEQ ID NO: 1 or 2 or 3 or 24);
- (ii) a heavy chain complementarity-determining region 2 (CDRH2) comprising, or alternatively consisting essentially of, or yet further consisting of a sequence of IGSDRRHT (aa 75 to aa 82 of SEQ ID NO: 1 or 2 or 3 or 24);
- (iii) a heavy chain complementarity-determining region 3 (CDRH3) comprising, or alternatively consisting essentially of, or yet further consisting of a sequence of VGPYDGYYGEFDY (aa 121 to aa 133 of SEQ ID NO: 1 or 2 or 3 or 24);
- (iv) a light chain complementarity-determining region 1 (CDRL1) comprising, or alternatively consisting essentially of, or yet further consisting of a sequence of QSLLDSDGKTF (aa 47 to aa 57 of SEQ ID NO: 7 or 8 or 9 or 25);

(v) a light chain complementarity-determining region 2 (CDRL2) comprising, or alternatively consisting essentially of, or yet further consisting of a sequence of LVS (aa 75 to aa 77 of SEQ ID NO: 7 or 8 or 9 or 25); and
(vi) a light chain complementarity-determining region 3 (CDRL3) comprising, or alternatively consisting essentially of, or yet further consisting of a sequence of WQGTHFP (aa 114 to aa 120 of SEQ ID NO: 7 or 8 or 9 or 25).

Embodiment 163

An antibody or a fragment thereof comprising, or alternatively consisting essentially of, or yet further consisting of one or two or three or four or five or all six of the following (i) to (vi):
(i) a heavy chain complementarity-determining region 1 (CDRH1) comprising, or alternatively consisting essentially of, or yet further consisting of a sequence of GFTFSRY (aa 50 to aa 56 of SEQ ID NO: 4 or 5 or 6 or 26);
(ii) a heavy chain complementarity-determining region 2 (CDRH2) comprising, or alternatively consisting essentially of, or yet further consisting of a sequence of SSGGSY (aa 76 to aa 81 of SEQ ID NO: 4 or 5 or 6 or 26);
(iii) a heavy chain complementarity-determining region 3 (CDRH3) comprising, or alternatively consisting essentially of, or yet further consisting of a sequence of ER (aa 121 to aa 122 of SEQ ID NO: 4 or 5 or 6 or 26);
(iv) a light chain complementarity-determining region 1 (CDRL1) comprising, or alternatively consisting essentially of, or yet further consisting of a sequence of QDISNY (aa 47 to aa 52 of SEQ ID NO: 10 or 11 or 12 or 27);
(v) a light chain complementarity-determining region 2 (CDRL2) comprising, or alternatively consisting essentially of, or yet further consisting of a sequence of YTS (aa 70 to aa 72 of SEQ ID NO: 10 or 11 or 12 or 27); and
(vi) a light chain complementarity-determining region 3 (CDRL3) comprising, or alternatively consisting essentially of, or yet further consisting of a sequence of QQ (aa 109 to aa 110 of SEQ ID NO: 10 or 11 or 12 or 27),
optionally wherein the antibody or fragment thereof comprises, or alternatively consists essentially of, or yet further consists of a light chain and a heavy chain, further optionally wherein the light chain is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identical to an amino acid sequence of any one or more of SEQ ID NOs: 7-12, 14, 25 or 27 or optionally a SEQ ID NO selected therefrom whose sequence comprises one or two or three CDR(s) of the antibody or a fragment thereof, and further optionally wherein the heavy chain is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identical to an amino acid sequence of any one or more of SEQ ID NOs: 7-12, 14, 25 or 27 or optionally a SEQ ID NO selected therefrom whose sequence comprises one or two or three CDR(s) of the antibody or a fragment thereof.

Embodiment 164

The antibody or a fragment thereof of embodiment 133 or 163, wherein the CDRH1 comprises, or consists essentially of, or yet further consists of a sequence of GFTFSRYG (aa 50 to aa 57 of SEQ ID NO: 4 or 5 or 6 or 26).

Embodiment 165

The antibody or a fragment thereof of any one of embodiments 133 or 163-164, wherein the CDRH1 comprises, or consists essentially of, or yet further consists of a sequence of aASGFTFSRYGMS (aa 47 to aa 59 of SEQ ID NO:26), wherein the small letter a is A (aa 47 to aa 59 of SEQ ID NO: 4 or 5) or wherein the small letter a is T (aa 47 to aa 59 of SEQ ID NO: 6).

Embodiment 166

The antibody or a fragment thereof of any one of embodiments 133 or 163-165, wherein the CDRH2 comprises, or consists essentially of, or yet further consists of a sequence of ISSGGSYT (aa 75 to aa 82 of SEQ ID NO: 4 or 5 or 6 or 26).

Embodiment 167

The antibody or a fragment thereof of any one of embodiments 133 or 163-166, wherein the CDRH2 comprises, or consists essentially of, or yet further consists of a sequence of TISSGGSYTY (aa 74 to aa 83 of SEQ ID NO: 4 or 5 or 6 or 26).

Embodiment 168

The antibody or a fragment thereof of any one of embodiments 133 or 163-167, wherein the CDRH3 comprises, or consists essentially of, or yet further consists of a sequence of ERHGGDGYWYFDV (aa 121 to aa 133 of SEQ ID NO: 4 or 5 or 6 or 26).

Embodiment 169

The antibody or a fragment thereof of any one of embodiments 133 or 163-168, wherein the CDRL1 comprises, or consists essentially of, or yet further consists of a sequence of RASQDISNYLN (aa 44 to aa 54 of SEQ ID NO: 10 or 11 or 12 or 27).

Embodiment 170

The antibody or a fragment thereof of any one of embodiments 133 or 163-169, wherein the CDRL2 comprises, or consists essentially of, or yet further consists of a sequence of YTSRLHS (aa 70 to aa 76 of SEQ ID NO: 10 or 11 or 12 or 27).

Embodiment 171

The antibody or a fragment thereof of any one of embodiments 133 or 163-170, wherein the CDRL2 comprises, or consists essentially of, or yet further consists of a sequence of YYTSRLHS (aa 69 to aa 76 of SEQ ID NO: 10 or 11 or 12 or 27).

Embodiment 172

The antibody or a fragment thereof of any one of embodiments 133 or 163-171, wherein the CDRL3 comprises, or consists essentially of, or yet further consists of a sequence of QQGNPLRT (aa 109 to aa 116 of SEQ ID NO: 10 or 11 or 12 or 27).

Embodiment 173

The antibody or a fragment thereof of embodiment 133 or 163, comprising, or alternatively consisting essentially of, or yet further consisting of one or two or three or four or five or all six of the following (i) to (vi):
  (i) a heavy chain complementarity-determining region 1 (CDRH1) comprising, or alternatively consisting essentially of, or yet further consisting of a sequence of GFTFSRY (aa 50 to aa 56 of SEQ ID NO: 4 or 5 or 6 or 26);
  (ii) a heavy chain complementarity-determining region 2 (CDRH2) comprising, or alternatively consisting essentially of, or yet further consisting of a sequence of SSGGSY (aa 76 to aa 81 of SEQ ID NO: 4 or 5 or 6 or 26);
  (iii) a heavy chain complementarity-determining region 3 (CDRH3) comprising, or alternatively consisting essentially of, or yet further consisting of a sequence of ERHGGDGYWYFDV (aa 121 to aa 133 of SEQ ID NO: 4 or 5 or 6 or 26);
  (iv) a light chain complementarity-determining region 1 (CDRL1) comprising, or alternatively consisting essentially of, or yet further consisting of a sequence of QDISNY (aa 47 to aa 52 of SEQ ID NO: 10 or 11 or 12 or 27);
  (v) a light chain complementarity-determining region 2 (CDRL2) comprising, or alternatively consisting essentially of, or yet further consisting of a sequence of YTS (aa 70 to aa 72 of SEQ ID NO: 10 or 11 or 12 or 27); and
  (vi) a light chain complementarity-determining region 3 (CDRL3) comprising, or alternatively consisting essentially of, or yet further consisting of a sequence of QQGNPLRT (aa 109 to aa 116 of SEQ ID NO: 10 or 11 or 12 or 27).

Embodiment 174

The antibody or a fragment thereof of any one of embodiments 133, 163, or 173, comprising, or alternatively consisting essentially of, or yet further consisting of one or two or three or four or five or all six of the following (i) to (vi):
  (i) a heavy chain complementarity-determining region 1 (CDRH1) comprising, or alternatively consisting essentially of, or yet further consisting of a sequence of GFTFSRYG (aa 50 to aa 57 of SEQ ID NO: 4 or 5 or 6 or 26);
  (ii) a heavy chain complementarity-determining region 2 (CDRH2) comprising, or alternatively consisting essentially of, or yet further consisting of a sequence of ISSGGSYT (aa 75 to aa 82 of SEQ ID NO: 4 or 5 or 6 or 26);
  (iii) a heavy chain complementarity-determining region 3 (CDRH3) comprising, or alternatively consisting essentially of, or yet further consisting of a sequence of ERHGGDGYWYFDV (aa 121 to aa 133 of SEQ ID NO: 4 or 5 or 6 or 26);
  (iv) a light chain complementarity-determining region 1 (CDRL1) comprising, or alternatively consisting essentially of, or yet further consisting of a sequence of QDISNY (aa 47 to aa 52 of SEQ ID NO: 10 or 11 or 12 or 27);
  (v) a light chain complementarity-determining region 2 (CDRL2) comprising, or alternatively consisting essentially of, or yet further consisting of a sequence of YTS (aa 70 to aa 72 of SEQ ID NO: 10 or 11 or 12 or 27); and
  (vi) a light chain complementarity-determining region 3 (CDRL3) comprising, or alternatively consisting essentially of, or yet further consisting of a sequence of QQGNPLRT (aa 109 to aa 116 of SEQ ID NO: 10 or 11 or 12 or 27).

Embodiment 175

The antibody or a fragment thereof of any one of embodiments 133, 163, or 173, comprising, or alternatively consisting essentially of, or yet further consisting of one or two or three or four or five or all six of the following (i) to (vi):
  (i) a heavy chain complementarity-determining region 1 (CDRH1) comprising, or alternatively consisting essentially of, or yet further consisting of a sequence of aASGFTFSRYGMS (aa 47 to aa 59 of SEQ ID NO:26), wherein the small letter a is A (aa 47 to aa 59 of SEQ ID NO: 4 or 5) or wherein the small letter a is T (aa 47 to aa 59 of SEQ ID NO: 6);
  (ii) a heavy chain complementarity-determining region 2 (CDRH2) comprising, or alternatively consisting essentially of, or yet further consisting of a sequence of TISSGGSYTY (aa 74 to aa 83 of SEQ ID NO: 4 or 5 or 6 or 26);
  (iii) a heavy chain complementarity-determining region 3 (CDRH3) comprising, or alternatively consisting essentially of, or yet further consisting of a sequence of ERHGGDGYWYFDV (aa 121 to aa 133 of SEQ ID NO: 4 or 5 or 6 or 26);
  (iv) a light chain complementarity-determining region 1 (CDRL1) comprising, or alternatively consisting essentially of, or yet further consisting of a sequence of RASQDISNYLN (aa 44 to aa 54 of SEQ ID NO: 10 or 11 or 12 or 27);
  (v) a light chain complementarity-determining region 2 (CDRL2) comprising, or alternatively consisting essentially of, or yet further consisting of a sequence of YYTSRLHS (aa 69 to aa 76 of SEQ ID NO: 10 or 11 or 12 or 27); and
  (vi) a light chain complementarity-determining region 3 (CDRL3) comprising, or alternatively consisting essentially of, or yet further consisting of a sequence of QQGNPLRT (aa 109 to aa 116 of SEQ ID NO: 10 or 11 or 12 or 27).

Embodiment 176

The antibody or a fragment thereof of any one of embodiments 133, 163, 173, or 175, comprising, or alternatively consisting essentially of, or yet further consisting of one or two or three or four or five or all six of the following (i) to (vi):
  (i) a heavy chain complementarity-determining region 1 (CDRH1) comprising, or alternatively consisting essentially of, or yet further consisting of a sequence of AASGFTFSRYGMS (aa 47 to aa 59 of SEQ ID NO: 4 or 5);

(ii) a heavy chain complementarity-determining region 2 (CDRH2) comprising, or alternatively consisting essentially of, or yet further consisting of a sequence of TISSGGSYTY (aa 74 to aa 83 of SEQ ID NO: 4 or 5 or 6 or 26);

(iii) a heavy chain complementarity-determining region 3 (CDRH3) comprising, or alternatively consisting essentially of, or yet further consisting of a sequence of ERHGGDGYWYFDV (aa 121 to aa 133 of SEQ ID NO: 4 or 5 or 6 or 26);

(iv) a light chain complementarity-determining region 1 (CDRL1) comprising, or alternatively consisting essentially of, or yet further consisting of a sequence of RASQDISNYLN (aa 44 to aa 54 of SEQ ID NO: 10 or 11 or 12 or 27);

(v) a light chain complementarity-determining region 2 (CDRL2) comprising, or alternatively consisting essentially of, or yet further consisting of a sequence of YYTSRLHS (aa 69 to aa 76 of SEQ ID NO: 10 or 11 or 12 or 27); and (vi) a light chain complementarity-determining region 3 (CDRL3) comprising, or alternatively consisting essentially of, or yet further consisting of a sequence of QQGNPLRT (aa 109 to aa 116 of SEQ ID NO: 10 or 11 or 12 or 27).

Embodiment 177

The antibody or a fragment thereof of any one of embodiments 133, 163, 173, or 175 comprising, or alternatively consisting essentially of, or yet further consisting of one or two or three or four or five or all six of the following (i) to (vi):

(i) a heavy chain complementarity-determining region 1 (CDRH1) comprising, or alternatively consisting essentially of, or yet further consisting of a sequence of TASGFTFSRYGMS (aa 47 to aa 59 of SEQ ID NO: 6);

(ii) a heavy chain complementarity-determining region 2 (CDRH2) comprising, or alternatively consisting essentially of, or yet further consisting of a sequence of TISSGGSYTY (aa 74 to aa 83 of SEQ ID NO: 4 or 5 or 6 or 26);

(iii) a heavy chain complementarity-determining region 3 (CDRH3) comprising, or alternatively consisting essentially of, or yet further consisting of a sequence of ERHGGDGYWYFDV (aa 121 to aa 133 of SEQ ID NO: 4 or 5 or 6 or 26);

(iv) a light chain complementarity-determining region 1 (CDRL1) comprising, or alternatively consisting essentially of, or yet further consisting of a sequence of RASQDISNYLN (aa 44 to aa 54 of SEQ ID NO: 10 or 11 or 12 or 27);

(v) a light chain complementarity-determining region 2 (CDRL2) comprising, or alternatively consisting essentially of, or yet further consisting of a sequence of YYTSRLHS (aa 69 to aa 76 of SEQ ID NO: 10 or 11 or 12 or 27); and (vi) a light chain complementarity-determining region 3 (CDRL3) comprising, or alternatively consisting essentially of, or yet further consisting of a sequence of QQGNPLRT (aa 109 to aa 116 of SEQ ID NO: 10 or 11 or 12 or 27).

Embodiment 178

The antibody or a fragment thereof of any one of embodiments 133, 163, or 173, comprising, or alternatively consisting essentially of, or yet further consisting of one or two or three or four or five or all six of the following (i) to (vi):

(i) a heavy chain complementarity-determining region 1 (CDRH1) comprising, or alternatively consisting essentially of, or yet further consisting of a sequence of GFTFSRY (aa 50 to aa 56 of SEQ ID NO: 4 or 5 or 6 or 26);

(ii) a heavy chain complementarity-determining region 2 (CDRH2) comprising, or alternatively consisting essentially of, or yet further consisting of a sequence of SSGGSY (aa 76 to aa 81 of SEQ ID NO: 4 or 5 or 6 or 26);

(iii) a heavy chain complementarity-determining region 3 (CDRH3) comprising, or alternatively consisting essentially of, or yet further consisting of a sequence of ERHGGDGYWYFDV (aa 121 to aa 133 of SEQ ID NO: 4 or 5 or 6 or 26);

(iv) a light chain complementarity-determining region 1 (CDRL1) comprising, or alternatively consisting essentially of, or yet further consisting of a sequence of RASQDISNYLN (aa 44 to aa 54 of SEQ ID NO: 10 or 11 or 12 or 27);

(v) a light chain complementarity-determining region 2 (CDRL2) comprising, or alternatively consisting essentially of, or yet further consisting of a sequence of YTSRLHS (aa 70 to aa 76 of SEQ ID NO: 10 or 11 or 12 or 27); and (vi) a light chain complementarity-determining region 3 (CDRL3) comprising, or alternatively consisting essentially of, or yet further consisting of a sequence of QQGNPLRT (aa 109 to aa 116 of SEQ ID NO: 10 or 11 or 12 or 27).

Embodiment 179

The antibody or a fragment thereof of any one of embodiments 133 or 163, comprising, or alternatively consisting essentially of, or yet further consisting of one or two or three or four or five or all six of the following (i) to (vi):

(i) a heavy chain complementarity-determining region 1 (CDRH1) comprising, or alternatively consisting essentially of, or yet further consisting of a sequence of GFTFSRYG (aa 50 to aa 57 of SEQ ID NO: 4 or 5 or 6 or 26);

(ii) a heavy chain complementarity-determining region 2 (CDRH2) comprising, or alternatively consisting essentially of, or yet further consisting of a sequence of ISSGGSYT (aa 75 to aa 82 of SEQ ID NO: 4 or 5 or 6 or 26).;

(iii) a heavy chain complementarity-determining region 3 (CDRH3) comprising, or alternatively consisting essentially of, or yet further consisting of a sequence ER (aa 121 to aa 122 of SEQ ID NO: 4 or 5 or 6 or 26);

(iv) a light chain complementarity-determining region 1 (CDRL1) comprising, or alternatively consisting essentially of, or yet further consisting of a sequence of QDISNY (aa 47 to aa 52 of SEQ ID NO: 10 or 11 or 12 or 27);

(v) a light chain complementarity-determining region 2 (CDRL2) comprising, or alternatively consisting essentially of, or yet further consisting of a sequence of YTS (aa 70 to aa 72 of SEQ ID NO: 10 or 11 or 12 or 27); and (vi) a light chain complementarity-determining region 3 (CDRL3) comprising, or alternatively consisting essentially of, or yet further consisting of a sequence of QQ (aa 109 to aa 110 of SEQ ID NO: 10 or 11 or 12 or 27).

Embodiment 180

The antibody or a fragment thereof of any one of embodiments 1-179, wherein the antibody comprises, or alternatively consists essentially of, or yet further consists of:
(i) CDRs 1-3 of a sequence selected from the group of: SEQ ID NOs: 1-6, 13, 24 or 26, or an equivalent of each thereof; and/or
(ii) CDRs 1-3 of a sequence selected from the group of: SEQ ID NOs: 7-12, 14, 25 or 27, or an equivalent of each thereof.

Embodiment 181

The antibody or a fragment thereof of any one of embodiments 1-180, wherein the antibody comprises, or alternatively consists essentially of, or yet further consists of:
(i) CDRs 1-3 of a sequence selected from the group of: SEQ ID NOs: 1-6, 13, 24 or 26; and/or
(ii) CDRs 1-3 of a sequence selected from the group of: SEQ ID NOs: 7-12, 14, 25 or 27.

Embodiment 182

An antibody or a fragment thereof comprising, or alternatively consisting essentially of, or yet further consisting of:
(i) CDRs 1-3 of a sequence selected from the group of: SEQ ID NOs: 1-6, 13, 24 or 26, or an equivalent of each thereof; and/or
(ii) CDRs 1-3 of a sequence selected from the group of: SEQ ID NOs: 7-12, 14, 25 or 27, or an equivalent of each thereof,
optionally wherein the antibody or fragment thereof comprises, or alternatively consists essentially of, or yet further consists of a light chain and a heavy chain, further optionally wherein the light chain is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identical to an amino acid sequence of any one or more of SEQ ID NOs: 7-12, 14, 25 or 27 or optionally a SEQ ID NO selected therefrom whose sequence comprises one or two or three CDR(s) of the antibody or a fragment thereof, and further optionally wherein the heavy chain is at least about 80%, or at least about 85%, or at least about 90%, or at least about 91%, or at least about 92%, or at least about 93%, or at least about 94%, or at least about 95%, or at least about 96%, or at least about 97%, or at least about 98%, or at least about 99% identical to an amino acid sequence of any one or more of SEQ ID NOs: 7-12, 14, 25 or 27 or optionally a SEQ ID NO selected therefrom whose sequence comprises one or two or three CDR(s) of the antibody or a fragment thereof.

Embodiment 183

The antibody or a fragment thereof of any one of embodiments 1-182, wherein the antibody is selected from the group of: a bispecific antibody, a trispecific antibody, a tetraspecific antibody, or a pentaspecific antibody.

Embodiment 184

The antibody or a fragment thereof of any one of embodiments 1-183, wherein the antibody is selected from the group of an IgA, an IgD, an IgE, an IgG, or an IgM antibody.

Embodiment 185

The antibody or a fragment thereof of any one of embodiments 1-184, wherein the antibody further comprises a constant region selected from the group of: an IgA constant region, an IgD constant region, an IgE constant region, an IgG constant region or an IgM constant region.

Embodiment 186

The antibody or a fragment thereof of embodiment 185, wherein the constant region is an IgG1 constant region.

Embodiment 187

The antibody or a fragment thereof of any one of embodiments 1-185, wherein the antibody further comprises a heavy chain (HC) constant region of SEQ ID NOs: 1-6, 13, 24 or 26, and/or a light chain (LC) constant region of SEQ ID NOs: 7-12, 14, 25 or 27.

Embodiment 188

The antibody or a fragment thereof of embodiment 187, wherein the HC constant region comprises, or alternatively consists essentially of, or yet further consists of a constant region of SEQ ID NOs: 1-6, 13, 24 or 26 (optionally a sequence selected from aa 145 to aa 473 of SEQ ID NOs: 1-6, 13, 24 or 26), or wherein the HC constant regions comprises, or alternatively consists essentially of, or yet further consists of a constant region of any one of SEQ ID NOs: 15-22.

Embodiment 189

The antibody or a fragment thereof of embodiment 187 or 188, wherein the LC constant region comprises, or alternatively consists essentially of, or yet further consists of a constant region of SEQ ID NOs: 7-12 or 27 (optionally a sequence selected from aa 133 to aa 239 of SEQ ID NOs: 7-9, 14 or 25, and/or aa 127 to aa 233 of SEQ ID NOs: 10-12 or 27), or wherein the LC constant regions comprises, or alternatively consists essentially of, or yet further consists of a constant region of SEQ ID NOs: 23.

Embodiment 190

An antibody or a fragment thereof that competes for binding to an epitope with an antibody or a fragment thereof of any one of embodiments 1-189.

Embodiment 191

An antibody or a fragment thereof that competes for binding to a tip chimeric peptide IhfA5-mIhfB4$_{NTHI}$ with an antibody or a fragment thereof of any one of embodiments 1-24, 34-57, 67-90, 100-123, 133-162 and 180-189.

Embodiment 192

The antibody or a fragment thereof of embodiment 191, wherein the tip chimeric peptide IhfA5-mIhfB4$_{NTHI}$ comprises, or alternatively consists essentially of, or yet further consists of RPGRNPX1TGDVVPVSARRVV-X-FSLHHRQPRLGRNPX1TGDSV (SEQ ID NO: 38), wherein "X" is an optional amino acid linker sequence, optionally comprising, or consisting essentially of, or yet further consisting of between 1 to 20 amino acids, and wherein "X1" is any amino acid or alternatively "X1" is selected from the amino acids Q, R, K, S, or T.

Embodiment 193

The antibody or a fragment thereof of embodiment 191 or 192, wherein the tip chimeric peptide IhfA5-mIhfB4$_{NTHI}$ comprises, or alternatively consists essentially of, or yet further consists of RPGRNPKTGDVVPVSARRVV-X-FSLHHRQPRLGRNPKTGDSV (SEQ ID NO: 39), wherein "X" is an optional amino acid linker sequence, optionally comprising, or consisting essentially of, or yet further consisting of between 1 to 20 amino acids.

Embodiment 194

The antibody or a fragment thereof of any one of embodiments 191-193, wherein the tip chimeric peptide IhfA5-mIhfB4$_{NTHI}$ comprises, or alternatively consists essentially of, or yet further consists of RPGRNPKTGDVVPVSARRVVGPSLFSLHHRQPRL-GRNPKTGDSV (SEQ ID NO: 40).

Embodiment 195

An antibody or a fragment thereof that competes for binding to a tail chimeric peptide IhfA3-IhfB2$_{NTHI}$ with an antibody or a fragment thereof of any one of embodiments 1, 3-15, 25-34, 36-47, 58-67, 69-81, 91-100, 102-114, 124-133, and 163-189

Embodiment 196

The antibody or a fragment thereof of embodiment 195, wherein the tail chimeric peptide IhfA3-IhfB2$_{NTHI}$ comprises, or alternatively consists essentially of, or yet further consists of FLEEIRLSLESGQDVKLSGF-X-TL-SAKEIENMVKDILEFISQ (SEQ ID NO: 41), wherein "X" is an optional amino acid linker sequence, optionally comprising, or consisting essentially of, or yet further consisting of between 1 to 20 amino acids, and/or wherein the tail-chimeric peptide IhfA3-IhfB2$_{NTHI}$ comprises, or consists essentially of, or yet further consists of FLEE-IRLSLESGQDVKLSGFGPSLTLSAKEIENMVKDILE-FISQ (SEQ ID NO: 50).

Embodiment 197

The antibody or a fragment thereof of any one of embodiments 192, 193, or 196, wherein the amino acid linker is selected from the group of: GGSGGS (SEQ ID NO: 42), GPSLKL (SEQ ID NO: 43), GGG (SEQ ID NO: 44), GPSL (SEQ ID NO: 45), GPS (SEQ ID NO: 46), PSLK (SEQ ID NO: 47), GPSLK (SEQ ID NO: 48), or SLKL (SEQ ID NO: 49).

Embodiment 198

The antibody or a fragment thereof of any one of embodiments 190-197, wherein the antibody is a polyclonal, a monoclonal or a humanized antibody.

Embodiment 199

An antigen binding fragment of the antibody of any one of embodiments 1-198.

Embodiment 200

The antigen binding fragment of embodiment 199, wherein the antigen binding fragment is selected from the group of Fab, F(ab')$_2$, Fab', scFv, or Fv.

Embodiment 201

The antibody or a fragment thereof of any one of embodiments 1-33, 67-132, or 180-198 or an antigen binding fragment of embodiment 199 or 200, wherein an equivalent to an amino acid sequence comprises a polypeptide having at least 80% amino acid identity to the amino acid sequence, and/or wherein an equivalent to the amino acid sequence comprises a polypeptide that is encoded by a polynucleotide that hybridizes under conditions of high stringency to the complement of the polynucleotide encoding the amino acid sequence.

Embodiment 202

The antibody or a fragment thereof of any one of embodiments 1-33, 67-132, or 180-198 or an antigen binding fragment of embodiment 199 or 200, wherein an equivalent to an amino acid sequence comprises a polypeptide having at least 90% amino acid identity to the amino acid sequence, and/or wherein an equivalent to the amino acid sequence comprises a polypeptide that is encoded by a polynucleotide that hybridizes under conditions of high stringency to the complement of the polynucleotide encoding the amino acid sequence.

Embodiment 203

The antibody or a fragment thereof of any one of embodiments 1-33, 67-132, or 180-198 or an antigen binding fragment of embodiment 199 or 200, wherein an equivalent to an amino acid sequence comprises a polypeptide having at least 95% amino acid identity to the amino acid sequence, and/or wherein an equivalent to the amino acid sequence comprises a polypeptide that is encoded by a polynucleotide that hybridizes under conditions of high stringency to the complement of the polynucleotide encoding the amino acid sequence.

Embodiment 204

The antibody or a fragment thereof of any one of embodiments 1-33, 67-132, or 180-198 or an antigen binding fragment of embodiment 199 or 200, wherein an equivalent to an amino acid sequence comprises a polypeptide having at least 96% amino acid identity to the amino acid sequence, and/or wherein an equivalent to the amino acid sequence comprises a polypeptide that is encoded by a polynucleotide that hybridizes under conditions of high stringency to the complement of the polynucleotide encoding the amino acid sequence.

Embodiment 205

The antibody or a fragment thereof of any one of embodiments 1-33, 67-132, or 180-198 or an antigen binding fragment of embodiment 199 or 200, wherein an equivalent to an amino acid sequence comprises a polypeptide having at least 97% amino acid identity to the amino acid sequence, and/or wherein an equivalent to the amino acid sequence comprises a polypeptide that is encoded by a polynucleotide that hybridizes under conditions of high stringency to the complement of the polynucleotide encoding the amino acid sequence.

Embodiment 206

The antibody or a fragment thereof of any one of embodiments 1-33, 67-132, or 180-198 or an antigen binding fragment of embodiment 199 or 200, wherein an equivalent to an amino acid sequence comprises a polypeptide having at least 98% amino acid identity to the amino acid sequence, and/or wherein an equivalent to the amino acid sequence comprises a polypeptide that is encoded by a polynucleotide that hybridizes under conditions of high stringency to the complement of the polynucleotide encoding the amino acid sequence.

Embodiment 207

The antibody or a fragment thereof of any one of embodiments 1-33, 67-132, or 180-198 or an antigen binding fragment of embodiment 199 or 200, wherein an equivalent to an amino acid sequence comprises a polypeptide having at least 99% amino acid identity to the amino acid sequence, and/or wherein an equivalent to the amino acid sequence comprises a polypeptide that is encoded by a polynucleotide that hybridizes under conditions of high stringency to the complement of the polynucleotide encoding the amino acid sequence.

Embodiment 208

The antibody or a fragment thereof of any one of embodiments 1-198 and 201-207 or the antigen binding fragment of any one of embodiments 199-207, wherein the antibody or fragment thereof is modified, and optionally wherein the modification is selected from the group of PEGylation, a PEG mimetic, polysialyation, HESylation or glycosylation.

Embodiment 209

The antibody or a fragment thereof of any one of embodiments 1-198 and 201-208 or the antigen binding fragment of any one of embodiments 199-208, further comprising a detectable marker or a purification marker.

Embodiment 210

A complementarity-determining region (CDR) of the antibody or a fragment thereof of any one of embodiments 1-198 and 201-209 or the antigen binding fragment of any one of embodiments 199-209.

Embodiment 211

The CDR of embodiment 210, wherein the CDR is selected from the group consisting of CDR1, CDR2 or CDR3.

Embodiment 212

A complementarity-determining region (CDR) comprises, or alternatively consists essentially of, or yet further consists of any one or more of the following:

(i) A complementarity-determining region (CDR) a heavy chain complementarity-determining region 1 (CDRH1) comprising, or alternatively consisting essentially of, or yet further consisting of a sequence selected from the group of: GFTFXXY (amino acid (aa) 50 to aa 56 of SEQ ID NO: 13), GFTFRTY (aa 50 to aa 56 of SEQ ID NO: 1 or 2 or 3 or 24), or GFTFSRY (aa 50 to aa 56 of SEQ ID NO: 4 or 5 or 6 or 26), wherein X is any amino acid or an amino acid at the aligned aa position of a sequence selected from SEQ ID NOs: 1-6; GFTFRTYA (aa 50 to aa 57 of SEQ ID NO: 1 or 2 or 3 or 24); aASGFTFRTYAMS (aa 47 to aa 59 of SEQ ID NO: 24), wherein the small letter a is A (aa 47 to aa 59 of SEQ ID NO: 1 or 2) or wherein the small letter a is K (aa 47 to aa 59 of SEQ ID NO: 3); GFTFSRYG (aa 50 to aa 57 of SEQ ID NO: 4 or 5 or 6 or 26); or aASGFTFSRYGMS (aa 47 to aa 59 of SEQ ID NO:26), wherein the small letter a is A (aa 47 to aa 59 of SEQ ID NO: 4 or 5) or wherein the small letter a is T (aa 47 to aa 59 of SEQ ID NO: 6);

(ii) a heavy chain complementarity-determining region 2 (CDRH2) comprising, or alternatively consisting essentially of, or yet further consisting of a sequence selected from the group of: XSXXXX (amino acid (aa) 76 to aa 81 of SEQ ID NO: 13), GSDRRH (aa 76 to aa 81 of SEQ ID NO: 1 or 2 or 3 or 24), or SSGGSY (aa 76 to aa 81 of SEQ ID NO: 4 or 5 or 6 or 26), wherein X is any amino acid or an amino acid at the aligned aa position of a sequence selected from SEQ ID NOs: 1-6; IGSDRRHT (aa 75 to aa 82 of SEQ ID NO: 1 or 2 or 3 or 24); IGSDRRHTY (aa 75 to aa 83 of SEQ ID NO: 1 or 2 or 3 or 24); TIGSDRRHTY (aa 74 to aa 83 of SEQ ID NO: 1 or 2 or 3 or 24); WVATIGSDR-RHTYYP (aa 71 to aa 85 of SEQ ID NO: 1 or 2 or 3 or 24); ISSGGSYT (aa 75 to aa 82 of SEQ ID NO: 4 or 5 or 6 or 26); or TISSGGSYTY (aa 74 to aa 83 of SEQ ID NO: 4 or 5 or 6 or 26);

(iii) a heavy chain complementarity-determining region 3 (CDRH3) comprising, or alternatively consisting essentially of, or yet further consisting of a sequence selected from the group of: XXXXXXXXYXXFDX (amino acid (aa) 121 to aa 133 of SEQ ID NO: 13), VGPYDGYYGEFDY (aa 121 to aa 133 of SEQ ID NO: 1 or 2 or 3 or 24), or ERHGGDGYWYFDV (aa 121 to aa 133 of SEQ ID NO: 4 or 5 or 6 or 26), wherein X is any amino acid or an amino acid at the aligned aa position of a sequence selected from SEQ ID NOs: 1-6; VGPYDGYYGEFDY (aa 121 to aa 133 of SEQ ID NO: 1 or 2 or 3 or 24); or ER (aa 121 to aa 122 of SEQ ID NO: 4 or 5 or 6 or 26);

(iv) a light chain complementarity-determining region 1 (CDRL1) comprising, or alternatively consisting essentially of, or yet further consisting of a sequence selected from the group of: QXXXXXXXXXX (aa 47 to aa 57 of SEQ ID NO: 14), QXXXXX (aa 47 to aa 52 of SEQ ID NO: 14), QSLLDSDGKTF (aa 47 to aa 57 of SEQ ID NO: 7 or 8 or 9 or 25), or QDISNY (aa 47 to aa 52 of SEQ ID NO: 10 or 11 or 12 or 27), wherein X is any amino acid or an amino acid at the aligned aa position of a sequence selected from SEQ ID NOs: 7-12; rSSQSLLDSDGKTFLN (aa 44 to aa 59 of SEQ ID NO: 25), wherein the smaller letter r is R (aa 44 to aa 59 of SEQ ID NO: 7 or 8) or wherein the smaller letter r is K (aa 44 to aa 59 of SEQ ID NO: 9); or RASQDIS-NYLN (aa 44 to aa 54 of SEQ ID NO: 10 or 11 or 12 or 27);

(v) a light chain complementarity-determining region 2 (CDRL2) comprising, or alternatively consisting essentially of, or yet further consisting of a sequence selected from the group of: XXS (aa 75 to aa 77 of SEQ ID NO: 14), LVS (aa 75 to aa 77 of SEQ ID NO: 7 or 8 or 9 or 25), or YTS (aa 70 to aa 72 of SEQ ID NO: 10 or 11 or 12 or 27), wherein X is any amino acid or an amino acid at the aligned aa position of a sequence selected from SEQ ID NOs: 7-12; LVSK1DS (aa 75 to aa 81 of SEQ ID NO: 25), wherein the smaller letter 1 is L (aa 75 to aa 81 of SEQ ID NO: 7 or 9) or wherein the smaller letter 1 is R (aa 75 to aa 81 of SEQ ID NO: 8); YLVSK1DS (aa 74 to aa 81 of SEQ ID NO: 25), wherein the smaller letter 1 is L (aa 74 to aa 81 of SEQ ID NO: 7 or 9) or wherein the smaller letter 1 is R (aa 74 to aa 81 of SEQ ID NO: 8); LVSK1DSG (aa 75 to aa 82 of SEQ ID NO: 25), wherein the smaller letter 1 is L (aa 75 to aa 82 of SEQ ID NO: 7 or 9) or wherein the smaller letter 1 is R (aa 75 to aa 82 of SEQ ID NO: 8); YLVSK1DSGV (aa 74 to aa 83 of SEQ ID NO: 25), wherein the smaller letter 1 is L (aa 74 to aa 83 of SEQ ID NO: 7 or 9) or wherein the smaller letter 1 is R (aa 74 to aa 83 of SEQ ID NO: 8); RLIYLVSK1DSGVPD (aa 71 to aa 85 of SEQ ID NO: 25), wherein the smaller letter 1 is L (aa 71 to aa 85 of SEQ ID NO: 7 or 9) or wherein the smaller letter 1 is R (aa 71 to aa 85 of SEQ ID NO: 8); YTSRLHS (aa 70 to aa 76 of SEQ ID NO: 10 or 11 or 12 or 27); or YYTSRLHS (aa 69 to aa 76 of SEQ ID NO: 10 or 11 or 12 or 27); and (vi) a light chain complementarity-determining region 3 (CDRL3) comprising, or alternatively consisting essentially of, or yet further consisting of a sequence selected from the group of: XQGXXXXXT (aa 114 to aa 122 of SEQ ID NO: 14), WQGTHFPYT (aa 114 to aa 122 of SEQ ID NO: 7 or 8 or 9 or 25), or QQGNPLRT (aa 109 to aa 116 of SEQ ID NO: 10 or 11 or 12 or 27), wherein X is any amino acid or an amino acid at the aligned aa position of a sequence selected from SEQ ID NOs: 7-12; WQGTHFP (aa 114 to aa 120 of SEQ ID NO: 7 or 8 or 9 or 25); WQGTHFPY (aa 114 to aa 121 of SEQ ID NO: 7 or 8 or 9 or 25); WQGTHFPYT (aa 114 to aa 122 of SEQ ID NO: 7 or 8 or 9 or 25); QQ (aa 109 to aa 110 of SEQ ID NO: 10 or 11 or 12 or 27).

Embodiment 213

An isolated polypeptide comprising an amino acid sequence selected from the group of SEQ ID NOs: 1-14 or 24-27, or an equivalent of each thereof.

Embodiment 214

The isolated polypeptide of embodiment 213, wherein the polypeptide further comprises a detectable or purification marker.

Embodiment 215

An isolated polynucleotide encoding the antibody or a fragment thereof of any one of embodiments 1-198 and 201-209, the antigen binding fragment of any one of embodiments 199-209, the CDR of any one of embodiment 210-212, and the isolated polypeptide of embodiment 213 or 214, or an equivalent of each thereof, and optionally operatively linked to a promoter and enhancer element.

Embodiment 216

The isolated polynucleotide sequence of embodiment 215, further comprising a signal peptide coding polynucleotide sequence located upstream of the variable domain, chain, or CDR.

Embodiment 217

The antibody or a fragment thereof of any one of embodiments 1-198 and 201-209, the antigen binding fragment of any one of embodiments 199-209, the CDR of any one of embodiment 210-212, and the isolated polypeptide of embodiment 213 or 214, further comprising a signal peptide located upstream of the variable domain, chains, or CDRs.

Embodiment 218

A vector comprising an isolated polynucleotide of embodiment 215 or 216.

Embodiment 219

The vector of embodiment 218, wherein the vector is a plasmid or a viral vector.

Embodiment 220

The vector of embodiment 219, wherein the viral vector is selected from a group consisting of a retroviral vector, a lentiviral vector, an adenoviral vector, and an adeno-associated viral vector.

Embodiment 221

A host cell comprising the polynucleotide of embodiment 215 or 216, or the vector of any one of embodiments 218-220.

Embodiment 222

A composition comprising a carrier and one or more of: an antibody or a fragment thereof of any of embodiments 1-198, 201-209 and 217, an antigen binding fragment of any one of embodiments 199-209 and 217, a CDR of any one of embodiments 210-212 and 217, an isolated polypeptide of embodiment 213 or 214, an isolated polynucleotide of embodiment 215 or 216, a vector of any one of embodiments 218-220, or a host cell of embodiment 221.

Embodiment 223

A method of producing an antibody or a fragment thereof of any one of embodiments 1-198, 201-209 and 217, comprising culturing a host cell comprising a polynucleotide encoding the antibody or fragment under conditions for expression of the antibody or fragment, and optionally isolating the antibody or fragment thereof.

Embodiment 224

The method of embodiment 223, wherein the host cell is a mammalian cell.

Embodiment 225

A method for inhibiting or competing with the binding of a DNABII polypeptide or protein to a microbial DNA, comprising contacting the DNABII polypeptide or protein with an antibody or a fragment thereof of any one of embodiments 1-24, 34-57, 67-90, 100-123, 133-162 and 180-198, 201-209 and 217, wherein the antibody or fragment thereof binds a tip region of a DNABII peptide.

Embodiment 226

A method to disrupt a biofilm, comprising contacting the biofilm with an antibody or a fragment thereof of any one of embodiments 1-24, 34-57, 67-90, 100-123, 133-162 and 180-198, 201-209 and 217, wherein the antibody or fragment thereof binds a tip region of a DNABII peptide.

Embodiment 227

A method to prevent formation of or to disrupt a biofilm on a surface comprising treating the surface susceptible to or containing a biofilm with an antibody or a fragment thereof of any one of embodiments 1-24, 34-57, 67-90, 100-123, 133-162 and 180-198, 201-209 and 217, wherein the antibody or fragment thereof binds a tip region of a DNABII peptide.

Embodiment 228

A method to prevent or disrupt a biofilm in a subject, comprising administering to the subject an antibody or a fragment thereof of any one of embodiments 1-24, 34-57, 67-90, 100-123, 133-162 and 180-198, 201-209 and 217, wherein the antibody or fragment thereof binds to a tip region of a DNABII peptide.

Embodiment 229

A method for inhibiting, preventing or treating a microbial infection that produces a biofilm in a subject, comprising administering to the subject an antibody or a fragment thereof of any one of embodiments 1-24, 34-57, 67-90, 100-123, 133-162 and 180-198, 201-209 and 217, wherein the antibody or fragment thereof binds to a tip region of a DNABII peptide.

Embodiment 230

A method to treat a condition characterized by the formation of a biofilm in a subject, comprising administering to the subject an antibody or a fragment thereof of any of embodiments 1-24, 34-57, 67-90, 100-123, 133-162 and 180-198, 201-209 and 217, wherein the antibody or fragment thereof binds to a tip region of a DNABII peptide.

Embodiment 231

The method of any one of embodiments 228 to 230, wherein the antibody or a fragment thereof reduce one or more of pro-inflammatory cytokines and increase one or more of anti-inflammatory cytokines in the subject.

Embodiment 232

The method of embodiment 230 or 231, wherein the condition is selected from the group consisting of: chronic non-healing wounds, *Burkholderia*, venous ulcers, diabetic foot ulcers, ear infections, sinus infections, urinary tract infections, gastrointestinal tract ailments, pulmonary infections, respiratory tract infections, cystic fibrosis, chronic obstructive pulmonary disease, catheter-associated infections, indwelling devices associated infections, infections associated with implanted prostheses, osteomyelitis, cellulitis, abscesses, and periodontal disease.

Embodiment 233

The method of any one of embodiments 225 to 232, further comprising detecting a biofilm by contacting an antibody that binds a DNABII polypeptide or an antigen binding fragment of the antibody with a sample suspected of containing a biofilm, and detecting the binding of the biofilm and the antibody or fragment thereof.

Embodiment 234

A method to detect a biofilm in a subject, comprising administering to the subject an antibody or a fragment thereof of any one of embodiments 1-198, 201-209 and 217, and detecting binding of the antibody or the fragment to the biofilm.

Embodiment 235

A method for detecting a microbial infection that produces a biofilm in a subject, comprising contacting an antibody or a fragment thereof of any one of embodiments 1-198, 201-209 and 217 with a biological sample suspected of comprising the biofilm and isolated from the subject and detecting the binding of the antibody or the fragment thereof to any biofilm in the sample.

Embodiment 236

A method for screening subjects having a biofilm, comprising contacting an antibody or a fragment thereof of any one of embodiments 1-198, 201-209 and 217 with a biological sample comprising the biofilm and isolated from the subject, and detecting the binding of the antibody or fragment thereof to any biofilm in the sample.

Embodiment 237

A method for conferring passive immunity in a subject, comprising administering to the subject an antibody or a fragment thereof of any one of embodiments 1-24, 34-57, 67-90, 100-123, 133-162 and 180-198, 201-209 and 217 that binds to a tip region of a DNABII peptide.

Embodiment 238

The method of any one of embodiments 225-237, wherein the biofilm is derived from a gram negative or a gram positive biofilm producing bacteria.

Embodiment 239

The method of any one of embodiments 225-238, wherein the biofilm comprises a DNABII protein.

Embodiment 240

The method of embodiment 239, wherein the biofilm comprises a histone-like protein from *E. coli* strain U93 (HU) or an integration host factor (IHF) binding protein.

Embodiment 241

A method to prepare an interfering nucleic acid comprising preparing a nucleic acid consisting of about 10-20 nucleotides that specifically binds a binding partner to an antibody or a fragment thereof of any of embodiments 1-198, 201-209 and 217, and optionally isolating the interfering nucleic acid prepared.

Embodiment 242

A non-physiological surface coated with an antibody or a fragment thereof of any of embodiments 1-198, 201-209 and 217; and optionally, wherein the surface is in an industrial setting.

Embodiment 243

A method to obtain antisera effective to disrupt a biofilm comprising immunizing a subject with a small molecule, and recovering antiserum from the subject, and optionally isolating polyclonal antiserum or monoclonal antibodies from the subject.

Embodiment 244

An antibody fragment of any one of embodiments 1-24, 34-57, 67-90, 100-123, 133-162 and 180-198, 201-209 and 217, wherein the fragment is selected from the group of Fab, F(ab')₂, Fab', scFv, or Fv, and wherein the antibody fragment specifically binds the tip region of a DNABII peptide.

Embodiment 245

The antibody or a fragment thereof of embodiment 244 or the method of any one of embodiments 225-230 and 70-74, wherein the DNABII peptide is an IHF peptide.

Embodiment 246

A composition comprising an antibody fragment of embodiment 244 or 245 and a pharmaceutical acceptable carrier.

Embodiment 247

A non-physiological surface coated with an antibody fragment of embodiment 244 or 245, and optionally, wherein the surface is in an industrial setting.

Embodiment 248

A kit comprising one or more of: an antibody or a fragment thereof of any one of embodiments 1-198, 201-209, 217, 244 and 245, an antigen binding fragment of any one of embodiments 199-209, a CDR of any one of embodiments 210-212 and 217, an isolated polypeptide of embodiment 213 or 214, a polynucleotide of embodiment 215 or 216, a vector of any one of embodiments 218-220, the host cell of embodiment 221, or the composition of embodiment 222 or 246; and optionally instructions for use.

```
SEQUENCE LISTING
SEQ ID NO: 1 (H10210 (1F8.F1 Humanized HC1))
Bold font indicates an exemplified variable region
while the bold, italic and underlined font
indicates exemplified CDRs.
MDPKGSLSWRILLFLSLAFELSYGEVKLVESGGGLVQPGGSLRLSCAAS*GFTFRTYAM*

SWVRQAPGKGLEWVAT*IGSDRRHT*YYPDSVKGRFTISRDNAKNTLYLQMNSLRAE

DTAVYYC*VGPYDGYYGEFDY*WGQGTLVTVSSASTKGPSVFPLAPSSKSTSGGTAALGCL

VKDYFPEPVTVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYT

QKSLSLSPG**

SEQ ID NO: 2 (H10211 (1F8.F1 Humanized HC2))
Bold font indicates an exemplified variable region
while the bold, italic and underlined font
indicates exemplified CDRs.
MDPKGSLSWRILLFLSLAFELSYGEVQLVESGGGLVQPGGSLRLSCAAS*GFTFRTYA*M

SWVRQAPGKGLEWVAT*IGSDRRHT*YYPDSVKGRFTISRDNSKNTLYLQMNSLRAE

DTAVYYC*VGPYDGYYGEFDY*YWGQGTLVTVSSASTKGPSVFPLAPSSKSTSGGTAALGC

LVKDYFPEPVTVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYT

QKSLSLSPG**
```

-continued

SEQ ID NO: 3 (H10212 (1F8.F1 Humanized HC3))
Bold font indicates an exemplified variable region
while the bold, italic and underlined font
indicates exemplified CDRs.
MDPKGSLSWRILLFLSLAFELSYG**EVKLVQSGAEVKKPGASVKVSCKAS*GFTFRTYA***

**MSWVRQAPGQRLEWVAT*IGSDRRHT*YYPDKFQGRVTITRDNAKNTLYMELSSLRS**

**EDTAVYYC*VGPYDGYYGEFDY*YWGQGTLVTVSS**ASTKGPSVFPLAPSSKSTSGGTAAL

GCLVKDYFPEPVTVSWNSGALTSGVHTFPAVLQSSGLYSLSSVVTVPSSSLGTQTYICN

HVNKPSNTKVDKKVEPKSCDKTHTCPPCPAPELLGGPSVFLFPPKPKDTLMISRTPEVT

VCVVVDVSHEDPEVKFNWYVDGVEVHNAKTKPREEQYNSTYRVVSVLTVLHQDWLNGKEY

KCKVSNKALPAPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVMHEALHNHYT

QKSLSLSPG**

SEQ ID NO: 4 (H10213 (11E7.C7 Humanized HC1))
Bold font indicates an exemplified variable region
while the bold, italic and underlined font
indicates exemplified CDRs.
MDPKGSLSWRILLFLSLAFELSYG**EVQLVESGGGLVKPGGSLRLSCAAS*GFTFSRYG***M

**SWVRQAPGKGLEWVAT*ISSGGSYT*YYTDSVKGRFTISRDNAKNSLYLQMNSLRAED**

**TAVYYC*ERHGGDGYWYFDV*WGQGTMVTVSS**ASTKGPSVFPLAPSSKSTSGGTAALGC

LVKDYFPEPVTVSWNSGALTSGVHTFPAVLQSSGLYSLSSVVTVPSSSLGTQTYICNV

NHKPSNTKVDKKVEPKSCDKTHTCPPCPAPELLGGPSVFLFPPKPKDTLMISRTPEVT

CVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCSVMHEALHN

HYTQKSLSLSPG**

SEQ ID NO: 5 (H10214 (11E7.C7 Humanized HC2))
Bold font indicates an exemplified variable region
while the bold, italic and underlined font
indicates exemplified CDRs.
MDPKGSLSWRILLFLSLAFELSYG**EVQLVESGGGLVKPGGSLRLSCAAS*GFTFSRYG***M

**SWVRQAPGKGLEWVST*ISSGGSYT*YYTDSVKGRFTISRDNAKNSLYLQMNSLRAED**

**TAVYYC*ERHGGDGYWYFDV*WGQGTMVTVSS**ASTKGPSVFPLAPSSKSTSGGTAALGCL

VKDYFPEPVTVSWNSGALTSGVHTFPAVLQSSGLYSLSSVVTVPSSSLGTQTYICNVNH

KPSNTKVDKKVEPKSCDKTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVKGFYPSDIAV

EWESNGQPENNYKTTPPVLDSDGSFFLYSKLTVDKSRWQQGNVFSCSVMHEALHNHYT

QKSLSLSPG**

SEQ ID NO: 6 (H10215 (11E7.C7 Humanized HC3))
Bold font indicates an exemplified variable region
while the bold, italic and underlined font
indicates exemplified CDRs.
MDPKGSLSWRILLFLSLAFELSYG**EVQLVESGGGLVQPGRSLRLSCTAS*GFTFSRYG***M

**SWVRQAPGKGLEWVAT*ISSGGSYT*YYTDSVKGRFTISRDNAKNILYLQMNSLKTEDTA**

**VYYC*ERHGGDGYWYFDV*WGQGTMVTVSS**ASTKGPSVFPLAPSSKSTSGGTAALGCLVK

DYFPEPVTVSWNSGALTSGVHTFPAVLQSSGLYSLSSVVTVPSSSLGTQTYICNVNHKP

SNTKVDKKVEPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFYPSDIAVE

WESNGQPENNYKTTPPVLDSDGSFFLYSKLTVDKSRWQQGNVFSCSVMHEALHNHYT

QKSLSLSPG**

SEQ ID NO: 7 (L10210 (1F8.F1 Humanized LC1))
Bold font indicates an exemplified variable region
while the bold, italic and underlined font
indicates exemplified CDRs.
METDTLLLWVLLLWVPGSTGD**VVMTQSPLSLPVTLGQPASISCRSS*QSLLDSDGKTF*L**

**NWLQQRPGQSPRRLIY*LVS*KLDSGVPDRFSGSGSGTDFTLKISRVEAEDVGVYYC*W***

***QGTHFPYT*FGQGTKLEIK**RTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSP

VTKSFNRGEC*

SEQ ID NO: 8 (L10211 (1F8.F1 Humanized LC2))
Bold font indicates an exemplified variable region
while the bold, italic and underlined font
indicates exemplified CDRs.
METDTLLLWVLLLWVPGSTGD**VVMTQSPLSLPVTLGQPASISCRSS*QSLLDSDGKTF*L**

**NWLQQRPGQSPRRLIY*LVS*KRDSGVPDRFSGSGSGTDFTLKISRVEAEDVGVYYC*W***

***QGTHFPYT*FGQGTKLEIK**RTVAAPSVFIFPPSDEQLKSGTASVVCLLNNFYPREAKV

QWKVDNALQSGNSQESVTEQDSKDSTYSLSSTLTLSKADYEKHKVYACEVTHQGLSSP

VTKSFNRGEC*

SEQ ID NO: 9 (L10212 (1F8.F1 Humanized LC3))
Bold font indicates an exemplified variable region
while the bold, italic and underlined font
indicates exemplified CDRs.
METDTLLLWVLLLWVPGSTGD**VVMTQSPDSLAVSLGERATINCKSS*QSLLDSDGKTF***

**LNWLQQKPGQPPKRLIY*LVS*KLDSGVPDRFSGSGSGTDFTLTISSLQAEDVAVYYC**

***WQGTHFPYT*FGQGTKLEIK**RTVAAPSVFIFPPSDEQLKSGTASVVCLLNNFYPREA

KVQWKVDNALQSGNSQESVTEQDSKDSTYSLSSTLTLSKADYEKHKVYACEVTHQGL

SSPVTKSFNRGEC*

SEQ ID NO: 10 (L10213 (11E7.C7 Humanized LC1))
Bold font indicates an exemplified variable region
while the bold, italic and underlined font
indicates exemplified CDRs.
METDTLLLWVLLLWVPGSTGD**IQMTQSPSSLSASVGDRVTITCRAS*QDISNY*LNWYQ**

**QKPGKAVKLLIY*YTS*RLHSGVPSRFSGSGSGTDYTLTISSLQPEDFATYFC*QQGNPLR***

TFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRG

EC*

SEQ ID NO: 11 (L10214 (11E7.C7 Humanized LC2))
Bold font indicates an exemplified variable region
while the bold, italic and underlined font
indicates exemplified CDRs.
METDTLLLWVLLLWVPGSTGD**IQMTQSPSSLSASVGDRVTITCRAS*QDISNY*LNWYQ**

**QKPGKAVKLLIY*YTS*RLHSGVPSRFSGSGSGTDYTLTISSLQPEDFATYYC*QQGNPLR***

***T*FGGGTKVEIK**RTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRG

EC*

-continued

SEQ ID NO: 12 (L10215 (11E7.C7 Humanized LC3))
Bold font indicates an exemplified variable region
while the bold, italic and underlined font
indicates exemplified CDRs.
METDTLLLWVLLLWVPGSTG**DIVMTQSPATLSLSPGERATLSCRAS*QDISNY*LNWYQ**

**QKPGQAVRLLIY*YTSR*LHSGIPARFSGSGSGTDYTLTISSLEPEDFAVYFC*QQGNPLR***

***T*FGGGTKVEIK**RTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGE

C*

SEQ ID NO: 13 (Heavy Chain Consensus Sequence)
MDPKGSLSWR ILLFLSLAFE LSYGEVqLVe SGgglvXPGg SlrlSCaASG  50

FTFXXYXMSW VRQAPGkgLE WVaTIXSXXX XTYYXDsvkG RfTIsRDNaK 100

NtLYlqmnSL raEDTAVYYC XXXXXXXXYXX FDXWGQGTXV TVSSASTKGP 150

SVFPLAPSSK STSGGTAALG CLVKDYFPEP VTVSWNSGAL TSGVHTFPAV 200

LQSSGLYSLS SVVTVPSSSL GTQTYICNVN HKPSNTKVDK KVEPKSCDKT 250

HTCPPCPAPE LLGGPSVFLF PPKPKDTLMI SRTPEVTCVV VDVSHEDPEV 300

KFNWYVDGVE VHNAKTKPRE EQYNSTYRVV SVLTVLHQDW LNGKEYKCKV 350

SNKALPAPIE KTISKAKGQP REPQVYTLPP SREEMTKNQV SLTCLVKGFY 400

PSDIAVEWES NGQPENNYKT TPPVLDSDGS FFLYSKLTVD KSRWQQGNVF 450

SCSVMHEALH NHYTQKSLSL SPG**                          475
Wherein X and a small letter can be substituted with any
amino acid or alternatively, with an amino acid selected
from SEQ ID NOs: 1-6, in the corresponding position.
In one embodiment, X may also indicate absence of an
amino acid residue.

SEQ ID NO: 14 (Light Chain Consensus Sequence)
METDTLLLWV LLLWVPGSTG DXvMTQSPXs Lsys1GXrat isCrXSQXXX  50

XXXXXXXLNW XQQkPGqaXX XLIYXXSX1X SGvPdRFSGS GSGTDXTLtI 100

SslXXEDXav YyCXQGXXXX XTFGXGTKXE IKRTVAAPSV FIFPPSDEQL 150

KSGTASVVCL LNNFYPREAK VQWKVDNALQ SGNSQESVTE QDSKDSTYSL 200

SSTLTLSKAD YEKHKVYACE VTHQGLSSPV TKSFNRGEC*           240
Wherein X and a small letter can be substituted with
any amino acid or alternatively, with an amino acid
selected from SEQ ID NOs: 7-12, in the corresponding
position. In one embodiment, X may also indicate
absence of an amino acid residue.

SEQ ID NO: 14 Human IgD constant region, Uniprot: P01880
APTKAPDVFPIISGCRHPKDNSPVVLACLITGYHPTSVTVTWYMGTQSQPQRTFPEIQR

RDSYYMTSSQLSTPLQQWRQGEYKCVVQHTASKSKKEIFRWPESPKAQASSVPTAQPQA

EGSLAKATTAPATTRNTGRGGEEKKKEKEKEEQEERETKTPECPSHTQPLGVYLLTPAV

QDLWLRDKATFTCFVVGSDLKDAHLTWEVAGKVPTGGVEEGLLERHSNGSQSQHSRLTL

PRSLWNAGTSVTCTLNHPSLPPQRLMALREPAAQAPVKLSLNLLASSDPPEAASWLLCE

VSGFSPPNILLMWLEDQREVNTSGFAPARPPPQPGSTTFWAWSVLRVPAPPSPQPATYT

CVVSHEDSRTLLNASRSLEVSYVTDHGPMK

SEQ ID NO: 15 Human IgG1 constant region, Uniprot: P01857
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREPQVYTLPPSR

DELTKNQVSLTCLVKGFYPSDIAVEWESNGQPENNYKTTPPVLDSDGSFFLYSKLTVDK

SRWQQGNVFSCSVMHEALHNHYTQKSLSLSPGK

SEQ ID NO: 16 Human IgG2 constant region, Uniprot: P01859
ASTKGPSVFPLAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCPAPPVAGPSV

FLFPPKPKDTLMISRTPEVTCVVVDVSHEDPEVQFNWYVDGVEVHNAKTKPREEQFNST

FRVVSVLTVVHQDWLNGKEYKCKVSNKGLPAPIEKTISKTKGQPREPQVYTLPPSREEM

TKNQVSLTCLVKGFYPSDISVEWESNGQPENNYKTTPPMLDSDGSFFLYSKLTVDKSRW

QQGNVFSCSVMHEALHNHYTQKSLSLSPGK

SEQ ID NO: 17 Human IgG3 constant region, Uniprot: P01860
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSC

DTPPPCPRCPEPKSCDTPPPCPRCPEPKSCDTPPPCPRCPAPELLGGPSVFLFPPKPKDTL

MISRTPEVTCVVVDVSHEDPEVQFKWYVDGVEVHNAKTKPREEQYNSTFRVVSVLTVLHQ

DWLNGKEYKCKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQGNIFSCSVMH

EALHNRFTQKSLSLSPGK

SEQ ID NO: 18 Human IgM constant region, Uniprot: P01871
GSASAPTLFPLVSCENSPSDTSSVAVGCLAQDFLPDSITLSWKYKNNSDISSTRGFPSVL

RGGKYAATSQVLLPSKDVMQGTDEHVVCKVQHPNGNKEKNVPLPVIAELPPKVSVFVPP

RDGFFGNPRKSKLICQATGFSPRQIQVSWLREGKQVGSGVTTDQVQAEAKESGPTTYKVT

TSTLTIKESDWLGQSMFTCRVDHRGLTFQQNASSMCVPDQDTAIRVFAIPPSFASIFLTK

SKLTCLVTDLTTYDSVTISWTRQNGEAVKTHTNISESHPNATFSAVGEASICEDDWNSGE

RFTCTVTHTDLPSPLKQTISRPKGVALHRPDVYLLPPAREQLNLRESATITCLVTGFSPA

DVFVQWMQRGQPLSPEKYVTSAPMPEPQAPGRYFAHSILTVSEEEWNTGETYTCVAHEA

LPNRVTERTVDKSTGKPTLYNVSLVMSDTAGTCY

SEQ ID NO: 19 Human IgG4 constant region, Uniprot: P01861
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPSCPAPEFLGGPSV

FLFPPKPKDTLMISRTPEVTCVVVDVSQEDPEVQFNWYVDGVEVHNAKTKPREEQFNST

YRVVSVLTVLHQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLYSRLTVDKSRW

QEGNVFSCSVMHEALHNHYTQKSLSLSLGK

SEQ ID NO: 20 Human IgA1 constant region, Uniprot: P01876
ASPTSPKVFPLSLCSTQPDGNVVIACLVQGFFPQEPLSVTWSESGQGVTARNFPPSQDAS

GDLYTTSSQLTLPATQCLAGKSVTCHVKHYTNPSQDVTVPCPVPSTPPTPSPSTPPTPSPS

CCHPRLSLHRPALEDLLLGSEANLTCTLTGLRDASGVTFTWTPSSGKSAVQGPPERDLC

GCYSVSSVLPGCAEPWNHGKTFTCTAAYPESKTPLTATLSKSGNTFRPEVHLLPPPSEEL

ALNELVTLTCLARGFSPKDVLVRWLQGSQELPREKYLTWASRQEPSQGTTTFAVTSILR

VAAEDWKKGDTFSCMVGHEALPLAFTQKTIDRLAGKPTHVNVSVVMAEVDGTCY

SEQ ID NO: 21 Human IgA2 constant region, Uniprot: P01877
ASPTSPKVFPLSLDSTPQDGNVVVACLVQGFFPQEPLSVTWSESGQNVTARNFPPSQDAS

GDLYTTSSQLTLPATQCPDGKSVTCHVKHYTNPSQDVTVPCPVPPPPCCHPRLSLHRPA

LEDLLLGSEANLTCTLTGLRDASGATFTWTPSSGKSAVQGPPERDLCGCYSVSSVLPGC

AQPWNHGETFTCTAAHPELKTPLTANITKSGNTFRPEVULLPPPSEELALNELVTLTCLA

RGFSPKDVLVRWLQGSQELPREKYLTWASRQEPSQGTTTFAVTSILRVAAEDWKKGDT

FSCMVGHEALPLAFTQKTIDRMAGKPTHVNVSVVMAEVDGTCY

SEQ ID NO: 22 Human Ig kappa constant region, Uniprot: P01834
TVAAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC

SEQ ID NO: 23 (Tip Heavy Chain Consensus Sequence)
MDPKGSLSWR ILLFLSLAFE LSYGEVkLVe SGgglvqPGg SirlSCaASG  50

FTFRTYAMSW VRQAPGkgLE WVATIGSDRR HTYYPDsvkG RfTIsRDNaK 100

NTLYlqmnSL RaEDTAVYYC VGPYDGYYGE FDYWGQGTLV TVSSASTKGP 150

SVFPLAPSSK STSGGTAALG CLVKDYFPEP VTVSWNSGAL TSGVHTFPAV 200

LQSSGLYSLS SVVTVPSSSL GTQTYICNVN HKPSNTKVDK KVEPKSCDKT 250

HTCPPCPAPE LLGGPSVFLF PPKPKDTLMI SRTPEVTCVV VDVSHEDPEV 300

KFNWYVDGVE VHNAKTKPRE EQYNSTYRVV SVLTVLHQDW LNGKEYKCKV 350

SNKALPAPIE KTISKAKGQP REPQVYTLPP SREEMTKNQV SLTCLVKGFY 400

PSDIAVEWES NGQPENNYKT TPPVXDSDGS FFLYSKLTVD KSRWQQGNVF 450

SCSVMEHALH NHYTQKSLSL SPQ**                           475
Wherein a small letter can be substituted with an amino
acid selected from SEQ ID NOs: 1-3 in the corresponding
position.

SEQ ID NO: 24 (Tip Light Chain Consensus Sequence)
METDTLLLWV LLLWVPGSTG DVVMTQSPlS LpVtLGqpAs IsCrSSQSLL  50

DSDGKTPLNW LQQrPGQsPr RLIYLVSKlD SGVPDRFSGS GSGTDFTLkI 300

SrveAEDVgV YYCWQGTHFP YTFGQGTKLE IKRTVAAPSV FIFPPSDEQL 350

KSGTASVVCL LNNTYPREAK VQWKVDNALQ SGNSQESVTE QDSKDSTYSL 200

SSTLTLSKAD YEKHKVYACE VTHQGLSSPV TKSFNRGEC**          240
Wherein a small letter can be substituted with an amino
acid selected from SEQ ID NOs: 7-9 in the corresponding
position.

SEQ ID NO: 25 (Tail Heavy Chain Consensus Sequence)
MDPKGSLSWR ILLFLSLAFE LSYGEVQLVE SGGGLVkPGg SLRLSCaASG  50

FTFSRYGMSW VRQAPGKGLE WVaTISSGGS YTYYTDSVKG RFTISRDNAK 100

NsLYLQMNSL raEDTAVYYC ERHGGDGYWY FDVWGQGTMV TVSSASTKGP 150

SVFPLAPSSK STSGGTAALG CLVKDYFPEP VTVSWNSGAL TSGVHTFPAV 200

LQSSGLYSLS SVVTVPSSSL GTQTYICNVN HKPSNTKVDK KVEPKSCDKT 250

HTCPPCPAPE LLGGPSVFLF PPKPKDTLMI SRTPEVTCVV VDVSHEDPEV 300

KFNWYVDGVE VHNAKTKPRE EQYNSTYRVV SVLTVLHQDW LNGKEYKCKV 350

SNKALPAPIE KTISKAKGQP REPQVYTLPP SREEMTKNQV SLTCLVKGFY 400

PSDIAVEWES NGQPENNYKT TPPVLDSDGS FFLYSKLTVD KSRWQQGNVF 450

SCSVMHEALH NHYTQKSLSL SPG**                          475
Wherein a small letter can be substituted with an amino
acid selected from SEQ ID NOs: 4-6 in the corresponding
position.

SEQ ID NO: 26 (Tail Light Chain Consensus Sequence)
METDTLLLWV LLLWVPGSTG DIqMTQSPss LSaSvGdRvT itCRASQDIS  50

NYLNWYQQKP GkAVkLLIYY TSRLHSGvPs RFSGSGSGTD YTLTISSLqP 100

```
EDFAtYfCQQ GNPLRTFGGG TKVEIKRTVA APSVFIFPPS DEQLKSGTAS    150

VVCLLNNFYP REAKVQWKVD NALQSGNSQE SVTEQDSKDS TYSLSSTLTL    200

SKADYEKMKV YACEVTHQGL SSPVTKSFNR GEC*                     234
```
Wherein a small letter can be substituted with an amino
acid selected from SEQ ID NOs: 10-12 in the corresponding
position.

SEQ ID NO: 28 (the consensus sequence that IHF binds)
WATCAANNNNTTR
Wherein W is A or T and R is a purine.

SEQ ID NO. 29 (*E. coli* hupA, Genbank
accession No.: AP_003818,
Last accessed Mar. 21, 2011)
MNKTQLIDVIAEKAELSKTQAKAALESTLAAITESLKEGDAVQLVGFGTFK

VNHRAERTGRNPQTGKEIKIAAANVPAFVSGKALKDAVK

SEQ ID NO. 30 (*E. coli* hupB, Genbank
accession No.: AP_001090.1,
Last accessed Mar. 21, 2011)
MNKSQLIDKIAAGADISKAAAGRALDAIIASVTESLKEGDDVALVGFG

TFAVKERAARTGRNPQTGKEITIAAAKVPSFRAGKALKDAVN

SEQ ID NO: 31 (IhfA, A tip fragment)
NFELRDKSSRPGRNPKTGDVV

SEQ ID NO: 32 (IhfB, B tip fragment)
SLHHRQPRLGRNPKTGDSVNL

SEQ ID NO: 33 (a peptide linker)
Gly-Pro-Ser-Leu-Lys-Leu

SEQ ID NO: 34 (a peptide linker)
Gly-Pro-Ser-Leu

SEQ ID NO: 35 (a peptide linker)
Pro-Ser-Leu-Lys

SEQ ID NO: 36 (a peptide linker)
Gly-Pro-Ser-Leu-Lys

SEQ ID NO: 37 (a peptide linker)
Ser-Leu-Lys-Leu

SEQ ID NO: 38 (tip-chimeric peptide IhfA5-mIhfB4$_{NTHI}$)
RPGRNPX$_1$TGDVVPVSARRVV-X-FSLHHRQPRLGRNPX$_1$TGDSV
wherein
"X" is an optional amino acid linker
sequence, optionally comprising, or consisting
essentially of, or yet further consisting of
between 1 to 20 amino acids wherein "X$_1$" is any
amino acid or alternatively "X$_1$" is selected
from the amino acids Q, R, K, S, or T.

SEQ ID NO: 39 (tip-chimeric peptide IhfA5-mIhfB4$_{NTHI}$
RPGRNPKTGDVVPVSARRVV-X-FSLHHRQPRLGRNPKTGDSV
wherein "X" is an optional amino acid linker
sequence optionally comprising between 1 to 20
amino acids.

SEQ ID NO: 40 (tip-chimeric peptide IhfA5-mIhfB4$_{NTHI}$
RPGRNPKTGDVVPVSARRVVGPSLFSLHHRQPRLGRNPKTGDSV SEQ ID NO: 41 (tail-chimeric peptide IhfA3-mIhfB4$_{NTHI}$
FLEEIRLSLESGQDVKLSGF-X-TLSAKEIENMVKDILEFISQ SEQ ID NO. 42: Non-limiting exemplary linker:
GGSGGS SEQ ID NO. 43: Non-limiting exemplary linker:
GPSLKL.

SEQ ID NO. 44: Non-limiting exemplary linker:
GGG.

-continued

SEQ ID NO. 45: Non-limiting exemplary linker:
GPSL.

SEQ ID NO. 46: Non-limiting exemplary linker:
GPS.

SEQ ID NO. 47: Non-limiting exemplary linker:
PSLK.

SEQ ID NO. 48: Non-limiting exemplary linker:
GPSLK.

SEQ ID NO. 49: Non-limiting exemplary linker:
SLKL.

SEQ ID NO: 50 (tail-chimeric peptide IhfA3-mIhfB4$_{NTHI}$)
FLEEIRLSLESGQDVKLSGFGPSLTLSAKEIENIVIVKDILEFISQ

---

What is claimed is:

1. An antibody or an antigen-binding fragment thereof comprising:
   (i) a heavy chain (HC) immunoglobulin variable domain comprising:
       a) a heavy chain complementarity-determining region 1 (CDRH1) comprising the amino acid sequence GFTFRTY (amino acids 50 to 56 of SEQ ID NO: 1);
       b) a heavy chain complementarity-determining region 2 (CDRH2) comprising the amino acid sequence GSDRRH (amino acids 76 to 81 of SEQ ID NO: 1); and
       c) a heavy chain complementarity-determining region 3 (CDRH3) comprising the amino acid sequence VGPYDGYYGEFDY (amino acids 121 to 133 of SEQ ID NO: 1); and
   (ii) a light chain (LC) immunoglobulin variable domain comprising:
       a) a light chain complementarity-determining region 1 (CDRL1) comprising the amino acid sequence QSLLDSDGKTF (amino acids 47 to 57 of SEQ ID NO: 7);
       b) a light chain complementarity-determining region 2 (CDRL2) comprising the amino acid sequence LVS (amino acids 75 to 77 of SEQ ID NO: 7); and
       c) a light chain complementarity-determining region 3 (CDRL3) comprising the amino acid sequence WQGTHFP (amino acids 114 to 120 of SEQ ID NO: 7).

2. The antibody or antigen-binding fragment of claim 1, wherein the heavy chain (HC) immunoglobulin variable domain comprises the amino acid sequence of amino acids 25 to 144 of SEQ ID NO: 1.

3. The antibody or antigen-binding fragment of claim 2, wherein the light chain (LC) immunoglobulin variable domain comprises the amino acid sequence of amino acids 21 to 132 of SEQ ID NO: 7, SEQ ID NO: 8, or SEQ ID NO: 9.

4. The antibody or antigen-binding fragment of claim 3, wherein the light chain (LC) immunoglobulin variable domain comprises the amino acid sequence of amino acids 21 to 132 of SEQ ID NO: 7.

5. The antibody or antigen-binding fragment of claim 3, wherein the light chain (LC) immunoglobulin variable domain comprises the amino acid sequence of amino acids 21 to 132 of SEQ ID NO: 8.

6. The antibody or antigen-binding fragment of claim 3, wherein the light chain (LC) immunoglobulin variable domain comprises the amino acid sequence of amino acids 21 to 132 of SEQ ID NO: 9.

7. The antibody or antigen-binding fragment of claim 1, wherein the CDRL3 comprises the amino acid sequence WQGTHFPYT (amino acids 114 to 122 of SEQ ID NO: 8).

8. The antibody or antigen-binding fragment of claim 1, wherein the antibody further comprises a constant region.

9. The antibody or antigen-binding fragment of claim 8, wherein the constant region is an IgA constant region, an IgD constant region, an IgE constant region, an IgG constant region or an IgM constant region.

10. The antibody or antigen-binding fragment of claim 8, wherein the constant region is an IgG1 constant region.

11. The antibody or antigen-binding fragment of claim 1, wherein the antigen-binding fragment is a Fab, F(ab')$_2$, Fab', scFv, or Fv.

12. The antibody or antigen-binding fragment of claim 1, wherein the antibody or antigen-binding fragment is modified.

13. The antibody or antigen-binding fragment of claim 12, wherein the antibody or antigen-binding fragment is modified by a process selected from PEGylation, polysialyation, HESylation or glycosylation.

14. The antibody or antigen-binding fragment of claim 1, wherein the antibody is a monoclonal antibody.

15. The antibody or antigen-binding fragment of claim 1, comprising a humanized or human framework.

16. A composition comprising a carrier and an antibody or antigen-binding fragment of claim 1.

17. An isolated polynucleotide encoding an antibody or antigen-binding fragment of claim 1, optionally operatively linked to a promoter and enhancer element.

18. A vector comprising a polynucleotide of claim 17.

19. A host cell comprising a polynucleotide of claim 17.

20. A method of producing an antibody or antigen-binding fragment of claim 1, comprising culturing a host cell comprising a polynucleotide encoding the antibody or antigen-binding fragment under conditions for expression of the antibody or antigen-binding fragment, and optionally isolating the antibody or antigen-binding fragment thereof.

21. A method of disrupting a biofilm, comprising contacting the biofilm with an effective amount of an antibody or antigen-binding fragment of claim 1.

22. A method of treating a condition characterized by the formation of a biofilm in a subject, comprising administering to the subject an effective amount of an antibody or antigen-binding fragment of claim 1.

23. A method to detect a biofilm in a subject, comprising administering to the subject an antibody or antigen-binding fragment of claim 1, and detecting binding of the antibody or antigen-binding fragment to the biofilm.

24. A method for conferring passive immunity in a subject, comprising administering to the subject an antibody or antigen-binding fragment of claim 1.

25. A non-physiological surface coated with an antibody or antigen-binding fragment of claim 1; optionally, wherein the surface is in an industrial setting.

26. A kit comprising an antibody or antigen-binding fragment of claim 1; and
optionally, instructions for use.

27. A monoclonal antibody or an antigen-binding fragment thereof, wherein the antibody comprises:
(i) a heavy chain (HC) immunoglobulin variable domain sequence comprising the amino acid sequence of amino acids 25 to 144 of SEQ ID NO: 1; and
(ii) a light chain (LC) immunoglobulin variable domain sequence comprising the amino acid sequence of amino acids 21 to 132 of SEQ ID NO: 7.

28. A monoclonal antibody or an antigen-binding fragment thereof, wherein the antibody comprises:
(i) a heavy chain (HC) immunoglobulin variable domain sequence comprising the amino acid sequence of amino acids 25 to 144 of SEQ ID NO: 1; and
(ii) a light chain (LC) immunoglobulin variable domain sequence comprising the amino acid sequence of amino acids 21 to 132 of SEQ ID NO: 8.

29. A monoclonal antibody or an antigen-binding fragment thereof, wherein the antibody comprises:
(i) a heavy chain (HC) immunoglobulin variable domain sequence comprising the amino acid sequence of amino acids 25 to 144 of SEQ ID NO: 1; and
(ii) a light chain (LC) immunoglobulin variable domain sequence comprising the amino acid sequence of amino acids 21 to 132 of SEQ ID NO: 9.

30. The antibody or antigen-binding fragment of claim 1, that binds the tip region of a DNABII peptide.

* * * * *

SEQUENCE LISTING

<160> NUMBER OF SEQ ID NOS: 50

<210> SEQ ID NO 1
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Lys Leu Val Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Arg Thr Tyr Ala Met Ser Trp Val Arg Gln Ala
    50                  55                  60

Pro Gly Lys Gly Leu Glu Trp Val Ala Thr Ile Gly Ser Asp Arg Arg
65                  70                  75                  80

His Thr Tyr Tyr Pro Asp Ser Val Lys Gly Arg Phe Thr Ile Ser Arg
                85                  90                  95

Asp Asn Ala Lys Asn Thr Leu Tyr Leu Gln Met Asn Ser Leu Arg Ala
            100                 105                 110

Glu Asp Thr Ala Val Tyr Tyr Cys Val Gly Pro Tyr Asp Gly Tyr Tyr
        115                 120                 125

Gly Glu Phe Asp Tyr Trp Gly Gln Gly Thr Leu Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470

<210> SEQ ID NO 2
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
                20                  25                  30

Gly Gly Leu Val Gln Pro Gly Gly Ser Leu Arg Leu Ser Cys Ala Ala
            35                  40                  45

Ser Gly Phe Thr Phe Arg Thr Tyr Ala Met Ser Trp Val Arg Gln Ala
        50                  55                  60

Pro Gly Lys Gly Leu Glu Trp Val Ala Thr Ile Gly Ser Asp Arg Arg
65                  70                  75                  80

His Thr Tyr Tyr Pro Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Val Gly Pro Tyr Asp Gly Tyr Tyr

```
            115                 120                 125
Gly Glu Phe Asp Tyr Trp Gly Gln Gly Thr Leu Val Thr Val Ser Ser
130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470

<210> SEQ ID NO 3
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

```
Met Asp Pro Lys Gly Ser Leu Ser Trp Arg Ile Leu Leu Phe Leu Ser
1               5                   10                  15

Leu Ala Phe Glu Leu Ser Tyr Gly Glu Val Lys Leu Val Gln Ser Gly
            20                  25                  30

Ala Glu Val Lys Lys Pro Gly Ala Ser Val Lys Val Ser Cys Lys Ala
            35                  40                  45

Ser Gly Phe Thr Phe Arg Thr Tyr Ala Met Ser Trp Val Arg Gln Ala
        50                  55                  60

Pro Gly Gln Arg Leu Glu Trp Val Ala Thr Ile Gly Ser Asp Arg Arg
65                  70                  75                  80

His Thr Tyr Tyr Pro Asp Lys Phe Gln Gly Arg Val Thr Ile Thr Arg
                85                  90                  95

Asp Asn Ala Lys Asn Thr Leu Tyr Met Glu Leu Ser Ser Leu Arg Ser
            100                 105                 110

Glu Asp Thr Ala Val Tyr Tyr Cys Val Gly Pro Tyr Asp Gly Tyr Tyr
            115                 120                 125

Gly Glu Phe Asp Tyr Trp Gly Gln Gly Thr Leu Val Thr Val Ser Ser
        130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
        210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
            245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
        340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
        370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
```

```
                420              425              430
Leu Tyr Ser Lys Leu Thr Val Asp Lys Ser Arg Trp Gln Gln Gly Asn
            435                  440                  445

Val Phe Ser Cys Ser Val Met His Glu Ala Leu His Asn His Tyr Thr
            450                  455                  460

Gln Lys Ser Leu Ser Leu Ser Pro Gly
465                 470

<210> SEQ ID NO 4
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30

Gly Gly Leu Val Lys Pro Gly Gly Ser Leu Arg Leu Ser Cys Ala Ala
        35                  40                  45

Ser Gly Phe Thr Phe Ser Arg Tyr Gly Met Ser Trp Val Arg Gln Ala
    50                  55                  60

Pro Gly Lys Gly Leu Glu Trp Val Ala Thr Ile Ser Ser Gly Gly Ser
65                  70                  75                  80

Tyr Thr Tyr Tyr Thr Asp Ser Val Lys Gly Arg Phe Thr Ile Ser Arg
                85                  90                  95

Asp Asn Ala Lys Asn Ser Leu Tyr Leu Gln Met Asn Ser Leu Arg Ala
            100                 105                 110

Glu Asp Thr Ala Val Tyr Tyr Cys Glu Arg His Gly Gly Asp Gly Tyr
        115                 120                 125

Trp Tyr Phe Asp Val Trp Gly Gln Gly Thr Met Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300
```

```
Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
        340                 345                 350

Lys Ala Leu Pro Ala Pro Ile Glu Lys Thr Ile Ser Lys Ala Lys Gly
    355                 360                 365

Gln Pro Arg Glu Pro Gln Val Tyr Thr Leu Pro Pro Ser Arg Glu Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
        420                 425                 430

Leu Tyr Ser Lys Leu Thr Val Asp Lys Ser Arg Trp Gln Gln Gly Asn
    435                 440                 445

Val Phe Ser Cys Ser Val Met His Glu Ala Leu His Asn His Tyr Thr
450                 455                 460

Gln Lys Ser Leu Ser Leu Ser Pro Gly
465                 470

<210> SEQ ID NO 5
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30

Gly Gly Leu Val Lys Pro Gly Gly Ser Leu Arg Leu Ser Cys Ala Ala
        35                  40                  45

Ser Gly Phe Thr Phe Ser Arg Tyr Gly Met Ser Trp Val Arg Gln Ala
    50                  55                  60

Pro Gly Lys Gly Leu Glu Trp Val Ser Thr Ile Ser Ser Gly Gly Ser
65                  70                  75                  80

Tyr Thr Tyr Tyr Thr Asp Ser Val Lys Gly Arg Phe Thr Ile Ser Arg
                85                  90                  95

Asp Asn Ala Lys Asn Ser Leu Tyr Leu Gln Met Asn Ser Leu Arg Ala
            100                 105                 110

Glu Asp Thr Ala Val Tyr Tyr Cys Glu Arg His Gly Gly Asp Gly Tyr
        115                 120                 125

Trp Tyr Phe Asp Val Trp Gly Gln Gly Thr Met Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190
```

```
Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Gln Thr
        210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly
465                 470

<210> SEQ ID NO 6
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30

Gly Gly Leu Val Gln Pro Gly Arg Ser Leu Arg Leu Ser Cys Thr Ala
        35                  40                  45

Ser Gly Phe Thr Phe Ser Arg Tyr Gly Met Ser Trp Val Arg Gln Ala
    50                  55                  60

Pro Gly Lys Gly Leu Glu Trp Val Ala Thr Ile Ser Ser Gly Gly Ser
```

```
                65                  70                  75                  80
Tyr Thr Tyr Tyr Thr Asp Ser Val Lys Gly Arg Phe Thr Ile Ser Arg
                    85                  90                  95
Asp Asn Ala Lys Asn Ile Leu Tyr Leu Gln Met Asn Ser Leu Lys Thr
                100                 105                 110
Glu Asp Thr Ala Val Tyr Tyr Cys Glu Arg His Gly Asp Gly Tyr
            115                 120                 125
Trp Tyr Phe Asp Val Trp Gly Gln Gly Thr Met Val Thr Val Ser Ser
        130                 135                 140
Ala Ser Thr Lys Gly Pro Ser Val Phe Pro Leu Ala Pro Ser Ser Lys
145                 150                 155                 160
Ser Thr Ser Gly Gly Thr Ala Ala Leu Gly Cys Leu Val Lys Asp Tyr
                165                 170                 175
Phe Pro Glu Pro Val Thr Val Ser Trp Asn Ser Gly Ala Leu Thr Ser
            180                 185                 190
Gly Val His Thr Phe Pro Ala Val Leu Gln Ser Ser Gly Leu Tyr Ser
        195                 200                 205
Leu Ser Ser Val Val Thr Val Pro Ser Ser Ser Leu Gly Thr Gln Thr
210                 215                 220
Tyr Ile Cys Asn Val Asn His Lys Pro Ser Asn Thr Lys Val Asp Lys
225                 230                 235                 240
Lys Val Glu Pro Lys Ser Cys Asp Lys Thr His Thr Cys Pro Pro Cys
                245                 250                 255
Pro Ala Pro Glu Leu Leu Gly Gly Pro Ser Val Phe Leu Phe Pro Pro
            260                 265                 270
Lys Pro Lys Asp Thr Leu Met Ile Ser Arg Thr Pro Glu Val Thr Cys
        275                 280                 285
Val Val Val Asp Val Ser His Glu Asp Pro Glu Val Lys Phe Asn Trp
        290                 295                 300
Tyr Val Asp Gly Val Glu Val His Asn Ala Lys Thr Lys Pro Arg Glu
305                 310                 315                 320
Glu Gln Tyr Asn Ser Thr Tyr Arg Val Val Ser Val Leu Thr Val Leu
                325                 330                 335
His Gln Asp Trp Leu Asn Gly Lys Glu Tyr Lys Cys Lys Val Ser Asn
            340                 345                 350
Lys Ala Leu Pro Ala Pro Ile Glu Lys Thr Ile Ser Lys Ala Lys Gly
        355                 360                 365
Gln Pro Arg Glu Pro Gln Val Tyr Thr Leu Pro Pro Ser Arg Glu Glu
    370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
                405                 410                 415
Asn Tyr Lys Thr Thr Pro Pro Val Leu Asp Ser Asp Gly Ser Phe Phe
            420                 425                 430
Leu Tyr Ser Lys Leu Thr Val Asp Lys Ser Arg Trp Gln Gln Gly Asn
        435                 440                 445
Val Phe Ser Cys Ser Val Met His Glu Ala Leu His Asn His Tyr Thr
    450                 455                 460
Gln Lys Ser Leu Ser Leu Ser Pro Gly
465                 470

<210> SEQ ID NO 7
```

<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Leu Asp Ser Asp Gly Lys Thr Phe Leu Asn Trp Leu Gln Gln Arg
    50                  55                  60

Pro Gly Gln Ser Pro Arg Arg Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Gly Thr His Phe Pro Tyr Thr Phe Gly Gln Gly Thr Lys
        115                 120                 125

Leu Glu Ile Lys Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 8
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Leu Ser Leu Pro
            20                  25                  30

Val Thr Leu Gly Gln Pro Ala Ser Ile Ser Cys Arg Ser Ser Gln Ser
        35                  40                  45

Leu Leu Asp Ser Asp Gly Lys Thr Phe Leu Asn Trp Leu Gln Gln Arg
    50                  55                  60

Pro Gly Gln Ser Pro Arg Arg Leu Ile Tyr Leu Val Ser Lys Arg Asp
65                  70                  75                  80

Ser Gly Val Pro Asp Arg Phe Ser Gly Ser Gly Ser Gly Thr Asp Phe
            85                  90                  95

Thr Leu Lys Ile Ser Arg Val Glu Ala Glu Asp Val Gly Val Tyr Tyr
            100                 105                 110

Cys Trp Gln Gly Thr His Phe Pro Tyr Thr Phe Gly Gln Gly Thr Lys
            115                 120                 125

Leu Glu Ile Lys Arg Thr Val Ala Ala Pro Ser Val Phe Ile Phe Pro
            130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
            195                 200                 205

Ala Asp Tyr Glu Lys His Lys Val Tyr Ala Cys Glu Val Thr His Gln
            210                 215                 220

Gly Leu Ser Ser Pro Val Thr Lys Ser Phe Asn Arg Gly Glu Cys
225                 230                 235

<210> SEQ ID NO 9
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Thr Asp Thr Leu Leu Leu Trp Val Leu Leu Leu Trp Val Pro
1               5                   10                  15

Gly Ser Thr Gly Asp Val Val Met Thr Gln Ser Pro Asp Ser Leu Ala
            20                  25                  30

Val Ser Leu Gly Glu Arg Ala Thr Ile Asn Cys Lys Ser Ser Gln Ser
            35                  40                  45

Leu Leu Asp Ser Asp Gly Lys Thr Phe Leu Asn Trp Leu Gln Gln Lys
50                  55                  60

Pro Gly Gln Pro Pro Lys Arg Leu Ile Tyr Leu Val Ser Lys Leu Asp
65                  70                  75                  80

Ser Gly Val Pro Asp Arg Phe Ser Gly Ser Gly Ser Gly Thr Asp Phe
            85                  90                  95

Thr Leu Thr Ile Ser Ser Leu Gln Ala Glu Asp Val Ala Val Tyr Tyr
            100                 105                 110

Cys Trp Gln Gly Thr His Phe Pro Tyr Thr Phe Gly Gln Gly Thr Lys
            115                 120                 125

Leu Glu Ile Lys Arg Thr Val Ala Ala Pro Ser Val Phe Ile Phe Pro
            130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
            165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys

```
                195                 200                 205
Ala Asp Tyr Glu Lys His Lys Val Tyr Ala Cys Glu Val Thr His Gln
        210                 215                 220

Gly Leu Ser Ser Pro Val Thr Lys Ser Phe Asn Arg Gly Glu Cys
225                 230                 235

<210> SEQ ID NO 10
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Ser Asn Tyr Leu Asn Trp Tyr Gln Gln Lys Pro Gly Lys Ala Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Phe Cys Gln Gln Gly Asn
            100                 105                 110

Pro Leu Arg Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 11
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Glu Thr Asp Thr Leu Leu Leu Trp Val Leu Leu Leu Trp Val Pro
1               5                   10                  15

Gly Ser Thr Gly Asp Ile Gln Met Thr Gln Ser Pro Ser Ser Leu Ser
```

```
                  20                  25                  30

Ala Ser Val Gly Asp Arg Val Thr Ile Thr Cys Arg Ala Ser Gln Asp
                35                  40                  45

Ile Ser Asn Tyr Leu Asn Trp Tyr Gln Gln Lys Pro Gly Lys Ala Val
            50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Thr Leu Thr Ile Ser
                    85                  90                  95

Ser Leu Gln Pro Glu Asp Phe Ala Thr Tyr Tyr Cys Gln Gln Gly Asn
                100                 105                 110

Pro Leu Arg Thr Phe Gly Gly Gly Thr Lys Val Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
        210                 215                 220

Thr Lys Ser Phe Asn Arg Gly Glu Cys
225                 230

<210> SEQ ID NO 12
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Glu Thr Asp Thr Leu Leu Leu Trp Val Leu Leu Leu Trp Val Pro
1               5                   10                  15

Gly Ser Thr Gly Asp Ile Val Met Thr Gln Ser Pro Ala Thr Leu Ser
                20                  25                  30

Leu Ser Pro Gly Glu Arg Ala Thr Leu Ser Cys Arg Ala Ser Gln Asp
            35                  40                  45

Ile Ser Asn Tyr Leu Asn Trp Tyr Gln Gln Lys Pro Gly Gln Ala Val
        50                  55                  60

Arg Leu Leu Ile Tyr Tyr Thr Ser Arg Leu His Ser Gly Ile Pro Ala
65                  70                  75                  80

Arg Phe Ser Gly Ser Gly Ser Gly Thr Asp Tyr Thr Leu Thr Ile Ser
                85                  90                  95

Ser Leu Glu Pro Glu Asp Phe Ala Val Tyr Phe Cys Gln Gln Gly Asn
            100                 105                 110

Pro Leu Arg Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140
```

-continued

```
Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 13
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Any amino acid, such as Q or K
<220> FEATURE:
<221> NAME/KEY: MOD_RES
<222> LOCATION: (30)..(30)
<223> OTHER INFORMATION: Any amino acid, such as E or Q
<220> FEATURE:
<221> NAME/KEY: MOD_RES
<222> LOCATION: (33)..(33)
<223> OTHER INFORMATION: Any amino acid, such as G or A
<220> FEATURE:
<221> NAME/KEY: MOD_RES
<222> LOCATION: (34)..(34)
<223> OTHER INFORMATION: Any amino acid, such as G or E
<220> FEATURE:
<221> NAME/KEY: MOD_RES
<222> LOCATION: (35)..(35)
<223> OTHER INFORMATION: Any amino acid, such as L or V
<220> FEATURE:
<221> NAME/KEY: MOD_RES
<222> LOCATION: (36)..(36)
<223> OTHER INFORMATION: Any amino acid, such as V or K
<220> FEATURE:
<221> NAME/KEY: MOD_RES
<222> LOCATION: (37)..(37)
<223> OTHER INFORMATION: Any amino acid, such as Q or K, or absent
<220> FEATURE:
<221> NAME/KEY: MOD_RES
<222> LOCATION: (40)..(40)
<223> OTHER INFORMATION: Any amino acid, such as R, G or A
<220> FEATURE:
<221> NAME/KEY: MOD_RES
<222> LOCATION: (42)..(42)
<223> OTHER INFORMATION: Any amino acid, such as L or V
<220> FEATURE:
<221> NAME/KEY: MOD_RES
<222> LOCATION: (43)..(43)
<223> OTHER INFORMATION: Any amino acid, such as R or K
<220> FEATURE:
<221> NAME/KEY: MOD_RES
<222> LOCATION: (44)..(44)
<223> OTHER INFORMATION: Any amino acid, such as L or V
<220> FEATURE:
<221> NAME/KEY: MOD_RES
<222> LOCATION: (47)..(47)
<223> OTHER INFORMATION: Any amino acid, such as T, A or K
<220> FEATURE:
<221> NAME/KEY: MOD_RES
<222> LOCATION: (54)..(54)
<223> OTHER INFORMATION: Any amino acid, such as S or R, or absent
<220> FEATURE:
```

```
<221> NAME/KEY: MOD_RES
<222> LOCATION: (55)..(55)
<223> OTHER INFORMATION: Any amino acid, such as R or T, or absent
<220> FEATURE:
<221> NAME/KEY: MOD_RES
<222> LOCATION: (57)..(57)
<223> OTHER INFORMATION: Any amino acid, such as G or A, or absent
<220> FEATURE:
<221> NAME/KEY: MOD_RES
<222> LOCATION: (67)..(67)
<223> OTHER INFORMATION: Any amino acid, such as K or Q
<220> FEATURE:
<221> NAME/KEY: MOD_RES
<222> LOCATION: (68)..(68)
<223> OTHER INFORMATION: Any amino acid, such as G or R
<220> FEATURE:
<221> NAME/KEY: MOD_RES
<222> LOCATION: (73)..(73)
<223> OTHER INFORMATION: Any amino acid, such as A or S
<220> FEATURE:
<221> NAME/KEY: MOD_RES
<222> LOCATION: (76)..(76)
<223> OTHER INFORMATION: Any amino acid, such as S or G, or absent
<220> FEATURE:
<221> NAME/KEY: MOD_RES
<222> LOCATION: (78)..(78)
<223> OTHER INFORMATION: Any amino acid, such as G or D, or absent
<220> FEATURE:
<221> NAME/KEY: MOD_RES
<222> LOCATION: (79)..(79)
<223> OTHER INFORMATION: Any amino acid, such as G or R, or absent
<220> FEATURE:
<221> NAME/KEY: MOD_RES
<222> LOCATION: (80)..(80)
<223> OTHER INFORMATION: Any amino acid, such as S or R, or absent
<220> FEATURE:
<221> NAME/KEY: MOD_RES
<222> LOCATION: (81)..(81)
<223> OTHER INFORMATION: Any amino acid, such as Y or H, or absent
<220> FEATURE:
<221> NAME/KEY: MOD_RES
<222> LOCATION: (85)..(85)
<223> OTHER INFORMATION: Any amino acid, such as T or P, or absent
<220> FEATURE:
<221> NAME/KEY: MOD_RES
<222> LOCATION: (87)..(87)
<223> OTHER INFORMATION: Any amino acid, such as S or K
<220> FEATURE:
<221> NAME/KEY: MOD_RES
<222> LOCATION: (88)..(88)
<223> OTHER INFORMATION: Any amino acid, such as V or F
<220> FEATURE:
<221> NAME/KEY: MOD_RES
<222> LOCATION: (89)..(89)
<223> OTHER INFORMATION: Any amino acid, such as K or Q
<220> FEATURE:
<221> NAME/KEY: MOD_RES
<222> LOCATION: (92)..(92)
<223> OTHER INFORMATION: Any amino acid, such as F or V
<220> FEATURE:
<221> NAME/KEY: MOD_RES
<222> LOCATION: (95)..(95)
<223> OTHER INFORMATION: Any amino acid, such as S or T
<220> FEATURE:
<221> NAME/KEY: MOD_RES
<222> LOCATION: (99)..(99)
<223> OTHER INFORMATION: Any amino acid, such as A or S
<220> FEATURE:
<221> NAME/KEY: MOD_RES
<222> LOCATION: (102)..(102)
<223> OTHER INFORMATION: Any amino acid, such as I, S or T
<220> FEATURE:
<221> NAME/KEY: MOD_RES
<222> LOCATION: (105)..(105)
<223> OTHER INFORMATION: Any amino acid, such as L or M
<220> FEATURE:
<221> NAME/KEY: MOD_RES
<222> LOCATION: (106)..(106)
<223> OTHER INFORMATION: Any amino acid, such as Q or E
```

```
<220> FEATURE:
<221> NAME/KEY: MOD_RES
<222> LOCATION: (107)..(107)
<223> OTHER INFORMATION: Any amino acid, such as M or L
<220> FEATURE:
<221> NAME/KEY: MOD_RES
<222> LOCATION: (108)..(108)
<223> OTHER INFORMATION: Any amino acid, such as N or S
<220> FEATURE:
<221> NAME/KEY: MOD_RES
<222> LOCATION: (111)..(111)
<223> OTHER INFORMATION: Any amino acid, such as K or R
<220> FEATURE:
<221> NAME/KEY: MOD_RES
<222> LOCATION: (112)..(112)
<223> OTHER INFORMATION: Any amino acid, such as T, A or S
<220> FEATURE:
<221> NAME/KEY: MOD_RES
<222> LOCATION: (121)..(121)
<223> OTHER INFORMATION: Any amino acid, such as E or V, or absent
<220> FEATURE:
<221> NAME/KEY: MOD_RES
<222> LOCATION: (122)..(122)
<223> OTHER INFORMATION: Any amino acid, such as R or G, or absent
<220> FEATURE:
<221> NAME/KEY: MOD_RES
<222> LOCATION: (123)..(123)
<223> OTHER INFORMATION: Any amino acid, such as H or P, or absent
<220> FEATURE:
<221> NAME/KEY: MOD_RES
<222> LOCATION: (124)..(124)
<223> OTHER INFORMATION: Any amino acid, such as G or Y, or absent
<220> FEATURE:
<221> NAME/KEY: MOD_RES
<222> LOCATION: (125)..(125)
<223> OTHER INFORMATION: Any amino acid, such as G or D, or absent
<220> FEATURE:
<221> NAME/KEY: MOD_RES
<222> LOCATION: (126)..(126)
<223> OTHER INFORMATION: Any amino acid, such as D or G, or absent
<220> FEATURE:
<221> NAME/KEY: MOD_RES
<222> LOCATION: (127)..(127)
<223> OTHER INFORMATION: Any amino acid, such as G or Y, or absent
<220> FEATURE:
<221> NAME/KEY: MOD_RES
<222> LOCATION: (129)..(129)
<223> OTHER INFORMATION: Any amino acid, such as W or G, or absent
<220> FEATURE:
<221> NAME/KEY: MOD_RES
<222> LOCATION: (130)..(130)
<223> OTHER INFORMATION: Any amino acid, such as Y or E, or absent
<220> FEATURE:
<221> NAME/KEY: MOD_RES
<222> LOCATION: (133)..(133)
<223> OTHER INFORMATION: Any amino acid, such as V or Y, or absent
<220> FEATURE:
<221> NAME/KEY: MOD_RES
<222> LOCATION: (139)..(139)
<223> OTHER INFORMATION: Any amino acid, such as M or L, or absent

<400> SEQUENCE: 13

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Xaa Leu Val Xaa Ser Gly
            20                  25                  30

Xaa Xaa Xaa Xaa Xaa Pro Gly Xaa Ser Xaa Xaa Xaa Ser Cys Xaa Ala
        35                  40                  45

Ser Gly Phe Thr Phe Xaa Xaa Tyr Xaa Met Ser Trp Val Arg Gln Ala
    50                  55                  60

Pro Gly Xaa Xaa Leu Glu Trp Val Xaa Thr Ile Xaa Ser Xaa Xaa Xaa
65                  70                  75                  80

Xaa Thr Tyr Tyr Xaa Asp Xaa Xaa Xaa Gly Arg Xaa Thr Ile Xaa Arg
```

```
                     85                  90                  95
Asp Asn Xaa Lys Asn Xaa Leu Tyr Xaa Xaa Xaa Ser Leu Xaa Xaa
            100                 105                 110

Glu Asp Thr Ala Val Tyr Tyr Cys Xaa Xaa Xaa Xaa Xaa Xaa Tyr
            115                 120                 125

Xaa Xaa Phe Asp Xaa Trp Gly Gln Gly Thr Xaa Val Thr Val Ser Ser
            130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
            195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
            275                 280                 285

Val Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
            355                 360                 365

Gln Pro Arg Glu Pro Gln Val Tyr Thr Leu Pro Pro Ser Arg Glu Glu
            370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
            435                 440                 445

Val Phe Ser Cys Ser Val Met His Glu Ala Leu His Asn His Tyr Thr
450                 455                 460

Gln Lys Ser Leu Ser Leu Ser Pro Gly
465                 470

<210> SEQ ID NO 14
<211> LENGTH: 239
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: Any amino acid, such as I or V, or absent
<220> FEATURE:
<221> NAME/KEY: MOD_RES
<222> LOCATION: (23)..(23)
<223> OTHER INFORMATION: Any amino acid, such as V or Q
<220> FEATURE:
<221> NAME/KEY: MOD_RES
<222> LOCATION: (29)..(29)
<223> OTHER INFORMATION: Any amino acid, such as A, S, D or L, or absent
<220> FEATURE:
<221> NAME/KEY: MOD_RES
<222> LOCATION: (30)..(30)
<223> OTHER INFORMATION: Any amino acid, such as T or S
<220> FEATURE:
<221> NAME/KEY: MOD_RES
<222> LOCATION: (32)..(32)
<223> OTHER INFORMATION: Any amino acid, such as S, A or P
<220> FEATURE:
<221> NAME/KEY: MOD_RES
<222> LOCATION: (33)..(33)
<223> OTHER INFORMATION: Any amino acid, such as L, A or V
<220> FEATURE:
<221> NAME/KEY: MOD_RES
<222> LOCATION: (34)..(34)
<223> OTHER INFORMATION: Any amino acid, such as S or T
<220> FEATURE:
<221> NAME/KEY: MOD_RES
<222> LOCATION: (35)..(35)
<223> OTHER INFORMATION: Any amino acid, such as P, V or L
<220> FEATURE:
<221> NAME/KEY: MOD_RES
<222> LOCATION: (37)..(37)
<223> OTHER INFORMATION: Any amino acid, such as E, D or Q, or absent
<220> FEATURE:
<221> NAME/KEY: MOD_RES
<222> LOCATION: (38)..(38)
<223> OTHER INFORMATION: Any amino acid, such as R or P
<220> FEATURE:
<221> NAME/KEY: MOD_RES
<222> LOCATION: (39)..(39)
<223> OTHER INFORMATION: Any amino acid, such as A or V
<220> FEATURE:
<221> NAME/KEY: MOD_RES
<222> LOCATION: (40)..(40)
<223> OTHER INFORMATION: Any amino acid, such as T or S
<220> FEATURE:
<221> NAME/KEY: MOD_RES
<222> LOCATION: (41)..(41)
<223> OTHER INFORMATION: Any amino acid, such as L or I
<220> FEATURE:
<221> NAME/KEY: MOD_RES
<222> LOCATION: (42)..(42)
<223> OTHER INFORMATION: Any amino acid, such as S, T or N
<220> FEATURE:
<221> NAME/KEY: MOD_RES
<222> LOCATION: (44)..(44)
<223> OTHER INFORMATION: Any amino acid, such as R or K
<220> FEATURE:
<221> NAME/KEY: MOD_RES
<222> LOCATION: (45)..(45)
<223> OTHER INFORMATION: Any amino acid, such as A or S, or absent
<220> FEATURE:
<221> NAME/KEY: MOD_RES
<222> LOCATION: (48)..(48)
<223> OTHER INFORMATION: Any amino acid, such as D or S, or absent
<220> FEATURE:
<221> NAME/KEY: MOD_RES
<222> LOCATION: (49)..(49)
<223> OTHER INFORMATION: Any amino acid, such as I or L, or absent
<220> FEATURE:
<221> NAME/KEY: MOD_RES
<222> LOCATION: (50)..(50)
<223> OTHER INFORMATION: Any amino acid, such as L or absent
```

-continued

```
<220> FEATURE:
<221> NAME/KEY: MOD_RES
<222> LOCATION: (51)..(51)
<223> OTHER INFORMATION: Any amino acid, such as D or absent
<220> FEATURE:
<221> NAME/KEY: MOD_RES
<222> LOCATION: (52)..(52)
<223> OTHER INFORMATION: Any amino acid, such as S or absent
<220> FEATURE:
<221> NAME/KEY: MOD_RES
<222> LOCATION: (53)..(53)
<223> OTHER INFORMATION: Any amino acid, such as D or absent
<220> FEATURE:
<221> NAME/KEY: MOD_RES
<222> LOCATION: (54)..(54)
<223> OTHER INFORMATION: Any amino acid, such as G or absent
<220> FEATURE:
<221> NAME/KEY: MOD_RES
<222> LOCATION: (55)..(55)
<223> OTHER INFORMATION: Any amino acid, such as S or K, or absent
<220> FEATURE:
<221> NAME/KEY: MOD_RES
<222> LOCATION: (56)..(56)
<223> OTHER INFORMATION: Any amino acid, such as N or T, or absent
<220> FEATURE:
<221> NAME/KEY: MOD_RES
<222> LOCATION: (57)..(57)
<223> OTHER INFORMATION: Any amino acid, such as Y or F, or absent
<220> FEATURE:
<221> NAME/KEY: MOD_RES
<222> LOCATION: (61)..(61)
<223> OTHER INFORMATION: Any amino acid, such as Y or L, or absent
<220> FEATURE:
<221> NAME/KEY: MOD_RES
<222> LOCATION: (64)..(64)
<223> OTHER INFORMATION: Any amino acid, such as K or R
<220> FEATURE:
<221> NAME/KEY: MOD_RES
<222> LOCATION: (67)..(67)
<223> OTHER INFORMATION: Any amino acid, such as Q or K
<220> FEATURE:
<221> NAME/KEY: MOD_RES
<222> LOCATION: (68)..(68)
<223> OTHER INFORMATION: Any amino acid, such as A, P or S
<220> FEATURE:
<221> NAME/KEY: MOD_RES
<222> LOCATION: (69)..(69)
<223> OTHER INFORMATION: Any amino acid, such as V or P, or absent
<220> FEATURE:
<221> NAME/KEY: MOD_RES
<222> LOCATION: (70)..(70)
<223> OTHER INFORMATION: Any amino acid, such as R or K, or absent
<220> FEATURE:
<221> NAME/KEY: MOD_RES
<222> LOCATION: (71)..(71)
<223> OTHER INFORMATION: Any amino acid, such as L or R, or absent
<220> FEATURE:
<221> NAME/KEY: MOD_RES
<222> LOCATION: (75)..(75)
<223> OTHER INFORMATION: Any amino acid, such as Y or L, or absent
<220> FEATURE:
<221> NAME/KEY: MOD_RES
<222> LOCATION: (76)..(76)
<223> OTHER INFORMATION: Any amino acid, such as T or V, or absent
<220> FEATURE:
<221> NAME/KEY: MOD_RES
<222> LOCATION: (78)..(78)
<223> OTHER INFORMATION: Any amino acid, such as R or K, or absent
<220> FEATURE:
<221> NAME/KEY: MOD_RES
<222> LOCATION: (79)..(79)
<223> OTHER INFORMATION: Any amino acid, such as L or R
<220> FEATURE:
<221> NAME/KEY: MOD_RES
<222> LOCATION: (80)..(80)
<223> OTHER INFORMATION: Any amino acid, such as H or D, or absent
<220> FEATURE:
<221> NAME/KEY: MOD_RES
<222> LOCATION: (83)..(83)
```

```
<223> OTHER INFORMATION: Any amino acid, such as I or V
<220> FEATURE:
<221> NAME/KEY: MOD_RES
<222> LOCATION: (85)..(85)
<223> OTHER INFORMATION: Any amino acid, such as A, S or D
<220> FEATURE:
<221> NAME/KEY: MOD_RES
<222> LOCATION: (96)..(96)
<223> OTHER INFORMATION: Any amino acid, such as Y or F, or absent
<220> FEATURE:
<221> NAME/KEY: MOD_RES
<222> LOCATION: (99)..(99)
<223> OTHER INFORMATION: Any amino acid, such as T or K
<220> FEATURE:
<221> NAME/KEY: MOD_RES
<222> LOCATION: (102)..(102)
<223> OTHER INFORMATION: Any amino acid, such as S or R
<220> FEATURE:
<221> NAME/KEY: MOD_RES
<222> LOCATION: (103)..(103)
<223> OTHER INFORMATION: Any amino acid, such as L or V
<220> FEATURE:
<221> NAME/KEY: MOD_RES
<222> LOCATION: (104)..(104)
<223> OTHER INFORMATION: Any amino acid, such as E or Q, or absent
<220> FEATURE:
<221> NAME/KEY: MOD_RES
<222> LOCATION: (105)..(105)
<223> OTHER INFORMATION: Any amino acid, such as P or A, or absent
<220> FEATURE:
<221> NAME/KEY: MOD_RES
<222> LOCATION: (108)..(108)
<223> OTHER INFORMATION: Any amino acid, such as F or V, or absent
<220> FEATURE:
<221> NAME/KEY: MOD_RES
<222> LOCATION: (109)..(109)
<223> OTHER INFORMATION: Any amino acid, such as A or G
<220> FEATURE:
<221> NAME/KEY: MOD_RES
<222> LOCATION: (110)..(110)
<223> OTHER INFORMATION: Any amino acid, such as V or T
<220> FEATURE:
<221> NAME/KEY: MOD_RES
<222> LOCATION: (112)..(112)
<223> OTHER INFORMATION: Any amino acid, such as F or Y
<220> FEATURE:
<221> NAME/KEY: MOD_RES
<222> LOCATION: (114)..(114)
<223> OTHER INFORMATION: Any amino acid, such as Q or W, or absent
<220> FEATURE:
<221> NAME/KEY: MOD_RES
<222> LOCATION: (117)..(117)
<223> OTHER INFORMATION: Any amino acid, such as N or T, or absent
<220> FEATURE:
<221> NAME/KEY: MOD_RES
<222> LOCATION: (118)..(118)
<223> OTHER INFORMATION: Any amino acid, such as P or H, or absent
<220> FEATURE:
<221> NAME/KEY: MOD_RES
<222> LOCATION: (119)..(119)
<223> OTHER INFORMATION: Any amino acid, such as F or absent
<220> FEATURE:
<221> NAME/KEY: MOD_RES
<222> LOCATION: (120)..(120)
<223> OTHER INFORMATION: Any amino acid, such as L or P, or absent
<220> FEATURE:
<221> NAME/KEY: MOD_RES
<222> LOCATION: (121)..(121)
<223> OTHER INFORMATION: Any amino acid, such as R or Y, or absent
<220> FEATURE:
<221> NAME/KEY: MOD_RES
<222> LOCATION: (125)..(125)
<223> OTHER INFORMATION: Any amino acid, such as G or Q, or absent
<220> FEATURE:
<221> NAME/KEY: MOD_RES
<222> LOCATION: (129)..(129)
<223> OTHER INFORMATION: Any amino acid, such as V or L, or absent

<400> SEQUENCE: 14
```

Met Glu Thr Asp Thr Leu Leu Leu Trp Val Leu Leu Leu Trp Val Pro
1               5                   10                  15

Gly Ser Thr Gly Asp Xaa Xaa Met Thr Gln Ser Pro Xaa Xaa Leu Xaa
                20                  25                  30

Xaa Xaa Xaa Gly Xaa Xaa Xaa Xaa Xaa Cys Xaa Xaa Ser Gln Xaa
            35                  40                  45

Xaa Xaa Xaa Xaa Xaa Xaa Xaa Xaa Leu Asn Trp Xaa Gln Gln Xaa
50                      55                  60

Pro Gly Xaa Xaa Xaa Xaa Xaa Leu Ile Tyr Xaa Xaa Ser Xaa Xaa Xaa
65                  70                  75                  80

Ser Gly Xaa Pro Xaa Arg Phe Ser Gly Ser Gly Ser Gly Thr Asp Xaa
                85                  90                  95

Thr Leu Xaa Ile Ser Xaa Xaa Xaa Xaa Glu Asp Xaa Xaa Xaa Tyr Xaa
            100                 105                 110

Cys Xaa Gln Gly Xaa Xaa Xaa Xaa Thr Phe Gly Xaa Gly Thr Lys
        115                 120                 125

Xaa Glu Ile Lys Arg Thr Val Ala Ala Pro Ser Val Phe Ile Phe Pro
130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
210                 215                 220

Gly Leu Ser Ser Pro Val Thr Lys Ser Phe Asn Arg Gly Glu Cys
225                 230                 235

<210> SEQ ID NO 15
<211> LENGTH: 384
<212> TYPE: PRT
<213> ORGANISM: Homo sapiens

<400> SEQUENCE: 15

Ala Pro Thr Lys Ala Pro Asp Val Phe Pro Ile Ile Ser Gly Cys Arg
1               5                   10                  15

His Pro Lys Asp Asn Ser Pro Val Val Leu Ala Cys Leu Ile Thr Gly
                20                  25                  30

Tyr His Pro Thr Ser Val Thr Val Thr Trp Tyr Met Gly Thr Gln Ser
            35                  40                  45

Gln Pro Gln Arg Thr Phe Pro Glu Ile Gln Arg Arg Asp Ser Tyr Tyr
        50                  55                  60

Met Thr Ser Ser Gln Leu Ser Thr Pro Leu Gln Gln Trp Arg Gln Gly
65                  70                  75                  80

Glu Tyr Lys Cys Val Val Gln His Thr Ala Ser Lys Ser Lys Lys Glu
                85                  90                  95

Ile Phe Arg Trp Pro Glu Ser Pro Lys Ala Gln Ala Ser Ser Val Pro
            100                 105                 110

Thr Ala Gln Pro Gln Ala Glu Gly Ser Leu Ala Lys Ala Thr Thr Ala
        115                 120                 125

Pro Ala Thr Thr Arg Asn Thr Gly Arg Gly Gly Glu Glu Lys Lys Lys

```
            130                 135                 140
Glu Lys Glu Lys Glu Glu Gln Glu Gly Arg Glu Thr Lys Thr Pro Glu
145                 150                 155                 160

Cys Pro Ser His Thr Gln Pro Leu Gly Val Tyr Leu Leu Thr Pro Ala
                165                 170                 175

Val Gln Asp Leu Trp Leu Arg Asp Lys Ala Thr Phe Thr Cys Phe Val
            180                 185                 190

Val Gly Ser Asp Leu Lys Asp Ala His Leu Thr Trp Glu Val Ala Gly
            195                 200                 205

Lys Val Pro Thr Gly Gly Val Glu Glu Gly Leu Leu Glu Arg His Ser
            210                 215                 220

Asn Gly Ser Gln Ser Gln His Ser Arg Leu Thr Leu Pro Arg Ser Leu
225                 230                 235                 240

Trp Asn Ala Gly Thr Ser Val Thr Cys Thr Leu Asn His Pro Ser Leu
                245                 250                 255

Pro Pro Gln Arg Leu Met Ala Leu Arg Glu Pro Ala Ala Gln Ala Pro
                260                 265                 270

Val Lys Leu Ser Leu Asn Leu Leu Ala Ser Ser Asp Pro Pro Glu Ala
            275                 280                 285

Ala Ser Trp Leu Leu Cys Glu Val Ser Gly Phe Ser Pro Pro Asn Ile
290                 295                 300

Leu Leu Met Trp Leu Glu Asp Gln Arg Glu Val Asn Thr Ser Gly Phe
305                 310                 315                 320

Ala Pro Ala Arg Pro Pro Gln Pro Gly Ser Thr Thr Phe Trp Ala
                325                 330                 335

Trp Ser Val Leu Arg Val Pro Ala Pro Pro Ser Pro Gln Pro Ala Thr
                340                 345                 350

Tyr Thr Cys Val Val Ser His Glu Asp Ser Arg Thr Leu Leu Asn Ala
                355                 360                 365

Ser Arg Ser Leu Glu Val Ser Tyr Val Thr Asp His Gly Pro Met Lys
370                 375                 380
```

<210> SEQ ID NO 16
<211> LENGTH: 330
<212> TYPE: PRT
<213> ORGANISM: Homo sapiens

<400> SEQUENCE: 16

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

-continued

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 17
<211> LENGTH: 326
<212> TYPE: PRT
<213> ORGANISM: Homo sapiens

<400> SEQUENCE: 17

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

```
Ser Thr Phe Arg Val Val Ser Val Leu Thr Val Val His Gln Asp Trp
                180                 185                 190
Leu Asn Gly Lys Glu Tyr Lys Cys Lys Val Ser Asn Lys Gly Leu Pro
            195                 200                 205
Ala Pro Ile Glu Lys Thr Ile Ser Lys Thr Lys Gly Gln Pro Arg Glu
210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ser Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 18
<211> LENGTH: 377
<212> TYPE: PRT
<213> ORGANISM: Homo sapiens

<400> SEQUENCE: 18

Ala Ser Thr Lys Gly Pro Ser Val Phe Pro Leu Ala Pro Cys Ser Arg
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Thr Cys Asn Val Asn His Lys Pro Ser Asn Thr Lys Val Asp Lys
                85                  90                  95
Arg Val Glu Leu Lys Thr Pro Leu Gly Asp Thr Thr His Thr Cys Pro
            100                 105                 110
Arg Cys Pro Glu Pro Lys Ser Cys Asp Thr Pro Pro Pro Cys Pro Arg
        115                 120                 125
Cys Pro Glu Pro Lys Ser Cys Asp Thr Pro Pro Pro Cys Pro Arg Cys
    130                 135                 140
Pro Glu Pro Lys Ser Cys Asp Thr Pro Pro Pro Cys Pro Arg Cys Pro
145                 150                 155                 160
Ala Pro Glu Leu Leu Gly Gly Pro Ser Val Phe Leu Phe Pro Pro Lys
                165                 170                 175
Pro Lys Asp Thr Leu Met Ile Ser Arg Thr Pro Glu Val Thr Cys Val
            180                 185                 190
Val Val Asp Val Ser His Glu Asp Pro Glu Val Gln Phe Lys Trp Tyr
        195                 200                 205
Val Asp Gly Val Glu Val His Asn Ala Lys Thr Lys Pro Arg Glu Glu
```

```
                     210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
            245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
        370                 375

<210> SEQ ID NO 19
<211> LENGTH: 452
<212> TYPE: PRT
<213> ORGANISM: Homo sapiens

<400> SEQUENCE: 19

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Leu Ser Trp Lys Tyr Lys Asn Asn Ser
        35                  40                  45

Asp Ile Ser Ser Thr Arg Gly Phe Pro Ser Val Leu Arg Gly Gly Lys
    50                  55                  60

Tyr Ala Ala Thr Ser Gln Val Leu Leu Pro Ser Lys Asp Val Met Gln
65                  70                  75                  80

Gly Thr Asp Glu His Val Val Cys Lys Val Gln His Pro Asn Gly Asn
                85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
    130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205
```

```
Asn Ala Ser Ser Met Cys Val Pro Asp Gln Asp Thr Ala Ile Arg Val
    210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
                260                 265                 270

Ile Ser Glu Ser His Pro Asn Ala Thr Phe Ser Ala Val Gly Glu Ala
                275                 280                 285

Ser Ile Cys Glu Asp Asp Trp Asn Ser Gly Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
                340                 345                 350

Val Thr Gly Phe Ser Pro Ala Asp Val Phe Val Gln Trp Met Gln Arg
                355                 360                 365

Gly Gln Pro Leu Ser Pro Glu Lys Tyr Val Thr Ser Ala Pro Met Pro
                370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Glu Ala Leu Pro Asn Arg Val Thr Glu Arg Thr Val Asp Lys Ser Thr
                420                 425                 430

Gly Lys Pro Thr Leu Tyr Asn Val Ser Leu Val Met Ser Asp Thr Ala
                435                 440                 445

Gly Thr Cys Tyr
    450

<210> SEQ ID NO 20
<211> LENGTH: 327
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
                100                 105                 110

Glu Phe Leu Gly Gly Pro Ser Val Phe Leu Phe Pro Pro Lys Pro Lys
                115                 120                 125
```

-continued

```
Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 21
<211> LENGTH: 353
<212> TYPE: PRT
<213> ORGANISM: Homo sapiens

<400> SEQUENCE: 21

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Glu
```

```
                         165                 170                 175
Arg Asp Leu Cys Gly Cys Tyr Ser Val Ser Ser Val Leu Pro Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Ser Glu Glu Leu
225                 230                 235                 240

Ala Leu Asn Glu Leu Val Thr Leu Thr Cys Leu Ala Arg Gly Phe Ser
                245                 250                 255

Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr

<210> SEQ ID NO 22
<211> LENGTH: 340
<212> TYPE: PRT
<213> ORGANISM: Homo sapiens

<400> SEQUENCE: 22

Ala Ser Pro Thr Ser Pro Lys Val Phe Pro Leu Ser Leu Asp Ser Thr
1               5                   10                  15

Pro Gln Asp Gly Asn Val Val Ala Cys Leu Val Gln Gly Phe Phe
        20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
```

```
                180             185             190
Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
        210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
        260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
        290                 295                 300

Glu Ala Leu Pro Leu Ala Phe Thr Gln Lys Thr Ile Asp Arg Met Ala
305                 310                 315                 320

Gly Lys Pro Thr His Val Asn Val Ser Val Val Met Ala Glu Val Asp
                325                 330                 335

Gly Thr Cys Tyr
            340

<210> SEQ ID NO 23
<211> LENGTH: 106
<212> TYPE: PRT
<213> ORGANISM: Homo sapiens

<400> SEQUENCE: 23

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 24
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: K or Q
<220> FEATURE:
<221> NAME/KEY: MOD_RES
<222> LOCATION: (30)..(30)
<223> OTHER INFORMATION: Q or E
<220> FEATURE:
<221> NAME/KEY: MOD_RES
```

-continued

```
<222> LOCATION: (33)..(33)
<223> OTHER INFORMATION: A or G
<220> FEATURE:
<221> NAME/KEY: MOD_RES
<222> LOCATION: (34)..(34)
<223> OTHER INFORMATION: E or G
<220> FEATURE:
<221> NAME/KEY: MOD_RES
<222> LOCATION: (35)..(35)
<223> OTHER INFORMATION: V or L
<220> FEATURE:
<221> NAME/KEY: MOD_RES
<222> LOCATION: (36)..(36)
<223> OTHER INFORMATION: K or V
<220> FEATURE:
<221> NAME/KEY: MOD_RES
<222> LOCATION: (37)..(37)
<223> OTHER INFORMATION: K or Q
<220> FEATURE:
<221> NAME/KEY: MOD_RES
<222> LOCATION: (40)..(40)
<223> OTHER INFORMATION: A or G
<220> FEATURE:
<221> NAME/KEY: MOD_RES
<222> LOCATION: (42)..(42)
<223> OTHER INFORMATION: V or L
<220> FEATURE:
<221> NAME/KEY: MOD_RES
<222> LOCATION: (43)..(43)
<223> OTHER INFORMATION: K or R
<220> FEATURE:
<221> NAME/KEY: MOD_RES
<222> LOCATION: (44)..(44)
<223> OTHER INFORMATION: V or L
<220> FEATURE:
<221> NAME/KEY: MOD_RES
<222> LOCATION: (47)..(47)
<223> OTHER INFORMATION: K or A
<220> FEATURE:
<221> NAME/KEY: MOD_RES
<222> LOCATION: (67)..(67)
<223> OTHER INFORMATION: Q or K
<220> FEATURE:
<221> NAME/KEY: MOD_RES
<222> LOCATION: (68)..(68)
<223> OTHER INFORMATION: R or G
<220> FEATURE:
<221> NAME/KEY: MOD_RES
<222> LOCATION: (87)..(87)
<223> OTHER INFORMATION: K or S
<220> FEATURE:
<221> NAME/KEY: MOD_RES
<222> LOCATION: (88)..(88)
<223> OTHER INFORMATION: F or V
<220> FEATURE:
<221> NAME/KEY: MOD_RES
<222> LOCATION: (89)..(89)
<223> OTHER INFORMATION: Q or K
<220> FEATURE:
<221> NAME/KEY: MOD_RES
<222> LOCATION: (92)..(92)
<223> OTHER INFORMATION: V or F
<220> FEATURE:
<221> NAME/KEY: MOD_RES
<222> LOCATION: (95)..(95)
<223> OTHER INFORMATION: T or S
<220> FEATURE:
<221> NAME/KEY: MOD_RES
<222> LOCATION: (99)..(99)
<223> OTHER INFORMATION: A or S
<220> FEATURE:
<221> NAME/KEY: MOD_RES
<222> LOCATION: (105)..(105)
<223> OTHER INFORMATION: M or L
<220> FEATURE:
<221> NAME/KEY: MOD_RES
<222> LOCATION: (106)..(106)
<223> OTHER INFORMATION: E or Q
<220> FEATURE:
```

```
<221> NAME/KEY: MOD_RES
<222> LOCATION: (107)..(107)
<223> OTHER INFORMATION: L or M
<220> FEATURE:
<221> NAME/KEY: MOD_RES
<222> LOCATION: (108)..(108)
<223> OTHER INFORMATION: S or N
<220> FEATURE:
<221> NAME/KEY: MOD_RES
<222> LOCATION: (112)..(112)
<223> OTHER INFORMATION: S or A

<400> SEQUENCE: 24
```

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Xaa Leu Val Xaa Ser Gly
            20                  25                  30

Xaa Xaa Xaa Xaa Xaa Pro Gly Xaa Ser Xaa Xaa Xaa Ser Cys Xaa Ala
        35                  40                  45

Ser Gly Phe Thr Phe Arg Thr Tyr Ala Met Ser Trp Val Arg Gln Ala
    50                  55                  60

Pro Gly Xaa Xaa Leu Glu Trp Val Ala Thr Ile Gly Ser Asp Arg Arg
65              70                  75                  80

His Thr Tyr Tyr Pro Asp Xaa Xaa Xaa Gly Arg Xaa Thr Ile Xaa Arg
                85                  90                  95

Asp Asn Xaa Lys Asn Thr Leu Tyr Xaa Xaa Xaa Ser Leu Arg Xaa
            100                 105                 110

Glu Asp Thr Ala Val Tyr Tyr Cys Val Gly Pro Tyr Asp Gly Tyr Tyr
            115                 120                 125

Gly Glu Phe Asp Tyr Trp Gly Gln Gly Thr Leu Val Thr Val Ser Ser
130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

```
Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Glu Glu
    370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
450                 455                 460

Gln Lys Ser Leu Ser Leu Ser Pro Gly
465                 470

<210> SEQ ID NO 25
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: D or L
<220> FEATURE:
<221> NAME/KEY: MOD_RES
<222> LOCATION: (32)..(32)
<223> OTHER INFORMATION: A or P
<220> FEATURE:
<221> NAME/KEY: MOD_RES
<222> LOCATION: (34)..(34)
<223> OTHER INFORMATION: S or T
<220> FEATURE:
<221> NAME/KEY: MOD_RES
<222> LOCATION: (37)..(37)
<223> OTHER INFORMATION: E or Q
<220> FEATURE:
<221> NAME/KEY: MOD_RES
<222> LOCATION: (38)..(38)
<223> OTHER INFORMATION: R or P
<220> FEATURE:
<221> NAME/KEY: MOD_RES
<222> LOCATION: (40)..(40)
<223> OTHER INFORMATION: T or S
<220> FEATURE:
<221> NAME/KEY: MOD_RES
<222> LOCATION: (42)..(42)
<223> OTHER INFORMATION: N or S
<220> FEATURE:
<221> NAME/KEY: MOD_RES
<222> LOCATION: (44)..(44)
<223> OTHER INFORMATION: K or R
<220> FEATURE:
<221> NAME/KEY: MOD_RES
<222> LOCATION: (64)..(64)
<223> OTHER INFORMATION: K or R
<220> FEATURE:
<221> NAME/KEY: MOD_RES
<222> LOCATION: (68)..(68)
<223> OTHER INFORMATION: P or S
<220> FEATURE:
<221> NAME/KEY: MOD_RES
<222> LOCATION: (70)..(70)
<223> OTHER INFORMATION: K or R
<220> FEATURE:
<221> NAME/KEY: MOD_RES
```

```
<222> LOCATION: (79)..(79)
<223> OTHER INFORMATION: L or R
<220> FEATURE:
<221> NAME/KEY: MOD_RES
<222> LOCATION: (99)..(99)
<223> OTHER INFORMATION: T or K
<220> FEATURE:
<221> NAME/KEY: MOD_RES
<222> LOCATION: (102)..(102)
<223> OTHER INFORMATION: S or R
<220> FEATURE:
<221> NAME/KEY: MOD_RES
<222> LOCATION: (103)..(103)
<223> OTHER INFORMATION: L or V
<220> FEATURE:
<221> NAME/KEY: MOD_RES
<222> LOCATION: (104)..(104)
<223> OTHER INFORMATION: Q or E
<220> FEATURE:
<221> NAME/KEY: MOD_RES
<222> LOCATION: (109)..(109)
<223> OTHER INFORMATION: A or G

<400> SEQUENCE: 25

Met Glu Thr Asp Thr Leu Leu Leu Trp Val Leu Leu Leu Trp Val Pro
  1               5                  10                  15

Gly Ser Thr Gly Asp Val Val Met Thr Gln Ser Pro Xaa Ser Leu Xaa
             20                  25                  30

Val Xaa Leu Gly Xaa Xaa Ala Xaa Ile Xaa Cys Xaa Ser Ser Gln Ser
         35                  40                  45

Leu Leu Asp Ser Asp Gly Lys Thr Phe Leu Asn Trp Leu Gln Gln Xaa
     50                  55                  60

Pro Gly Gln Xaa Pro Xaa Arg Leu Ile Tyr Leu Val Ser Lys Xaa Asp
 65                  70                  75                  80

Ser Gly Val Pro Asp Arg Phe Ser Gly Ser Gly Ser Gly Thr Asp Phe
             85                  90                  95

Thr Leu Xaa Ile Ser Xaa Xaa Xaa Ala Glu Asp Val Xaa Val Tyr Tyr
            100                 105                 110

Cys Trp Gln Gly Thr His Phe Pro Tyr Thr Phe Gly Gln Gly Thr Lys
            115                 120                 125

Leu Glu Ile Lys Arg Thr Val Ala Ala Pro Ser Val Phe Ile Phe Pro
        130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys
225                 230                 235

<210> SEQ ID NO 26
<211> LENGTH: 473
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (37)..(37)
<223> OTHER INFORMATION: Q or K
<220> FEATURE:
<221> NAME/KEY: MOD_RES
<222> LOCATION: (40)..(40)
<223> OTHER INFORMATION: R or G
<220> FEATURE:
<221> NAME/KEY: MOD_RES
<222> LOCATION: (47)..(47)
<223> OTHER INFORMATION: T or A
<220> FEATURE:
<221> NAME/KEY: MOD_RES
<222> LOCATION: (73)..(73)
<223> OTHER INFORMATION: A or S
<220> FEATURE:
<221> NAME/KEY: MOD_RES
<222> LOCATION: (102)..(102)
<223> OTHER INFORMATION: I or S
<220> FEATURE:
<221> NAME/KEY: MOD_RES
<222> LOCATION: (111)..(111)
<223> OTHER INFORMATION: K or R
<220> FEATURE:
<221> NAME/KEY: MOD_RES
<222> LOCATION: (112)..(112)
<223> OTHER INFORMATION: T or A

<400> SEQUENCE: 26
```

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30

Gly Gly Leu Val Xaa Pro Gly Xaa Ser Leu Arg Leu Ser Cys Xaa Ala
        35                  40                  45

Ser Gly Phe Thr Phe Ser Arg Tyr Gly Met Ser Trp Val Arg Gln Ala
    50                  55                  60

Pro Gly Lys Gly Leu Glu Trp Val Xaa Thr Ile Ser Ser Gly Gly Ser
65                  70                  75                  80

Tyr Thr Tyr Tyr Thr Asp Ser Val Lys Gly Arg Phe Thr Ile Ser Arg
                85                  90                  95

Asp Asn Ala Lys Asn Xaa Leu Tyr Leu Gln Met Asn Ser Leu Xaa Xaa
            100                 105                 110

Glu Asp Thr Ala Val Tyr Tyr Cys Glu Arg His Gly Gly Asp Gly Tyr
        115                 120                 125

Trp Tyr Phe Asp Val Trp Gly Gln Gly Thr Met Val Thr Val Ser Ser
    130                 135                 140

Ala Ser Thr Lys Gly Pro Ser Val Phe Pro Leu Ala Pro Ser Ser Lys
145                 150                 155                 160

Ser Thr Ser Gly Gly Thr Ala Ala Leu Gly Cys Leu Val Lys Asp Tyr
                165                 170                 175

Phe Pro Glu Pro Val Thr Val Ser Trp Asn Ser Gly Ala Leu Thr Ser
            180                 185                 190

Gly Val His Thr Phe Pro Ala Val Leu Gln Ser Ser Gly Leu Tyr Ser
        195                 200                 205

Leu Ser Ser Val Val Thr Val Pro Ser Ser Ser Leu Gly Thr Gln Thr
    210                 215                 220

Tyr Ile Cys Asn Val Asn His Lys Pro Ser Asn Thr Lys Val Asp Lys
225                 230                 235                 240

Lys Val Glu Pro Lys Ser Cys Asp Lys Thr His Thr Cys Pro Pro Cys
                245                 250                 255

Pro Ala Pro Glu Leu Leu Gly Gly Pro Ser Val Phe Leu Phe Pro Pro

-continued

```
                     260                 265                 270
Lys Pro Lys Asp Thr Leu Met Ile Ser Arg Thr Pro Glu Val Thr Cys
                275                 280                 285

Val Val Asp Val Ser His Glu Asp Pro Glu Val Lys Phe Asn Trp
            290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
                355                 360                 365

Gln Pro Arg Glu Pro Gln Val Tyr Thr Leu Pro Pro Ser Arg Glu Glu
            370                 375                 380

Met Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
                435                 440                 445

Val Phe Ser Cys Ser Val Met His Glu Ala Leu His Asn His Tyr Thr
450                 455                 460

Gln Lys Ser Leu Ser Leu Ser Pro Gly
465                 470

<210> SEQ ID NO 27
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: V or Q
<220> FEATURE:
<221> NAME/KEY: MOD_RES
<222> LOCATION: (29)..(29)
<223> OTHER INFORMATION: A or S
<220> FEATURE:
<221> NAME/KEY: MOD_RES
<222> LOCATION: (30)..(30)
<223> OTHER INFORMATION: T or S
<220> FEATURE:
<221> NAME/KEY: MOD_RES
<222> LOCATION: (33)..(33)
<223> OTHER INFORMATION: L or A
<220> FEATURE:
<221> NAME/KEY: MOD_RES
<222> LOCATION: (35)..(35)
<223> OTHER INFORMATION: P or V
<220> FEATURE:
<221> NAME/KEY: MOD_RES
<222> LOCATION: (37)..(37)
<223> OTHER INFORMATION: E or D
<220> FEATURE:
<221> NAME/KEY: MOD_RES
<222> LOCATION: (39)..(39)
<223> OTHER INFORMATION: A or V
<220> FEATURE:
<221> NAME/KEY: MOD_RES
```

```
<222> LOCATION: (41)..(41)
<223> OTHER INFORMATION: L or I
<220> FEATURE:
<221> NAME/KEY: MOD_RES
<222> LOCATION: (42)..(42)
<223> OTHER INFORMATION: S or T
<220> FEATURE:
<221> NAME/KEY: MOD_RES
<222> LOCATION: (62)..(62)
<223> OTHER INFORMATION: Q or K
<220> FEATURE:
<221> NAME/KEY: MOD_RES
<222> LOCATION: (65)..(65)
<223> OTHER INFORMATION: R or K
<220> FEATURE:
<221> NAME/KEY: MOD_RES
<222> LOCATION: (78)..(78)
<223> OTHER INFORMATION: I or V
<220> FEATURE:
<221> NAME/KEY: MOD_RES
<222> LOCATION: (80)..(80)
<223> OTHER INFORMATION: A or S
<220> FEATURE:
<221> NAME/KEY: MOD_RES
<222> LOCATION: (99)..(99)
<223> OTHER INFORMATION: E or Q
<220> FEATURE:
<221> NAME/KEY: MOD_RES
<222> LOCATION: (105)..(105)
<223> OTHER INFORMATION: V or T
<220> FEATURE:
<221> NAME/KEY: MOD_RES
<222> LOCATION: (107)..(107)
<223> OTHER INFORMATION: F or Y

<400> SEQUENCE: 27

Met Glu Thr Asp Thr Leu Leu Leu Trp Val Leu Leu Leu Trp Val Pro
 1               5                  10                  15

Gly Ser Thr Gly Asp Ile Xaa Met Thr Gln Ser Pro Xaa Xaa Leu Ser
            20                  25                  30

Xaa Ser Xaa Gly Xaa Arg Xaa Thr Xaa Xaa Cys Arg Ala Ser Gln Asp
        35                  40                  45

Ile Ser Asn Tyr Leu Asn Trp Tyr Gln Gln Lys Pro Gly Xaa Ala Val
    50                  55                  60

Xaa Leu Leu Ile Tyr Tyr Thr Ser Arg Leu His Ser Gly Xaa Pro Xaa
65                  70                  75                  80

Arg Phe Ser Gly Ser Gly Ser Gly Thr Asp Tyr Thr Leu Thr Ile Ser
                85                  90                  95

Ser Leu Xaa Pro Glu Asp Phe Ala Xaa Tyr Xaa Cys Gln Gln Gly Asn
            100                 105                 110

Pro Leu Arg Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220
```

```
Thr Lys Ser Phe Asn Arg Gly Glu Cys
225                 230
```

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Trp Ala Thr Cys Ala Ala Asn Asn Asn Thr Thr Arg
1               5                   10
```

<210> SEQ ID NO 29
<211> LENGTH: 90
<212> TYPE: PRT
<213> ORGANISM: Escherichia coli

<400> SEQUENCE: 29

```
Met Asn Lys Thr Gln Leu Ile Asp Val Ile Ala Glu Lys Ala Glu Leu
1               5                   10                  15

Ser Lys Thr Gln Ala Lys Ala Ala Leu Glu Ser Thr Leu Ala Ala Ile
                20                  25                  30

Thr Glu Ser Leu Lys Glu Gly Asp Ala Val Gln Leu Val Gly Phe Gly
            35                  40                  45

Thr Phe Lys Val Asn His Arg Ala Glu Arg Thr Gly Arg Asn Pro Gln
        50                  55                  60

Thr Gly Lys Glu Ile Lys Ile Ala Ala Ala Asn Val Pro Ala Phe Val
65                  70                  75                  80

Ser Gly Lys Ala Leu Lys Asp Ala Val Lys
                85                  90
```

<210> SEQ ID NO 30
<211> LENGTH: 90
<212> TYPE: PRT
<213> ORGANISM: Escherichia coli

<400> SEQUENCE: 30

```
Met Asn Lys Ser Gln Leu Ile Asp Lys Ile Ala Ala Gly Ala Asp Ile
1               5                   10                  15

Ser Lys Ala Ala Ala Gly Arg Ala Leu Asp Ala Ile Ile Ala Ser Val
                20                  25                  30

Thr Glu Ser Leu Lys Glu Gly Asp Asp Val Ala Leu Val Gly Phe Gly
            35                  40                  45

Thr Phe Ala Val Lys Glu Arg Ala Ala Arg Thr Gly Arg Asn Pro Gln
        50                  55                  60

Thr Gly Lys Glu Ile Thr Ile Ala Ala Ala Lys Val Pro Ser Phe Arg
65                  70                  75                  80

Ala Gly Lys Ala Leu Lys Asp Ala Val Asn
                85                  90
```

<210> SEQ ID NO 31
<211> LENGTH: 21
<212> TYPE: PRT
<213> ORGANISM: Haemophilus influenzae

<400> SEQUENCE: 31

```
Asn Phe Glu Leu Arg Asp Lys Ser Ser Arg Pro Gly Arg Asn Pro Lys
1               5                   10                  15
```

Thr Gly Asp Val Val
            20

<210> SEQ ID NO 32
<211> LENGTH: 21
<212> TYPE: PRT
<213> ORGANISM: Haemophilus influenzae

<400> SEQUENCE: 32

Ser Leu His His Arg Gln Pro Arg Leu Gly Arg Asn Pro Lys Thr Gly
1               5                   10                  15

Asp Ser Val Asn Leu
            20

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Pro Ser Leu Lys Leu
1               5

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Pro Ser Leu
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Ser Leu Lys
1

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Pro Ser Leu Lys
1               5

<210> SEQ ID NO 37
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 37

Ser Leu Lys Leu
1

<210> SEQ ID NO 38
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (21)..(40)
<223> OTHER INFORMATION: Any amino acid
<220> FEATURE:
<221> NAME/KEY: MISC_FEATURE
<222> LOCATION: (21)..(40)
<223> OTHER INFORMATION: This region may encompass 1-20 residues
<220> FEATURE:
<221> NAME/KEY: MOD_RES
<222> LOCATION: (55)..(55)
<223> OTHER INFORMATION: Any amino acid

<400> SEQUENCE: 38

Arg Pro Gly Arg Asn Pro Xaa Thr Gly Asp Val Val Pro Val Ser Ala
1               5                   10                  15

Arg Arg Val Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Xaa Thr Gly Asp Ser Val
    50                  55                  60

<210> SEQ ID NO 39
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(40)
<223> OTHER INFORMATION: Any amino acid
<220> FEATURE:
<221> NAME/KEY: MISC_FEATURE
<222> LOCATION: (21)..(40)
<223> OTHER INFORMATION: This region may encompass 1-20 residues

<400> SEQUENCE: 39

Arg Pro Gly Arg Asn Pro Lys Thr Gly Asp Val Val Pro Val Ser Ala
1               5                   10                  15

Arg Arg Val Val Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Phe Ser Leu His His Arg Gln Pro
        35                  40                  45

Arg Leu Gly Arg Asn Pro Lys Thr Gly Asp Ser Val
    50                  55                  60
```

<210> SEQ ID NO 40
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Arg Pro Gly Arg Asn Pro Lys Thr Gly Asp Val Val Pro Val Ser Ala
1               5                   10                  15

Arg Arg Val Val Gly Pro Ser Leu Phe Ser Leu His His Arg Gln Pro
            20                  25                  30

Arg Leu Gly Arg Asn Pro Lys Thr Gly Asp Ser Val
        35                  40

<210> SEQ ID NO 41
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(40)
<223> OTHER INFORMATION: Any amino acid
<220> FEATURE:
<221> NAME/KEY: MISC_FEATURE
<222> LOCATION: (21)..(40)
<223> OTHER INFORMATION: This region may encompass 1-20 residues

<400> SEQUENCE: 41

Phe Leu Glu Glu Ile Arg Leu Ser Leu Glu Ser Gly Gln Asp Val Lys
1               5                   10                  15

Leu Ser Gly Phe Xaa Xaa Xaa Xaa Xaa Xaa Xaa Xaa Xaa Xaa
            20                  25                  30

Xaa Xaa Xaa Xaa Xaa Xaa Xaa Xaa Thr Leu Ser Ala Lys Glu Ile Glu
        35                  40                  45

Asn Met Val Lys Asp Ile Leu Glu Phe Ile Ser Gln
    50                  55                  60

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly Ser Gly Gly Ser
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Pro Ser Leu Lys Leu
1               5

```
<210> SEQ ID NO 44
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Gly Gly
1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Pro Ser Leu
1

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Pro Ser
1

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Pro Ser Leu Lys
1

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gly Pro Ser Leu Lys
1               5

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 49

Ser Leu Lys Leu
1

<210> SEQ ID NO 50
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Phe Leu Glu Glu Ile Arg Leu Ser Leu Glu Ser Gly Gln Asp Val Lys
1               5                   10                  15

Leu Ser Gly Phe Gly Pro Ser Leu Thr Leu Ser Ala Lys Glu Ile Glu
            20                  25                  30

Asn Met Val Lys Asp Ile Leu Glu Phe Ile Ser Gln
        35                  40
```